US009994844B2

(12) United States Patent
Siegfried et al.

(10) Patent No.: US 9,994,844 B2
(45) Date of Patent: Jun. 12, 2018

(54) PARENTAL RNAI SUPPRESSION OF CHROMATIN REMODELING GENES TO CONTROL COLEOPTERAN PESTS

(71) Applicants: Dow AgroSciences LLC, Indianapolis, IN (US); The Board of Regents of the University of Nebraska, Lincoln, NE (US)

(72) Inventors: Blair D. Siegfried, Lincoln, NE (US); Kenneth E. Narva, Zionsville, IN (US); Kanika Arora, Indianapolis, IN (US); Sarah E. Worden, Indianapolis, IN (US); Chitvan Khajuria, Chesterfield, MO (US); Elane Fishilevich, Indianapolis, IN (US); Nicholas P. Storer, Kensington, MD (US); Meghan Frey, Greenwood, IN (US); Ronda L. Hamm, Carmel, IN (US); Ana M. Velez, Lincoln, NE (US)

(73) Assignees: Dow AgroSciences LLC, Indianapolis, IN (US); The Board of Regents of the University of Nebraska, Lincoln, NE (US)

( * ) Notice: Subject to any disclaimer, the term of this patent is extended or adjusted under 35 U.S.C. 154(b) by 0 days. days.

(21) Appl. No.: 14/971,188

(22) Filed: Dec. 16, 2015

(65) Prior Publication Data

US 2016/0208251 A1 Jul. 21, 2016
US 2017/0369873 A9 Dec. 28, 2017

Related U.S. Application Data

(63) Continuation-in-part of application No. 13/646,485, filed on Oct. 5, 2012, now Pat. No. 9,770,035.

(60) Provisional application No. 62/092,768, filed on Dec. 16, 2014, provisional application No. 62/170,076, filed on Jun. 2, 2015, provisional application No. 61/544,214, filed on Oct. 6, 2011, provisional application No. 61/544,227, filed on Oct. 6, 2011, provisional application No. 61/544,217, filed on Oct. 6, 2011.

(51) Int. Cl.

| | |
|---|---|
| ***C12N 15/113*** | (2010.01) |
| ***A01N 63/02*** | (2006.01) |
| ***C12N 15/82*** | (2006.01) |
| ***A01N 57/16*** | (2006.01) |

(52) U.S. Cl.
CPC ............ *C12N 15/113* (2013.01); *A01N 57/16* (2013.01); *C12N 15/8218* (2013.01); *C12N 15/8286* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2012/0174258 A1 | 7/2012 | Narva et al. | | |
| 2013/0058890 A1 | 3/2013 | Raemaekers et al. | | |
| 2013/0097730 A1 * | 4/2013 | Narva | ................ | C12N 15/8286 800/279 |
| 2016/0230186 A1 * | 8/2016 | Baum | ................ | C12N 15/8286 |

FOREIGN PATENT DOCUMENTS

| | | |
|---|---|---|
| WO | 2007035650 | 3/2007 |

OTHER PUBLICATIONS

Khajuria et al, 2015, Insect Biochemistry and Molecular Biology, 63:54-62.*
Thomas et al, 2001, Plant J., 25:417-425.*
Gkhajuria, Chitvan et al., 'Parental RNA interference of genes involved in embryonic development of the western corn rootworm, *Diabrotica virgifera* virgifera LeConte', Insect Biochemistry and Molecular Biology, Epub. May 22, 2015, vol. 63, pp. 54-62.
Ho, Lena et al., "Chromatin remodelling during development,", Nature, Jan. 28, 2010, pp. 474-484, vol. 463, No. 7280 (NIH Public Access Author Manuscript Version internal pp. 1-24).
Mito, Taro et al., "Kruppel acts as a gap gene regulating expression of hunchback and even-skipped in the intermediate germ cricket Glyllus bimaculatus," Developmental Biology, Epub. Apr. 17, 2006, vol. 294, No. 2, pp. 471-481.
NCBI, GenBank accession No. XM_003742362.1 (Jun. 14, 2012).
NCBI, GenBank accession No. XM_007547345.1 (Apr. 22, 2014).
Search Report and Written Opinion for PCT/US2015/066082, dated Apr. 15, 2016.
Search Report and Written Opinion for PCT/US2015/066134, dated Apr. 22, 2016.

* cited by examiner

*Primary Examiner* — Jason Deveau Rosen
(74) *Attorney, Agent, or Firm* — Sean M. Russell; Magleby Cataxinos & Greenwood

(57) ABSTRACT

This disclosure concerns nucleic acid molecules and methods of use thereof for control of coleopteran pests through RNA interference-mediated inhibition of target coding and transcribed non-coding sequences in coleopteran pests. The disclosure also concerns methods for making transgenic plants that express nucleic acid molecules useful for the control of coleopteran pests, and the plant cells and plants obtained thereby.

38 Claims, 16 Drawing Sheets

```
Score =  492 bits (256), Expect = e-137
Identities = 307/330 (93%), Gaps = 1/330 (0%)
 Strand = Plus / Minus

Query: 1    ccattctcgctgcatttgctcaatcctacatacactttaactccttcttgggttttag 60
            ||||||||| ||||| ||||||||||||||||||||||||||||||||||||||||||||
Sbjct: 1185 ccattctcgttgcatcttgctcaatcctacatacactttaactccttcttgggttttag 1126

Query: 61   cccttctctacttcaattttcaatcttctaagcaagaatggttttaatacagcatgcag 120
            || |||||| ||||||  ||||||||||||||||||||||||||||||||||||||||| 
Sbjct: 1125 ccgtttctccacttcagctttcaatcttctaagcaagaatggttttaatacagcatgcaa 1066

Query: 121  cctctccaccatggagttgcctcccagacattgactggtgttaaaccaggcatcgaaatc 180
             ||||| |||| || |||| |||||||||||||||||||||| |||||||||||||||||
Sbjct: 1065 tctctcgaccaaggcgttgtctcccagacattgactggtgttgaaccaggcatcgaaatc 1006

Query: 181  atcagatgagttaaaaacgtctggcagtaagaagttgagaagagaccagagttcatgtaa 240
            ||| |||||||| ||||| ||||||||||||||||||||||||| ||||||||| |||||
Sbjct: 1005 atccgatgagttgaaaacatctggcagtaagaagttgagaagagcccagagttcgtgtaa 946

Query: 241  attgttttgtaatggagtacctgttagcagtagcctgttggtattcttgaattccctgag 300
            ||||||||||||||||||||||||||||||||||||||| ||| ||||||| ||||||||
Sbjct: 945  attgttttgtaatggagtacctgttagcagtagcctgttagtagtcttgaactccctgag 886

Query: 301  aatttcggaaagcttagtctttttcatttt 330
            |||||||||||||||||  |||||||||||
Sbjct: 885  aatttcggaaagcttag-atttttcatttt 857
```

FIG. 4

SEQUENCE LISTING

<160> NUMBER OF SEQ ID NOS: 171

<210> SEQ ID NO 1
<211> LENGTH: 4768
<212> TYPE: DNA
<213> ORGANISM: Diabrotica virgifera

<400> SEQUENCE: 1
caagtggcca tggcatgcca cagggtcccc ctggacaacc aggtcagcaa caccaaggcc 60
gaactgctga taatttacat gccttacaaa aagcaataga tacaatggaa gaaaaaggta 120
tgcaagaaga tcagaggtat tcacagttac tggcgttacg tgctagatcc agtggtcaac 180
catctaacgg agttcttaca ccgctgcaaa tgaatcaact tagaaatcaa attatggcat 240
acaggtgcct agcgaggagc caaccaattc ctccttcaat aatgttgggg ctgcaaggaa 300
agaggcctga cggttcacca cagtttccta cacctccgtc aagtccgttt caaccacaag 360
gacctggtgc accccctggt ccggaacaac caccagctaa tgcagaaaac gtagcagagc 420
cagcagcacc agtaggaccg caaggtgcac aaggacctcc taaccaacag agagctcaaa 480
ctagccagtt agtccccaat aagcaaactc gtttcactac catgcccaaa ccatctggac 540
tagatccact agttcttctt caagagaggg aaactagggt ggcagctaga atcgctgcta 600
gaatagaaca atgtagtaac ttacctacca atctttcaga caaagtccgc atgcaagcac 660
agatagaatt gagagctttg cggtgcctta atttccaaag gcaactaaga agcgaaattt 720
tgaactgtat taggagagat ataacgcttg aatctgctgt aaattttaaa gcatataaaa 780
gaacgaagcg acagggtcta aaagaatcga gagctacaga gaagttagaa aaacaacaga 840
agttagaagc agaaagaaag agaagacaga agaaccaaga atttttgaat gctgtattga 900
acaatggaaa agaattcaag gaattccaca agcagaatca agcgaaatta gctaagatta 960
ataaagctgt tattaattat cacgctaatg ctgaaagaga gcaaaagaaa gaagcagaaa 1020
ggagagagaa ggaacgtatg atcagattga tggcagaaga tgaagaaggt tatagacagt 1080
tgatcgatca aaagaaagac aaacgtctag cgttcttgct ttcccaaaca gatgaatata 1140
tcagtaactt aacagagatg gtgaaaatgc acaaagtcga acaaagtaac aagaagcggg 1200
aagaagaacg acggaagaga aggcaagaca aaatgcagca gcctgacagg aaagtcacag 1260
ttatcgaaat ggctactggg aataaggtta gtggagaaaa cgctccgact gtccaggaac 1320
ttcctgaatg gttacagact catcctggtt gggagatgat agatacagaa gacgaggacg 1380
agaatgacga atatagaatg gacgattatg aagaaaataa tcaagtcgat gctacagaaa 1440
tcattcagaa agccaaggtt gaggatgacg aatatcacaa gaatgccaca gaggaacaga 1500
cgtactacgg tattgcacat acagtgagcg agtcagtatc agaacaggcc tccattatga 1560
taaacggtga actgaaagag taccaggtca aaggactgga atggatggta tccttgtaca 1620
acaacaatct taatggtatc ctagcagacg agatgggttt gggtaagact attcaaacca 1680
ttggcctgat cacctacttg atggagaaaa aaaagttgaa tgggccattt ttgatcattg 1740
tgccgttatc cactatatct aattggatgt tggagttcga aaaatgggct ccttctgttg 1800
tggtcgtctc ctacaaaggc tcacctggtc acaggaaatt gcttcagggt cagatgaagt 1860
cagcaaaatt caatgttctt cttactactt atgaatatat cattaaagat aagggaattc 1920
tttcaaaagt accgtttaag tatatgatcg tggacgaggg tcacagaatg aagaaccatc 1980
attgcaagtt gacccagact ttgaacactc actacgcagc tcctttccgc cttctcttaa 2040
ccggtactcc tctacaaaac aaactaccag aactgtgggc gttgcttaac ttcttacttc 2100
cgtctatttt caagagttgt tccactttcg agcaatggtt caacgcccct ttcgcaacca 2160
cgggagaaaa ggttgaactt aacgaagaag aaaccatcct tatcatccga cgtcttcaca 2220
aagtcctgcg acctttcctc ttaagacgtc tcaaaaagga agtagagtct cagcttcccg 2280
acaaagtcga atacattatc aaatgcgaga tgtccggttt gcaaaaagtg ttgtaccaac 2340
acatgcagag caagggagtt ctgctcaccg acgggtccga aaagggtaat aggggccgag 2400
gtggagctaa ggctatcatg aataccatca tgcaactgcg gaagctgtgt aatcatcctt 2460
tcatgttcca aatgatcgaa gaaaagtatt gtgaatatgt aggcatgggt gggggactca 2520
catcagggcc ggatatatac agatcttctg gtaaatttga acttctggat cgggtattgc 2580
caaagctcaa ggcgactgac cacagagtcc tactgttctg tcaaatgacg acgttgatga 2640
acatcatgga agactacttc atttggagag gttacaaata tcttcgtctg gatggtatgg 2700
taaaagcgga agatcgggcg gaactactca agaagttcaa tgacaaacaa agcgaatatt 2760
ttgtgtttct attgtcaaca agagcaggag gtcttggact caacttgcaa agtgctgata 2820
ctgttatcat ctttgattct gactggaatc ctcaccagga tttacaagct caagatcgtg 2880
cccatcgtat aggccagcaa aatgaagtca gggtcctacg tttaatgaca gttaattcag 2940
tggaagaaag aatcttagct gcagctaaat acaaacttat aatggacgag aaagtaatcc 3000
aagctggtat gttcgatcag aagtctacag gctcagagag acatcagttt ttgcagagta 3060
ttttacacca tgacggaagc gacgaagaag aggaaaacga agttcctgat gacgaaacag 3120
tgaaccagat gttggcccga agggaaaacg aatttcagct tttccagaag atggatcagg 3180
aaagaaagga agaagatgaa aagaccggaa agtcgcgact tattcaagaa agcgaattgc 3240
ccgaatggct gttgaagcaa gacgatgaaa tctactcgtg gggccttgat gatccagatg 3300
ctgttttagg aaggggtagt aggcaaagaa aagaagttga ttatgttgac agcctgacgg 3360
agaaagagtg gcttaaggct attgacgaag agggagaatt tgaggaagaa caagaaggtg 3420
ataaagaagg tctcagaaag aaaagaggga ggaagaggaa gaagcgcgat gatgacgaag 3480
aggcaagcca aattaagaga agaaaggtgc atctagccga gatcaagatg aagaaaaaga 3540
tgaagaggct tatggaagtt gttgtgaact acagggatag ggatggtaga gtattgagcg 3600
aaccgtttat gaaacttcca tcaaagaagg agttacctga atattacgat acgattaaga 3660
aacctattga tattgaaaaa gtcgttgcca acgtagaaga aggaaaatat ttcacgatgc 3720
acgatttgga aagagatttc gacttgctgt gccaaaacgc ccaacaatac aacgaagaag 3780
actccatgat ctacgaggac agcctcgttc ttcgacaggt gtttagaagc gcgagggaaa 3840
agatcgacgg tacctcagac cacgacgaca acgccgatgg accggcggtg gctcagatca 3900
aacgacctcg tggtagacct cgaaaacaca agagacccga agagatcgag gccgaagcgg 3960
cggctcagaa agctatggag gaggcatcga agctgagagc tcaagctgag gcggaagagc 4020
ttagatctaa ggtggaggag gcatctcaga gagccaaaga ggaagcgaaa gcaagggagg 4080
aagccaaagc tagggaagaa gccgaaatcg agaacatgga ggagattccc acaagcacat 4140
gatctataga gcaaccggaa acaaaaaggc aaaaaagaaa tattatatag aaaagatgta 4200
catgttcaat ggagatacat tttcgctgag ttacaacggg taatgctttt acaacggata 4260
ttttgacgta tgaatgttga cgttcagatg aagtatattt ataaaataat ccagaccttt 4320
acgttttggt tgatttgttt tctgtattgt tcagtttatt gaacaaccat taatagcagc 4380
ttacctaaat gatttagaaa agcatctgag ttatttagat aagttttgag attatattta 4440

```
ttaactttaa tattactatc tttattatag catattgtaa ttattttttc ctgtccttct   4500

ttcgttgtgt ggtagataat ccgagagtca acagttataa gcaaatgaaa ttcagttaaa   4560

cctcaaatgt acaaaatgat caaattaatg tttacaattt atttttttac cacgcacatc   4620

cactattact attgtcagtc attgagatat cattttatat agctccatgt ctgtcttcct   4680

caatttacag agaagcaatt agacaagtaa tgacataata tggtgctgaa ataatgtgct   4740

tgatagtgat gttgaaaaag taactatt                                      4768
```

<210> SEQ ID NO 2
<211> LENGTH: 1375
<212> TYPE: PRT
<213> ORGANISM: Diabrotica virgifera

<400> SEQUENCE: 2

```
Met Pro Gln Gly Pro Pro Gly Gln Pro Gly Gln Gln His Gln Gly Arg
1               5                   10                  15

Thr Ala Asp Asn Leu His Ala Leu Gln Lys Ala Ile Asp Thr Met Glu
            20                  25                  30

Glu Lys Gly Met Gln Glu Asp Gln Arg Tyr Ser Gln Leu Leu Ala Leu
        35                  40                  45

Arg Ala Arg Ser Ser Gly Gln Pro Ser Asn Gly Val Leu Thr Pro Leu
    50                  55                  60

Gln Met Asn Gln Leu Arg Asn Gln Ile Met Ala Tyr Arg Cys Leu Ala
65                  70                  75                  80

Arg Ser Gln Pro Ile Pro Pro Ser Ile Met Leu Gly Leu Gln Gly Lys
                85                  90                  95

Arg Pro Asp Gly Ser Pro Gln Phe Pro Thr Pro Pro Ser Ser Pro Phe
            100                 105                 110

Gln Pro Gln Gly Pro Gly Ala Pro Pro Gly Pro Glu Gln Pro Pro Ala
        115                 120                 125

Asn Ala Glu Asn Val Ala Glu Pro Ala Ala Pro Val Gly Pro Gln Gly
    130                 135                 140

Ala Gln Gly Pro Pro Asn Gln Gln Arg Ala Gln Thr Ser Gln Leu Val
145                 150                 155                 160

Pro Asn Lys Gln Thr Arg Phe Thr Thr Met Pro Lys Pro Ser Gly Leu
                165                 170                 175

Asp Pro Leu Val Leu Leu Gln Glu Arg Glu Thr Arg Val Ala Ala Arg
            180                 185                 190

Ile Ala Ala Arg Ile Glu Gln Cys Ser Asn Leu Pro Thr Asn Leu Ser
        195                 200                 205

Asp Lys Val Arg Met Gln Ala Gln Ile Glu Leu Arg Ala Leu Arg Cys
    210                 215                 220

Leu Asn Phe Gln Arg Gln Leu Arg Ser Glu Ile Leu Asn Cys Ile Arg
225                 230                 235                 240

Arg Asp Ile Thr Leu Glu Ser Ala Val Asn Phe Lys Ala Tyr Lys Arg
                245                 250                 255

Thr Lys Arg Gln Gly Leu Lys Glu Ser Arg Ala Thr Glu Lys Leu Glu
            260                 265                 270

Lys Gln Gln Lys Leu Glu Ala Glu Arg Lys Arg Arg Gln Lys Asn Gln
        275                 280                 285

Glu Phe Leu Asn Ala Val Leu Asn Asn Gly Lys Glu Phe Lys Glu Phe
    290                 295                 300

His Lys Gln Asn Gln Ala Lys Leu Ala Lys Ile Asn Lys Ala Val Ile
305                 310                 315                 320
```

```
Asn Tyr His Ala Asn Ala Glu Arg Glu Gln Lys Lys Glu Ala Glu Arg
                325                 330                 335

Arg Glu Lys Glu Arg Met Ile Arg Leu Met Ala Glu Asp Glu Glu Gly
            340                 345                 350

Tyr Arg Gln Leu Ile Asp Gln Lys Lys Asp Lys Arg Leu Ala Phe Leu
        355                 360                 365

Leu Ser Gln Thr Asp Glu Tyr Ile Ser Asn Leu Thr Glu Met Val Lys
    370                 375                 380

Met His Lys Val Glu Gln Ser Asn Lys Lys Arg Glu Glu Glu Arg Arg
385                 390                 395                 400

Lys Arg Arg Gln Asp Lys Met Gln Gln Pro Asp Arg Lys Val Thr Val
                405                 410                 415

Ile Glu Met Ala Thr Gly Asn Lys Val Ser Gly Glu Asn Ala Pro Thr
            420                 425                 430

Val Gln Glu Leu Pro Glu Trp Leu Gln Thr His Pro Gly Trp Glu Met
        435                 440                 445

Ile Asp Thr Glu Asp Glu Asp Glu Asn Asp Glu Tyr Arg Met Asp Asp
    450                 455                 460

Tyr Glu Glu Asn Asn Gln Val Asp Ala Thr Glu Ile Ile Gln Lys Ala
465                 470                 475                 480

Lys Val Glu Asp Asp Glu Tyr His Lys Asn Ala Thr Glu Glu Gln Thr
                485                 490                 495

Tyr Tyr Gly Ile Ala His Thr Val Ser Glu Ser Val Ser Glu Gln Ala
            500                 505                 510

Ser Ile Met Ile Asn Gly Glu Leu Lys Glu Tyr Gln Val Lys Gly Leu
        515                 520                 525

Glu Trp Met Val Ser Leu Tyr Asn Asn Asn Leu Asn Gly Ile Leu Ala
    530                 535                 540

Asp Glu Met Gly Leu Gly Lys Thr Ile Gln Thr Ile Gly Leu Ile Thr
545                 550                 555                 560

Tyr Leu Met Glu Lys Lys Lys Leu Asn Gly Pro Phe Leu Ile Ile Val
                565                 570                 575

Pro Leu Ser Thr Ile Ser Asn Trp Met Leu Glu Phe Glu Lys Trp Ala
            580                 585                 590

Pro Ser Val Val Val Val Ser Tyr Lys Gly Ser Pro Gly His Arg Lys
        595                 600                 605

Leu Leu Gln Gly Gln Met Lys Ser Ala Lys Phe Asn Val Leu Leu Thr
    610                 615                 620

Thr Tyr Glu Tyr Ile Ile Lys Asp Lys Gly Ile Leu Ser Lys Val Pro
625                 630                 635                 640

Phe Lys Tyr Met Ile Val Asp Glu Gly His Arg Met Lys Asn His His
                645                 650                 655

Cys Lys Leu Thr Gln Thr Leu Asn Thr His Tyr Ala Ala Pro Phe Arg
            660                 665                 670

Leu Leu Leu Thr Gly Thr Pro Leu Gln Asn Lys Leu Pro Glu Leu Trp
        675                 680                 685

Ala Leu Leu Asn Phe Leu Leu Pro Ser Ile Phe Lys Ser Cys Ser Thr
    690                 695                 700

Phe Glu Gln Trp Phe Asn Ala Pro Phe Ala Thr Thr Gly Glu Lys Val
705                 710                 715                 720

Glu Leu Asn Glu Glu Glu Thr Ile Leu Ile Ile Arg Arg Leu His Lys
                725                 730                 735
```

```
Val Leu Arg Pro Phe Leu Leu Arg Arg Leu Lys Lys Glu Val Glu Ser
            740                 745                 750

Gln Leu Pro Asp Lys Val Glu Tyr Ile Ile Lys Cys Glu Met Ser Gly
        755                 760                 765

Leu Gln Lys Val Leu Tyr Gln His Met Gln Ser Lys Gly Val Leu Leu
    770                 775                 780

Thr Asp Gly Ser Glu Lys Gly Asn Arg Gly Arg Gly Gly Ala Lys Ala
785                 790                 795                 800

Ile Met Asn Thr Ile Met Gln Leu Arg Lys Leu Cys Asn His Pro Phe
                805                 810                 815

Met Phe Gln Met Ile Glu Glu Lys Tyr Cys Glu Tyr Val Gly Met Gly
            820                 825                 830

Gly Gly Leu Thr Ser Gly Pro Asp Ile Tyr Arg Ser Ser Gly Lys Phe
        835                 840                 845

Glu Leu Leu Asp Arg Val Leu Pro Lys Leu Lys Ala Thr Asp His Arg
    850                 855                 860

Val Leu Leu Phe Cys Gln Met Thr Thr Leu Met Asn Ile Met Glu Asp
865                 870                 875                 880

Tyr Phe Ile Trp Arg Gly Tyr Lys Tyr Leu Arg Leu Asp Gly Met Val
                885                 890                 895

Lys Ala Glu Asp Arg Ala Glu Leu Leu Lys Lys Phe Asn Asp Lys Gln
            900                 905                 910

Ser Glu Tyr Phe Val Phe Leu Leu Ser Thr Arg Ala Gly Gly Leu Gly
        915                 920                 925

Leu Asn Leu Gln Ser Ala Asp Thr Val Ile Ile Phe Asp Ser Asp Trp
    930                 935                 940

Asn Pro His Gln Asp Leu Gln Ala Gln Asp Arg Ala His Arg Ile Gly
945                 950                 955                 960

Gln Gln Asn Glu Val Arg Val Leu Arg Leu Met Thr Val Asn Ser Val
                965                 970                 975

Glu Glu Arg Ile Leu Ala Ala Ala Lys Tyr Lys Leu Ile Met Asp Glu
            980                 985                 990

Lys Val Ile Gln Ala Gly Met Phe  Asp Gln Lys Ser Thr  Gly Ser Glu
        995                 1000                1005

Arg His  Gln Phe Leu Gln Ser  Ile Leu His His Asp  Gly Ser Asp
    1010                1015                1020

Glu Glu  Glu Glu Asn Glu Val  Pro Asp Asp Glu Thr  Val Asn Gln
    1025                1030                1035

Met Leu  Ala Arg Arg Glu Asn  Glu Phe Gln Leu Phe  Gln Lys Met
    1040                1045                1050

Asp Gln  Glu Arg Lys Glu Glu  Asp Glu Lys Thr Gly  Lys Ser Arg
    1055                1060                1065

Leu Ile  Gln Glu Ser Glu Leu  Pro Glu Trp Leu Leu  Lys Gln Asp
    1070                1075                1080

Asp Glu  Ile Tyr Ser Trp Gly  Leu Asp Asp Pro Asp  Ala Val Leu
    1085                1090                1095

Gly Arg  Gly Ser Arg Gln Arg  Lys Glu Val Asp Tyr  Val Asp Ser
    1100                1105                1110

Leu Thr  Glu Lys Glu Trp Leu  Lys Ala Ile Asp Glu  Glu Gly Glu
    1115                1120                1125

Phe Glu  Glu Glu Gln Glu Gly  Asp Lys Glu Gly Leu  Arg Lys Lys
    1130                1135                1140

Arg Gly  Arg Lys Arg Lys Lys  Arg Asp Asp Asp Glu  Glu Ala Ser
```

```
    1145                1150                1155

Gln Ile  Lys Arg Arg Lys Val  His Leu Ala Glu Ile  Lys Met Lys
    1160                1165                1170

Lys Lys  Met Lys Arg Leu Met  Glu Val Val Val Asn  Tyr Arg Asp
    1175                1180                1185

Arg Asp  Gly Arg Val Leu Ser  Glu Pro Phe Met Lys  Leu Pro Ser
    1190                1195                1200

Lys Lys  Glu Leu Pro Glu Tyr  Tyr Asp Thr Ile Lys  Lys Pro Ile
    1205                1210                1215

Asp Ile  Glu Lys Val Val Ala  Asn Val Glu Glu Gly  Lys Tyr Phe
    1220                1225                1230

Thr Met  His Asp Leu Glu Arg  Asp Phe Asp Leu Leu  Cys Gln Asn
    1235                1240                1245

Ala Gln  Gln Tyr Asn Glu Glu  Asp Ser Met Ile Tyr  Glu Asp Ser
    1250                1255                1260

Leu Val  Leu Arg Gln Val Phe  Arg Ser Ala Arg Glu  Lys Ile Asp
    1265                1270                1275

Gly Thr  Ser Asp His Asp Asp  Asn Ala Asp Gly Pro  Ala Val Ala
    1280                1285                1290

Gln Ile  Lys Arg Pro Arg Gly  Arg Pro Arg Lys His  Lys Arg Pro
    1295                1300                1305

Glu Glu  Ile Glu Ala Glu Ala  Ala Ala Gln Lys Ala  Met Glu Glu
    1310                1315                1320

Ala Ser  Lys Leu Arg Ala Gln  Ala Glu Ala Glu Glu  Leu Arg Ser
    1325                1330                1335

Lys Val  Glu Glu Ala Ser Gln  Arg Ala Lys Glu Glu  Ala Lys Ala
    1340                1345                1350

Arg Glu  Glu Ala Lys Ala Arg  Glu Glu Ala Glu Ile  Glu Asn Met
    1355                1360                1365

Glu Glu  Ile Pro Thr Ser Thr
    1370                1375
```

<210> SEQ ID NO 3
<211> LENGTH: 5147
<212> TYPE: DNA
<213> ORGANISM: Diabrotica virgifera

<400> SEQUENCE: 3

```
tcacgtgcct ccacaaggcc atgttcctcc acagggtcac gtgcctccac aaggccatgt     60

tcctccacag ggacatcttc ctccacaggg ccatattcca ccacagggtc atggtccaac    120

gcagggccac atacctcctc aggggcatgt tccaccacaa ggacatatac ctcctcaagg    180

gcatgcaccc ccacaaggac atgcaccacc acaggggcat cctggcgttc ctcctggtca    240

tcagagtcat cctcaagggc atccacaaac accagggcat cctggacctg gacatatacc    300

acctggtgga gcaatgcacc cagggcatta tccaagtggc catggcatgc cacagggtcc    360

ccctggacaa ccaggtcagc aacaccaagg ccgaactgct gataatttac atgccttaca    420

aaaagcaata gatacaatgg aagaaaaagg tatgcaagaa gatcagaggt attcacagtt    480

actggcgtta cgtgctagat ccagtggtca accatctaac ggagttctta caccgctgca    540

aatgaatcaa cttagaaatc aaattatggc atacaggtgc ctagcgagga gccaaccaat    600

tcctccttca ataatgttgg ggctgcaagg aaagaggcct gacggttcac cacagtttcc    660

tacacctccg tcaagtccgt ttcaaccaca aggacctggt gcaccccctg gtccggaaca    720
```

-continued

```
accaccagct aatgcagaaa acgtagcaga gccagcagca ccagtaggac cgcaaggtgc    780
acaaggacct cctaaccaac agagagctca aactagccag ttagtcccca ataagcaaac    840
tcgtttcact accatgccca aaccatctgg actagatcca ctagttcttc ttcaagagag    900
ggaaactagg gtggcagcta gaatcgctgc tagaatagaa caatgtagta acttacctac    960
caatctttca gacaaagtcc gcatgcaagc acagatagaa ttgagagctt tgcggtgcct   1020
caatttccaa aggcaactaa gaagcgaaat tttgaactgt attaggagag atataacgct   1080
tgaatctgct gtaaatttta aagcatataa aagaacgaag cgacagggtc taaaagaatc   1140
gagagctaca gagaagttag aaaaacaaca gaagttagaa gcagaaagaa agagaagaca   1200
gaagaaccaa gaatttttga atgctgtatt gaacaatgga aaagaattca aggaattcca   1260
caagcagaat caagcgaaat tagctaagat taataaagct gttattaatt atcacgctaa   1320
tgctgaaaga gagcaaaaga aagaagcaga aaggagagag aaggaacgta tgatcagatt   1380
gatggcagaa gatgaagaag gttatagaaa gctcattgat caaaagaaag acaaacgtct   1440
agcgttcttg ctttcgcaaa cagatgagta tataactaac ctcacggaga tggtaaagca   1500
acacaagttg gaacaaacca ataaaaagaa agaggaggaa aaacgcaaga agaagcagca   1560
gaaaatgcaa caaccagata ggaaagttac agttctggaa actgcaacag gtaaaaaagt   1620
aacaggagag gctgctccta cactgcgaca agttcaagaa tggttaatcc aacatcctgg   1680
atgggagatg gtcgatacag atgatgagga tgatgaaaac ggggagaaga gggatgatga   1740
ctatgatgaa aatcaagaag tggatgatgc aaaagaagtt attaaaaaag ctaaagttga   1800
agatgacgaa tatcacaaaa acacaaaaga agaacagact tactacagta ttgctcacac   1860
tgttcatgaa gtggtaacag aacaagcatc cattctggtt aatggaaagc ttaaggaata   1920
tcaaattaga gggttagaat ggatggtgtc tttgtacaat aacaatctga atggtattct   1980
agcagatgag atgggtctag gtaaaaccat tcaaacgatt ggcttgttga cctatttgat   2040
ggaaaaaaag aagataaatg gaccgttttt gatcatagtg ccactttcaa ccatttctaa   2100
ttggatgttg gaatttcaaa agtgggcccc tactgtagtt gtcatttcat acaaaggctc   2160
tcctgtggtt agaaaagtga tccagagcca gttaaaagct gctaaattca atgtgcttct   2220
cactacctac gagtacatta ttaaggacaa gggtgtatta gcaaaaatcc catttaaata   2280
tatgatcata gatgagggtc atcgtatgaa aaaccaccac tgcaaattga ctcaagtcct   2340
gaatacgcac tatttggcgc cctacagact cctgcttact ggtactcccc tacaaaataa   2400
attaccagaa ttatgggcct tgttgaattt cttgttgcct tcgattttca agagttgctc   2460
cacttttgaa caatggttca atgcgccatt cgcaacaaca ggagaaaagg ttgagttaaa   2520
cgaagaagaa actatcctta tcatccgtcg tcttcacaaa gtactcaggc cgtttctcct   2580
gagacgtctc aagaaagaag tcgaatctca gcttccagac aaagtggaat atatcataaa   2640
gtgtgacatg tcgggcctac aaaaggttct ctatgcacac atgcagagca agggtgtgtt   2700
acttaccgat ggttccgaga agggcagtaa aggaaggga tctaaggcac tgatgaacac    2760
cattatgcag ctgaggaaac tgtgcaatca tccgtttatg ttccaaaata tcgaagagaa   2820
atattgtgat catgttggta ttgctggtgg agtggtttct ggacccgaca cttatagggt   2880
atctggtaag tttgagctct tggacagaat attgcccaaa atgaaagcaa ctaaccatag   2940
gattcttctt ttctgtcaaa tgactcaatt aatgaccatc atggaagatt atctaaattg   3000
gagaggattc aaatatcttc gtcttgatgg tacaatcaaa tcagaagatc gcggggacct   3060
attatcgaaa tttaatgata aaaatagtga atattttttg tttttgctat ctacacgggc   3120
```

```
tggaggtctg ggacttaatt tgcagacagc tgatactgtg attatcttcg attccgattg   3180
gaatcctcat caggatttac aagctcagga tcgagctcat cgtattggac agcaaaatga   3240
ggtccgagtt ttgcgtttga tgactgttaa ctctgttgag gaacgaattt tagctgcagc   3300
taaatacaag cttactatgg acgaaaaggt cattcaagct ggtatgttcg atcagaagtc   3360
tacgggatct gaaaggcagc agtttcttca gagtatttta cacaatgatg gtagtgatga   3420
agaagaggaa aatgaagtgc ctgatgacga aaccgtcaac caaatgatag ctaggacaga   3480
ggatgagttt cagctcttcc aaaaaatgga tacggaaaga aaagaggaga atgaaaaact   3540
tggtcagcat aaaaagtcgc gattggttca agaatgtgaa cttccggatt ggctgacaaa   3600
gccagatgaa gatgatggct ggggtgatga ttatactgaa gcgctattgg gcagaggaac   3660
caggcagcga aaggaagttg attatgctga tagtttaaca gaaaaggaat ggttaaaggc   3720
tatcgatgaa gacggagact acgatgaaga agaagaggaa gaaaaagtac aaaagaagag   3780
gggtaggaag agaaggaagc gtgacgattc tgacgatgac accagcagtt ctacgagaag   3840
gcgtaagcta ccccaaagtc aggtagaagc taggctaaag agaaaaatga aaaagttgat   3900
gaacatagtt acaaattata aagacaggga tggacgacag cttagcgatc aattcattaa   3960
attgcctcca aggaaagagt atccagacta ttatactatt attaaaaagc ctatagatat   4020
tagcaagata ttaaattata tagatgatgg aaagtactct gatttctccg atctggaacg   4080
agacttcatg cttctctgcc agaatgctca aatctataac gaagaagcgt cgttgattca   4140
cgaagacagc atcgtactgc agtcggtctt ttcgagtgcc aagcagaaga tcgaagcctc   4200
cccggattcg gacgacgaaa aagatgacaa taattccgat gtagaaactc ctaagaataa   4260
aaataaacct ggtaaaggca agagacgacc cggcaggcct aggaggtcgg cgaaaaaata   4320
catttcggac gacgatgacg acgactgaag agtttaggtg taagagaaat gagaatgaaa   4380
ttcttattgc aaaagttgta catatgaagg tgttgttatt ctttaccaaa gctggtaaat   4440
gtttgattta aagggaaact ggaacttttc tcttggtttt agatagtact atagataggt   4500
tttgataggg aataacaggt tcaagattcg ccccagttga aatttgctta aatgatcaaa   4560
gagtacttaa gtataatgaa tcacgattgt ttaaatttta acttgcactt agtgacaaaa   4620
aaataacagc ttataaataa atttacgtag caagaatgat cctattgatt aagaatgaat   4680
gagcctctcc aaagatagtc caaaaagtgt ttcagggtga aaaggagttg tgaaaaatac   4740
aagatggtct gctaagcaac cttctttgta acaaaaatca tgtttttcca gaaatttttt   4800
tttattttat taatatagtc ctcttttatc tcaatacaac gcgattccag cgattttcca   4860
aacttcttta tgccgtcgga ataaggcccc acctagattg gatccgtatt tctcctatca   4920
gatccgatcc gacgtcggat tgaaagcaaa ctcaaggtat taaggtatgg ctgcacttac   4980
attggatccc catcctccga tccgatatag ggcgattgat aggagaagct acagcagaga   5040
agcagttcga cgtcggccga tatcggatcg gtcttctcac tacagtgtag gcactgcgct   5100
ttaatacctt ccctaataac actaaacatt ccatgtatgt tcctaga                 5147
```

<210> SEQ ID NO 4
<211> LENGTH: 1344
<212> TYPE: PRT
<213> ORGANISM: Diabrotica virgifera

<400> SEQUENCE: 4

```
Met His Pro Gly His Tyr Pro Ser Gly His Gly Met Pro Gln Gly Pro
1               5                   10                  15
```

```
Pro Gly Gln Pro Gly Gln Gln His Gln Gly Arg Thr Ala Asp Asn Leu
            20                  25                  30

His Ala Leu Gln Lys Ala Ile Asp Thr Met Glu Glu Lys Gly Met Gln
        35                  40                  45

Glu Asp Gln Arg Tyr Ser Gln Leu Leu Ala Leu Arg Ala Arg Ser Ser
    50                  55                  60

Gly Gln Pro Ser Asn Gly Val Leu Thr Pro Leu Gln Met Asn Gln Leu
65                  70                  75                  80

Arg Asn Gln Ile Met Ala Tyr Arg Cys Leu Ala Arg Ser Gln Pro Ile
                85                  90                  95

Pro Pro Ser Ile Met Leu Gly Leu Gln Gly Lys Arg Pro Asp Gly Ser
            100                 105                 110

Pro Gln Phe Pro Thr Pro Pro Ser Ser Pro Phe Gln Pro Gln Gly Pro
        115                 120                 125

Gly Ala Pro Pro Gly Pro Glu Gln Pro Pro Ala Asn Ala Glu Asn Val
    130                 135                 140

Ala Glu Pro Ala Ala Pro Val Gly Pro Gln Gly Ala Gln Gly Pro Pro
145                 150                 155                 160

Asn Gln Gln Arg Ala Gln Thr Ser Gln Leu Val Pro Asn Lys Gln Thr
                165                 170                 175

Arg Phe Thr Thr Met Pro Lys Pro Ser Gly Leu Asp Pro Leu Val Leu
            180                 185                 190

Leu Gln Glu Arg Glu Thr Arg Val Ala Ala Arg Ile Ala Ala Arg Ile
        195                 200                 205

Glu Gln Cys Ser Asn Leu Pro Thr Asn Leu Ser Asp Lys Val Arg Met
    210                 215                 220

Gln Ala Gln Ile Glu Leu Arg Ala Leu Arg Cys Leu Asn Phe Gln Arg
225                 230                 235                 240

Gln Leu Arg Ser Glu Ile Leu Asn Cys Ile Arg Arg Asp Ile Thr Leu
                245                 250                 255

Glu Ser Ala Val Asn Phe Lys Ala Tyr Lys Arg Thr Lys Arg Gln Gly
            260                 265                 270

Leu Lys Glu Ser Arg Ala Thr Glu Lys Leu Glu Lys Gln Gln Lys Leu
        275                 280                 285

Glu Ala Glu Arg Lys Arg Arg Gln Lys Asn Gln Glu Phe Leu Asn Ala
    290                 295                 300

Val Leu Asn Asn Gly Lys Glu Phe Lys Glu Phe His Lys Gln Asn Gln
305                 310                 315                 320

Ala Lys Leu Ala Lys Ile Asn Lys Ala Val Ile Asn Tyr His Ala Asn
                325                 330                 335

Ala Glu Arg Glu Gln Lys Lys Glu Ala Glu Arg Arg Glu Lys Glu Arg
            340                 345                 350

Met Ile Arg Leu Met Ala Glu Asp Glu Glu Gly Tyr Arg Lys Leu Ile
        355                 360                 365

Asp Gln Lys Lys Asp Lys Arg Leu Ala Phe Leu Leu Ser Gln Thr Asp
    370                 375                 380

Glu Tyr Ile Thr Asn Leu Thr Glu Met Val Lys Gln His Lys Leu Glu
385                 390                 395                 400

Gln Thr Asn Lys Lys Lys Glu Glu Glu Lys Arg Lys Lys Lys Gln Gln
                405                 410                 415

Lys Met Gln Gln Pro Asp Arg Lys Val Thr Val Leu Glu Thr Ala Thr
            420                 425                 430
```

-continued

```
Gly Lys Lys Val Thr Gly Glu Ala Ala Pro Thr Leu Arg Gln Val Gln
        435                 440                 445

Glu Trp Leu Ile Gln His Pro Gly Trp Glu Met Val Asp Thr Asp Asp
    450                 455                 460

Glu Asp Asp Glu Asn Gly Glu Lys Arg Asp Asp Asp Tyr Asp Glu Asn
465                 470                 475                 480

Gln Glu Val Asp Asp Ala Lys Glu Val Ile Lys Lys Ala Lys Val Glu
                485                 490                 495

Asp Asp Glu Tyr His Lys Asn Thr Lys Glu Glu Gln Thr Tyr Tyr Ser
            500                 505                 510

Ile Ala His Thr Val His Glu Val Val Thr Glu Gln Ala Ser Ile Leu
        515                 520                 525

Val Asn Gly Lys Leu Lys Glu Tyr Gln Ile Arg Gly Leu Glu Trp Met
    530                 535                 540

Val Ser Leu Tyr Asn Asn Asn Leu Asn Gly Ile Leu Ala Asp Glu Met
545                 550                 555                 560

Gly Leu Gly Lys Thr Ile Gln Thr Ile Gly Leu Leu Thr Tyr Leu Met
                565                 570                 575

Glu Lys Lys Lys Ile Asn Gly Pro Phe Leu Ile Ile Val Pro Leu Ser
            580                 585                 590

Thr Ile Ser Asn Trp Met Leu Glu Phe Gln Lys Trp Ala Pro Thr Val
        595                 600                 605

Val Val Ile Ser Tyr Lys Gly Ser Pro Val Val Arg Lys Val Ile Gln
    610                 615                 620

Ser Gln Leu Lys Ala Ala Lys Phe Asn Val Leu Leu Thr Thr Tyr Glu
625                 630                 635                 640

Tyr Ile Ile Lys Asp Lys Gly Val Leu Ala Lys Ile Pro Phe Lys Tyr
                645                 650                 655

Met Ile Ile Asp Glu Gly His Arg Met Lys Asn His His Cys Lys Leu
            660                 665                 670

Thr Gln Val Leu Asn Thr His Tyr Leu Ala Pro Tyr Arg Leu Leu Leu
        675                 680                 685

Thr Gly Thr Pro Leu Gln Asn Lys Leu Pro Glu Leu Trp Ala Leu Leu
    690                 695                 700

Asn Phe Leu Leu Pro Ser Ile Phe Lys Ser Cys Ser Thr Phe Glu Gln
705                 710                 715                 720

Trp Phe Asn Ala Pro Phe Ala Thr Thr Gly Glu Lys Val Glu Leu Asn
                725                 730                 735

Glu Glu Glu Thr Ile Leu Ile Ile Arg Arg Leu His Lys Val Leu Arg
            740                 745                 750

Pro Phe Leu Leu Arg Arg Leu Lys Lys Glu Val Glu Ser Gln Leu Pro
        755                 760                 765

Asp Lys Val Glu Tyr Ile Ile Lys Cys Asp Met Ser Gly Leu Gln Lys
    770                 775                 780

Val Leu Tyr Ala His Met Gln Ser Lys Gly Val Leu Leu Thr Asp Gly
785                 790                 795                 800

Ser Glu Lys Gly Ser Lys Gly Arg Gly Ser Lys Ala Leu Met Asn Thr
                805                 810                 815

Ile Met Gln Leu Arg Lys Leu Cys Asn His Pro Phe Met Phe Gln Asn
            820                 825                 830

Ile Glu Glu Lys Tyr Cys Asp His Val Gly Ile Ala Gly Gly Val Val
        835                 840                 845

Ser Gly Pro Asp Thr Tyr Arg Val Ser Gly Lys Phe Glu Leu Leu Asp
```

```
    850                 855                 860

Arg Ile Leu Pro Lys Met Lys Ala Thr Asn His Arg Ile Leu Leu Phe
865                 870                 875                 880

Cys Gln Met Thr Gln Leu Met Thr Ile Met Glu Asp Tyr Leu Asn Trp
                885                 890                 895

Arg Gly Phe Lys Tyr Leu Arg Leu Asp Gly Thr Ile Lys Ser Glu Asp
            900                 905                 910

Arg Gly Asp Leu Leu Ser Lys Phe Asn Asp Lys Asn Ser Glu Tyr Phe
        915                 920                 925

Leu Phe Leu Leu Ser Thr Arg Ala Gly Gly Leu Gly Leu Asn Leu Gln
    930                 935                 940

Thr Ala Asp Thr Val Ile Ile Phe Asp Ser Asp Trp Asn Pro His Gln
945                 950                 955                 960

Asp Leu Gln Ala Gln Asp Arg Ala His Arg Ile Gly Gln Gln Asn Glu
                965                 970                 975

Val Arg Val Leu Arg Leu Met Thr Val Asn Ser Val Glu Glu Arg Ile
            980                 985                 990

Leu Ala Ala Ala Lys Tyr Lys Leu  Thr Met Asp Glu Lys  Val Ile Gln
        995                 1000                1005

Ala Gly  Met Phe Asp Gln Lys  Ser Thr Gly Ser Glu  Arg Gln Gln
    1010                 1015                 1020

Phe Leu  Gln Ser Ile Leu His  Asn Asp Gly Ser Asp  Glu Glu Glu
    1025                 1030                 1035

Glu Asn  Glu Val Pro Asp Asp  Glu Thr Val Asn Gln  Met Ile Ala
    1040                 1045                 1050

Arg Thr  Glu Asp Glu Phe Gln  Leu Phe Gln Lys Met  Asp Thr Glu
    1055                 1060                 1065

Arg Lys  Glu Glu Asn Glu Lys  Leu Gly Gln His Lys  Lys Ser Arg
    1070                 1075                 1080

Leu Val  Gln Glu Cys Glu Leu  Pro Asp Trp Leu Thr  Lys Pro Asp
    1085                 1090                 1095

Glu Asp  Asp Gly Trp Gly Asp  Asp Tyr Thr Glu Ala  Leu Leu Gly
    1100                 1105                 1110

Arg Gly  Thr Arg Gln Arg Lys  Glu Val Asp Tyr Ala  Asp Ser Leu
    1115                 1120                 1125

Thr Glu  Lys Glu Trp Leu Lys  Ala Ile Asp Glu Asp  Gly Asp Tyr
    1130                 1135                 1140

Asp Glu  Glu Glu Glu Glu Glu  Lys Val Gln Lys Lys  Arg Gly Arg
    1145                 1150                 1155

Lys Arg  Arg Lys Arg Asp Asp  Ser Asp Asp Asp Thr  Ser Ser Ser
    1160                 1165                 1170

Thr Arg  Arg Arg Lys Leu Pro  Gln Ser Gln Val Glu  Ala Arg Leu
    1175                 1180                 1185

Lys Arg  Lys Met Lys Lys Leu  Met Asn Ile Val Thr  Asn Tyr Lys
    1190                 1195                 1200

Asp Arg  Asp Gly Arg Gln Leu  Ser Asp Gln Phe Ile  Lys Leu Pro
    1205                 1210                 1215

Pro Arg  Lys Glu Tyr Pro Asp  Tyr Tyr Thr Ile Ile  Lys Lys Pro
    1220                 1225                 1230

Ile Asp  Ile Ser Lys Ile Leu  Asn Tyr Ile Asp Asp  Gly Lys Tyr
    1235                 1240                 1245

Ser Asp  Phe Ser Asp Leu Glu  Arg Asp Phe Met Leu  Leu Cys Gln
    1250                 1255                 1260
```

Asn Ala Gln Ile Tyr Asn Glu Glu Ala Ser Leu Ile His Glu Asp
1265 1270 1275

Ser Ile Val Leu Gln Ser Val Phe Ser Ser Ala Lys Gln Lys Ile
1280 1285 1290

Glu Ala Ser Pro Asp Ser Asp Asp Glu Lys Asp Asp Asn Asn Ser
1295 1300 1305

Asp Val Glu Thr Pro Lys Asn Lys Asn Lys Pro Gly Lys Gly Lys
1310 1315 1320

Arg Arg Pro Gly Arg Pro Arg Arg Ser Ala Lys Lys Tyr Ile Ser
1325 1330 1335

Asp Asp Asp Asp Asp Asp
1340

<210> SEQ ID NO 5
<211> LENGTH: 5134
<212> TYPE: DNA
<213> ORGANISM: Diabrotica virgifera

<400> SEQUENCE: 5
acagttaaat attgaaaatg gcctggtgtt ttgataaaac ggaagaggcg aatttctagt 60
agcattttaa ggtttcattt gcatttaaaa caaattcatg tattataaaa tgtaggatac 120
gtttcctcgt atccatctac ttaatttagg ataacaataa agggtgtgag acagttaaat 180
attgaaaatg gccagtgctt cattattacc caaaactttc acttctattg gtggcaaagc 240
cctacctacc aactcacaac aaaacattca gtcaaaattt aaagagatta cagttccacc 300
aggaaatact cctcaagatg ttaaagaagg ccccagtcac caatcaaatc caaaccattt 360
ggcttctctt caaaaggcca ttgaaactat ggaagagaag ggcttacaag ctgatcctag 420
atattcacag ttacttgcat tgcgagctag cattcctggg gcagaagaaa atggttctcc 480
cttctcaaac aaccaaatca agcaattaag aaaccaaata atggcttaca ggtgtttggc 540
aagaaatcaa cctgttccaa acaatttagt attaggtttg catggaaaaa ctcctgaaaa 600
agttccacat attgtacctc caccgcaacc tcaagaagta cctaatgggg gcgatccagg 660
accttcaaca agttctgctg ctgctgtagc tcctagaaca ccacaaaagc tgccagcaaa 720
accaattgag gctcagcttg tcaacagaga accaagagtc actactttat ctaaaccatc 780
ttccatagac cctgttgttc tattacaaga acgagaaaac agggtagcag ctcgtatagc 840
agcgaggatt gaacaagtca gtaatctgcc gactgatatg tctgaggcat tacgtattcg 900
ggcacaaata gaactcagag ctttgagatg tctaaacctc cagagacaac ttcgtagtga 960
ggttttgagc tgtattcgac gggacacaac attagaaaca gcagtaaatg taaaagcgtt 1020
taaacggacc aaacgtcaag gtcttcgaga agctagagca acagaaaaac ttgagaaaca 1080
acaaaagctg gaagcagaga gaaagaaacg ccagaagaac caagagttct taaacaatgt 1140
gatggcacac gctaaagatt tcaaagaatt ccacaggcag aaccaagcaa aactttctaa 1200
acttaataaa gctattctta cttatcacgc taatgcggag agagaacaaa agaaggaaca 1260
agagagaaga gaaaaggaac gtatgaagaa attgatggca gaagatgaag aaggttatag 1320
acagttgatc gatcaaaaga aagacaaacg tctagcgttc ttgctttcgc aaacagatga 1380
gtatataact aacctcacgg agatggtaaa gcaacacaag ttggaacaaa ccaataaaaa 1440
gaaagaggag gaaaaacgca agaagaagca gcagaaaatg caacaaccag ataggaaagt 1500
tacagttctg gaaactgcaa caggtaaaaa agtaacagga gaggctgctc ctacactgcg 1560

-continued

```
acaagttcag gaatggttaa tccaacatcc tggatgggag atggtcgata cagatgatga   1620
ggatgatgaa aacggggaga agagggatga tgactatgat gaaaatcaag aagtggatga   1680
tgcaaaagaa gttattaaaa aagctaaagt tgaagatgac gaatatcaca aaaacacaaa   1740
agaagaacag acttactaca gtattgctca cactgttcat gaagtggtaa cagaacaagc   1800
atccattctg gttaatggaa agcttaagga atatcaaatt agagggttag aatggatggt   1860
gtctttgtac aataacaatc tgaatggtat tctagcagat gagatgggtc taggtaaaac   1920
cattcaaacg attggcttgt tgacctattt gatggaaaaa aagaagataa atggaccgtt   1980
tttgatcata gtgccacttt caaccatttc taattggatg ttggaatttc aaaagtgggc   2040
ccctactgta gttgtcattt catacaaagg ctctcctgtg gttagaaaag tgatccagag   2100
ccagttaaaa gctgctaaat tcaatgtgct tctcactacc tacgagtaca ttattaagga   2160
caagggtgta ttagcaaaaa tcccatttaa atatatgatc atagatgagg gtcatcgtat   2220
gaaaaaccac cactgcaaat tgactcaagt cctgaatacg cactatttgg cgccctacag   2280
actcctgctt actggtactc ccctacaaaa taaattacca gaattatggg ccttgttgaa   2340
tttcttgttg ccttcgattt tcaagagttg ctccactttt gaacaatggt tcaatgcgcc   2400
attcgcaaca acaggagaaa aggttgagtt aaacgaagaa gaaactatcc ttatcatccg   2460
tcgtcttcac aaagtactca ggccgtttct cctgagacgt ctcaagaaag aagtcgaatc   2520
tcagcttcca gacaaagtgg aatatatcat aaagtgtgac atgtcgggcc tacaaaaggt   2580
tctctatgca cacatgcaga gcaagggtgt gttacttacc gatggttccg agaagggcag   2640
taaaggaagg ggatctaagg cactgatgaa caccattatg cagctgagga aactgtgcaa   2700
tcatccgttt atgttccaaa atatcgaaga gaaatattgt gatcatgttg gtattgctgg   2760
tggagtggtt tctggacccg acacttatag ggtatctggt aagtttgagc tcttggacag   2820
aatattgccc aaaatgaaag caactaacca taggattctt cttttctgtc aaatgactca   2880
attaatgacc atcatggaag attatctaaa ttggagagga ttcaaatatc ttcgtcttga   2940
tggtacaatc aaatcagaag atcgcgggga cctattatcg aaatttaatg ataaaaaatag   3000
tgaatatttt ttgtttttgc tatctacacg ggctggaggt ctgggactta atttgcagac   3060
agctgatact gtgattatct tcgattccga ttggaatcct catcaggatt tacaagctca   3120
ggatcgagct catcgtattg gacagcaaaa tgaggtccga gttttgcgtt tgatgactgt   3180
taactctgtt gaggaacgaa ttttagctgc agctaaatac aagcttacta tggacgaaaa   3240
ggtcattcaa gctggtatgt tcgatcagaa gtctacaggc tcagagagac atcagttttt   3300
gcagagtatt ttacaccatg acggaagcga cgaagaagag gaaaacgaag ttcctgatga   3360
cgaaacagtg aaccagatgt tggcccgaag ggaaaacgaa tttcagcttt tccagaagat   3420
ggatcaggaa agaaaggaag aagatgaaaa gaccggaaag tcgcgactta ttcaagaaag   3480
cgaattgccc gaatggctgt tgaagcaaga cgatgaaatc tactcgtggg gccttgatga   3540
tccagatgct gttttaggaa ggggtagtag gcaaagaaaa gaagttgatt atgttgacag   3600
cctgacggag aaagagtggc ttaaggctat tgacgaagag ggagaatttg aggaagaaca   3660
agaaggtgat aaagaaggtc tcagaaagaa aagagggagg aagaggaaga agcgcgatga   3720
tgacgaagag gcaagccaaa ttaagagaag aaaggtgcat ctagccgaga tcaagatgaa   3780
gaaaaagatg aagaggctta tggaagttgt tgtgaactac agggacaggg atggtagagt   3840
attgagcgaa ccgtttatga aacttccatc aaagaaggag ttacctgagt attacgatac   3900
gattaagaaa cctattgata ttgaaaaagt cgttgccaac gtagaagaag gaaaatattt   3960
```

-continued

```
cacgatgcac gatttggaaa gagatttcga cttgctgtgc caaaacgccc aacaatacaa   4020

cgaagaagac tccatgatct acgaggacag cctcgttctt cgacaggtgt ttagaagcgc   4080

gagggaaaag atcgacggta cctcagacca cgacgacaac gccgatggac cggcggtggc   4140

tcagatcaaa cgacctcgtg gtagacctcg aaaacacaag agacccgaag agatcgaggc   4200

cgaagcggcg gctcagaaag ctatggagga ggcatcgaag ctgagagctc aagctgaggc   4260

ggaagagctt agatctaagg tggaggaggc atctcagaga gccaaagagg aagcgaaagc   4320

aagggaggaa gccaaagcta gggaagaagc cgaaatcgag aacatggagg agattcccac   4380

aagcacatga tctatagagc aaccggaaac aaaaaggcaa aaaagaaata ttatatagaa   4440

aagatgtaca tgttcaatgg agatacattt tcgccgagtt acaacgggta atgcttttac   4500

aacggatatt ttgacgtatg aatgttgacg ttcagatgaa gtatatttat aaaataatcc   4560

agacctttac gttttggttg atttgttttc tgtattgttc agtttattga acaaccatta   4620

atagcagctt acctaaatga tttagaaaag catctgagtt atttagataa gttttgagat   4680

tatatttatt aactttaata ttactatctt tattatagca tattgtaatt atttttttcct   4740

gtccttcttt cgttgtgtgg tagataatcc gagagtcaac agttataagc aaatgaaatt   4800

cagttaaacc tcaaatgtac aaaatgatca aattaatgtt tacaatttat ttttttacca   4860

cgcacattca ctattactat tgtcagtcat tgagatatca ttttatatag ctccatgtct   4920

gtcttcctca atttacagag aagcaattag acaagtaatg acataaatatg gtgctgaaat   4980

aatgtgcttg atagtgatgt tcacaaagta actattcgtt acaaagtact cgttacttac   5040

aaataccgaa actaacgatt actatacaga gaggcaaatc gttactttga ttacactgat   5100

tacttcgtat caatcgtatc agagcgagta acga                               5134
```

```
<210> SEQ ID NO 6
<211> LENGTH: 1400
<212> TYPE: PRT
<213> ORGANISM: Diabrotica virgifera

<400> SEQUENCE: 6

Met Ala Ser Ala Ser Leu Leu Pro Lys Thr Phe Thr Ser Ile Gly Gly
1               5                   10                  15

Lys Ala Leu Pro Thr Asn Ser Gln Gln Asn Ile Gln Ser Lys Phe Lys
            20                  25                  30

Glu Ile Thr Val Pro Pro Gly Asn Thr Pro Gln Asp Val Lys Glu Gly
        35                  40                  45

Pro Ser His Gln Ser Asn Pro Asn His Leu Ala Ser Leu Gln Lys Ala
    50                  55                  60

Ile Glu Thr Met Glu Glu Lys Gly Leu Gln Ala Asp Pro Arg Tyr Ser
65                  70                  75                  80

Gln Leu Leu Ala Leu Arg Ala Ser Ile Pro Gly Ala Glu Glu Asn Gly
                85                  90                  95

Ser Pro Phe Ser Asn Asn Gln Ile Lys Gln Leu Arg Asn Gln Ile Met
            100                 105                 110

Ala Tyr Arg Cys Leu Ala Arg Asn Gln Pro Val Pro Asn Asn Leu Val
        115                 120                 125

Leu Gly Leu His Gly Lys Thr Pro Glu Lys Val Pro His Ile Val Pro
    130                 135                 140

Pro Pro Gln Pro Gln Glu Val Pro Asn Gly Gly Asp Pro Gly Pro Ser
145                 150                 155                 160
```

-continued

```
Thr Ser Ser Ala Ala Ala Val Ala Pro Arg Thr Pro Gln Lys Leu Pro
                165                 170                 175

Ala Lys Pro Ile Glu Ala Gln Leu Val Asn Arg Glu Pro Arg Val Thr
            180                 185                 190

Thr Leu Ser Lys Pro Ser Ser Ile Asp Pro Val Val Leu Leu Gln Glu
        195                 200                 205

Arg Glu Asn Arg Val Ala Ala Arg Ile Ala Ala Arg Ile Glu Gln Val
    210                 215                 220

Ser Asn Leu Pro Thr Asp Met Ser Glu Ala Leu Arg Ile Arg Ala Gln
225                 230                 235                 240

Ile Glu Leu Arg Ala Leu Arg Cys Leu Asn Leu Gln Arg Gln Leu Arg
                245                 250                 255

Ser Glu Val Leu Ser Cys Ile Arg Arg Asp Thr Thr Leu Glu Thr Ala
            260                 265                 270

Val Asn Val Lys Ala Phe Lys Arg Thr Lys Arg Gln Gly Leu Arg Glu
        275                 280                 285

Ala Arg Ala Thr Glu Lys Leu Glu Lys Gln Gln Lys Leu Glu Ala Glu
    290                 295                 300

Arg Lys Lys Arg Gln Lys Asn Gln Glu Phe Leu Asn Asn Val Met Ala
305                 310                 315                 320

His Ala Lys Asp Phe Lys Glu Phe His Arg Gln Asn Gln Ala Lys Leu
                325                 330                 335

Ser Lys Leu Asn Lys Ala Ile Leu Thr Tyr His Ala Asn Ala Glu Arg
            340                 345                 350

Glu Gln Lys Lys Glu Gln Glu Arg Arg Glu Lys Glu Arg Met Lys Lys
        355                 360                 365

Leu Met Ala Glu Asp Glu Glu Gly Tyr Arg Gln Leu Ile Asp Gln Lys
    370                 375                 380

Lys Asp Lys Arg Leu Ala Phe Leu Leu Ser Gln Thr Asp Glu Tyr Ile
385                 390                 395                 400

Thr Asn Leu Thr Glu Met Val Lys Gln His Lys Leu Glu Gln Thr Asn
                405                 410                 415

Lys Lys Lys Glu Glu Glu Lys Arg Lys Lys Lys Gln Gln Lys Met Gln
            420                 425                 430

Gln Pro Asp Arg Lys Val Thr Val Leu Glu Thr Ala Thr Gly Lys Lys
        435                 440                 445

Val Thr Gly Glu Ala Ala Pro Thr Leu Arg Gln Val Gln Glu Trp Leu
    450                 455                 460

Ile Gln His Pro Gly Trp Glu Met Val Asp Thr Asp Asp Glu Asp Asp
465                 470                 475                 480

Glu Asn Gly Glu Lys Arg Asp Asp Asp Tyr Asp Glu Asn Gln Glu Val
                485                 490                 495

Asp Asp Ala Lys Glu Val Ile Lys Lys Ala Lys Val Glu Asp Asp Glu
            500                 505                 510

Tyr His Lys Asn Thr Lys Glu Glu Gln Thr Tyr Tyr Ser Ile Ala His
        515                 520                 525

Thr Val His Glu Val Val Thr Glu Gln Ala Ser Ile Leu Val Asn Gly
    530                 535                 540

Lys Leu Lys Glu Tyr Gln Ile Arg Gly Leu Glu Trp Met Val Ser Leu
545                 550                 555                 560

Tyr Asn Asn Asn Leu Asn Gly Ile Leu Ala Asp Glu Met Gly Leu Gly
                565                 570                 575

Lys Thr Ile Gln Thr Ile Gly Leu Leu Thr Tyr Leu Met Glu Lys Lys
```

-continued

```
            580                 585                 590

Lys Ile Asn Gly Pro Phe Leu Ile Ile Val Pro Leu Ser Thr Ile Ser
        595                 600                 605

Asn Trp Met Leu Glu Phe Gln Lys Trp Ala Pro Thr Val Val Val Ile
    610                 615                 620

Ser Tyr Lys Gly Ser Pro Val Val Arg Lys Val Ile Gln Ser Gln Leu
625                 630                 635                 640

Lys Ala Ala Lys Phe Asn Val Leu Leu Thr Thr Tyr Glu Tyr Ile Ile
            645                 650                 655

Lys Asp Lys Gly Val Leu Ala Lys Ile Pro Phe Lys Tyr Met Ile Ile
            660                 665                 670

Asp Glu Gly His Arg Met Lys Asn His His Cys Lys Leu Thr Gln Val
        675                 680                 685

Leu Asn Thr His Tyr Leu Ala Pro Tyr Arg Leu Leu Leu Thr Gly Thr
    690                 695                 700

Pro Leu Gln Asn Lys Leu Pro Glu Leu Trp Ala Leu Leu Asn Phe Leu
705                 710                 715                 720

Leu Pro Ser Ile Phe Lys Ser Cys Ser Thr Phe Glu Gln Trp Phe Asn
            725                 730                 735

Ala Pro Phe Ala Thr Thr Gly Glu Lys Val Glu Leu Asn Glu Glu Glu
            740                 745                 750

Thr Ile Leu Ile Ile Arg Arg Leu His Lys Val Leu Arg Pro Phe Leu
        755                 760                 765

Leu Arg Arg Leu Lys Lys Glu Val Glu Ser Gln Leu Pro Asp Lys Val
    770                 775                 780

Glu Tyr Ile Ile Lys Cys Asp Met Ser Gly Leu Gln Lys Val Leu Tyr
785                 790                 795                 800

Ala His Met Gln Ser Lys Gly Val Leu Leu Thr Asp Gly Ser Glu Lys
            805                 810                 815

Gly Ser Lys Gly Arg Gly Ser Lys Ala Leu Met Asn Thr Ile Met Gln
            820                 825                 830

Leu Arg Lys Leu Cys Asn His Pro Phe Met Phe Gln Asn Ile Glu Glu
        835                 840                 845

Lys Tyr Cys Asp His Val Gly Ile Ala Gly Gly Val Val Ser Gly Pro
    850                 855                 860

Asp Thr Tyr Arg Val Ser Gly Lys Phe Glu Leu Leu Asp Arg Ile Leu
865                 870                 875                 880

Pro Lys Met Lys Ala Thr Asn His Arg Ile Leu Leu Phe Cys Gln Met
            885                 890                 895

Thr Gln Leu Met Thr Ile Met Glu Asp Tyr Leu Asn Trp Arg Gly Phe
            900                 905                 910

Lys Tyr Leu Arg Leu Asp Gly Thr Ile Lys Ser Glu Asp Arg Gly Asp
        915                 920                 925

Leu Leu Ser Lys Phe Asn Asp Lys Asn Ser Glu Tyr Phe Leu Phe Leu
    930                 935                 940

Leu Ser Thr Arg Ala Gly Gly Leu Gly Leu Asn Leu Gln Thr Ala Asp
945                 950                 955                 960

Thr Val Ile Ile Phe Asp Ser Asp Trp Asn Pro His Gln Asp Leu Gln
            965                 970                 975

Ala Gln Asp Arg Ala His Arg Ile Gly Gln Gln Asn Glu Val Arg Val
            980                 985                 990

Leu Arg Leu Met Thr Val Asn Ser  Val Glu Glu Arg Ile  Leu Ala Ala
        995                 1000                1005
```

```
Ala Lys  Tyr Lys Leu Thr Met  Asp Glu Lys Val Ile  Gln Ala Gly
    1010                 1015                 1020

Met Phe  Asp Gln Lys Ser Thr  Gly Ser Glu Arg His  Gln Phe Leu
    1025                 1030                 1035

Gln Ser  Ile Leu His His Asp  Gly Ser Asp Glu Glu  Glu Glu Asn
    1040                 1045                 1050

Glu Val  Pro Asp Asp Glu Thr  Val Asn Gln Met Leu  Ala Arg Arg
    1055                 1060                 1065

Glu Asn  Glu Phe Gln Leu Phe  Gln Lys Met Asp Gln  Glu Arg Lys
    1070                 1075                 1080

Glu Glu  Asp Glu Lys Thr Gly  Lys Ser Arg Leu Ile  Gln Glu Ser
    1085                 1090                 1095

Glu Leu  Pro Glu Trp Leu Leu  Lys Gln Asp Asp Glu  Ile Tyr Ser
    1100                 1105                 1110

Trp Gly  Leu Asp Asp Pro Asp  Ala Val Leu Gly Arg  Gly Ser Arg
    1115                 1120                 1125

Gln Arg  Lys Glu Val Asp Tyr  Val Asp Ser Leu Thr  Glu Lys Glu
    1130                 1135                 1140

Trp Leu  Lys Ala Ile Asp Glu  Glu Gly Glu Phe Glu  Glu Glu Gln
    1145                 1150                 1155

Glu Gly  Asp Lys Glu Gly Leu  Arg Lys Lys Arg Gly  Arg Lys Arg
    1160                 1165                 1170

Lys Lys  Arg Asp Asp Asp Glu  Glu Ala Ser Gln Ile  Lys Arg Arg
    1175                 1180                 1185

Lys Val  His Leu Ala Glu Ile  Lys Met Lys Lys Lys  Met Lys Arg
    1190                 1195                 1200

Leu Met  Glu Val Val Val Asn  Tyr Arg Asp Arg Asp  Gly Arg Val
    1205                 1210                 1215

Leu Ser  Glu Pro Phe Met Lys  Leu Pro Ser Lys Lys  Glu Leu Pro
    1220                 1225                 1230

Glu Tyr  Tyr Asp Thr Ile Lys  Lys Pro Ile Asp Ile  Glu Lys Val
    1235                 1240                 1245

Val Ala  Asn Val Glu Glu Gly  Lys Tyr Phe Thr Met  His Asp Leu
    1250                 1255                 1260

Glu Arg  Asp Phe Asp Leu Leu  Cys Gln Asn Ala Gln  Gln Tyr Asn
    1265                 1270                 1275

Glu Glu  Asp Ser Met Ile Tyr  Glu Asp Ser Leu Val  Leu Arg Gln
    1280                 1285                 1290

Val Phe  Arg Ser Ala Arg Glu  Lys Ile Asp Gly Thr  Ser Asp His
    1295                 1300                 1305

Asp Asp  Asn Ala Asp Gly Pro  Ala Val Ala Gln Ile  Lys Arg Pro
    1310                 1315                 1320

Arg Gly  Arg Pro Arg Lys His  Lys Arg Pro Glu Glu  Ile Glu Ala
    1325                 1330                 1335

Glu Ala  Ala Ala Gln Lys Ala  Met Glu Glu Ala Ser  Lys Leu Arg
    1340                 1345                 1350

Ala Gln  Ala Glu Ala Glu Glu  Leu Arg Ser Lys Val  Glu Glu Ala
    1355                 1360                 1365

Ser Gln  Arg Ala Lys Glu Glu  Ala Lys Ala Arg Glu  Glu Ala Lys
    1370                 1375                 1380

Ala Arg  Glu Glu Ala Glu Ile  Glu Asn Met Glu Glu  Ile Pro Thr
    1385                 1390                 1395
```

-continued

Ser Thr
    1400

<210> SEQ ID NO 7
<211> LENGTH: 538
<212> TYPE: DNA
<213> ORGANISM: Diabrotica virgifera

<400> SEQUENCE: 7
agtgtattag caaaaatccc atttaaatat atgatcatag atgagggtca tcgtatgaaa 60
aaccaccact gcaaattgac tcaagtcctg aatacgcact atttggcgcc ctacagactc 120
ctgcttactg gtactcccct acaaaataaa ttaccagaat tatgggcctt gttgaatttc 180
ttgttgcctt cgattttcaa gagttgctcc acttttgaac aatggttcaa tgcgccattc 240
gcaacaacag gagaaaaggt tgagttaaac gaagaagaaa ctatccttat catccgtcgt 300
cttcacaaag tactcaggcc gtttctcctg agacgtctca agaaagaagt cgaatctcag 360
cttccagaca aagtggaata tatcataaag tgtgacatgt cgggcctaca aaaggttctc 420
tatgcacaca tgcagagcaa gggtgtgtta cttaccgatg gttccgagaa gggcagtaaa 480
ggaaggggat ctaaggacaa ctagatgaac accattatgc agctgaggaa actgtgct 538

<210> SEQ ID NO 8
<211> LENGTH: 352
<212> TYPE: DNA
<213> ORGANISM: Diabrotica virgifera

<400> SEQUENCE: 8
ttgaactgta ttaggagaga tataacgctt gaatctgctg taaattttaa agcatataaa 60
agaacgaagc gacagggtct aaaagaatcg agagctacag agaagttaga aaaacaacag 120
aagttagaag cagaaagaaa gagaagacag aagaaccaag aatttttgaa tgctgtattg 180
aacaatggaa aagaattcaa ggaattccac aagcagaatc aagcgaaatt agctaagatt 240
aataaagctg ttattaatta tcacgctaat gctgaaagag agcaaaagaa agaagcagaa 300
aggagagaga aggaacgtat gatcagattg atggcagaag atgaagaagg tt 352

<210> SEQ ID NO 9
<211> LENGTH: 178
<212> TYPE: PRT
<213> ORGANISM: Diabrotica virgifera

<400> SEQUENCE: 9

Ser Val Leu Ala Lys Ile Pro Phe Lys Tyr Met Ile Ile Asp Glu Gly
1               5                   10                  15

His Arg Met Lys Asn His His Cys Lys Leu Thr Gln Val Leu Asn Thr
            20                  25                  30

His Tyr Leu Ala Pro Tyr Arg Leu Leu Leu Thr Gly Thr Pro Leu Gln
        35                  40                  45

Asn Lys Leu Pro Glu Leu Trp Ala Leu Leu Asn Phe Leu Leu Pro Ser
    50                  55                  60

Ile Phe Lys Ser Cys Ser Thr Phe Glu Gln Trp Phe Asn Ala Pro Phe
65                  70                  75                  80

Ala Thr Thr Gly Glu Lys Val Glu Leu Asn Glu Glu Glu Thr Ile Leu
                85                  90                  95

Ile Ile Arg Arg Leu His Lys Val Leu Arg Pro Phe Leu Leu Arg Arg
            100                 105                 110

Leu Lys Lys Glu Val Glu Ser Gln Leu Pro Asp Lys Val Glu Tyr Ile

-continued

```
        115                 120                 125

Ile Lys Cys Asp Met Ser Gly Leu Gln Lys Val Leu Tyr Ala His Met
    130                 135                 140

Gln Ser Lys Gly Val Leu Leu Thr Asp Gly Ser Glu Lys Gly Ser Lys
145                 150                 155                 160

Gly Arg Gly Ser Lys Asp Asn Met Asn Thr Ile Met Gln Leu Arg Lys
                165                 170                 175

Leu Cys


<210> SEQ ID NO 10
<211> LENGTH: 459
<212> TYPE: DNA
<213> ORGANISM: Diabrotica virgifera

<400> SEQUENCE: 10

atgagggtca tcgtatgaaa aaccaccact gcaaattgac tcaagtcctg aatacgcact     60

atttggcgcc ctacagactc ctgcttactg gtactcccct acaaaataaa ttaccagaat    120

tatgggcctt gttgaatttc ttgttgcctt cgattttcaa gagttgctcc acttttgaac    180

aatggttcaa tgcgccattc gcaacaacag gagaaaaggt tgagttaaac gaagaagaaa    240

ctatccttat catccgtcgt cttcacaaag tactcaggcc gtttctcctg agacgtctca    300

agaaagaagt cgaatctcag cttccagaca aagtggaata tatcataaag tgtgacatgt    360

cgggcctaca aaaggttctc tatgcacaca tgcagagcaa gggtgtgtta cttaccgatg    420

gttccgagaa gggcagtaaa ggaaggggat ctaaggaca                          459


<210> SEQ ID NO 11
<211> LENGTH: 503
<212> TYPE: DNA
<213> ORGANISM: Artificial Sequence
<220> FEATURE:
<223> OTHER INFORMATION: YFP coding region

<400> SEQUENCE: 11

caccatgggc tccagcggcg ccctgctgtt ccacggcaag atcccctacg tggtggagat     60

ggagggcaat gtggatggcc acaccttcag catccgcggc aagggctacg gcgatgccag    120

cgtgggcaag gtggatgccc agttcatctg caccaccggc gatgtgcccg tgccctggag    180

caccctggtg accaccctga cctacggcgc ccagtgcttc gccaagtacg gccccgagct    240

gaaggatttc tacaagagct gcatgcccga tggctacgtg caggagcgca ccatcacctt    300

cgagggcgat ggcaatttca agacccgcgc cgaggtgacc ttcgagaatg gcagcgtgta    360

caatcgcgtg aagctgaatg gccagggctt caagaaggat ggccacgtgc tgggcaagaa    420

tctggagttc aatttcaccc cccactgcct gtacatctgg ggcgatcagg ccaatcacgg    480

cctgaagagc gccttcaaga tct                                            503


<210> SEQ ID NO 12
<211> LENGTH: 20
<212> TYPE: DNA
<213> ORGANISM: Artificial Sequence
<220> FEATURE:
<223> OTHER INFORMATION: T7 phage promoter

<400> SEQUENCE: 12

taatacgact cactataggg                                                 20


<210> SEQ ID NO 13
```

<211> LENGTH: 48
<212> TYPE: DNA
<213> ORGANISM: Artificial Sequence
<220> FEATURE:
<223> OTHER INFORMATION: Primer BrahmaVar2_FT7

<400> SEQUENCE: 13
ttaatacgac tcactatagg gagaatgagg gtcatcgtat gaaaaacc 48

<210> SEQ ID NO 14
<211> LENGTH: 24
<212> TYPE: DNA
<213> ORGANISM: Artificial Sequence
<220> FEATURE:
<223> OTHER INFORMATION: Primer BrahmaVar2_R

<400> SEQUENCE: 14
tgtccttaga tccccttcct ttac 24

<210> SEQ ID NO 15
<211> LENGTH: 24
<212> TYPE: DNA
<213> ORGANISM: Artificial Sequence
<220> FEATURE:
<223> OTHER INFORMATION: Primer BrahmaVar2_F

<400> SEQUENCE: 15
atgagggtca tcgtatgaaa aacc 24

<210> SEQ ID NO 16
<211> LENGTH: 48
<212> TYPE: DNA
<213> ORGANISM: Artificial Sequence
<220> FEATURE:
<223> OTHER INFORMATION: Primer BrahmaVar2_RT7

<400> SEQUENCE: 16
ttaatacgac tcactatagg gagatgtcct tagatcccct tcctttac 48

<210> SEQ ID NO 17
<211> LENGTH: 38
<212> TYPE: DNA
<213> ORGANISM: Artificial Sequence
<220> FEATURE:
<223> OTHER INFORMATION: Primer Brahma352_FT7

<400> SEQUENCE: 17
taatacgact cactataggg aaccttcttc atcttctg 38

<210> SEQ ID NO 18
<211> LENGTH: 39
<212> TYPE: DNA
<213> ORGANISM: Artificial Sequence
<220> FEATURE:
<223> OTHER INFORMATION: Primer Brahma352_RT7

<400> SEQUENCE: 18
taatacgact cactataggg ttgaactgta ttaggagag 39

<210> SEQ ID NO 19
<211> LENGTH: 47
<212> TYPE: DNA
<213> ORGANISM: Artificial Sequence
<220> FEATURE:
<223> OTHER INFORMATION: Primer YFP-F_T7

<400> SEQUENCE: 19

-continued ttaatacgac tcactatagg gagacaccat gggctccagc ggcgccc 47

<210> SEQ ID NO 20
<211> LENGTH: 47
<212> TYPE: DNA
<213> ORGANISM: Artificial Sequence
<220> FEATURE:
<223> OTHER INFORMATION: Primer YFP-R_T7

<400> SEQUENCE: 20
ttaatacgac tcactatagg gagaagatct tgaaggcgct cttcagg 47

<210> SEQ ID NO 21
<211> LENGTH: 218
<212> TYPE: DNA
<213> ORGANISM: Diabrotica virgifera

<400> SEQUENCE: 21
tagctctgat gacagagccc atcgagtttc aagccaaaca gttgcataaa gctatcagcg 60
gattgggaac tgatgaaagt acaatmgtmg aaattttaag tgtmcacaac aacgatgaga 120
ttataagaat ttcccaggcc tatgaaggat tgtaccaacg mtcattggaa tctgatatca 180
aaggagatac ctcaggaaca ttaaaaaaga attattag 218

<210> SEQ ID NO 22
<211> LENGTH: 424
<212> TYPE: DNA
<213> ORGANISM: Diabrotica virgifera
<220> FEATURE:
<221> NAME/KEY: misc_feature
<222> LOCATION: (393)..(395)
<223> OTHER INFORMATION: n is a, c, g, or t

<400> SEQUENCE: 22
ttgttacaag ctggagaact tctctttgct ggaaccgaag agtcagtatt taatgctgta 60
ttctgtcaaa gaaataaacc acaattgaat ttgatattcg acaaatatga agaaattgtt 120
gggcatccca ttgaaaaagc cattgaaaac gagttttcag gaaatgctaa acaagccatg 180
ttacacctta tccagagcgt aagagatcaa gttgcatatt tggtaaccag gctgcatgat 240
tcaatggcag gcgtcggtac tgacgataga actttaatca gaattgttgt ttcgagatct 300
gaaatcgatc tagaggaaat caaacaatgc tatgaagaaa tctacagtaa aaccttggct 360
gataggatag cggatgacac atctggcgac tannnaaaag ccttattagc cgttgttggt 420
taag 424

<210> SEQ ID NO 23
<211> LENGTH: 397
<212> TYPE: DNA
<213> ORGANISM: Diabrotica virgifera

<400> SEQUENCE: 23
agatgttggc tgcatctaga gaattacaca agttcttcca tgattgcaag gatgtactga 60
gcagaatagt ggaaaaacag gtatccatgt ctgatgaatt gggaagggac gcaggagctg 120
tcaatgccct tcaacgcaaa caccagaact tcctccaaga cctacaaaca ctccaatcga 180
acgtccaaca aatccaagaa gaatcagcta aacttcaagc tagctatgcc ggtgatagag 240
ctaaagaaat caccaacagg gagcaggaag tggtagcagc ctgggcagcc ttgcagatcg 300
cttgcgatca gagacacgga aaattgagcg atactggtga tctattcaaa ttctttaact 360

-continued tggtacgaac gttgatgcag tggatggacg aatggac 397

<210> SEQ ID NO 24
<211> LENGTH: 490
<212> TYPE: DNA
<213> ORGANISM: Diabrotica virgifera

<400> SEQUENCE: 24
gcagatgaac accagcgaga aaccaagaga tgttagtggt gttgaattgt tgatgaacaa 60
ccatcagaca ctcaaggctg agatcgaagc cagagaagac aactttacgg cttgtatttc 120
tttaggaaag gaattgttga gccgtaatca ctatgctagt gctgatatta aggataaatt 180
ggtcgcgttg acgaatcaaa ggaatgctgt actacagagg tgggaagaaa gatgggagaa 240
cttgcaactc atcctcgagg tataccaatt cgccagagat gcggccgtcg ccgaagcatg 300
gttgatcgca caagaacctt acttgatgag ccaagaacta ggacacacca ttgacgacgt 360
tgaaaacttg ataaagaaac acgaagcgtt cgaaaaatcg gcagcggcgc aagaagagag 420
attcagtgct ttggagagac tgacgacgtt cgaattgaga gaaataaaga ggaaacaaga 480
agctgcccag 490

<210> SEQ ID NO 25
<211> LENGTH: 330
<212> TYPE: DNA
<213> ORGANISM: Diabrotica virgifera

<400> SEQUENCE: 25
agtgaaatgt tagcaaatat aacatccaag tttcgtaatt gtacttgctc agttagaaaa 60
tattctgtag tttcactatc ttcaaccgaa aatagaataa atgtagaacc tcgcgaactt 120
gcctttcctc caaaatatca agaacctcga caagtttggt tggagagttt agatacgata 180
gacgacaaaa aattgggtat tcttgagctg catcctgatg tttttgctac taatccaaga 240
atagatatta tacatcaaaa tgttagatgg caaagtttat atagatatgt aagctatgct 300
catacaaagt caagatttga agtgagaggt 330

<210> SEQ ID NO 26
<211> LENGTH: 320
<212> TYPE: DNA
<213> ORGANISM: Diabrotica virgifera

<400> SEQUENCE: 26
caaagtcaag atttgaagtg agaggtggag gtcgaaaacc gtggccgcaa aagggattgg 60
gacgtgctcg acatggttca attagaagtc cactttggag aggtggagga gttgttcatg 120
gaccaaaatc tccaacccct catttttaca tgattccatt ctacacccgt ttgctgggtt 180
tgactagcgc actttcagta aaatttgccc aagatgactt gcacgttgtg gatagtctag 240
atctgccaac tgacgaacaa agttatatag aagagctggt caaaagccgc ttttggggt 300 ccttcttgtt ttatttgtag 320

<210> SEQ ID NO 27
<211> LENGTH: 46
<212> TYPE: DNA
<213> ORGANISM: Artificial Sequence
<220> FEATURE:
<223> OTHER INFORMATION: Primer Ann-F1_T7

<400> SEQUENCE: 27
ttaatacgac tcactatagg gagagctcca acagtggttc cttatc 46

-continued

<210> SEQ ID NO 28
<211> LENGTH: 29
<212> TYPE: DNA
<213> ORGANISM: Artificial Sequence
<220> FEATURE:
<223> OTHER INFORMATION: Primer Ann-R1

<400> SEQUENCE: 28
ctaataattc ttttttaatg ttcctgagg 29

<210> SEQ ID NO 29
<211> LENGTH: 22
<212> TYPE: DNA
<213> ORGANISM: Artificial Sequence
<220> FEATURE:
<223> OTHER INFORMATION: Primer Ann-F1

<400> SEQUENCE: 29
gctccaacag tggttcctta tc 22

<210> SEQ ID NO 30
<211> LENGTH: 53
<212> TYPE: DNA
<213> ORGANISM: Artificial Sequence
<220> FEATURE:
<223> OTHER INFORMATION: Primer Ann-R1_T7

<400> SEQUENCE: 30
ttaatacgac tcactatagg gagactaata attctttttt aatgttcctg agg 53

<210> SEQ ID NO 31
<211> LENGTH: 48
<212> TYPE: DNA
<213> ORGANISM: Artificial Sequence
<220> FEATURE:
<223> OTHER INFORMATION: Primer Ann-F2_T7

<400> SEQUENCE: 31
ttaatacgac tcactatagg gagattgtta caagctggag aacttctc 48

<210> SEQ ID NO 32
<211> LENGTH: 24
<212> TYPE: DNA
<213> ORGANISM: Artificial Sequence
<220> FEATURE:
<223> OTHER INFORMATION: Primer Ann-R2

<400> SEQUENCE: 32
cttaaccaac aacggctaat aagg 24

<210> SEQ ID NO 33
<211> LENGTH: 24
<212> TYPE: DNA
<213> ORGANISM: Artificial Sequence
<220> FEATURE:
<223> OTHER INFORMATION: Primer Ann-F2

<400> SEQUENCE: 33
ttgttacaag ctggagaact tctc 24

<210> SEQ ID NO 34
<211> LENGTH: 48
<212> TYPE: DNA
<213> ORGANISM: Artificial Sequence
<220> FEATURE:

<223> OTHER INFORMATION: Primer Ann-R2T7

<400> SEQUENCE: 34
ttaatacgac tcactatagg gagacttaac caacaacggc taataagg 48

<210> SEQ ID NO 35
<211> LENGTH: 47
<212> TYPE: DNA
<213> ORGANISM: Artificial Sequence
<220> FEATURE:
<223> OTHER INFORMATION: Primer Betasp2-F1_T7

<400> SEQUENCE: 35
ttaatacgac tcactatagg gagaagatgt tggctgcatc tagagaa 47

<210> SEQ ID NO 36
<211> LENGTH: 22
<212> TYPE: DNA
<213> ORGANISM: Artificial Sequence
<220> FEATURE:
<223> OTHER INFORMATION: Primer Betasp2-R1

<400> SEQUENCE: 36
gtccattcgt ccatccactg ca 22

<210> SEQ ID NO 37
<211> LENGTH: 23
<212> TYPE: DNA
<213> ORGANISM: Artificial Sequence
<220> FEATURE:
<223> OTHER INFORMATION: Primer Betasp2-F1

<400> SEQUENCE: 37
agatgttggc tgcatctaga gaa 23

<210> SEQ ID NO 38
<211> LENGTH: 46
<212> TYPE: DNA
<213> ORGANISM: Artificial Sequence
<220> FEATURE:
<223> OTHER INFORMATION: Primer Betasp-R1_T7

<400> SEQUENCE: 38
ttaatacgac tcactatagg gagagtccat tcgtccatcc actgca 46

<210> SEQ ID NO 39
<211> LENGTH: 46
<212> TYPE: DNA
<213> ORGANISM: Artificial Sequence
<220> FEATURE:
<223> OTHER INFORMATION: Primer Betasp2-F2_T7

<400> SEQUENCE: 39
ttaatacgac tcactatagg gagagcagat gaacaccagc gagaaa 46

<210> SEQ ID NO 40
<211> LENGTH: 22
<212> TYPE: DNA
<213> ORGANISM: Artificial Sequence
<220> FEATURE:
<223> OTHER INFORMATION: Primer Betasp2-R2

<400> SEQUENCE: 40
ctgggcagct tcttgtttcc tc 22

<210> SEQ ID NO 41
<211> LENGTH: 22
<212> TYPE: DNA
<213> ORGANISM: Artificial Sequence
<220> FEATURE:
<223> OTHER INFORMATION: Primer Betasp2-F2

<400> SEQUENCE: 41
gcagatgaac accagcgaga aa 22

<210> SEQ ID NO 42
<211> LENGTH: 46
<212> TYPE: DNA
<213> ORGANISM: Artificial Sequence
<220> FEATURE:
<223> OTHER INFORMATION: Primer Betasp2-R2_T7

<400> SEQUENCE: 42
ttaatacgac tcactatagg gagactgggc agcttcttgt ttcctc 46

<210> SEQ ID NO 43
<211> LENGTH: 51
<212> TYPE: DNA
<213> ORGANISM: Artificial Sequence
<220> FEATURE:
<223> OTHER INFORMATION: Primer L4-F1_T7

<400> SEQUENCE: 43
ttaatacgac tcactatagg gagaagtgaa atgttagcaa atataacatc c 51

<210> SEQ ID NO 44
<211> LENGTH: 26
<212> TYPE: DNA
<213> ORGANISM: Artificial Sequence
<220> FEATURE:
<223> OTHER INFORMATION: Primer L4-R1

<400> SEQUENCE: 44
acctctcact tcaaatcttg actttg 26

<210> SEQ ID NO 45
<211> LENGTH: 27
<212> TYPE: DNA
<213> ORGANISM: Artificial Sequence
<220> FEATURE:
<223> OTHER INFORMATION: Primer L4-F1

<400> SEQUENCE: 45
agtgaaatgt tagcaaatat aacatcc 27

<210> SEQ ID NO 46
<211> LENGTH: 50
<212> TYPE: DNA
<213> ORGANISM: Artificial Sequence
<220> FEATURE:
<223> OTHER INFORMATION: Primer L4-R1_T7

<400> SEQUENCE: 46
ttaatacgac tcactatagg gagaacctct cacttcaaat cttgactttg 50

<210> SEQ ID NO 47
<211> LENGTH: 50
<212> TYPE: DNA
<213> ORGANISM: Artificial Sequence
<220> FEATURE:
<223> OTHER INFORMATION: Primer L4-F2_T7

<400> SEQUENCE: 47
ttaatacgac tcactatagg gagacaaagt caagatttga agtgagaggt 50

<210> SEQ ID NO 48
<211> LENGTH: 25
<212> TYPE: DNA
<213> ORGANISM: Artificial Sequence
<220> FEATURE:
<223> OTHER INFORMATION: Primer L4-R2

<400> SEQUENCE: 48
ctacaaataa aacaagaagg acccc 25

<210> SEQ ID NO 49
<211> LENGTH: 26
<212> TYPE: DNA
<213> ORGANISM: Artificial Sequence
<220> FEATURE:
<223> OTHER INFORMATION: Primer L4-F2

<400> SEQUENCE: 49
caaagtcaag atttgaagtg agaggt 26

<210> SEQ ID NO 50
<211> LENGTH: 49
<212> TYPE: DNA
<213> ORGANISM: Artificial Sequence
<220> FEATURE:
<223> OTHER INFORMATION: Primer L4-R2_T7

<400> SEQUENCE: 50
ttaatacgac tcactatagg gagactacaa ataaaacaag aaggacccc 49

<210> SEQ ID NO 51
<211> LENGTH: 23
<212> TYPE: DNA
<213> ORGANISM: Artificial Sequence
<220> FEATURE:
<223> OTHER INFORMATION: Primer YFP-R

<400> SEQUENCE: 51
agatcttgaa ggcgctcttc agg 23

<210> SEQ ID NO 52
<211> LENGTH: 23
<212> TYPE: DNA
<213> ORGANISM: Artificial Sequence
<220> FEATURE:
<223> OTHER INFORMATION: Primer YFP-F

<400> SEQUENCE: 52
caccatgggc tccagcggcg ccc 23

<210> SEQ ID NO 53
<211> LENGTH: 370
<212> TYPE: DNA
<213> ORGANISM: Artificial Sequence
<220> FEATURE:
<223> OTHER INFORMATION: GFP partial coding region

<400> SEQUENCE: 53
aagtgatgct acatacggaa agcttaccct taaatttatt tgcactactg gaaaactacc 60
tgttccatgg ccaacacttg tcactacttt ctcttatggt gttcaatgct tttcccgtta 120
tccggatcat atgaaacggc atgacttttt caagagtgcc atgcccgaag gttatgtaca 180
ggaacgcact atatctttca aagatgacgg gaactacaag acgcgtgctg aagtcaagtt 240
tgaaggtgat acccttgtta atcgtatcga gttaaaaggt attgatttta aagaagatgg 300
aaacattctc ggacacaaac tcgagtacaa ctataactca cacaatgtat acatcacggc 360
agacaaacaa 370

<210> SEQ ID NO 54
<211> LENGTH: 43
<212> TYPE: DNA
<213> ORGANISM: Artificial Sequence
<220> FEATURE:
<223> OTHER INFORMATION: Primer GFP_T7F

<400> SEQUENCE: 54
taatacgact cactataggg aaggtgatgc tacatacgga aag 43

<210> SEQ ID NO 55
<211> LENGTH: 38
<212> TYPE: DNA
<213> ORGANISM: Artificial Sequence
<220> FEATURE:
<223> OTHER INFORMATION: Primer GFP_T7R

<400> SEQUENCE: 55
taatacgact cactataggg ttgtttgtct gccgtgat 38

<210> SEQ ID NO 56
<211> LENGTH: 222
<212> TYPE: DNA
<213> ORGANISM: Solanum tuberosum

<400> SEQUENCE: 56
gactagtacc ggttgggaaa ggtatgtttc tgcttctacc tttgatatat atataataat 60
tatcactaat tagtagtaat atagtatttc aagtattttt ttcaaaataa aagaatgtag 120
tatatagcta ttgcttttct gtagtttata agtgtgtata ttttaattta taacttttct 180
aatatatgac caaaacatgg tgatgtgcag gttgatccgc gg 222

<210> SEQ ID NO 57
<211> LENGTH: 812
<212> TYPE: DNA
<213> ORGANISM: Artificial Sequence
<220> FEATURE:
<223> OTHER INFORMATION: Brahma v1 hpRNA encoding sequence

<400> SEQUENCE: 57
gcgccctaca gactcctgct tactggtact cccctacaaa ataaattacc agaattatgg 60
gccttgttga atttcttgtt gccttcgatt ttcaagagtt gctccacttt tgaacaatgg 120
ttcaatgcgc cattcgcaac aacaggagaa aaggttgagt taaacgaaga agaaactatc 180
cttatcatcc gtcgtcttca caaagtactc aggccgtttc tcctgagacg tctcaagaaa 240
gaagtcgaat ctcagcttcc agacaaagtg gaatatatca taaagtgtga catgtgacta 300
gtaccggttg ggaaaggtat gtttctgctt ctacctttga tatatatata ataattatca 360
ctaattagta gtaatatagt atttcaagta tttttttcaa aataaaagaa tgtagtatat 420
agctattgct tttctgtagt ttataagtgt gtatatttta atttataact tttctaatat 480
atgaccaaaa catggtgatg tgcaggttga tccgcggaca tgtcacactt tatgatatat 540
tccactttgt ctggaagctg agattcgact tctttcttga gacgtctcag gagaaacggc 600

-continued

```
ctgagtactt tgtgaagacg acggatgata aggatagttt cttcttcgtt taactcaacc    660

ttttctcctg ttgttgcgaa tggcgcattg aaccattgtt caaaagtgga gcaactcttg    720

aaaatcgaag gcaacaagaa attcaacaag gcccataatt ctggtaattt attttgtagg    780

ggagtaccag taagcaggag tctgtagggc gc                                  812
```

<210> SEQ ID NO 58
<211> LENGTH: 822
<212> TYPE: DNA
<213> ORGANISM: Artificial Sequence
<220> FEATURE:
<223> OTHER INFORMATION: Brahma v2 hpRNA encoding sequence

<400> SEQUENCE: 58

```
catataaaag aacgaagcga cagggtctaa aagaatcgag agctacagag aagttagaaa     60

aacaacagaa gttagaagca gaaagaaaga gaagacagaa gaaccaagaa tttttgaatg    120

ctgtattgaa caatggaaaa gaattcaagg aattccacaa gcagaatcaa gcgaaattag    180

ctaagattaa taaagctgtt attaattatc acgctaatgc tgaaagagag caaaagaaag    240

aagcagaaag gagagagaag gaacgtatga tcagattgat ggcagaagat gaagaaggtt    300

gactagtacc ggttgggaaa ggtatgtttc tgcttctacc tttgatatat atataataat    360

tatcactaat tagtagtaat atagtatttc aagtattttt ttcaaaataa aagaatgtag    420

tatatagcta ttgcttttct gtagtttata agtgtgtata ttttaattta taacttttct    480

aatatatgac caaaacatgg tgatgtgcag gttgatccgc ggaaccttct tcatcttctg    540

ccatcaatct gatcatacgt tccttctctc tcctttctgc ttctttcttt tgctctcttt    600

cagcattagc gtgataatta ataacagctt tattaatctt agctaatttc gcttgattct    660

gcttgtggaa ttccttgaat tcttttccat tgttcaatac agcattcaaa aattcttggt    720

tcttctgtct tctctttctt tctgcttcta acttctgttg tttttctaac ttctctgtag    780

ctctcgattc ttttagaccc tgtcgcttcg ttcttttata tg                       822
```

<210> SEQ ID NO 59
<211> LENGTH: 22
<212> TYPE: DNA
<213> ORGANISM: Artificial Sequence
<220> FEATURE:
<223> OTHER INFORMATION: T20VN primer
<220> FEATURE:
<221> NAME/KEY: misc_feature
<222> LOCATION: (22)..(22)
<223> OTHER INFORMATION: n is a, c, g, or t

<400> SEQUENCE: 59

```
tttttttttt tttttttttt vn                                              22
```

<210> SEQ ID NO 60
<211> LENGTH: 19
<212> TYPE: DNA
<213> ORGANISM: Artificial Sequence
<220> FEATURE:
<223> OTHER INFORMATION: Primer P5U76S(F)

<400> SEQUENCE: 60

```
tgtgatgttg gtggcgtat                                                  19
```

<210> SEQ ID NO 61
<211> LENGTH: 24
<212> TYPE: DNA
<213> ORGANISM: Artificial Sequence -continued
<220> FEATURE:
<223> OTHER INFORMATION: Primer P5U76A(R)

<400> SEQUENCE: 61
tgttaaataa aaccccaaag atcg 24

<210> SEQ ID NO 62
<211> LENGTH: 20
<212> TYPE: DNA
<213> ORGANISM: Artificial Sequence
<220> FEATURE:
<223> OTHER INFORMATION: Primer TIPmxF

<400> SEQUENCE: 62
gagggtaatg ccaactggtt 20

<210> SEQ ID NO 63
<211> LENGTH: 24
<212> TYPE: DNA
<213> ORGANISM: Artificial Sequence
<220> FEATURE:
<223> OTHER INFORMATION: Primer TIPmxR

<400> SEQUENCE: 63
gcaatgtaac cgagtgtctc tcaa 24

<210> SEQ ID NO 64
<211> LENGTH: 32
<212> TYPE: DNA
<213> ORGANISM: Artificial Sequence
<220> FEATURE:
<223> OTHER INFORMATION: Primer HXTIP

<400> SEQUENCE: 64
tttttggctt agagttgatg gtgtactgat ga 32

<210> SEQ ID NO 65
<211> LENGTH: 151
<212> TYPE: DNA
<213> ORGANISM: Escherichia coli

<400> SEQUENCE: 65
gaccgtaagg cttgatgaaa caacgcggcg agctttgatc aacgaccttt tggaaacttc 60
ggcttcccct ggagagagcg agattctccg cgctgtagaa gtcaccattg ttgtgcacga 120
cgacatcatt ccgtggcgtt atccagctaa g 151

<210> SEQ ID NO 66
<211> LENGTH: 69
<212> TYPE: DNA
<213> ORGANISM: Artificial Sequence
<220> FEATURE:
<223> OTHER INFORMATION: AAD1 partial coding region

<400> SEQUENCE: 66
tgttcggttc cctctaccaa gcacagaacc gtcgcttcag caacacctca gtcaaggtga 60
tggatgttg 69

<210> SEQ ID NO 67
<211> LENGTH: 25
<212> TYPE: DNA
<213> ORGANISM: Artificial Sequence
<220> FEATURE:
<223> OTHER INFORMATION: Primer ST-LS1-F

<400> SEQUENCE: 67
gtatgtttct gcttctacct ttgat 25

<210> SEQ ID NO 68
<211> LENGTH: 29
<212> TYPE: DNA
<213> ORGANISM: Artificial Sequence
<220> FEATURE:
<223> OTHER INFORMATION: Primer ST-LS1-R

<400> SEQUENCE: 68
ccatgttttg gtcatatatt agaaaagtt 29

<210> SEQ ID NO 69
<211> LENGTH: 34
<212> TYPE: DNA
<213> ORGANISM: Artificial Sequence
<220> FEATURE:
<223> OTHER INFORMATION: Probe ST-LS1-P

<400> SEQUENCE: 69
agtaatatag tatttcaagt atttttttca aaat 34

<210> SEQ ID NO 70
<211> LENGTH: 20
<212> TYPE: DNA
<213> ORGANISM: Artificial Sequence
<220> FEATURE:
<223> OTHER INFORMATION: Primer GAAD1-F

<400> SEQUENCE: 70
tgttcggttc cctctaccaa 20

<210> SEQ ID NO 71
<211> LENGTH: 22
<212> TYPE: DNA
<213> ORGANISM: Artificial Sequence
<220> FEATURE:
<223> OTHER INFORMATION: Primer GAAD1-R

<400> SEQUENCE: 71
caacatccat caccttgact ga 22

<210> SEQ ID NO 72
<211> LENGTH: 24
<212> TYPE: DNA
<213> ORGANISM: Artificial Sequence
<220> FEATURE:
<223> OTHER INFORMATION: Probe GAAD1-P

<400> SEQUENCE: 72
cacagaaccg tcgcttcagc aaca 24

<210> SEQ ID NO 73
<211> LENGTH: 18
<212> TYPE: DNA
<213> ORGANISM: Artificial Sequence
<220> FEATURE:
<223> OTHER INFORMATION: Primer IVR1-F

<400> SEQUENCE: 73
tggcggacga cgacttgt 18

<210> SEQ ID NO 74
<211> LENGTH: 19

-continued

<212> TYPE: DNA
<213> ORGANISM: Artificial Sequence
<220> FEATURE:
<223> OTHER INFORMATION: Primer IVR1-R

<400> SEQUENCE: 74
aaagtttgga ggctgccgt 19

<210> SEQ ID NO 75
<211> LENGTH: 26
<212> TYPE: DNA
<213> ORGANISM: Artificial Sequence
<220> FEATURE:
<223> OTHER INFORMATION: Probe IVR1-P

<400> SEQUENCE: 75
cgagcagacc gccgtgtact tctacc 26

<210> SEQ ID NO 76
<211> LENGTH: 19
<212> TYPE: DNA
<213> ORGANISM: Artificial Sequence
<220> FEATURE:
<223> OTHER INFORMATION: Primer SPC1A

<400> SEQUENCE: 76
cttagctgga taacgccac 19

<210> SEQ ID NO 77
<211> LENGTH: 19
<212> TYPE: DNA
<213> ORGANISM: Artificial Sequence
<220> FEATURE:
<223> OTHER INFORMATION: Primer SPC1S

<400> SEQUENCE: 77
gaccgtaagg cttgatgaa 19

<210> SEQ ID NO 78
<211> LENGTH: 21
<212> TYPE: DNA
<213> ORGANISM: Artificial Sequence
<220> FEATURE:
<223> OTHER INFORMATION: Probe TQSPEC

<400> SEQUENCE: 78
cgagattctc cgcgctgtag a 21

<210> SEQ ID NO 79
<211> LENGTH: 5146
<212> TYPE: DNA
<213> ORGANISM: Diabrotica virgifera

<400> SEQUENCE: 79
ttgagaacga gaacacgaac gagtgtatcg tcgtgtttct ttttctttgg ttattgtgta 60
aattaattac aaacgtgtta aaatttactt aaagttagtg atttgtgtat ttatagtttg 120
taagtgatgg catcagatga agaagtggag gattctttcg ccggggagga agatgccccc 180
gacgatacgg ctgaacaaat agataacgat cctgattctg aagatggtgt tcctaaagga 240
ggggaagaag atgatgatta tgaaccagaa gattccagaa agaaaaagaa gggaaagaaa 300
agaaaagcca ggggagaaga aaagaaaggc aagaaaaaga agaaaaagcg aaagaatgat 360
agtggggatg aaagtgactt tggagaagat gataatggag gtggggactc agattatgca 420

-continued

```
agcagtagta aaagaggaag gaaaaagggt tctactaaac actcttctgc atcatcaaca    480
ccaacaccag ctagtgactc tggcacagga ggcatgccca ccatcgagca agtttgttca    540
acatttggtt taactgatgt cgagcttgac tattcagatg ctgatatgca aaacttgacc    600
acctataagt tgttccaaca gcatgtgaga ccgctccttg ctaaggaaaa tccaaaggtt    660
cctatgtcaa agttgatgat gttggttgct gcaaaatggc gcgaattttc taattcaaac    720
cccaatctgc aaagcgaaaa tgaaccgtct gctgcaactt caaccacatc tgaagaaagt    780
tatccaaaaa ctaatcgttc gagagcatcc aaggaagcag cacaaaagat agtagaggct    840
gactctgagc catatgatga cgaatttgat gacgaagacg aggaggaaaa agaagagaaa    900
ggaaagaaaa aaaagagtaa tagaggaagg cctagtaaaa agaaggctac taaagtacca    960
actttaaaga ttaaactagg aaagaggaag cgtggaagtt cggatgaaga gggcgatctt   1020
agtggaggtg gctctgatcg cgattctgat gctgagtttg agcagatgct acaagaagct   1080
gaagaaccaa aatccaacaa atctaccact ggtgaagaat ccgcacagcc atcagaatca   1140
cctgcagatg aaaatccacc accaaaacgc aaagcgaaaa ccaaaattgg ttgcaaaaca   1200
aagagaaaga agaaaacaaa gagtggtaaa cctgaagatg aaaattatga acatcaagat   1260
tactgcgagg tatgtcaaca aggtggagaa attatcctct gtgatacttg ccctagagct   1320
taccacttgg tttgcctgga acctgaatta gaagaagccc ctgaaggaaa gtggagttgc   1380
cctcattgtg agaatgaagg tccggctgaa caagatgatg acgagcatca agaattctgc   1440
agggtttgca aagatggtgg cgaacttttg tgttgcgatt cctgtacatc tgcgtaccac   1500
acgcactgtc ttaacccgcc acttcccgaa atacctgacg gcgattggaa atgtcctagg   1560
tgcggttgtc cgcctcttgt gggcaaagtt gcgaaaattc ttacgtggaa atgggttgat   1620
gatcctccta aaaagaagga caatggtgaa gaggagcctc ctacacgaca tagagagtac   1680
tttgttaagt ggcatgagct atcatattgg cattgtagtt ggataaccga gcttcaattg   1740
gatgtatatc atcctctcat gtttcgaagt tattcaagaa agtgggacat ggaagagcct   1800
cctaaacttg aagaacctat ggatgaagct gacactagat gtagcagatt cctgaaaatg   1860
ggtggaaaca acaacgacga tgaactcgaa gagaagtatt acagatacgg aataaaacca   1920
gaatggctaa tagtccatcg tgtcatcaac caccgtacga tgcgagacgg aagaactttg   1980
tacttagtaa aatggcgaga gctaacttac gatcaagcta cctgggaaga agattctgac   2040
gatatcccag ccctaaagtc tgccatcgaa tattacacag attcaagagc tgctaattta   2100
tccggagctg gaggtaagct aaagaagaaa gttggaagga agccgaaagc taaagaactt   2160
atcgatgacg acgatagaaa cggtcctcgc agatatactc caccgccaga taagccctgc   2220
agtgatctga agaagaaact agacaaacaa ccctcatatt tggacgagag tggattgctt   2280
cacgagtacc aactagaggg tcttaactgg cttcgttatt cgtgggccaa cggtatagac   2340
actatcttag ccgacgagat gggtctcggt aaaaccattc aaaccattgt cttcttgtat   2400
tcgctctaca aggaaggtca ctgcaaaggt ccgtttctaa ttagtgtccc actttcaacg   2460
atcatcaatt gggagagaga attcgaaaat tgggcacctg atttttattg tattacatat   2520
gttggtgaca aggactgcag agccgtgatt cgtgagaacg aactcagttt cgaagatggt   2580
gctgtcagag gaggtcgagc ttcgagaatc agagccggtt ccatcaagtt taacgttttg   2640
ttgaccagct acgaattaat ttcgatcgat tcggcatgtc tcggttctat cgaatgggcc   2700
gttttggtag tcgatgaagc tcatagattg aaaagcaatc aatcaaaatt cttcaaaatc   2760
ttaaacgctt ataatatagc ttataaactc ctcttgaccg gaacaccgct tcaaaacaac   2820
```

-continued

```
ctcgaagaat tgttccattt gttgaacttc ctcaacggtc agaaattcaa cgatctccaa   2880
aacttccaag ccgaattcgc cgacatttcg aaagaagacc aagtgaagaa attgcacgag   2940
atgttgggac ctcatatgct gcgtcgtctc aaggccgatg tgctgaagag catgccttcg   3000
aaatctgaat ttatcgtcag agtcgaatta tcgcccatgc agaagaaata ttataaatat   3060
attttgacga ggaactttga agctttaaat cctaaaggag gcggacagtc ggtatcttta   3120
cttaacatta tgatggatct caagaaatgt tgcaaccatc cctatctttt cccagccgcc   3180
tcggaagaag ctccgctggg tccccatggt aattgggatg taggtcattt gattaaggct   3240
tcaggaaagt tggtgctatt agcgaagatg ttgaagatcc ttagagaaca gggtcacaga   3300
gtgttgatct tctcgcaaat gacgaagatg ttggatataa tggaagattt tcttgaagga   3360
gaagggtata aatacgaacg tattgatggg gctattactg gtaatctccg tcaagaagct   3420
atcgataggt ttaacgctcc aggtgctccc cagtttgttt tccttttgtc cactaaagct   3480
ggtggtttgg gcatcaatct tgctacagca gatactgtaa tcatctatga ttccgattgg   3540
aatccccaca atgatattca ggcattctcc agagctcatc gtatcggtca agccaacaag   3600
gtgatgatct accgttttgt aacacgtaac agtgtggaag aacgtgttac gcaagtagcc   3660
aagcggaaaa tgatgttaac tcacttggta gtcagacctg gaatgggcgg aaaaggtgcc   3720
aactttacta agcaagagtt ggacgatatt ctcagattcg gtactgaaga attgtttaaa   3780
gaaagtgaag gcaaagaaga cgaagccatt cactacgacg acaaagctgt gggagaattg   3840
ctggatcgtt ctaaagaagg catagaacag aaagagagtt gggcgaacga atatctcagt   3900
tcatttaaag tggctagtta tgttacaaaa gaaggggaag ttgaggaaga agttgacact   3960
gagattatta aacaagaagc ggaaaatacc gatccggcct actggatcaa gctgcttaga   4020
catcattatg agcaacaaca ggaagatata gctaggacgt taggaaaagg caaaagagtg   4080
aggaaacagg ttaattataa tgacggagga atgacaactg acacacgaga agatacgaca   4140
tggcaagaaa atctctctga ttaccattct gacttttctg cgggatcgga tgaggataag   4200
gaagacgata aggaagacga tgattcgatg agaagaacga cgccgattta agcagaagga   4260
gtcgaagaaa gatggaaagg aaagacgaga aggatcgtcc tttaccaccg ttactagcca   4320
gagttggcgg caatattgaa gtactcggtt ttaatgccag gcagcgtaaa gcgttcctta   4380
atgctattat gcgctacgga atgccaccac aagacgcttt caattcacag tggctggtga   4440
gagatcttcg aggaaaatct gagaagatat tcaaggctta cgtgtctctc tttatgaggc   4500
atctttgcga acctggtgca gataatgctg atacgtttgc ggacggtgtg ccgagggaag   4560
gactgagtag gcaacatgtt ttgacaagga ttggtgtgat gtcacttata agaaagaagg   4620
ttcaggagtt cgaacacatc aacggcgagt atagcatgcc ggaagtaatc aaaaagagca   4680
ttatggatca aaataaaatc aatgccgccg gcaccgccac cacaagcgaa gcagaaacgc   4740
ctaaaagtgc tactaccagt actagtgcta cgccagctac aagtgctgct cccagtcccg   4800
ctcccacaca aggagaagat aaagataagg ataaagattc cgttcagagt gacgaaaata   4860
aagataaaga agtggttaat aaaacggaaa ccgaagatga agagaagaaa acgggagaat   4920
cttcaacaga aaagccgaaa actgaaccgg aagaagtgaa agaagcttct ccgaaaaccg   4980
aaattcctga agctagttcc gaagctgata aatctgagat caaatccgaa gtcgatacct   5040
cgtctgtaac cagcgaggaa aagaaagaag agaaagagga agaggccaaa aaagaagaac   5100
ccgaagagac caaaatggaa atacaggagg aggaacttgt taaaga                  5146
```

<210> SEQ ID NO 80
<211> LENGTH: 1974
<212> TYPE: PRT
<213> ORGANISM: Diabrotica virgifera

<400> SEQUENCE: 80

Met Ala Ser Asp Glu Glu Val Glu Asp Ser Phe Ala Gly Glu Glu Asp
1 5 10 15

Ala Pro Asp Asp Thr Ala Glu Gln Ile Asp Asn Asp Pro Asp Ser Glu
20 25 30

Asp Gly Val Pro Lys Gly Gly Glu Glu Asp Asp Asp Tyr Glu Pro Glu
35 40 45

Asp Ser Arg Lys Lys Lys Lys Gly Lys Lys Arg Lys Ala Arg Gly Glu
50 55 60

Glu Lys Lys Gly Lys Lys Lys Lys Lys Lys Arg Lys Asn Asp Ser Gly
65 70 75 80

Asp Glu Ser Asp Phe Gly Glu Asp Asp Asn Gly Gly Gly Asp Ser Asp
85 90 95

Tyr Ala Ser Ser Ser Lys Arg Gly Arg Lys Lys Gly Ser Thr Lys His
100 105 110

Ser Ser Ala Ser Ser Thr Pro Thr Pro Ala Ser Asp Ser Gly Thr Gly
115 120 125

Gly Met Pro Thr Ile Glu Gln Val Cys Ser Thr Phe Gly Leu Thr Asp
130 135 140

Val Glu Leu Asp Tyr Ser Asp Ala Asp Met Gln Asn Leu Thr Thr Tyr
145 150 155 160

Lys Leu Phe Gln Gln His Val Arg Pro Leu Leu Ala Lys Glu Asn Pro
165 170 175

Lys Val Pro Met Ser Lys Leu Met Met Leu Val Ala Ala Lys Trp Arg
180 185 190

Glu Phe Ser Asn Ser Asn Pro Asn Leu Gln Ser Glu Asn Glu Pro Ser
195 200 205

Ala Ala Thr Ser Thr Thr Ser Glu Glu Ser Tyr Pro Lys Thr Asn Arg
210 215 220

Ser Arg Ala Ser Lys Glu Ala Ala Gln Lys Ile Val Glu Ala Asp Ser
225 230 235 240

Glu Pro Tyr Asp Asp Glu Phe Asp Asp Glu Asp Glu Glu Glu Lys Glu
245 250 255

Glu Lys Gly Lys Lys Lys Lys Ser Asn Arg Gly Arg Pro Ser Lys Lys
260 265 270

Lys Ala Thr Lys Val Pro Thr Leu Lys Ile Lys Leu Gly Lys Arg Lys
275 280 285

Arg Gly Ser Ser Asp Glu Glu Gly Asp Leu Ser Gly Gly Gly Ser Asp
290 295 300

Arg Asp Ser Asp Ala Glu Phe Glu Gln Met Leu Gln Glu Ala Glu Glu
305 310 315 320

Pro Lys Ser Asn Lys Ser Thr Thr Gly Glu Glu Ser Ala Gln Pro Ser
325 330 335

Glu Ser Pro Ala Asp Glu Asn Pro Pro Pro Lys Arg Lys Ala Lys Thr
340 345 350

Lys Ile Gly Cys Lys Thr Lys Arg Lys Lys Lys Thr Lys Ser Gly Lys
355 360 365

Pro Glu Asp Glu Asn Tyr Glu His Gln Asp Tyr Cys Glu Val Cys Gln
370 375 380

-continued

Gln Gly Gly Glu Ile Ile Leu Cys Asp Thr Cys Pro Arg Ala Tyr His
385 390 395 400

Leu Val Cys Leu Glu Pro Glu Leu Glu Glu Ala Pro Glu Gly Lys Trp
405 410 415

Ser Cys Pro His Cys Glu Asn Glu Gly Pro Ala Glu Gln Asp Asp Asp
420 425 430

Glu His Gln Glu Phe Cys Arg Val Cys Lys Asp Gly Gly Glu Leu Leu
435 440 445

Cys Cys Asp Ser Cys Thr Ser Ala Tyr His Thr His Cys Leu Asn Pro
450 455 460

Pro Leu Pro Glu Ile Pro Asp Gly Asp Trp Lys Cys Pro Arg Cys Gly
465 470 475 480

Cys Pro Pro Leu Val Gly Lys Val Ala Lys Ile Leu Thr Trp Lys Trp
485 490 495

Val Asp Asp Pro Pro Lys Lys Lys Asp Asn Gly Glu Glu Glu Pro Pro
500 505 510

Thr Arg His Arg Glu Tyr Phe Val Lys Trp His Glu Leu Ser Tyr Trp
515 520 525

His Cys Ser Trp Ile Thr Glu Leu Gln Leu Asp Val Tyr His Pro Leu
530 535 540

Met Phe Arg Ser Tyr Ser Arg Lys Trp Asp Met Glu Glu Pro Pro Lys
545 550 555 560

Leu Glu Glu Pro Met Asp Glu Ala Asp Thr Arg Cys Ser Arg Phe Leu
565 570 575

Lys Met Gly Gly Asn Asn Asn Asp Asp Glu Leu Glu Glu Lys Tyr Tyr
580 585 590

Arg Tyr Gly Ile Lys Pro Glu Trp Leu Ile Val His Arg Val Ile Asn
595 600 605

His Arg Thr Met Arg Asp Gly Arg Thr Leu Tyr Leu Val Lys Trp Arg
610 615 620

Glu Leu Thr Tyr Asp Gln Ala Thr Trp Glu Glu Asp Ser Asp Asp Ile
625 630 635 640

Pro Ala Leu Lys Ser Ala Ile Glu Tyr Tyr Thr Asp Ser Arg Ala Ala
645 650 655

Asn Leu Ser Gly Ala Gly Gly Lys Leu Lys Lys Lys Val Gly Arg Lys
660 665 670

Pro Lys Ala Lys Glu Leu Ile Asp Asp Asp Asp Arg Asn Gly Pro Arg
675 680 685

Arg Tyr Thr Pro Pro Pro Asp Lys Pro Cys Ser Asp Leu Lys Lys Lys
690 695 700

Leu Asp Lys Gln Pro Ser Tyr Leu Asp Glu Ser Gly Leu Leu His Glu
705 710 715 720

Tyr Gln Leu Glu Gly Leu Asn Trp Leu Arg Tyr Ser Trp Ala Asn Gly
725 730 735

Ile Asp Thr Ile Leu Ala Asp Glu Met Gly Leu Gly Lys Thr Ile Gln
740 745 750

Thr Ile Val Phe Leu Tyr Ser Leu Tyr Lys Glu Gly His Cys Lys Gly
755 760 765

Pro Phe Leu Ile Ser Val Pro Leu Ser Thr Ile Ile Asn Trp Glu Arg
770 775 780

Glu Phe Glu Asn Trp Ala Pro Asp Phe Tyr Cys Ile Thr Tyr Val Gly
785 790 795 800

-continued

```
Asp Lys Asp Cys Arg Ala Val Ile Arg Glu Asn Glu Leu Ser Phe Glu
                805                 810                 815

Asp Gly Ala Val Arg Gly Gly Arg Ala Ser Arg Ile Arg Ala Gly Ser
            820                 825                 830

Ile Lys Phe Asn Val Leu Leu Thr Ser Tyr Glu Leu Ile Ser Ile Asp
        835                 840                 845

Ser Ala Cys Leu Gly Ser Ile Glu Trp Ala Val Leu Val Val Asp Glu
    850                 855                 860

Ala His Arg Leu Lys Ser Asn Gln Ser Lys Phe Phe Lys Ile Leu Asn
865                 870                 875                 880

Ala Tyr Asn Ile Ala Tyr Lys Leu Leu Leu Thr Gly Thr Pro Leu Gln
                885                 890                 895

Asn Asn Leu Glu Glu Leu Phe His Leu Leu Asn Phe Leu Asn Gly Gln
            900                 905                 910

Lys Phe Asn Asp Leu Gln Asn Phe Gln Ala Glu Phe Ala Asp Ile Ser
        915                 920                 925

Lys Glu Asp Gln Val Lys Lys Leu His Glu Met Leu Gly Pro His Met
    930                 935                 940

Leu Arg Arg Leu Lys Ala Asp Val Leu Lys Ser Met Pro Ser Lys Ser
945                 950                 955                 960

Glu Phe Ile Val Arg Val Glu Leu Ser Pro Met Gln Lys Lys Tyr Tyr
                965                 970                 975

Lys Tyr Ile Leu Thr Arg Asn Phe Glu Ala Leu Asn Pro Lys Gly Gly
            980                 985                 990

Gly Gln Ser Val Ser Leu Leu Asn  Ile Met Met Asp Leu  Lys Lys Cys
        995                 1000                1005

Cys Asn  His Pro Tyr Leu Phe  Pro Ala Ala Ser Glu  Glu Ala Pro
    1010                1015                1020

Leu Gly  Pro His Gly Asn Trp  Asp Val Gly His Leu  Ile Lys Ala
    1025                1030                1035

Ser Gly  Lys Leu Val Leu Leu  Ala Lys Met Leu Lys  Ile Leu Arg
    1040                1045                1050

Glu Gln  Gly His Arg Val Leu  Ile Phe Ser Gln Met  Thr Lys Met
    1055                1060                1065

Leu Asp  Ile Met Glu Asp Phe  Leu Glu Gly Glu Gly  Tyr Lys Tyr
    1070                1075                1080

Glu Arg  Ile Asp Gly Ala Ile  Thr Gly Asn Leu Arg  Gln Glu Ala
    1085                1090                1095

Ile Asp  Arg Phe Asn Ala Pro  Gly Ala Pro Gln Phe  Val Phe Leu
    1100                1105                1110

Leu Ser  Thr Lys Ala Gly Gly  Leu Gly Ile Asn Leu  Ala Thr Ala
    1115                1120                1125

Asp Thr  Val Ile Ile Tyr Asp  Ser Asp Trp Asn Pro  His Asn Asp
    1130                1135                1140

Ile Gln  Ala Phe Ser Arg Ala  His Arg Ile Gly Gln  Ala Asn Lys
    1145                1150                1155

Val Met  Ile Tyr Arg Phe Val  Thr Arg Asn Ser Val  Glu Glu Arg
    1160                1165                1170

Val Thr  Gln Val Ala Lys Arg  Lys Met Met Leu Thr  His Leu Val
    1175                1180                1185

Val Arg  Pro Gly Met Gly Gly  Lys Gly Ala Asn Phe  Thr Lys Gln
    1190                1195                1200

Glu Leu  Asp Asp Ile Leu Arg  Phe Gly Thr Glu Glu  Leu Phe Lys
```

1205 1210 1215

Glu Ser Glu Gly Lys Glu Asp Glu Ala Ile His Tyr Asp Asp Lys
1220 1225 1230

Ala Val Gly Glu Leu Leu Asp Arg Ser Lys Glu Gly Ile Glu Gln
1235 1240 1245

Lys Glu Ser Trp Ala Asn Glu Tyr Leu Ser Ser Phe Lys Val Ala
1250 1255 1260

Ser Tyr Val Thr Lys Glu Gly Glu Val Glu Glu Glu Val Asp Thr
1265 1270 1275

Glu Ile Ile Lys Gln Glu Ala Glu Asn Thr Asp Pro Ala Tyr Trp
1280 1285 1290

Ile Lys Leu Leu Arg His His Tyr Glu Gln Gln Gln Glu Asp Ile
1295 1300 1305

Ala Arg Thr Leu Gly Lys Gly Lys Arg Val Arg Lys Gln Val Asn
1310 1315 1320

Tyr Asn Asp Gly Gly Met Thr Thr Asp Thr Arg Glu Asp Thr Thr
1325 1330 1335

Trp Gln Glu Asn Leu Ser Asp Tyr His Ser Asp Phe Ser Ala Gly
1340 1345 1350

Ser Asp Glu Asp Lys Glu Asp Asp Asp Phe Asp Glu Lys Asn Asp
1355 1360 1365

Ala Asp Leu Ser Arg Arg Ser Arg Arg Lys Met Glu Arg Lys Asp
1370 1375 1380

Glu Lys Asp Arg Pro Leu Pro Pro Leu Leu Ala Arg Val Gly Gly
1385 1390 1395

Asn Ile Glu Val Leu Gly Phe Asn Ala Arg Gln Arg Lys Ala Phe
1400 1405 1410

Leu Asn Ala Ile Met Arg Tyr Gly Met Pro Pro Gln Asp Ala Phe
1415 1420 1425

Asn Ser Gln Trp Leu Val Arg Asp Leu Arg Gly Lys Ser Glu Lys
1430 1435 1440

Ile Phe Lys Ala Tyr Val Ser Leu Phe Met Arg His Leu Cys Glu
1445 1450 1455

Pro Gly Ala Asp Asn Ala Asp Thr Phe Ala Asp Gly Val Pro Arg
1460 1465 1470

Glu Gly Leu Ser Arg Gln His Val Leu Thr Arg Ile Gly Val Met
1475 1480 1485

Ser Leu Ile Arg Lys Lys Val Gln Glu Phe Glu His Ile Asn Gly
1490 1495 1500

Glu Tyr Ser Met Pro Glu Val Ile Lys Lys Ser Ile Met Asp Gln
1505 1510 1515

Asn Lys Ile Asn Ala Ala Gly Thr Ala Thr Thr Ser Glu Ala Glu
1520 1525 1530

Thr Pro Lys Ser Ala Thr Thr Ser Thr Ser Ala Thr Pro Ala Thr
1535 1540 1545

Ser Ala Ala Pro Ser Pro Ala Pro Thr Gln Gly Glu Asp Lys Asp
1550 1555 1560

Lys Asp Lys Asp Ser Val Gln Ser Asp Glu Asn Lys Asp Lys Glu
1565 1570 1575

Val Val Asn Lys Thr Glu Thr Glu Asp Glu Glu Lys Lys Thr Gly
1580 1585 1590

Glu Ser Ser Thr Glu Lys Pro Lys Thr Glu Pro Glu Glu Val Lys
1595 1600 1605

```
Glu Ala  Ser Pro Lys Thr Glu  Thr Pro Glu Ala Ser  Ser Glu Ala
    1610                 1615                 1620

Asp Lys  Ser Glu Ile Lys Ser  Glu Val Asp Thr Ser  Ser Val Thr
    1625                 1630                 1635

Ser Glu  Glu Lys Lys Glu Glu  Lys Glu Glu Glu Ala  Lys Lys Glu
    1640                 1645                 1650

Glu Pro  Glu Glu Thr Lys Met  Glu Ile Gln Glu Glu  Glu Leu Val
    1655                 1660                 1665

Lys Glu  Glu Lys Lys Glu Glu  Glu Asp Asp Lys Lys  Lys Glu Glu
    1670                 1675                 1680

Val Lys  Lys Glu Val Glu Lys  Lys Glu Glu Asp Asp  Val Met Val
    1685                 1690                 1695

Ile Asp  Asp Asp Lys Asp Lys  Lys Asp Lys Lys Glu  Ile Asp Leu
    1700                 1705                 1710

Glu Ala  Lys Lys Arg Phe Met  Phe Asn Ile Ala Asp  Gly Gly Phe
    1715                 1720                 1725

Thr Glu  Leu His Thr Leu Trp  Leu Asn Glu Glu Lys  Ala Ala Ser
    1730                 1735                 1740

Pro Gly  Arg Glu Tyr Glu Ile  Trp His Arg Arg His  Asp Tyr Trp
    1745                 1750                 1755

Leu Leu  Ala Gly Ile Val Thr  His Gly Tyr Gly Arg  Trp Gln Asp
    1760                 1765                 1770

Ile Gln  Ala Asp Ala Arg Phe  Ala Ile Ile Asn Glu  Pro Phe Lys
    1775                 1780                 1785

Met Asp  Val Gly Lys Gly Asn  Phe Leu Glu Ile Lys  Asn Lys Phe
    1790                 1795                 1800

Leu Ala  Arg Arg Phe Lys Leu  Leu Glu Gln Ala Leu  Val Ile Glu
    1805                 1810                 1815

Glu Gln  Leu Arg Arg Ala Ala  Tyr Leu Asn Leu Thr  Gln Asp Pro
    1820                 1825                 1830

Asn His  Pro Ala Met Ser Leu  Asn Ala Arg Phe Ala  Glu Val Glu
    1835                 1840                 1845

Cys Leu  Ala Glu Ser His Gln  His Leu Ser Lys Glu  Ser Leu Ala
    1850                 1855                 1860

Gly Asn  Lys Pro Ala Asn Ala  Val Leu His Lys Val  Leu Asn Gln
    1865                 1870                 1875

Leu Glu  Glu Leu Leu Ser Asp  Met Lys Ser Asp Val  Ser Arg Leu
    1880                 1885                 1890

Pro Ala  Thr Leu Ala Arg Ile  Pro Pro Val Ala Gln  Arg Leu Gln
    1895                 1900                 1905

Met Ser  Glu Arg Ser Ile Leu  Ser Arg Leu Ala Ala  Thr Ser Ser
    1910                 1915                 1920

Ser Asn  Thr Gln Ser Thr Thr  Gln Val Met Ser Gln  Phe Pro Pro
    1925                 1930                 1935

Gly Phe  Ser Ala Gly Ser Leu  Pro Gly Phe Thr Gly  Ser Thr Gly
    1940                 1945                 1950

Asn Phe  Ser Asn Phe Arg Pro  Gln Tyr Ser Val Pro  Gly Gln Pro
    1955                 1960                 1965

Pro Ala  Gly Phe Pro Ser
    1970
```

<210> SEQ ID NO 81
<211> LENGTH: 3076

<212> TYPE: DNA
<213> ORGANISM: Diabrotica virgifera

<400> SEQUENCE: 81

```
agcggcggca gcacgcagca ggcaacactg gcaacagcag ttttttttaac gcgcggtggc     60
tgagaattga gaatgctgtt gtaaatttct ttgttaatca aataaaactt tgtttcaaca    120
tattgcaaaa ttcatctaaa cgttcaacat gtcacaaact gaaggctcga cagaggcgag    180
cgtaagtgcc tcagaaccaa tggaagaagc agagaactcg gaattggctc aaaatgaaga    240
atcttcttca gatactacct ctaagggtga agagttcgag gtcaaagtgg cttctgacag    300
aggaaaaaga tttgactact tgttgaaaca gactgaaatc ttttcacatt ttatgaacca    360
aacaaaatct cccagtaaac caaaaactgg gaggcctaaa aaagagaaga gtgatacatc    420
tgatttaaga catcgtaaaa ctgaacaaga agaagatgaa gaacttttag cagaaaccaa    480
ccttaaaaca aagactacaa ctcgttttga tgcctcacca ccctacatca aacatgggga    540
aatgagagat tatcaagtcc gtggtttgaa ctggatgatt tctttgtatg aacatggcat    600
caatggtatt ttagcagatg agatgggttt gggtaaaact ttacaaacca tatctctgct    660
tggatatatg aagcactata aaagtacacc tggtcctcat attgtcattg ttcctaaatc    720
taccttatca aactggatga atgagttcga gaagtggtgt ccaaccttga gagccgtttg    780
tctcattggt gatcaagagg ctaggagctc atttatcaga gatacgatga tgcctggtga    840
atgggatgtt tgtgtaacct cgtacgaaat gtgtattaaa gaaaaatctg tatttaaaaa    900
gttcaactgg agatatatgg tcattgacga agctcatcgt ataaaaaatg aaaaatctaa    960
gctttccgaa attctcaggg agttcaagac tactaacagg ctactgctaa caggtactcc   1020
attacaaaac aatttacacg aactctgggc tcttctcaac ttcttactgc cagatgtttt   1080
caactcatcg gatgatttcg atgcctggtt caacaccagt caatgtctgg gagacaacgc   1140
cttggtcgag agattgcatg ctgtattaaa accattcttg cttagaagat tgaaagctga   1200
agtggagaaa cggctaaaac ccaagaagga gttaaaagtg tatgtaggat tgagcaagat   1260
gcaacgagaa tggtatacca aagtgctgat gaaggatatt gatatagtga atggtgcagg   1320
aaaggtagaa aaaatgcgac tacagaatat tctcatgcag ttaagaaaat gcacaaatca   1380
cccctacctt tttgatggcg ctgagcccgg accaccttac acaaccgatg aacatctcgt   1440
gtacaattgc ggtaaaatgg tgttgctgga taaactgctt cccaaattga aggaacagga   1500
atctcgtgta cttatcttct ctcagatgac ccgtatgttg gatatacttg aagattattg   1560
tcattggcga cagtaccaat attgtcgttt ggatggtcaa accccacacg aagacagaca   1620
gagacaaatc aacgagtata acgaagacaa tagccaaaag tttatcttta tgttgtcaac   1680
tagagccggt ggattgggta tcaatttggc cacagctgat gtagttatta tatatgattc   1740
ggattggaat ccccagatgg atctgcaagc catggacaga gcgcatagaa ttggtcagaa   1800
gaaacaagtc agagttttca ggtttattac cgaaaacact gtggaagaaa aaatcgtcga   1860
aagagctgaa gtaaaattac gtttagacaa attagttatc cagcagggtc gtttagccga   1920
ttccaaagca cagactctaa acaaagacga aatgttgaac atgatccggc acggtgccaa   1980
ccacgtattt gcttctaagg attccgaaat aacagatgaa gatatcgata gtatattgga   2040
aaagggagaa atgaagaccg ctcagctagc tcagaagatg gaaaccatgg gcgaatcgtc   2100
acttcgcaac ttcacagtcg aaacacccac tgaatcagtc taccaattcg aaggagaaga   2160
ttatcgtgag aagcagaaaa ccatcggctt gagcaactgg atagaacctc ccaaaagaga   2220
```

-continued

```
aaggaaggcc aactatgccg tcgatgctta cttcagagaa gctttaaggg tttctgagcc   2280

taaagcgcct aaggctccaa gaccaccaaa acagcccatc gtacaagatt tccagttttt   2340

cccgccgaga ttattcgaac ttttggacca ggagatctac ttttacagga aatctttggg   2400

atataaggtt ccgaaaaact tagaacttgg acctgacgcg tccaagcaac agaaagaaga   2460

gcaaagaaaa atagatgagt cagaaccgct caccgaagac gaacagcaag aaaaagaaaa   2520

cttgttaacg caaggtttca ccaattggag taaacgcgat ttcaatcagt tcatcaaagc   2580

caacgagaaa tatggtaggg acgatattga gaacatcgcc aaggatgttg aaggcaaaac   2640

gcctgaagaa gttatggaat attctgcggt gttttgggaa agatgtcatg aattacagga   2700

tattgataga ataatggccc agattgagag aggagaaact aaaatacaaa gaagagctag   2760

tattaagaag gcacttgatg ctaaaatggc aagatatcgt gcaccattcc atcagctgag   2820

aatttcttac ggcaccaaca aaggcaagaa ctacatggag gacgaagaca ggtttttggt   2880

gtgtatgttg cacaagttgg gtttcgatag agaaaacgtt tatgaagagt taagagcagc   2940

tgtacgtgcg tcaccacaat tcagatttga ttggttctta aaatcgagaa ctgccatgga   3000

gctgcaaagg agatgcaaca cattgataac gttaatagaa agagaaaatg ctgaattgga   3060

ggaaagagaa aaaatt                                                    3076
```

<210> SEQ ID NO 82
<211> LENGTH: 976
<212> TYPE: PRT
<213> ORGANISM: Diabrotica virgifera

<400> SEQUENCE: 82

```
Met Ser Gln Thr Glu Gly Ser Thr Glu Ala Ser Val Ser Ala Ser Glu
1               5                   10                  15

Pro Met Glu Glu Ala Glu Asn Ser Glu Leu Ala Gln Asn Glu Glu Ser
            20                  25                  30

Ser Ser Asp Thr Thr Ser Lys Gly Glu Glu Phe Glu Val Lys Val Ala
        35                  40                  45

Ser Asp Arg Gly Lys Arg Phe Asp Tyr Leu Leu Lys Gln Thr Glu Ile
    50                  55                  60

Phe Ser His Phe Met Asn Gln Thr Lys Ser Pro Ser Lys Pro Lys Thr
65                  70                  75                  80

Gly Arg Pro Lys Lys Glu Lys Ser Asp Thr Ser Asp Leu Arg His Arg
                85                  90                  95

Lys Thr Glu Gln Glu Glu Asp Glu Glu Leu Leu Ala Glu Thr Asn Leu
            100                 105                 110

Lys Thr Lys Thr Thr Thr Arg Phe Asp Ala Ser Pro Pro Tyr Ile Lys
        115                 120                 125

His Gly Glu Met Arg Asp Tyr Gln Val Arg Gly Leu Asn Trp Met Ile
    130                 135                 140

Ser Leu Tyr Glu His Gly Ile Asn Gly Ile Leu Ala Asp Glu Met Gly
145                 150                 155                 160

Leu Gly Lys Thr Leu Gln Thr Ile Ser Leu Leu Gly Tyr Met Lys His
                165                 170                 175

Tyr Lys Ser Thr Pro Gly Pro His Ile Val Ile Val Pro Lys Ser Thr
            180                 185                 190

Leu Ser Asn Trp Met Asn Glu Phe Glu Lys Trp Cys Pro Thr Leu Arg
        195                 200                 205

Ala Val Cys Leu Ile Gly Asp Gln Glu Ala Arg Ser Ser Phe Ile Arg
    210                 215                 220
```

```
Asp Thr Met Met Pro Gly Glu Trp Asp Val Cys Val Thr Ser Tyr Glu
225                 230                 235                 240

Met Cys Ile Lys Glu Lys Ser Val Phe Lys Lys Phe Asn Trp Arg Tyr
                245                 250                 255

Met Val Ile Asp Glu Ala His Arg Ile Lys Asn Glu Lys Ser Lys Leu
            260                 265                 270

Ser Glu Ile Leu Arg Glu Phe Lys Thr Thr Asn Arg Leu Leu Leu Thr
        275                 280                 285

Gly Thr Pro Leu Gln Asn Asn Leu His Glu Leu Trp Ala Leu Leu Asn
    290                 295                 300

Phe Leu Leu Pro Asp Val Phe Asn Ser Ser Asp Asp Phe Asp Ala Trp
305                 310                 315                 320

Phe Asn Thr Ser Gln Cys Leu Gly Asp Asn Ala Leu Val Glu Arg Leu
                325                 330                 335

His Ala Val Leu Lys Pro Phe Leu Leu Arg Arg Leu Lys Ala Glu Val
            340                 345                 350

Glu Lys Arg Leu Lys Pro Lys Lys Glu Leu Lys Val Tyr Val Gly Leu
        355                 360                 365

Ser Lys Met Gln Arg Glu Trp Tyr Thr Lys Val Leu Met Lys Asp Ile
    370                 375                 380

Asp Ile Val Asn Gly Ala Gly Lys Val Glu Lys Met Arg Leu Gln Asn
385                 390                 395                 400

Ile Leu Met Gln Leu Arg Lys Cys Thr Asn His Pro Tyr Leu Phe Asp
                405                 410                 415

Gly Ala Glu Pro Gly Pro Pro Tyr Thr Thr Asp Glu His Leu Val Tyr
            420                 425                 430

Asn Cys Gly Lys Met Val Leu Leu Asp Lys Leu Leu Pro Lys Leu Lys
        435                 440                 445

Glu Gln Glu Ser Arg Val Leu Ile Phe Ser Gln Met Thr Arg Met Leu
    450                 455                 460

Asp Ile Leu Glu Asp Tyr Cys His Trp Arg Gln Tyr Gln Tyr Cys Arg
465                 470                 475                 480

Leu Asp Gly Gln Thr Pro His Glu Asp Arg Gln Arg Gln Ile Asn Glu
                485                 490                 495

Tyr Asn Glu Asp Asn Ser Gln Lys Phe Ile Phe Met Leu Ser Thr Arg
            500                 505                 510

Ala Gly Gly Leu Gly Ile Asn Leu Ala Thr Ala Asp Val Val Ile Ile
        515                 520                 525

Tyr Asp Ser Asp Trp Asn Pro Gln Met Asp Leu Gln Ala Met Asp Arg
    530                 535                 540

Ala His Arg Ile Gly Gln Lys Lys Gln Val Arg Val Phe Arg Phe Ile
545                 550                 555                 560

Thr Glu Asn Thr Val Glu Glu Lys Ile Val Glu Arg Ala Glu Val Lys
                565                 570                 575

Leu Arg Leu Asp Lys Leu Val Ile Gln Gln Gly Arg Leu Ala Asp Ser
            580                 585                 590

Lys Ala Gln Thr Leu Asn Lys Asp Glu Met Leu Asn Met Ile Arg His
        595                 600                 605

Gly Ala Asn His Val Phe Ala Ser Lys Asp Ser Glu Ile Thr Asp Glu
    610                 615                 620

Asp Ile Asp Ser Ile Leu Glu Lys Gly Glu Met Lys Thr Ala Gln Leu
625                 630                 635                 640
```

```
Ala Gln Lys Met Glu Thr Met Gly Glu Ser Ser Leu Arg Asn Phe Thr
                645                 650                 655

Val Glu Thr Pro Thr Glu Ser Val Tyr Gln Phe Glu Gly Glu Asp Tyr
            660                 665                 670

Arg Glu Lys Gln Lys Thr Ile Gly Leu Ser Asn Trp Ile Glu Pro Pro
        675                 680                 685

Lys Arg Glu Arg Lys Ala Asn Tyr Ala Val Asp Ala Tyr Phe Arg Glu
    690                 695                 700

Ala Leu Arg Val Ser Glu Pro Lys Ala Pro Lys Ala Pro Arg Pro Pro
705                 710                 715                 720

Lys Gln Pro Ile Val Gln Asp Phe Gln Phe Phe Pro Pro Arg Leu Phe
                725                 730                 735

Glu Leu Leu Asp Gln Glu Ile Tyr Phe Tyr Arg Lys Ser Leu Gly Tyr
            740                 745                 750

Lys Val Pro Lys Asn Leu Glu Leu Gly Pro Asp Ala Ser Lys Gln Gln
        755                 760                 765

Lys Glu Glu Gln Arg Lys Ile Asp Glu Ser Glu Pro Leu Thr Glu Asp
    770                 775                 780

Glu Gln Gln Glu Lys Glu Asn Leu Leu Thr Gln Gly Phe Thr Asn Trp
785                 790                 795                 800

Ser Lys Arg Asp Phe Asn Gln Phe Ile Lys Ala Asn Glu Lys Tyr Gly
                805                 810                 815

Arg Asp Asp Ile Glu Asn Ile Ala Lys Asp Val Glu Gly Lys Thr Pro
            820                 825                 830

Glu Glu Val Met Glu Tyr Ser Ala Val Phe Trp Glu Arg Cys His Glu
        835                 840                 845

Leu Gln Asp Ile Asp Arg Ile Met Ala Gln Ile Glu Arg Gly Glu Thr
    850                 855                 860

Lys Ile Gln Arg Arg Ala Ser Ile Lys Lys Ala Leu Asp Ala Lys Met
865                 870                 875                 880

Ala Arg Tyr Arg Ala Pro Phe His Gln Leu Arg Ile Ser Tyr Gly Thr
                885                 890                 895

Asn Lys Gly Lys Asn Tyr Met Glu Asp Glu Asp Arg Phe Leu Val Cys
            900                 905                 910

Met Leu His Lys Leu Gly Phe Asp Arg Glu Asn Val Tyr Glu Glu Leu
        915                 920                 925

Arg Ala Ala Val Arg Ala Ser Pro Gln Phe Arg Phe Asp Trp Phe Leu
    930                 935                 940

Lys Ser Arg Thr Ala Met Glu Leu Gln Arg Arg Cys Asn Thr Leu Ile
945                 950                 955                 960

Thr Leu Ile Glu Arg Glu Asn Ala Glu Leu Glu Glu Arg Glu Lys Ile
                965                 970                 975


<210> SEQ ID NO 83
<211> LENGTH: 4137
<212> TYPE: DNA
<213> ORGANISM: Diabrotica virgifera

<400> SEQUENCE: 83

atggaaggct cagagtcgga aaattcagct tctggttccg gttcagaaaa tgagagcaaa      60

agtgattcca gtaacaactc tggaagcgct tctggtagtt cttcttcgga cggttccgat     120

acaggcgaag aaactgtaga aaatggatcg gccaataaaa gtagtagtaa aagtgacgga     180

gaagaagtac ttgaagaaag taacgggtgt agccaagatt caaactctat acctcctgct     240
```

-continued

```
agtccagata gttcgagtaa attcgatact accaaagatt taagttctga taggagttcg    300
gatccctcta gcatcagacg atcagttagg tcgcgaagag agccggaaag acttcagagt    360
aaagacagtg atagggcttc gagtgataaa agcaacaaaa gtgctgaaga ttggaaatac    420
aatgacgcta gttcgtcaga gtctgaacca gaagtaaaag aacgcccccc acctagtaaa    480
cgcgtaggtg ccagagcgcg aacgactgtg ataaaaaaga aaaagtccaa gaaaagaagc    540
caatacagtt cagaagatga ggaaacgagc gacgaaagcg atgaggatag taggagagct    600
gtgtccagaa ggaaggctac tacagttagt tacaaggaag aaagtgagga tgagaaaacg    660
gattccgagg atttgctaga agttgataat aatgaaccgg tagaacctgt cccggaagaa    720
aaatgtgaaa caatagaaag aattttggca acgagaagag gaaaaattgg agttaccgga    780
aacattacta cagtctacta tgtagaagaa aatggtgatc cgaatgaagg agttgatgaa    840
aaggatttag atagtacaga agatcagtat ctaatcaaat ggaaagattg ggctcatatt    900
cacaacacat gggaatcaga caaaagttta cgagaacaga aagtaaaggg gatgaaaaaa    960
ttggaaaatt atatcaaaaa agaagtcgaa attcaacagt ggcttaaata ttctactcct   1020
gaggatgtgg aatattatga atgtcaaatg gagttatctc aggatctttt gaagagtttc   1080
aacgaggtcg agaggataat agcaaagtac aataagcctg atggggtaa agattattat   1140
attaaatggc aaagtcttcc atatgctgaa tcgacttggg aagattcagt tctaattcaa   1200
cgaaaatggc ctgaccaaat aaatgaattc gaagctaggg agcaatcaag tatgacccca   1260
acgagacact gtaaagtact caaacataga cccaaattcc acgaagtcaa gacccagcct   1320
gaatatatga tgggcaaaga acagactttg atactgcgtg attaccaaat acatggtctc   1380
aactggatga tacattcctg gtcaaaagaa aactctgtta tattagcaga cgagatgggg   1440
ctcggtaaaa cgattcagac aatttgcttt ctatactatc tcttcaatac tcaccacctc   1500
cacggaccat ttttgtgtgt tgtgcccctt tctacaatga cgtcgtggca gagggaaatg   1560
acacagtggg cacccgactt gaactttgtc acatacttgg gagatgttca gtccagagat   1620
acgattcgcc aatatgaatg gtgctttgaa gggtcaaaaa ggctaaagtt caatgcaatt   1680
ctcacaacgt atgaaattgt tttgaaggat aaagcatttt taggaagtct cagctgggct   1740
gtgttactag tagatgaagc tcacaggttg aaaaacgatg attctttgtt gtacaaagct   1800
ttaatggaat ttgacactaa tcacaggctt cttattactg gtactccttt acaaaatagt   1860
ttaaaagaac tttgggcgct gctacatttt atcatgcccg ctaagtttga aacatgggac   1920
gaattcaaaa gagaacacga aaacaccaca aactccacaa actataccaa actccacaaa   1980
caacttgaac cgtttatttt aagacgggta aagaaagatg tagaaaaatc tctccccgct   2040
aaagtagaac aaattcttag ggtagagatg acgtctatcc agaaacaata ctataagtgg   2100
atattaacaa aaaattataa tgccttgaga agaggagtca aaggatccac aacaaccttc   2160
ttaaatattg tgatagaact gaagaaatgt tgtaaccatt cgtctttgat caagccccca   2220
gatattgaaa cacaatacaa tcaacacgac gttttgcagc aacttctcag aggttcggga   2280
aaattagtgc ttctggataa attgcttatc cgtttgcgca atactggcca tagagtacta   2340
atcttctcgc agatggtccg gatgttggac attcttgccg aatatttgca gcttcgacat   2400
ttcccgtttc agaggctaga tggtggcatc aagggagagc tgcgacgtca agccttagat   2460
catttcaatg ctgaagggtc tcaagatttt tgcttccttc tttcaactcg cgcagggggc   2520
ttgggcatta atttagctac tgctgatact gtgataattt ttgattcgga ctggaatcct   2580
caaaacgatc ttcaagcgca ggcaagagct cataggatcg gtcaaaagaa ccaagtcaac   2640
```

```
atttataggt tagttactgc tagatctgta gaggaagaaa ttgtagaaag ggcaaaacaa   2700

aaaatggtac tggatcatct tgtaattcag agaatggaca cgacgggaag aaccgttttg   2760

gacaaaaagg ggtcttctaa taataatccg tttaacaaag aagatctgac ggcgattttg   2820

aaatttggag ctgaggaatt atttaaagat gaagatgacg atgaggaacc aaactgtgat   2880

attgacgaaa ttcttcgacg agctgagacc agagatgaag ctccttcatt ggttggagat   2940

gaactacttt cggcatttaa agtagcaagt ttcgccgctt ttgacgaaga tgccgagccc   3000

tcaccagtca acaatgttgt taacgacgat gaaagtaaag actgggatga aattattcca   3060

gaaaaacttc gtatcaaggc agaggaagag gaaaagaaca aggaaatgga agatctttat   3120

cttcctccgc gaagtcgaaa aactcttcaa cagattaatc aatctgaaag tgacggggaa   3180

gaaggcaaag gtaggaagaa aacgaagaaa gatggagatg aatcgggagg ttccagtggc   3240

gatgatgaca ctgacgagga aaaacctaaa aaacgaggaa ggccaccagc aaaccccaga   3300

gaaaagttca agaacttcac tgatgctgag attagaaggt ttataaaaag ttataagaaa   3360

tttagtggac ccttaaagcg attagaggca gttgcttgtg atgctgaatt gcaagaaaaa   3420

ccattagctg agttacggaa attgggagaa cttcttcatg agaggtgcag ggcatttatg   3480

aatgaacaag ctaaagaaaa tacagagtct aacactcaag acgaacccaa aggtcgcaaa   3540

agaggaccat cgtttaaaat tggaggagtg tctgtaaatg ccaaaacgat gatggcttgt   3600

gaggaagagt tagaaccatt agatgaagtc attccagctg atccaaatga acgattacgt   3660

tgggtttttg atgtaaaaac gaagtcgtct cactttgatg tggactgggg tatggaagag   3720

gacactaagt tattgaaagg aatttatcac tatggtcttg gctcatggga gcaaataaaa   3780

ttggatccat tattaggcat tggtgataaa attttcctta ataatgaaga taaaaagccg   3840

caggctaaac atcttttatc aagagcagaa tacttattaa agattatgaa aaagcaatta   3900

gatctaaaga agggggttca aaaaccaaaa agacagagga aaaaagaaca aaaagttctt   3960

actaaggaaa ttattgatga cgatgaaagc tcaaatgatg tttcatcatt accaagttcc   4020

gctccagtta cagtatcagt agctccggtt gttaaaaagg taaagaaaga agtgaaaaaa   4080

gaaaaggagg ataaagaaga atcctcgccc gagaaaaagg aaaaaaaaga aggataa      4137
```

```
<210> SEQ ID NO 84
<211> LENGTH: 1724
<212> TYPE: PRT
<213> ORGANISM: Diabrotica virgifera

<400> SEQUENCE: 84

Met Glu Gly Ser Glu Ser Glu Asn Ser Ala Ser Gly Ser Gly Ser Glu
1               5                   10                  15

Asn Glu Ser Lys Ser Asp Ser Ser Asn Asn Ser Gly Ser Ala Ser Gly
            20                  25                  30

Ser Ser Ser Ser Asp Gly Ser Asp Thr Gly Glu Glu Thr Val Glu Asn
        35                  40                  45

Gly Ser Ala Asn Lys Ser Ser Ser Lys Ser Asp Gly Glu Glu Val Leu
    50                  55                  60

Glu Glu Ser Asn Gly Cys Ser Gln Asp Ser Asn Ser Ile Pro Pro Ala
65                  70                  75                  80

Ser Pro Asp Ser Ser Ser Lys Phe Asp Thr Thr Lys Asp Leu Ser Ser
                85                  90                  95

Asp Arg Ser Ser Asp Pro Ser Ser Ile Arg Arg Ser Val Arg Ser Arg
            100                 105                 110
```

-continued

```
Arg Glu Pro Glu Arg Leu Gln Ser Lys Asp Ser Asp Arg Ala Ser Ser
        115                 120                 125

Asp Lys Ser Asn Lys Ser Ala Glu Asp Trp Lys Tyr Asn Asp Ala Ser
    130                 135                 140

Ser Ser Glu Ser Glu Pro Glu Val Lys Glu Arg Pro Pro Pro Ser Lys
145                 150                 155                 160

Arg Val Gly Ala Arg Ala Arg Thr Thr Val Ile Lys Lys Lys Lys Ser
                165                 170                 175

Lys Lys Arg Ser Gln Tyr Ser Ser Glu Asp Glu Glu Thr Ser Asp Glu
            180                 185                 190

Ser Asp Glu Asp Ser Arg Arg Ala Val Ser Arg Arg Lys Ala Thr Thr
        195                 200                 205

Val Ser Tyr Lys Glu Glu Ser Glu Asp Glu Lys Thr Asp Ser Glu Asp
    210                 215                 220

Leu Leu Glu Val Asp Asn Asn Glu Pro Val Glu Pro Val Pro Glu Glu
225                 230                 235                 240

Lys Cys Glu Thr Ile Glu Arg Ile Leu Ala Thr Arg Arg Gly Lys Ile
                245                 250                 255

Gly Val Thr Gly Asn Ile Thr Thr Val Tyr Tyr Val Glu Glu Asn Gly
            260                 265                 270

Asp Pro Asn Glu Gly Val Asp Glu Lys Asp Leu Asp Ser Thr Glu Asp
        275                 280                 285

Gln Tyr Leu Ile Lys Trp Lys Asp Trp Ala His Ile His Asn Thr Trp
    290                 295                 300

Glu Ser Asp Lys Ser Leu Arg Glu Gln Lys Val Lys Gly Met Lys Lys
305                 310                 315                 320

Leu Glu Asn Tyr Ile Lys Lys Glu Val Glu Ile Gln Gln Trp Leu Lys
                325                 330                 335

Tyr Ser Thr Pro Glu Asp Val Glu Tyr Tyr Glu Cys Gln Met Glu Leu
            340                 345                 350

Ser Gln Asp Leu Leu Lys Ser Phe Asn Glu Val Glu Arg Ile Ile Ala
        355                 360                 365

Lys Tyr Asn Lys Pro Asp Gly Gly Lys Asp Tyr Tyr Ile Lys Trp Gln
    370                 375                 380

Ser Leu Pro Tyr Ala Glu Ser Thr Trp Glu Asp Ser Val Leu Ile Gln
385                 390                 395                 400

Arg Lys Trp Pro Asp Gln Ile Asn Glu Phe Glu Ala Arg Glu Gln Ser
                405                 410                 415

Ser Met Thr Pro Thr Arg His Cys Lys Val Leu Lys His Arg Pro Lys
            420                 425                 430

Phe His Glu Val Lys Thr Gln Pro Glu Tyr Met Met Gly Lys Glu Gln
        435                 440                 445

Thr Leu Ile Leu Arg Asp Tyr Gln Ile His Gly Leu Asn Trp Met Ile
    450                 455                 460

His Ser Trp Ser Lys Glu Asn Ser Val Ile Leu Ala Asp Glu Met Gly
465                 470                 475                 480

Leu Gly Lys Thr Ile Gln Thr Ile Cys Phe Leu Tyr Tyr Leu Phe Asn
                485                 490                 495

Thr His His Leu His Gly Pro Phe Leu Cys Val Val Pro Leu Ser Thr
            500                 505                 510

Met Thr Ser Trp Gln Arg Glu Met Thr Gln Trp Ala Pro Asp Leu Asn
        515                 520                 525
```

Phe Val Thr Tyr Leu Gly Asp Val Gln Ser Arg Asp Thr Ile Arg Gln
    530                 535                 540

Tyr Glu Trp Cys Phe Glu Gly Ser Lys Arg Leu Lys Phe Asn Ala Ile
545                 550                 555                 560

Leu Thr Thr Tyr Glu Ile Val Leu Lys Asp Lys Ala Phe Leu Gly Ser
                565                 570                 575

Leu Ser Trp Ala Val Leu Leu Val Asp Glu Ala His Arg Leu Lys Asn
            580                 585                 590

Asp Asp Ser Leu Leu Tyr Lys Ala Leu Met Glu Phe Asp Thr Asn His
        595                 600                 605

Arg Leu Leu Ile Thr Gly Thr Pro Leu Gln Asn Ser Leu Lys Glu Leu
    610                 615                 620

Trp Ala Leu Leu His Phe Ile Met Pro Ala Lys Phe Glu Thr Trp Asp
625                 630                 635                 640

Glu Phe Lys Arg Glu His Glu Asn Thr Thr Asn Ser Thr Asn Tyr Thr
                645                 650                 655

Lys Leu His Lys Gln Leu Glu Pro Phe Ile Leu Arg Arg Val Lys Lys
            660                 665                 670

Asp Val Glu Lys Ser Leu Pro Ala Lys Val Glu Gln Ile Leu Arg Val
        675                 680                 685

Glu Met Thr Ser Ile Gln Lys Gln Tyr Tyr Lys Trp Ile Leu Thr Lys
    690                 695                 700

Asn Tyr Asn Ala Leu Arg Arg Gly Val Lys Gly Ser Thr Thr Thr Phe
705                 710                 715                 720

Leu Asn Ile Val Ile Glu Leu Lys Lys Cys Cys Asn His Ser Ser Leu
                725                 730                 735

Ile Lys Pro Pro Asp Ile Glu Thr Gln Tyr Asn Gln His Asp Val Leu
            740                 745                 750

Gln Gln Leu Leu Arg Gly Ser Gly Lys Leu Val Leu Leu Asp Lys Leu
        755                 760                 765

Leu Ile Arg Leu Arg Asn Thr Gly His Arg Val Leu Ile Phe Ser Gln
    770                 775                 780

Met Val Arg Met Leu Asp Ile Leu Ala Glu Tyr Leu Gln Leu Arg His
785                 790                 795                 800

Phe Pro Phe Gln Arg Leu Asp Gly Gly Ile Lys Gly Glu Leu Arg Arg
                805                 810                 815

Gln Ala Leu Asp His Phe Asn Ala Glu Gly Ser Gln Asp Phe Cys Phe
            820                 825                 830

Leu Leu Ser Thr Arg Ala Gly Gly Leu Gly Ile Asn Leu Ala Thr Ala
        835                 840                 845

Asp Thr Val Ile Ile Phe Asp Ser Asp Trp Asn Pro Gln Asn Asp Leu
    850                 855                 860

Gln Ala Gln Ala Arg Ala His Arg Ile Gly Gln Lys Asn Gln Val Asn
865                 870                 875                 880

Ile Tyr Arg Leu Val Thr Ala Arg Ser Val Glu Glu Glu Ile Val Glu
                885                 890                 895

Arg Ala Lys Gln Lys Met Val Leu Asp His Leu Val Ile Gln Arg Met
            900                 905                 910

Asp Thr Thr Gly Arg Thr Val Leu Asp Lys Lys Gly Ser Ser Asn Asn
        915                 920                 925

Asn Pro Phe Asn Lys Glu Asp Leu Thr Ala Ile Leu Lys Phe Gly Ala
    930                 935                 940

Glu Glu Leu Phe Lys Asp Glu Asp Asp Asp Glu Glu Pro Asn Cys Asp

```
945                 950                 955                 960

Ile Asp Glu Ile Leu Arg Arg Ala Glu Thr Arg Asp Glu Ala Pro Ser
                965                 970                 975

Leu Val Gly Asp Glu Leu Leu Ser Ala Phe Lys Val Ala Ser Phe Ala
            980                 985                 990

Ala Phe Asp Glu Asp Ala Glu Pro  Ser Pro Val Asn Asn  Val Val Asn
        995                 1000                1005

Asp Asp  Glu Ser Lys Asp Trp  Asp Glu Ile Ile Pro  Glu Lys Leu
    1010                 1015                 1020

Arg Ile  Lys Ala Glu Glu Glu  Glu Lys Asn Lys Glu  Met Glu Asp
    1025                 1030                 1035

Leu Tyr  Leu Pro Pro Arg Ser  Arg Lys Thr Leu Gln  Gln Ile Asn
    1040                 1045                 1050

Gln Ser  Glu Ser Asp Gly Glu  Glu Gly Lys Gly Arg  Lys Lys Thr
    1055                 1060                 1065

Lys Lys  Asp Gly Asp Glu Ser  Gly Gly Ser Ser Gly  Asp Asp Asp
    1070                 1075                 1080

Thr Asp  Glu Glu Lys Pro Lys  Lys Arg Gly Arg Pro  Pro Ala Asn
    1085                 1090                 1095

Pro Arg  Glu Lys Phe Lys Asn  Phe Thr Asp Ala Glu  Ile Arg Arg
    1100                 1105                 1110

Phe Ile  Lys Ser Tyr Lys Lys  Phe Ser Gly Pro Leu  Lys Arg Leu
    1115                 1120                 1125

Glu Ala  Val Ala Cys Asp Ala  Glu Leu Gln Glu Lys  Pro Leu Ala
    1130                 1135                 1140

Glu Leu  Arg Lys Leu Gly Glu  Leu Leu His Glu Arg  Cys Arg Ala
    1145                 1150                 1155

Phe Met  Asn Glu Gln Ala Lys  Glu Asn Thr Glu Ser  Asn Thr Gln
    1160                 1165                 1170

Asp Glu  Pro Lys Gly Arg Lys  Arg Gly Pro Ser Phe  Lys Ile Gly
    1175                 1180                 1185

Gly Val  Ser Val Asn Ala Lys  Thr Met Met Ala Cys  Glu Glu Glu
    1190                 1195                 1200

Leu Glu  Pro Leu Asp Glu Val  Ile Pro Ala Asp Pro  Asn Glu Arg
    1205                 1210                 1215

Leu Arg  Trp Val Phe Asp Val  Lys Thr Lys Ser Ser  His Phe Asp
    1220                 1225                 1230

Val Asp  Trp Gly Met Glu Glu  Asp Thr Lys Leu Leu  Lys Gly Ile
    1235                 1240                 1245

Tyr His  Tyr Gly Leu Gly Ser  Trp Glu Gln Ile Lys  Leu Asp Pro
    1250                 1255                 1260

Leu Leu  Gly Ile Gly Asp Lys  Ile Phe Leu Asn Asn  Glu Asp Lys
    1265                 1270                 1275

Lys Pro  Gln Ala Lys His Leu  Leu Ser Arg Ala Glu  Tyr Leu Leu
    1280                 1285                 1290

Lys Ile  Met Lys Lys Gln Leu  Asp Leu Lys Lys Gly  Val Gln Lys
    1295                 1300                 1305

Pro Lys  Arg Gln Arg Lys Lys  Glu Gln Lys Val Leu  Thr Lys Glu
    1310                 1315                 1320

Ile Ile  Asp Asp Asp Glu Ser  Ser Asn Asp Val Ser  Ser Leu Pro
    1325                 1330                 1335

Ser Ser  Ala Pro Val Thr Val  Ser Val Ala Pro Val  Val Lys Lys
    1340                 1345                 1350
```

```
Val Lys Lys Glu Val Lys Lys Glu Lys Glu Asp Lys Glu Glu Ser
    1355                1360                1365

Ser Pro Glu Lys Lys Glu Lys Lys Lys Asp Lys Lys Lys Glu Lys
    1370                1375                1380

Lys Thr Ser Gly Pro Met His Phe Ser Thr Asn Glu Pro Val Ala
    1385                1390                1395

Leu Asn Val Leu Gly Asp Leu Asp Pro Leu Ile Phe Asn Glu Cys
    1400                1405                1410

Lys Glu Lys Met Arg Pro Val Lys Lys Ala Leu Lys Ala Leu Asp
    1415                1420                1425

Asn Pro Asp Glu Ser Leu Pro Glu Ala Glu Gln Val Gln His Thr
    1430                1435                1440

Arg Asp Cys Leu Leu Gln Ile Gly Glu Gln Ile Asn Thr Cys Leu
    1445                1450                1455

Leu Lys Tyr Thr Asp Pro Glu Lys Ile Lys Glu Trp Arg Ser Asn
    1460                1465                1470

Leu Trp Tyr Phe Val Ser Lys Phe Thr Glu Tyr Asp Ala Lys Lys
    1475                1480                1485

Leu Tyr Lys Leu Tyr Lys Lys Ala Cys Lys Lys Thr Asp Lys Ile
    1490                1495                1500

Glu Thr Lys Lys Glu Lys Lys Ala Glu Lys Arg Ala Glu His Leu
    1505                1510                1515

Glu Lys Glu Arg Glu Glu Thr Ala Ser Thr Ser Ala Asp Lys Val
    1520                1525                1530

Lys Lys Ile Lys Ile Pro Arg Thr Glu Lys Lys Asp Ala Lys Glu
    1535                1540                1545

His Lys Arg Lys His Asp Ser Asp Ser Glu Glu Ser Pro Lys Lys
    1550                1555                1560

His Arg Ser Glu Lys Lys Glu Arg Arg Ala Lys Glu Lys Lys Arg
    1565                1570                1575

Ser Arg Asp Glu Thr Ser Glu Asp Asp Gln Glu Tyr Arg Phe Asn
    1580                1585                1590

Arg His Arg Lys Pro Gly Asn Tyr Arg His Asp Gln His Ala Pro
    1595                1600                1605

Gln Asp Arg Trp Ser Gly Gly Gln Gln Glu Arg Phe Ser Gly Asp
    1610                1615                1620

His Lys Arg Gln Gln Asp Tyr His Arg Gly Ala Gly Phe His Arg
    1625                1630                1635

Asp Arg Asp Tyr Gln Arg Tyr Asp Lys Gly Ser Pro Glu Lys Asn
    1640                1645                1650

Asn Asp Trp Arg Gln Tyr Pro Arg Gly Arg Glu Ile Met Pro Pro
    1655                1660                1665

Met Pro Gly Gly Gln Pro Met Gly Met Gly Gly Gly Tyr Tyr Pro
    1670                1675                1680

Pro Asn Tyr Asn Gln Gly Gln Gly Tyr Ala Pro Glu Gln Pro Phe
    1685                1690                1695

Pro Pro Arg Asp Arg Phe Pro Leu Gly Asp Trp Arg Pro Pro Asp
    1700                1705                1710

Arg Gly Gly Tyr Arg Tyr Asp Arg Arg Gln Gln
    1715                1720
```

<210> SEQ ID NO 85
<211> LENGTH: 767

<212> TYPE: DNA
<213> ORGANISM: Diabrotica virgifera

<400> SEQUENCE: 85
tacgagatgt tcatcggttg tgtaaggtgg tccgggctca gcgccatcaa aaaggtaggg 60
gtgattggtg cattttctca actgcatgaa aatattctgt agccgcattt ttgccacctg 120
tgcaccattc agtatatcaa tatccttcat tagcactttg gtattaccat tctcgctgca 180
ttttgctcaa tcctacatac acttttaact ccttcttggg ttttagccct ttctctactt 240
caattttcaa tcttctaagc aagaatggtt ttaatacagc atgcagcctc tccaccatgg 300
agttgcctcc cagacattga ctggtgttaa accaggcatc gaaatcatca gatgagttaa 360
aaacgtctgg cagtaagaag ttgagaagag accagagttc atgtaaattg ttttgtaatg 420
gagtacctgt tagcagtagc ctgttggtat tcttgaattc cctgagaatt tcggaaagct 480
tagtcttttt catttttat acgatgagct tcatcaacga ccagatatct ccacttgaac 540
ttttttaata gagattttc tttaatacac atttcatacg aggttataca gacatcccat 600
tcaccaggca tcatcgtatc tctgataatt gagttcctag cctcttgatc gccaatgaga 660
caaacagctc tcaaggttgg acaccactgc tggaactcat tcatccaatt tgataaggta 720
gatttaggaa caacgacaaa tatgaggacc aggtgtactt ttatagt 767

<210> SEQ ID NO 86
<211> LENGTH: 110
<212> TYPE: PRT
<213> ORGANISM: Diabrotica virgifera

<400> SEQUENCE: 86

Lys Met Lys Lys Thr Lys Leu Ser Glu Ile Leu Arg Glu Phe Lys Asn
1 5 10 15

Thr Asn Arg Leu Leu Leu Thr Gly Thr Pro Leu Gln Asn Asn Leu His
20 25 30

Glu Leu Trp Ser Leu Leu Asn Phe Leu Leu Pro Asp Val Phe Asn Ser
35 40 45

Ser Asp Asp Phe Asp Ala Trp Phe Asn Thr Ser Gln Cys Leu Gly Gly
50 55 60

Asn Ser Met Val Glu Arg Leu His Ala Val Leu Lys Pro Phe Leu Leu
65 70 75 80

Arg Arg Leu Lys Ile Glu Val Glu Lys Gly Leu Lys Pro Lys Lys Glu
85 90 95

Leu Lys Val Tyr Val Gly Leu Ser Lys Met Gln Arg Glu Trp
100 105 110

<210> SEQ ID NO 87
<211> LENGTH: 3074
<212> TYPE: DNA
<213> ORGANISM: Diabrotica virgifera

<400> SEQUENCE: 87
ctttgttaat caaataaaac tttgtttcaa catattgcaa aattcatcta aacgttcaac 60
atgtcacaaa ctgaaggctc gacagaggcg agcgtaagtg cctcagaacc aatggaagaa 120
gcagagaact cggaattggc tcaaaatgaa gaatcttctt cagatactac ctctaagggt 180
gaagagttcg aggtcaaagt ggcttctgac agaggaaaaa gatttgacta cttgttgaaa 240
cagactgaaa tcttttcaca ttttatgaac caaacaaaat ctcccagtaa accaaaaact 300
gggaggccta aaaaagagaa gagtgataca tctgatttaa gacatcgtaa aactgaacaa 360

-continued

```
gaagaagatg aagaactttt agcagaaacc aaccttaaaa caaagactac aactcgtttt    420
gatgcctcac caccctacat caaacatggg gaaatgagag attatcaagt ccgtggtttg    480
aactggatga tttctttgta tgaacatggc atcaatggta ttttagcaga tgagatgggt    540
ttgggtaaaa ctttacaaac catatctctg cttggatata tgaagcacta taaaagtaca    600
cctggtcctc atattgtcat tgttcctaaa tctaccttat caaactggat gaatgagttc    660
gagaagtggt gtccaacctt gagagccgtt tgtctcattg gtgatcaaga ggctaggagc    720
tcatttatca gagatacgat gatgcctggt gaatgggatg tttgtgtaac ctcgtacgaa    780
atgtgtatta aagaaaaatc tgtatttaaa aagttcaact ggagatatat ggtcattgac    840
gaagctcatc gtataaaaaa tgaaaaatct aagctttccg aaattctcag ggagttcaag    900
actactaaca ggctactgct aacaggtact ccattacaaa acaatttaca cgaactctgg    960
gctcttctca acttcttact gccagatgtt ttcaactcat cggatgattt cgatgcctgg   1020
ttcaacacca gtcaatgtct gggagacaac gccttggtcg agagattgca tgctgtatta   1080
aaaccattct tgcttagaag attgaaagct gaagtggaga aacggctaaa acccaagaag   1140
gagttaaaag tgtatgtagg attgagcaag atgcaacgag aatggtatac caaagtgctg   1200
atgaaggata ttgatatagt gaatggtgca ggaaaggtag aaaaaatgcg actacagaat   1260
attctcatgc agttaagaaa atgcacaaat caccccctacc tttttgatgg cgctgagccc   1320
ggaccacctt acacaaccga tgaacatctc gtgtacaatt gcggtaaaat ggtgttgctg   1380
gataaactgc ttcccaaatt gaaggaacag gaatctcgtg tacttatctt ctctcagatg   1440
acccgtatgt tggatatact tgaagattac tgtcattggc gacagtacca atattgtcgt   1500
ttggatggtc aaaccccaca cgaagacaga cagagacaaa tcaacgagta taacgaagac   1560
aatagccaaa agtttatctt tatgttgtca actagagccg gtggattggg tatcaatttg   1620
gccacagctg atgtagttat tatatatgat tcggattgga atccccagat ggatctgcaa   1680
gccatggaca gagcgcatag aattggtcag aagaaacaag tcagagtttt caggtttatt   1740
accgaaaaca ctgtggaaga aaaaatcgtc gaaagagctg aagtaaaatt acgtttagac   1800
aaattagtta tccagcaggg tcgtttagcc gattccaaag cacagactct aaacaaagac   1860
gaaatgttga acatgatccg gcacggtgcc aaccacgtat ttgcttctaa ggattccgaa   1920
ataacagatg aagatatcga tagtatattg gaaaagggag aaatgaagac cgctcagcta   1980
gctcagaaga tggaaaccat gggcgaatcg tcacttcgca acttcacagt cgaaacaccc   2040
actgaatcag tctaccaatt cgaaggagaa gattatcgtg agaagcagaa aaccatcggc   2100
ttgagcaact ggatagaacc tcccaaaaga gaaaggaagg ccaactatgc cgtcgatgct   2160
tacttcagag aagctttaag ggtttctgag cctaaagcgc ctaaggctcc aagaccacca   2220
aaacagccca tcgtacaaga tttccagttt ttcccgccga gattattcga acttttggac   2280
caggagatct acttttacag gaaatctttg ggatataagg ttccgaaaaa cttagaactt   2340
ggacctgacg cgtccaagca acagaaagaa gagcaaagaa aaatagatga gtcagaaccg   2400
ctcaccgaag acgaacagca agaaaaagaa aacttgttaa cgcaaggttt caccaattgg   2460
agtaaacgcg atttcaatca gttcatcaaa gccaacgaga aatatggtag ggacgatatt   2520
gagaacatcg ccaaggatgt tgaaggcaaa acgcctgaag aagttatgga atattctgcg   2580
gtgttttggg aaagatgtca tgaattacag gatattgata gaataatggc ccagattgag   2640
agaggagaaa ctaaaataca aagaagagct agtattaaga aggcacttga tgctaaaatg   2700
```

```
gcaagatatc gtgcaccatt ccatcagctg agaatttctt acggcaccaa caaaggcaag   2760

aactacatgg aggacgaaga caggtttttg gtgtgtatgt tgcacaagtt gggtttcgat   2820

agagaaaacg tttatgaaga gttaagagca gctgtacgtg cgtcaccaca attcagattt   2880

gattggttct taaaatcgag aactgccatg gagctgcaaa ggagatgcaa cacattgata   2940

acgttaatag aaagagaaaa tgctgaattg gaggaaagag aaaaaattga taaaaagaaa   3000

aaagtttcca aatcttcaaa tcttggaggt attcctgccc aaatcagctc gaaatcttca   3060

cagaaacgga agaa                                                     3074


<210> SEQ ID NO 88
<211> LENGTH: 987
<212> TYPE: PRT
<213> ORGANISM: Diabrotica virgifera

<400> SEQUENCE: 88

Met Glu Glu Ala Glu Asn Ser Glu Leu Ala Gln Asn Glu Glu Ser Ser
1               5                   10                  15

Ser Asp Thr Thr Ser Lys Gly Glu Glu Phe Glu Val Lys Val Ala Ser
            20                  25                  30

Asp Arg Gly Lys Arg Phe Asp Tyr Leu Leu Lys Gln Thr Glu Ile Phe
        35                  40                  45

Ser His Phe Met Asn Gln Thr Lys Ser Pro Ser Lys Pro Lys Thr Gly
    50                  55                  60

Arg Pro Lys Lys Glu Lys Ser Asp Thr Ser Asp Leu Arg His Arg Lys
65                  70                  75                  80

Thr Glu Gln Glu Glu Asp Glu Glu Leu Leu Ala Glu Thr Asn Leu Lys
                85                  90                  95

Thr Lys Thr Thr Thr Arg Phe Asp Ala Ser Pro Pro Tyr Ile Lys His
            100                 105                 110

Gly Glu Met Arg Asp Tyr Gln Val Arg Gly Leu Asn Trp Met Ile Ser
        115                 120                 125

Leu Tyr Glu His Gly Ile Asn Gly Ile Leu Ala Asp Glu Met Gly Leu
    130                 135                 140

Gly Lys Thr Leu Gln Thr Ile Ser Leu Leu Gly Tyr Met Lys His Tyr
145                 150                 155                 160

Lys Ser Thr Pro Gly Pro His Ile Val Ile Val Pro Lys Ser Thr Leu
                165                 170                 175

Ser Asn Trp Met Asn Glu Phe Glu Lys Trp Cys Pro Thr Leu Arg Ala
            180                 185                 190

Val Cys Leu Ile Gly Asp Gln Glu Ala Arg Ser Ser Phe Ile Arg Asp
        195                 200                 205

Thr Met Met Pro Gly Glu Trp Asp Val Cys Val Thr Ser Tyr Glu Met
    210                 215                 220

Cys Ile Lys Glu Lys Ser Val Phe Lys Lys Phe Asn Trp Arg Tyr Met
225                 230                 235                 240

Val Ile Asp Glu Ala His Arg Ile Lys Asn Glu Lys Ser Lys Leu Ser
                245                 250                 255

Glu Ile Leu Arg Glu Phe Lys Thr Thr Asn Arg Leu Leu Leu Thr Gly
            260                 265                 270

Thr Pro Leu Gln Asn Asn Leu His Glu Leu Trp Ala Leu Leu Asn Phe
        275                 280                 285

Leu Leu Pro Asp Val Phe Asn Ser Ser Asp Asp Phe Asp Ala Trp Phe
    290                 295                 300
```

-continued

```
Asn Thr Ser Gln Cys Leu Gly Asp Asn Ala Leu Val Glu Arg Leu His
305                 310                 315                 320

Ala Val Leu Lys Pro Phe Leu Leu Arg Arg Leu Lys Ala Glu Val Glu
                325                 330                 335

Lys Arg Leu Lys Pro Lys Lys Glu Leu Lys Val Tyr Val Gly Leu Ser
            340                 345                 350

Lys Met Gln Arg Glu Trp Tyr Thr Lys Val Leu Met Lys Asp Ile Asp
        355                 360                 365

Ile Val Asn Gly Ala Gly Lys Val Glu Lys Met Arg Leu Gln Asn Ile
    370                 375                 380

Leu Met Gln Leu Arg Lys Cys Thr Asn His Pro Tyr Leu Phe Asp Gly
385                 390                 395                 400

Ala Glu Pro Gly Pro Pro Tyr Thr Thr Asp Glu His Leu Val Tyr Asn
                405                 410                 415

Cys Gly Lys Met Val Leu Leu Asp Lys Leu Leu Pro Lys Leu Lys Glu
            420                 425                 430

Gln Glu Ser Arg Val Leu Ile Phe Ser Gln Met Thr Arg Met Leu Asp
        435                 440                 445

Ile Leu Glu Asp Tyr Cys His Trp Arg Gln Tyr Gln Tyr Cys Arg Leu
    450                 455                 460

Asp Gly Gln Thr Pro His Glu Asp Arg Gln Arg Gln Ile Asn Glu Tyr
465                 470                 475                 480

Asn Glu Asp Asn Ser Gln Lys Phe Ile Phe Met Leu Ser Thr Arg Ala
                485                 490                 495

Gly Gly Leu Gly Ile Asn Leu Ala Thr Ala Asp Val Val Ile Ile Tyr
            500                 505                 510

Asp Ser Asp Trp Asn Pro Gln Met Asp Leu Gln Ala Met Asp Arg Ala
        515                 520                 525

His Arg Ile Gly Gln Lys Lys Gln Val Arg Val Phe Arg Phe Ile Thr
    530                 535                 540

Glu Asn Thr Val Glu Glu Lys Ile Val Glu Arg Ala Glu Val Lys Leu
545                 550                 555                 560

Arg Leu Asp Lys Leu Val Ile Gln Gln Gly Arg Leu Ala Asp Ser Lys
                565                 570                 575

Ala Gln Thr Leu Asn Lys Asp Glu Met Leu Asn Met Ile Arg His Gly
            580                 585                 590

Ala Asn His Val Phe Ala Ser Lys Asp Ser Glu Ile Thr Asp Glu Asp
        595                 600                 605

Ile Asp Ser Ile Leu Glu Lys Gly Glu Met Lys Thr Ala Gln Leu Ala
    610                 615                 620

Gln Lys Met Glu Thr Met Gly Glu Ser Ser Leu Arg Asn Phe Thr Val
625                 630                 635                 640

Glu Thr Pro Thr Glu Ser Val Tyr Gln Phe Glu Gly Glu Asp Tyr Arg
                645                 650                 655

Glu Lys Gln Lys Thr Ile Gly Leu Ser Asn Trp Ile Glu Pro Pro Lys
            660                 665                 670

Arg Glu Arg Lys Ala Asn Tyr Ala Val Asp Ala Tyr Phe Arg Glu Ala
        675                 680                 685

Leu Arg Val Ser Glu Pro Lys Ala Pro Lys Ala Pro Arg Pro Pro Lys
    690                 695                 700

Gln Pro Ile Val Gln Asp Phe Gln Phe Phe Pro Pro Arg Leu Phe Glu
705                 710                 715                 720

Leu Leu Asp Gln Glu Ile Tyr Phe Tyr Arg Lys Ser Leu Gly Tyr Lys
```

```
                725                 730                 735

Val Pro Lys Asn Leu Glu Leu Gly Pro Asp Ala Ser Lys Gln Gln Lys
            740                 745                 750

Glu Glu Gln Arg Lys Ile Asp Glu Ser Glu Pro Leu Thr Glu Asp Glu
        755                 760                 765

Gln Gln Glu Lys Glu Asn Leu Leu Thr Gln Gly Phe Thr Asn Trp Ser
    770                 775                 780

Lys Arg Asp Phe Asn Gln Phe Ile Lys Ala Asn Glu Lys Tyr Gly Arg
785                 790                 795                 800

Asp Asp Ile Glu Asn Ile Ala Lys Asp Val Glu Gly Lys Thr Pro Glu
                805                 810                 815

Glu Val Met Glu Tyr Ser Ala Val Phe Trp Glu Arg Cys His Glu Leu
            820                 825                 830

Gln Asp Ile Asp Arg Ile Met Ala Gln Ile Glu Arg Gly Glu Thr Lys
        835                 840                 845

Ile Gln Arg Arg Ala Ser Ile Lys Lys Ala Leu Asp Ala Lys Met Ala
    850                 855                 860

Arg Tyr Arg Ala Pro Phe His Gln Leu Arg Ile Ser Tyr Gly Thr Asn
865                 870                 875                 880

Lys Gly Lys Asn Tyr Met Glu Asp Glu Asp Arg Phe Leu Val Cys Met
                885                 890                 895

Leu His Lys Leu Gly Phe Asp Arg Glu Asn Val Tyr Glu Glu Leu Arg
            900                 905                 910

Ala Ala Val Arg Ala Ser Pro Gln Phe Arg Phe Asp Trp Phe Leu Lys
        915                 920                 925

Ser Arg Thr Ala Met Glu Leu Gln Arg Arg Cys Asn Thr Leu Ile Thr
    930                 935                 940

Leu Ile Glu Arg Glu Asn Ala Glu Leu Glu Glu Arg Glu Lys Ile Asp
945                 950                 955                 960

Lys Lys Lys Lys Val Ser Lys Ser Ser Asn Leu Gly Gly Ile Pro Ala
                965                 970                 975

Gln Ile Ser Ser Lys Ser Ser Gln Lys Arg Lys
            980                 985


<210> SEQ ID NO 89
<211> LENGTH: 4998
<212> TYPE: DNA
<213> ORGANISM: Diabrotica virgifera

<400> SEQUENCE: 89

tttcaaataa aatttgttcc ttgataataa aaaaacaaag aaaatggagg ttaatccaat      60

aattagaact cgacatattg taaaattaat gaaaaatggc cgcaaaatat tatgtactaa     120

gattgccctg attctacaat atctcgagtt aaaattattg gattaaagtt tagtaaacgt     180

cattttgttt gttttttgtt caaggaacaa attttatttg aaaattcttt ttatctcttt     240

tagtttacga actagaacct tataaataat tcaattgttc agcagccaaa aatacataaa     300

aaatttgaaa aggtcacagt gtctagctga cccctagatt cagtttaaaa attaaaaata     360

ttattaatcg tcgggataat cgtagaacga ataacttgaa tactgcgcgt tactatttac     420

attagagcct aggttggtgc catctgaagg taacgggacc ggcaaaggcc ttgatggttt     480

gcgaggtcgg tatgttcctc tagaaccggc gtttgacggg ccacctggtt ttaaacgggg     540

tctgccagga ccccgccgca ttgatggggt ttgagcagta gaactgctag cttgagcagc     600

tccagaaact tccaaaaagc agtgggacgg tgatgaatgc atcgaagctg cagacatagt     660
```

-continued

```
agtagaatct ggagacggtt gatccgttaa aaagatacta ccaggtcccg gtgatgtaga    720
gacagaagaa ctattagata tctggcggcc aagccctgtc gtacggcttc gagatcctct    780
aggccgtccc cttcgagatg accctcttcc aggaagcctt ggtttgacag ttgtgccgta    840
tacattgtat acagtatatt tattcgtaat tgccgaatca gattcatcat tgtaaatgtc    900
tacgccatca tctatcagaa tgtcgttaga attgacactt aatggactgt tgggcccact    960
ttcgacgaca gtactagtag cttcttctaa tgtaactgat tccagtttag ctttttttggg  1020
ttccatgcca actggtattg tcttatattg taattttcgt ttcctgtcta actcttcgga   1080
agtattatcg attttcaaat gatatttttg taccaattca tcatcatcca acagcaagga   1140
caccacttcc ttgggcttga gtgtatccgg tttaaagtta ccaccgctaa tgaccaattt   1200
ttgaatctcg ctcttttctc tagccctttg taagatgcgt tcttcaatag aacctttaca   1260
aattaatctg tacaccgtca cctgcttggt ctgacccaac cgatgggccc tgtccatagc   1320
ctgctggtcc acagtcgggt tccaatcact gtcgtagaaa attacagtat ctgcagcagt   1380
taaattgata ccaagtccac cagctcttgt cgacagtaga aaaacaaaaa tgtctgctct   1440
ggcttggaaa tcagcaacca tatcccttcg ttctgatatt tttgatgaac catctaacct   1500
catatactta tgatgcctgt gccacatgta ttcttctaaa agatcaatca tctttgtcat   1560
ctgcgaatat attaaaacgc gatgtccttc ctctttgagt cttttaagga gtccatcaag   1620
taccgacagt tttccagaat cggtaactaa actctcctta tctggtatca caatattcga   1680
aaaaccgtta acaggtctca aattatcaac tgcattaaac ggtcgaggat gtaaagtttc   1740
tgctgattta taattcaatt tattgttggt cgctttcgac cagtaagaat taagagagtt   1800
gaaactaaat tcgtctagat gacgctgtag atcccacgct gctctacgag aataacaata   1860
taagccgagt ggggccgccg ataccctagg catacaataa aaaagaaagg cgggaatttc   1920
agtctttgta cattggaaca cctgagttaa cctctttatg taaggaaaat cagtcaatat   1980
attttgtatc tggttcactc tatggtcatt aactcttaaa agtgcatcat ttcctgcgtt   2040
aagttcttta gtttttaatc taatattttt atgttcaaca gtttctggag tggaatgaaa   2100
cacatgatcg gtatgtgtgt aaaacactct atttcctttg ttttgttcag taaaaactaa   2160
atcaccaaat acatcactac ttcgaatctg atattgattt aaacggaaaa aattcctcaa   2220
ctgtaatgtc ggccgtttc taaaggatat gtcccatagt tttctataat ataatatttc   2280
attggatttt tggcattcgt aataatgttt ccacctgtgc aaaatattcc cttgaaatat   2340
cctaaaaaca tcttcagctg ataaacccaa aaagtgacaa aaattaaaaa tggtgggatg   2400
caaaccatct tgaatagcat cttttatgtc tcctggtttg aaaatgaagt gtttcctaat   2460
tttctccatt aaaatttctc gaacattgaa atcataaatt tgataaggaa ctgtgtactg   2520
caaagaactt attctaatgg gagatttggc gtctcttctc tcaaaaagtt cgggatggtt   2580
gcaaaccttt ctaaactgca tcaccaaatt catcaaattt gaagtaaaat tcttatctac   2640
agtgtgagaa tctcccccgc caactgtgta attcaagaga tcttcaattt tgattttttg   2700
ttttagagcc aaatacaata aattctgtct tgtggtcagt ggacagtaga ccattacttc   2760
tattttatca gacagttcat tttcaacatc tttcttgatt ctcctcaaca taaaaggttt   2820
taaaatcata tgtaaacgag ataagtgttt ttcatcgata ccagttttgt tttcagcatg   2880
gctttcaatg tcttttgaaa accattcgtt gaactcctca tgtgagtcaa agagtgttgg   2940
cataataaaa tgcaataagg cccatagctc cgccatactg ttttgtattg gggtaccact   3000
```

```
caacaacaat ctgttcctgc aactaaaacc taatagagtc ttccatctca ttgaactagt   3060

acttttgata gcctgtgctt catctagtat catgtattgc cattttattc tattaaagta   3120

ttttatatct gttataacta tttggtagga agttaccaca atgtgaaaac tagcgtcttt   3180

tgtatacatg tctttcaaat cccaaaactg ccttaaaatt tttctttcgt ttggatttcc   3240

ccaatagggc accactttaa aatccggcac aaacttggcc acttcttgct gccaattgtg   3300

cagggttgag gccggagata ttatcaaaaa agggccccag acagaatatt tttcagctat   3360

gtgacaaaga aacgcaatac tttgaacagt tttgcctaga cccatttcat cagctagaat   3420

accactgatt ccctgagagt ataaatttgc caaccaattc atccctctta gttgatatcc   3480

ttttaatttg cctctaaaca tattaggttg tggctgttca ccctctccat tgggaaattc   3540

attaagacac gaattggctt gttggtcaaa atgtctagtc cttgcttttt cactctgaaa   3600

tgcatctaat gcattctttt tggccatttc cttcatactt tcactatcgt aagtatcaca   3660

acttaatttt attgaacttt cctcgtctag ctggcttaaa attagcaact gttcttcagg   3720

agaagcctgt cccaatttct tggacatgaa atgagcatac agctcagtct gagtaataag   3780

aaagtttaat ttcctctgtt gtcgcttggc ttctaccaac tcgtggtcaa tttttctttg   3840

ttcttctgct tctttctcta accgtttctt aacttctcta tcaaaacgcc gtgagcgttt   3900

ccagtaagca atattctcac gtgataacct cttcatcctc catggctgtt ctttgactat   3960

tcgagcgctt tggagagctt tttgacgtgc atatttaaca caatgtgatg ccactcgttt   4020

gcactgcagt agcatttcct tgtgtttgtt aatttttgat ctatgttgct ttccaatttc   4080

tttttgact atattagtaa ataattttcg ccgctttatg gtcatcatat cttcccattt   4140

ccgtctggac tcttcatctt tgaatttttt tgttttttc tttggtatat gaagtcctaa   4200

aggaggagga ggtagagact gatttggaat gacaagtcca tattcagatg gcaaatactt   4260

atcagctata tcgtcgatgc tttggaaatc cattccattt tggagattca aatctaaaca   4320

tggttcatcc gaaatagcat ccaaaatatc aggatggtat agtggagact taaatgtgtc   4380

ttctatttta attttatttt tcttgacagg tactggtaga tttttttcta catgtggata   4440

aagatctact gcactgatca atccagctcc atagtatgca taattatcaa aattctcttt   4500

tctttttctt aaggattttt gatatgaatg caacctcata acatgcttat attgtacatc   4560

atccggacta ctatctgaac tttcttgtag aacatcagca agccatttcc tcctagttga   4620

aacagtttta agattgtaat actcattggt agagtgaggt tctgaatctt ttaaaataga   4680

atctatattg acatcactca gattgcccat gccatcatca gaatcgtcag agtcgctact   4740

taactgtaat tggttgtgta catctcgtaa aaacatatta gtgtcgacag cttgctcaac   4800

tcttcttaca tgaactggtt tagctgtata tgatctatta gtttgatcaa ggtagctgtt   4860

ggtgggtaat attttgtatg atttatccct gccgttccac attttttcta aatgtaataa   4920

actgttttca gaatatctat ataaattaag ctaatataat tttacattac attacattct   4980

caattagttc attttta                                                  4998
```

<210> SEQ ID NO 90
<211> LENGTH: 1512
<212> TYPE: PRT
<213> ORGANISM: Diabrotica virgifera

<400> SEQUENCE: 90

```
Met Trp Asn Gly Arg Asp Lys Ser Tyr Lys Ile Leu Pro Thr Asn Ser
1               5                   10                  15
```

-continued

```
Tyr Leu Asp Gln Thr Asn Arg Ser Tyr Thr Ala Lys Pro Val His Val
            20                  25                  30

Arg Arg Val Glu Gln Ala Val Asp Thr Asn Met Phe Leu Arg Asp Val
        35                  40                  45

His Asn Gln Leu Gln Leu Ser Ser Asp Ser Asp Asp Ser Asp Asp Gly
    50                  55                  60

Met Gly Asn Leu Ser Asp Val Asn Ile Asp Ser Ile Leu Lys Asp Ser
65                  70                  75                  80

Glu Pro His Ser Thr Asn Glu Tyr Tyr Asn Leu Lys Thr Val Ser Thr
                85                  90                  95

Arg Arg Lys Trp Leu Ala Asp Val Leu Gln Glu Ser Ser Asp Ser Ser
            100                 105                 110

Pro Asp Asp Val Gln Tyr Lys His Val Met Arg Leu His Ser Tyr Gln
        115                 120                 125

Lys Ser Leu Arg Lys Arg Lys Glu Asn Phe Asp Asn Tyr Ala Tyr Tyr
    130                 135                 140

Gly Ala Gly Leu Ile Ser Ala Val Asp Leu Tyr Pro His Val Glu Lys
145                 150                 155                 160

Asn Leu Pro Val Pro Val Lys Lys Asn Lys Ile Lys Ile Glu Asp Thr
                165                 170                 175

Phe Lys Ser Pro Leu Tyr His Pro Asp Ile Leu Asp Ala Ile Ser Asp
            180                 185                 190

Glu Pro Cys Leu Asp Leu Asn Leu Gln Asn Gly Met Asp Phe Gln Ser
        195                 200                 205

Ile Asp Asp Ile Ala Asp Lys Tyr Leu Pro Ser Glu Tyr Gly Leu Val
    210                 215                 220

Ile Pro Asn Gln Ser Leu Pro Pro Pro Pro Leu Gly Leu His Ile Pro
225                 230                 235                 240

Lys Lys Lys Thr Lys Lys Phe Lys Asp Glu Glu Ser Arg Arg Lys Trp
                245                 250                 255

Glu Asp Met Met Thr Ile Lys Arg Arg Lys Leu Phe Thr Asn Ile Val
            260                 265                 270

Lys Lys Glu Ile Gly Lys Gln His Arg Ser Lys Ile Asn Lys His Lys
        275                 280                 285

Glu Met Leu Leu Gln Cys Lys Arg Val Ala Ser His Cys Val Lys Tyr
    290                 295                 300

Ala Arg Gln Lys Ala Leu Gln Ser Ala Arg Ile Val Lys Glu Gln Pro
305                 310                 315                 320

Trp Arg Met Lys Arg Leu Ser Arg Glu Asn Ile Ala Tyr Trp Lys Arg
                325                 330                 335

Ser Arg Arg Phe Asp Arg Glu Val Lys Lys Arg Leu Glu Lys Glu Ala
            340                 345                 350

Glu Glu Gln Arg Lys Ile Asp His Glu Leu Val Glu Ala Lys Arg Gln
        355                 360                 365

Gln Arg Lys Leu Asn Phe Leu Ile Thr Gln Thr Glu Leu Tyr Ala His
    370                 375                 380

Phe Met Ser Lys Lys Leu Gly Gln Ala Ser Pro Glu Glu Gln Leu Leu
385                 390                 395                 400

Ile Leu Ser Gln Leu Asp Glu Glu Ser Ser Ile Lys Leu Ser Cys Asp
                405                 410                 415

Thr Tyr Asp Ser Glu Ser Met Lys Glu Met Ala Lys Lys Asn Ala Leu
            420                 425                 430

Asp Ala Phe Gln Ser Glu Lys Ala Arg Thr Arg His Phe Asp Gln Gln
```

```
        435                 440                 445

Ala Asn Ser Cys Leu Asn Glu Phe Pro Asn Gly Glu Gly Glu Gln Pro
    450                 455                 460

Gln Pro Asn Met Phe Arg Gly Lys Leu Lys Gly Tyr Gln Leu Arg Gly
465                 470                 475                 480

Met Asn Trp Leu Ala Asn Leu Tyr Ser Gln Gly Ile Ser Gly Ile Leu
                485                 490                 495

Ala Asp Glu Met Gly Leu Gly Lys Thr Val Gln Ser Ile Ala Phe Leu
            500                 505                 510

Cys His Ile Ala Glu Lys Tyr Ser Val Trp Gly Pro Phe Leu Ile Ile
        515                 520                 525

Ser Pro Ala Ser Thr Leu His Asn Trp Gln Gln Glu Val Ala Lys Phe
    530                 535                 540

Val Pro Asp Phe Lys Val Val Pro Tyr Trp Gly Asn Pro Asn Glu Arg
545                 550                 555                 560

Lys Ile Leu Arg Gln Phe Trp Asp Leu Lys Asp Met Tyr Thr Lys Asp
                565                 570                 575

Ala Ser Phe His Ile Val Val Thr Ser Tyr Gln Ile Val Ile Thr Asp
            580                 585                 590

Ile Lys Tyr Phe Asn Arg Ile Lys Trp Gln Tyr Met Ile Leu Asp Glu
        595                 600                 605

Ala Gln Ala Ile Lys Ser Thr Ser Ser Met Arg Trp Lys Thr Leu Leu
    610                 615                 620

Gly Phe Ser Cys Arg Asn Arg Leu Leu Leu Ser Gly Thr Pro Ile Gln
625                 630                 635                 640

Asn Ser Met Ala Glu Leu Trp Ala Leu Leu His Phe Ile Met Pro Thr
                645                 650                 655

Leu Phe Asp Ser His Glu Glu Phe Asn Glu Trp Phe Ser Lys Asp Ile
            660                 665                 670

Glu Ser His Ala Glu Asn Lys Thr Gly Ile Asp Glu Lys His Leu Ser
        675                 680                 685

Arg Leu His Met Ile Leu Lys Pro Phe Met Leu Arg Arg Ile Lys Lys
    690                 695                 700

Asp Val Glu Asn Glu Leu Ser Asp Lys Ile Glu Val Met Val Tyr Cys
705                 710                 715                 720

Pro Leu Thr Thr Arg Gln Asn Leu Leu Tyr Leu Ala Leu Lys Gln Lys
                725                 730                 735

Ile Lys Ile Glu Asp Leu Leu Asn Tyr Thr Val Gly Gly Gly Asp Ser
            740                 745                 750

His Thr Val Asp Lys Asn Phe Thr Ser Asn Leu Met Asn Leu Val Met
        755                 760                 765

Gln Phe Arg Lys Val Cys Asn His Pro Glu Leu Phe Glu Arg Arg Asp
    770                 775                 780

Ala Lys Ser Pro Ile Arg Ile Ser Ser Leu Gln Tyr Thr Val Pro Tyr
785                 790                 795                 800

Gln Ile Tyr Asp Phe Asn Val Arg Glu Ile Leu Met Glu Lys Ile Arg
                805                 810                 815

Lys His Phe Ile Phe Lys Pro Gly Asp Ile Lys Asp Ala Ile Gln Asp
            820                 825                 830

Gly Leu His Pro Thr Ile Phe Asn Phe Cys His Phe Leu Gly Leu Ser
        835                 840                 845

Ala Glu Asp Val Phe Arg Ile Phe Gln Gly Asn Ile Leu His Arg Trp
    850                 855                 860
```

```
Lys His Tyr Tyr Glu Cys Gln Lys Ser Asn Glu Ile Leu Tyr Tyr Arg
865                 870                 875                 880

Lys Leu Trp Asp Ile Ser Phe Arg Lys Arg Pro Thr Leu Gln Leu Arg
                885                 890                 895

Asn Phe Phe Arg Leu Asn Gln Tyr Gln Ile Arg Ser Ser Asp Val Phe
            900                 905                 910

Gly Asp Leu Val Phe Thr Glu Gln Asn Lys Gly Asn Arg Val Phe Tyr
        915                 920                 925

Thr His Thr Asp His Val Phe His Ser Thr Pro Glu Thr Val Glu His
    930                 935                 940

Lys Asn Ile Arg Leu Lys Thr Lys Glu Leu Asn Ala Gly Asn Asp Ala
945                 950                 955                 960

Leu Leu Arg Val Asn Asp His Arg Val Asn Gln Ile Gln Asn Ile Leu
                965                 970                 975

Thr Asp Phe Pro Tyr Ile Lys Arg Leu Thr Gln Val Phe Gln Cys Thr
            980                 985                 990

Lys Thr Glu Ile Pro Ala Phe Leu  Phe Tyr Cys Met Pro  Arg Val Ser
        995                 1000                1005

Ala Ala  Pro Leu Gly Leu Tyr  Cys Tyr Ser Arg Arg  Ala Ala Trp
    1010                1015                1020

Asp Leu  Gln Arg His Leu Asp  Glu Phe Ser Phe Asn  Ser Leu Asn
    1025                1030                1035

Ser Tyr  Trp Ser Lys Ala Thr  Asn Asn Lys Leu Asn  Tyr Lys Ser
    1040                1045                1050

Ala Glu  Thr Leu His Pro Arg  Pro Phe Asn Ala Val  Asp Asn Leu
    1055                1060                1065

Arg Pro  Val Asn Gly Phe Ser  Asn Ile Val Ile Pro  Asp Lys Glu
    1070                1075                1080

Ser Leu  Val Thr Asp Ser Gly  Lys Leu Ser Val Leu  Asp Gly Leu
    1085                1090                1095

Leu Lys  Arg Leu Lys Glu Glu  Gly His Arg Val Leu  Ile Tyr Ser
    1100                1105                1110

Gln Met  Thr Lys Met Ile Asp  Leu Leu Glu Glu Tyr  Met Trp His
    1115                1120                1125

Arg His  His Lys Tyr Met Arg  Leu Asp Gly Ser Ser  Lys Ile Ser
    1130                1135                1140

Glu Arg  Arg Asp Met Val Ala  Asp Phe Gln Ala Arg  Ala Asp Ile
    1145                1150                1155

Phe Val  Phe Leu Leu Ser Thr  Arg Ala Gly Gly Leu  Gly Ile Asn
    1160                1165                1170

Leu Thr  Ala Ala Asp Thr Val  Ile Phe Tyr Asp Ser  Asp Trp Asn
    1175                1180                1185

Pro Thr  Val Asp Gln Gln Ala  Met Asp Arg Ala His  Arg Leu Gly
    1190                1195                1200

Gln Thr  Lys Gln Val Thr Val  Tyr Arg Leu Ile Cys  Lys Gly Ser
    1205                1210                1215

Ile Glu  Glu Arg Ile Leu Gln  Arg Ala Arg Glu Lys  Ser Glu Ile
    1220                1225                1230

Gln Lys  Leu Val Ile Ser Gly  Gly Asn Phe Lys Pro  Asp Thr Leu
    1235                1240                1245

Lys Pro  Lys Glu Val Val Ser  Leu Leu Leu Asp Asp  Asp Glu Leu
    1250                1255                1260
```

-continued

```
Val Gln  Lys Tyr His Leu Lys  Ile Asp Asn Thr Ser  Glu Glu Leu
    1265                 1270                 1275

Asp Arg  Lys Arg Lys Leu Gln  Tyr Lys Thr Ile Pro  Val Gly Met
    1280                 1285                 1290

Glu Pro  Lys Lys Ala Lys Leu  Glu Ser Val Thr Leu  Glu Glu Ala
    1295                 1300                 1305

Thr Ser  Thr Val Val Glu Ser  Gly Pro Asn Ser Pro  Leu Ser Val
    1310                 1315                 1320

Asn Ser  Asn Asp Ile Leu Ile  Asp Asp Gly Val Asp  Ile Tyr Asn
    1325                 1330                 1335

Asp Glu  Ser Asp Ser Ala Ile  Thr Asn Lys Tyr Thr  Val Tyr Asn
    1340                 1345                 1350

Val Tyr  Gly Thr Thr Val Lys  Pro Arg Leu Pro Gly  Arg Gly Ser
    1355                 1360                 1365

Ser Arg  Arg Gly Arg Pro Arg  Gly Ser Arg Ser Arg  Thr Thr Gly
    1370                 1375                 1380

Leu Gly  Arg Gln Ile Ser Asn  Ser Ser Ser Val Ser  Thr Ser Pro
    1385                 1390                 1395

Gly Pro  Gly Ser Ile Phe Leu  Thr Asp Gln Pro Ser  Pro Asp Ser
    1400                 1405                 1410

Thr Thr  Met Ser Ala Ala Ser  Met His Ser Ser Pro  Ser His Cys
    1415                 1420                 1425

Phe Leu  Glu Val Ser Gly Ala  Ala Gln Ala Ser Ser  Ser Thr Ala
    1430                 1435                 1440

Gln Thr  Pro Ser Met Arg Arg  Gly Pro Gly Arg Pro  Arg Leu Lys
    1445                 1450                 1455

Pro Gly  Gly Pro Ser Asn Ala  Gly Ser Arg Gly Thr  Tyr Arg Pro
    1460                 1465                 1470

Arg Lys  Pro Ser Arg Pro Leu  Pro Val Pro Leu Pro  Ser Asp Gly
    1475                 1480                 1485

Thr Asn  Leu Gly Ser Asn Val  Asn Ser Asn Ala Gln  Tyr Ser Ser
    1490                 1495                 1500

Tyr Ser  Phe Tyr Asp Tyr Pro  Asp Asp
    1505                 1510
```

<210> SEQ ID NO 91
<211> LENGTH: 8026
<212> TYPE: DNA
<213> ORGANISM: Diabrotica virgifera

<400> SEQUENCE: 91

```
cgtcgctatg tcatataaga ccaatgcgtc atttttgctg aacgcgtaaa atgtagaaaa      60

caggtctatt ttgcaaattt ttaagttacg tggactacct aattgtatat taaactatta     120

gaaagacgat aatcatattt tttactgcgg atgattaacc ttaatgtgaa tattttgtga     180

taacatgatg agaattcgaa gatgagtgac gaaactccgg gggtagggca gggtgctctg     240

cccccgagag agggccaaag ccttcgactc cttgcagagc gccctactag tggtgctacg     300

gtaagggtag cccaggttgt tggtggtcag tatgtgttga caacacaatc acatggtatg     360

ccagctctag cacagattgc tgctgggaat cccaacgtca ctcgtctgat aagcatcagt     420

ccaactagag gtggacaatc gtccccacta aggcccagtt tggccaatca gtcgatcgtt     480

aatgttctta ccaagtctcg accaaatcct aatgtacgct tacagttatt tcaatccggt     540

gagagttctg gaaacaatgt ccagcatagt ccccattcga gatcactcaa aaggccgttg     600
```

-continued

```
tcttccacgg gtgaaaaaaa agatagctac gcttctaagc tgcaacatgt aatgaaccat    660
cgcattgttc gctcaaaatt aatgaaagaa aagtataatg aacatcttct agaggcctat    720
tatttagaga ccggaaataa cattctagat ttatatcaat ttgccaaaag acctaaaacc    780
caagcgtatc tagcttatct taaggaacat gccatcgatc ctcgagatta tcctgaactt    840
cagactacaa caactgttac tgtaccgcaa acgacgccta atacaccaac tgctacctct    900
gtcagctctc tgcccggtat ctctcatagt tacgccatcc agactaccag ttctactgta    960
acgacaccag aaagtaacag taacacctct acgccgaaat cagtatctgt caaagtgaag   1020
tctacatcac ttccgaatac tgttagtcaa gagatgattg tagagaaggc gaaacaagaa   1080
gcgtacgtgg tccaacgaat agccgattta cagaaggaag gaatatggtc tgaaaggaga   1140
cttcccaaag tgcaagagat gcctcggcct aaagcgcatt gggacttttt gatcgaagaa   1200
atggtctggt tggcagctga ttttgcgcag gaacgcaaat ggaagaaagc cgccgcgaaa   1260
aaatgtgcca gaatggtaca gaagtatttc caagacaagg cgctcgccgc ccaaaaagcg   1320
gaaaaggctc acgaacaaaa tcttagaagg atagccgcgt tctgtgcaaa ggagattaag   1380
atcttttgga acaacgtcga aaaactcgtc gagtataaac agaatacaat cttggaggag   1440
aagcggaaaa aggcgctcga tcagcagctt agttttatcg tggatcagac tgagaagtat   1500
tcgcagttgc ttgccgaagg aatgaataag accgcagaac agcctcctag ttcagcgcca   1560
tctcgatcag tgtctcgaac gcagtctgat acagaattcg atccggatct tcagagcgat   1620
gaagacgacg aagagaccat tgctcgagaa gaagctttag gtaacgaagg acataaagaa   1680
gaaatcgaag cgctacagaa agaatctcag atggaattag acgatttact agaggacgat   1740
ttcctgaggg attacctttt aaatcgagac acgatccgat tcagcgaatc cgaagattcg   1800
gacgatgaca cggactcgaa aaaagaatct ttcaaaggcg acaaagaaca gtctgacgat   1860
tctgaatctt ctaaagaaga agatacggaa gacgagagcg aagatgaatc tatgaaggtt   1920
actgaatcgg ttgttaaaga agaacacgac gagttgaaaa tattagtaga agattctcaa   1980
aaagagggag aaattaagac tgaacaagat acaaaaagacg accttatcaa tgacgcagct   2040
gctatagctg aaagtatcca acctaaagga aacaccctgt cttctactaa tgtatcaaca   2100
aatataccat ttttattaaa atatacgcta agagaatacc agcacatcgg tttggattgg   2160
ctggtaacta tgttcgacag aaaactgaac ggtatattag cagatgaaat gggtttaggc   2220
aaaacaatac aaacgatagc tcttctagca cacttggcgt gcgagaagga aaactggggc   2280
ccccatctga tagtagtccc cacttctgtg atgctgaatt gggaaatgga atgcaaaaag   2340
tggtgtccgg cttttaaaat tctaacgtat tacggaacgc agaaggaaag aaaatttaaa   2400
cggataggat ggacgaagcc taacgcgttt cacatatgca ttacttcgta caagctagtc   2460
attcaggacc accagagttt caggaggaaa aagtggaagt atctgatact ggacgaggcc   2520
caaaacatca agaatttcaa gtcgcaacga tggcagctgt tgttaaattt tcaaactcaa   2580
caacgtctgc tgttgactgg tacacctttg cagaacaacc tcatggaatt gtggtccctt   2640
atgcattttt taatgccgaa cgtatttcag tcgcatagag agttcaaaga atggttttcg   2700
aatccggtga caggaatgat tgaaggaaat tctgaataca acgaaagtat tatcaagaga   2760
ctgcacaagg tattaagacc atttcttcta aggcggttga aaagcgaagt ggaaaaacaa   2820
atgccaaaaa agtacgaaca cgtggtcatg tgtaggctat ccaaacgaca gaggtatttg   2880
tatgatgact acatgtcccg agcaaaaacg agggaaactt taactactgg aaatctgttg   2940
agtgttataa atgtgctgat gcagctgagg aaagtgtgta atcatccgaa tctatttgaa   3000
```

-continued

```
attagaccaa cgacatcgcc ttttcagtgt gacaacatcc ggcttcatat tccatccatt   3060
gtatattcag ctttagatta cgatcctgat aagcacgtga accttcaagc tttaaatctt   3120
ctactaatca tgcaagaaat ccactttggt tcgtaccagt gttaccggat gagacaatca   3180
agaaattcca agaaaatttt cgaaatggaa acgaattcta gcaaaaatcc accaccttgt   3240
ccgccatgta agttagccat gcgagttcta acagacaaac cttcagccac tgacgaaaag   3300
aatgagaaga aagacatgca agctttaagt cagccgcctc cattgcaagt taaaggaatg   3360
agccagccta acatgaagat gaaggtttct ggagtgcaat ttgttccaca gagcatactt   3420
aaatcaattc cagtagtgaa catatcacaa ggggctacag gtcaaatcgg agcacctgtt   3480
agtgtgacat ctgtattaaa accacaagac aaaatatctg ctagttttgc acagctagtt   3540
caaacgtcta ctggcaaaca cttgttacta acgtcgaatc ccaacattac gacgagccca   3600
gtgacaacta caacaccagg tggacaaaaa ttgaccttcc tatcgaagca gcccgtttct   3660
acgattggta atgcgggcca tgctgtaacg aaagcttatg tcaaatttca gttaacgtct   3720
gttacgacag catcaacttt cacaacagtt acgacagtca actccaatac gatatctgta   3780
gctaaaagtg aagataacaa agggatgcga atgtctgttg gtaatgatta tataggtaaa   3840
ctttattcta aacaaaatag cctggacgtg cgatggaata gcggcgaaaa acatttaggt   3900
ttaacaaatg aagacgatcc caaaggtgaa cgaaagaaga gactttccct catgtcacgc   3960
atcaacaaga tccgttgctc agctcttcca ctgtacggcc gagatttcca agaagctgtc   4020
aaaatatata cgcctaacca gctggatgtt tggaacgggg gtcatattca ctgcttgaac   4080
acactgtaca ataaggatgc caggaatgaa acgacggatt gtctccaaga cgcgttgttt   4140
aatcctgaaa gaagattgga agctctaaaa gatacttttg atcgatttat attctatgta   4200
ccttctgtga aagtggcgga acccgaactg caagtgtggc atcctccacc gagtaaatat   4260
tggggccaaa aacacgagaa acaacttata cagaaactat tcctaaaacc tgcaacacct   4320
cttcatagta tagcatctgc aatggtaacg cagtttccag atcctaggct tattcaatat   4380
gactgtggga agttacaaac tctggatata ctattgagga agttaaaact gggaagtcat   4440
cgagtattga tcttcacgca gatgacgaaa atgttggatg tactagaggc atttttgaat   4500
taccacggtc atatatatct taggttagat ggtaccacaa aagttgatca aagacaagtg   4560
ttgatggaga ggttcaacgg tgataaacgt attttcgctt ttattttgtc cacgcgttcc   4620
gggggcgtgg gtgtaaattt aaccggagcg gatactgtga tattttatga ttccgattgg   4680
aatccaacta tggacgcgca agcgcaagat cgttgtcacc gaatcggtca aacgagagac   4740
gtacacattt acaggctagt tagcgagcga acgatagagg agaatatatt gaagaaggcc   4800
aatcagaaac gattgctcgg agatctggcg atcgaagggg gtaatttcac aacggcgtac   4860
ttcaagagtt cgacgattca ggacttattc aacatagacc aaaacgaaga aagcgcatct   4920
gcccgaatgt cagaagttgt cgaactgaga aaagaaagag agaaggccct cagcacagac   4980
ctggttcatt ctgctgacga taaagccacc gtcggtgctc tcgaaaatgc tttcgaagca   5040
tgcgaggacg accaggacgt ccaagccgcg aaaacggcca aagccgaagc tgttgcagat   5100
cttgcagagt ttgatgaaaa cattcctctg gatgatcaag agaaagaacc tgagatcagc   5160
aaggcggaac aggaaattaa taatattata gaaaagttaa ctcccataga aaaatacgcc   5220
atgaatttca tcgaggcaac agaatctgcg tggtctgcag aacagcttgc agctgctgca   5280
agagagatcg aagaacagaa aaaggaatgg gagcagaacc gtctggcggc gatgcgagaa   5340
```

-continued

```
gaggaggaac gtcgtgctcg agagttagaa gaagaatctg atatcatcac gtattcaaga   5400
gatgacgcca ccaaccaggt tagctcaaaa aacaaaaaaa tcaataggta taataaaatt   5460
ttaagtaata aaagggttag gctcaaaaaa gatggagatg aagacgttga gaaaaaagat   5520
gacgtcgaga aaaaagatgg agttgaaaaa aggttgaaga agactaggac acgaaggctg   5580
tctcaaaaaa gcaaagatgt agaggtcgaa gaaccggatg cttgtgaatc acaagaagaa   5640
tctcaaatta acggagggga tacggataat agtgatagtg attctgattc tgatagcgaa   5700
tcttcatctt ccatggaatc taaaactacc ttaaaccacg ttgatccaaa ttcacctaga   5760
actaggtcta ggggcacagt ggctattaac ctttggacac tcgatgtcag cccgattttg   5820
cctggagaaa aaccgatgaa aaaatacggg gagaaccata gaaaaaatat taagagggtt   5880
agatctgtgt ctgaaaacga taacgatgga gataaagacg gtagaaagcg attgaggagg   5940
aaatacccca ccagtttaga aacatcagaa gaagaaaaca gtaaccagtc aagagaaaaa   6000
tctactaaga aacgtgccaa ggtagcaccc aaagggaaaa cttgtaaagt aattttaagt   6060
aatatactga acgataaacg atttaaagtc aacttaaaag aagacattga gatttcagtg   6120
agcacacaaa ttaatgagac ttccaccagc tcaaaccaga atcaaaccaa agattgcgag   6180
tctagtcaac atgagaatag caatttagat gaacagaatg attctcttga caatacagaa   6240
gttacctcat ccgaacttag taaattaact ggttgtactg aaatagataa taacgaaagt   6300
agtaaacagg aaaatgaaga attagacgaa tctatactcg aagataaata tgatgaagat   6360
ttcattacaa acaaaaatga agacatagat gaagaaacac tccttgaaga agataatcag   6420
atagagcagg ttgaaaataa aaatattgat agcacgaaag atgaaaaaca gggtgatgac   6480
agtaatgttt cagatgtagg tcatttaagt aaagataacg ataatgagga aaaaatggaa   6540
gtaacagaaa gtgttgacga ggaaaatggt gatatcaata agaaagtaga tgaagatgag   6600
agcgttaaag ataaaagaga aaggagaaaa ggtaatgagg aagatgataa tacagacaat   6660
gaagaaaaca tccaaaagtc agaaaatgat gagggcgata ttaaaaagca aggaaatcaa   6720
gatgaagaag tagaagagaa aaccttagga aattctactg aatcagttaa cgaaatagca   6780
aatgaaataa gtagatgcaa acctttaaat gagcagcaca acgaattggt agatgaagta   6840
gtaaatgaca caagtaatat ggatgaatat ataaaaaaat cggaaaattc caaagttgta   6900
gaaaagacaa gtgaagaaat actattcaac gatagggga atcaagattc atcgtcccag   6960
gatgtaaaag atgaagagat atcatcccac aacagaggag atgaaaaggt gtcattccac   7020
gataggatag ataaagaggt attacctgaa tgtaggaaag aggaagagaa acacaataga   7080
aaaaatgaag tactatcaca aactataaaa gatgaagagg cacagtccca caataggaaa   7140
gatgaatcgg gtacatttcc aaacgtagca gatatagaaa atagacttaa caacaaagtt   7200
cctcacgtcg ataatggtca taccgaaacg gtcagaatgt ctaaattggt aacgtctaat   7260
agaaatgcca atttcaggtc tcctgaaacg agaagaagct tcagaaagtg tggtaaaatt   7320
tcgaacaatc agactttaga cggttgggtg aaacggtcgc ctgtattacc tgtcgaagct   7380
gctaaagtaa acgataactc aaaatataaa aatgttggtt cgcccgagtt atagggagat   7440
ttgactgtgg aaagaggaga aatttaaaag tttttgatag ttaaaaaagt gtttattgat   7500
caatgtacac tgcaataagg taataactca aaaataattt atttctttac agttttcttc   7560
ttcatccact cctggacaaa ggcctcacga agtgttttac aagtttcttt gataacgggt   7620
aaaaccaaaa aatagtaaag ttcgcataac cttctggcta atgtctagtc ttagggttca   7680
agtcgcgcaa gcgcccagac cgaccgcttt acgtgccttc cgaatgacgg cggcggctca   7740
```

```
gaacaatttc ttaatgtcag tgccaggaat ctaacctaga tcctctagct tgttaagtca   7800

gtaataaaca ttagttcaac ggacatattg tcactttatt gcgcatgcgt ttatcattac   7860

tgagtcttga gttctgccta gccgtaccgt tgacatattc gtaaagattg tagtaataag   7920

gcatgcatca gatctttata gatttcaaac atgcttatga ctcagttaca attcgtccaa   7980

gactatggaa tggtatagtt gagctggaca tacctaagaa attagc                  8026


<210> SEQ ID NO 92
<211> LENGTH: 2410
<212> TYPE: PRT
<213> ORGANISM: Diabrotica virgifera

<400> SEQUENCE: 92

Met Ser Asp Glu Thr Pro Gly Val Gly Gln Gly Ala Leu Pro Pro Arg
1               5                   10                  15

Glu Gly Gln Ser Leu Arg Leu Leu Ala Glu Arg Pro Thr Ser Gly Ala
            20                  25                  30

Thr Val Arg Val Ala Gln Val Val Gly Gly Gln Tyr Val Leu Thr Thr
        35                  40                  45

Gln Ser His Gly Met Pro Ala Leu Ala Gln Ile Ala Ala Gly Asn Pro
    50                  55                  60

Asn Val Thr Arg Leu Ile Ser Ile Ser Pro Thr Arg Gly Gly Gln Ser
65                  70                  75                  80

Ser Pro Leu Arg Pro Ser Leu Ala Asn Gln Ser Ile Val Asn Val Leu
                85                  90                  95

Thr Lys Ser Arg Pro Asn Pro Asn Val Arg Leu Gln Leu Phe Gln Ser
            100                 105                 110

Gly Glu Ser Ser Gly Asn Asn Val Gln His Ser Pro His Ser Arg Ser
        115                 120                 125

Leu Lys Arg Pro Leu Ser Ser Thr Gly Glu Lys Lys Asp Ser Tyr Ala
    130                 135                 140

Ser Lys Leu Gln His Val Met Asn His Arg Ile Val Arg Ser Lys Leu
145                 150                 155                 160

Met Lys Glu Lys Tyr Asn Glu His Leu Leu Glu Ala Tyr Tyr Leu Glu
                165                 170                 175

Thr Gly Asn Asn Ile Leu Asp Leu Tyr Gln Phe Ala Lys Arg Pro Lys
            180                 185                 190

Thr Gln Ala Tyr Leu Ala Tyr Leu Lys Glu His Ala Ile Asp Pro Arg
        195                 200                 205

Asp Tyr Pro Glu Leu Gln Thr Thr Thr Thr Val Thr Val Pro Gln Thr
    210                 215                 220

Thr Pro Asn Thr Pro Thr Ala Thr Ser Val Ser Ser Leu Pro Gly Ile
225                 230                 235                 240

Ser His Ser Tyr Ala Ile Gln Thr Thr Ser Ser Thr Val Thr Thr Pro
                245                 250                 255

Glu Ser Asn Ser Asn Thr Ser Thr Pro Lys Ser Val Ser Val Lys Val
            260                 265                 270

Lys Ser Thr Ser Leu Pro Asn Thr Val Ser Gln Glu Met Ile Val Glu
        275                 280                 285

Lys Ala Lys Gln Glu Ala Tyr Val Val Gln Arg Ile Ala Asp Leu Gln
    290                 295                 300

Lys Glu Gly Ile Trp Ser Glu Arg Arg Leu Pro Lys Val Gln Glu Met
305                 310                 315                 320
```

-continued

```
Pro Arg Pro Lys Ala His Trp Asp Phe Leu Ile Glu Glu Met Val Trp
                325                 330                 335

Leu Ala Ala Asp Phe Ala Gln Glu Arg Lys Trp Lys Lys Ala Ala Ala
            340                 345                 350

Lys Lys Cys Ala Arg Met Val Gln Lys Tyr Phe Gln Asp Lys Ala Leu
        355                 360                 365

Ala Ala Gln Lys Ala Glu Lys Ala His Glu Gln Asn Leu Arg Arg Ile
    370                 375                 380

Ala Ala Phe Cys Ala Lys Glu Ile Lys Ile Phe Trp Asn Asn Val Glu
385                 390                 395                 400

Lys Leu Val Glu Tyr Lys Gln Asn Thr Ile Leu Glu Glu Lys Arg Lys
                405                 410                 415

Lys Ala Leu Asp Gln Gln Leu Ser Phe Ile Val Asp Gln Thr Glu Lys
            420                 425                 430

Tyr Ser Gln Leu Leu Ala Glu Gly Met Asn Lys Thr Ala Glu Gln Pro
        435                 440                 445

Pro Ser Ser Ala Pro Ser Arg Ser Val Ser Arg Thr Gln Ser Asp Thr
    450                 455                 460

Glu Phe Asp Pro Asp Leu Gln Ser Asp Glu Asp Asp Glu Glu Thr Ile
465                 470                 475                 480

Ala Arg Glu Glu Ala Leu Gly Asn Glu Gly His Lys Glu Glu Ile Glu
                485                 490                 495

Ala Leu Gln Lys Glu Ser Gln Met Glu Leu Asp Asp Leu Leu Glu Asp
            500                 505                 510

Asp Phe Leu Arg Asp Tyr Leu Leu Asn Arg Asp Thr Ile Arg Phe Ser
        515                 520                 525

Glu Ser Glu Asp Ser Asp Asp Asp Thr Asp Ser Lys Lys Glu Ser Phe
    530                 535                 540

Lys Gly Asp Lys Glu Gln Ser Asp Asp Ser Glu Ser Ser Lys Glu Glu
545                 550                 555                 560

Asp Thr Glu Asp Glu Ser Glu Asp Glu Ser Met Lys Val Thr Glu Ser
                565                 570                 575

Val Val Lys Glu Glu His Asp Glu Leu Lys Ile Leu Val Glu Asp Ser
            580                 585                 590

Gln Lys Glu Gly Glu Ile Lys Thr Glu Gln Asp Thr Lys Asp Asp Leu
        595                 600                 605

Ile Asn Asp Ala Ala Ala Ile Ala Glu Ser Ile Gln Pro Lys Gly Asn
    610                 615                 620

Thr Leu Ser Ser Thr Asn Val Ser Thr Asn Ile Pro Phe Leu Leu Lys
625                 630                 635                 640

Tyr Thr Leu Arg Glu Tyr Gln His Ile Gly Leu Asp Trp Leu Val Thr
                645                 650                 655

Met Phe Asp Arg Lys Leu Asn Gly Ile Leu Ala Asp Glu Met Gly Leu
            660                 665                 670

Gly Lys Thr Ile Gln Thr Ile Ala Leu Leu Ala His Leu Ala Cys Glu
        675                 680                 685

Lys Glu Asn Trp Gly Pro His Leu Ile Val Val Pro Thr Ser Val Met
    690                 695                 700

Leu Asn Trp Glu Met Glu Cys Lys Lys Trp Cys Pro Ala Phe Lys Ile
705                 710                 715                 720

Leu Thr Tyr Tyr Gly Thr Gln Lys Glu Arg Lys Phe Lys Arg Ile Gly
                725                 730                 735

Trp Thr Lys Pro Asn Ala Phe His Ile Cys Ile Thr Ser Tyr Lys Leu
```

-continued

```
        740                 745                 750

Val Ile Gln Asp His Gln Ser Phe Arg Arg Lys Lys Trp Lys Tyr Leu
    755                 760                 765

Ile Leu Asp Glu Ala Gln Asn Ile Lys Asn Phe Lys Ser Gln Arg Trp
    770                 775                 780

Gln Leu Leu Leu Asn Phe Gln Thr Gln Gln Arg Leu Leu Leu Thr Gly
785                 790                 795                 800

Thr Pro Leu Gln Asn Asn Leu Met Glu Leu Trp Ser Leu Met His Phe
                805                 810                 815

Leu Met Pro Asn Val Phe Gln Ser His Arg Glu Phe Lys Glu Trp Phe
            820                 825                 830

Ser Asn Pro Val Thr Gly Met Ile Glu Gly Asn Ser Glu Tyr Asn Glu
    835                 840                 845

Ser Ile Ile Lys Arg Leu His Lys Val Leu Arg Pro Phe Leu Leu Arg
    850                 855                 860

Arg Leu Lys Ser Glu Val Glu Lys Gln Met Pro Lys Lys Tyr Glu His
865                 870                 875                 880

Val Val Met Cys Arg Leu Ser Lys Arg Gln Arg Tyr Leu Tyr Asp Asp
                885                 890                 895

Tyr Met Ser Arg Ala Lys Thr Arg Glu Thr Leu Thr Thr Gly Asn Leu
            900                 905                 910

Leu Ser Val Ile Asn Val Leu Met Gln Leu Arg Lys Val Cys Asn His
    915                 920                 925

Pro Asn Leu Phe Glu Ile Arg Pro Thr Thr Ser Pro Phe Gln Cys Asp
    930                 935                 940

Asn Ile Arg Leu His Ile Pro Ser Ile Val Tyr Ser Ala Leu Asp Tyr
945                 950                 955                 960

Asp Pro Asp Lys His Val Asn Leu Gln Ala Leu Asn Leu Leu Leu Ile
                965                 970                 975

Met Gln Glu Ile His Phe Gly Ser Tyr Gln Cys Tyr Arg Met Arg Gln
            980                 985                 990

Ser Arg Asn Ser Lys Lys Ile Phe  Glu Met Glu Thr Asn  Ser Ser Lys
        995                 1000                1005

Asn Pro  Pro Pro Cys Pro Pro  Cys Lys Leu Ala Met  Arg Val Leu
    1010                1015                1020

Thr Asp  Lys Pro Ser Ala Thr  Asp Glu Lys Asn Glu  Lys Lys Asp
    1025                1030                1035

Met Gln  Ala Leu Ser Gln Pro  Pro Pro Leu Gln Val  Lys Gly Met
    1040                1045                1050

Ser Gln  Pro Asn Met Lys Met  Lys Val Ser Gly Val  Gln Phe Val
    1055                1060                1065

Pro Gln  Ser Ile Leu Lys Ser  Ile Pro Val Val Asn  Ile Ser Gln
    1070                1075                1080

Gly Ala  Thr Gly Gln Ile Gly  Ala Pro Val Ser Val  Thr Ser Val
    1085                1090                1095

Leu Lys  Pro Gln Asp Lys Ile  Ser Ala Ser Phe Ala  Gln Leu Val
    1100                1105                1110

Gln Thr  Ser Thr Gly Lys His  Leu Leu Leu Thr Ser  Asn Pro Asn
    1115                1120                1125

Ile Thr  Thr Ser Pro Val Thr  Thr Thr Thr Pro Gly  Gly Gln Lys
    1130                1135                1140

Leu Thr  Phe Leu Ser Lys Gln  Pro Val Ser Thr Ile  Gly Asn Ala
    1145                1150                1155
```

```
Gly His  Ala Val Thr Lys Ala  Tyr Val Lys Phe Gln  Leu Thr Ser
    1160                 1165                 1170

Val Thr  Thr Ala Ser Thr Phe  Thr Thr Val Thr Thr  Val Asn Ser
    1175                 1180                 1185

Asn Thr  Ile Ser Val Ala Lys  Ser Glu Asp Asn Lys  Gly Met Arg
    1190                 1195                 1200

Met Ser  Val Gly Asn Asp Tyr  Ile Gly Lys Leu Tyr  Ser Lys Gln
    1205                 1210                 1215

Asn Ser  Leu Asp Val Arg Trp  Asn Ser Gly Glu Lys  His Leu Gly
    1220                 1225                 1230

Leu Thr  Asn Glu Asp Asp Pro  Lys Gly Glu Arg Lys  Lys Arg Leu
    1235                 1240                 1245

Ser Leu  Met Ser Arg Ile Asn  Lys Ile Arg Cys Ser  Ala Leu Pro
    1250                 1255                 1260

Leu Tyr  Gly Arg Asp Phe Gln  Glu Ala Val Lys Ile  Tyr Thr Pro
    1265                 1270                 1275

Asn Gln  Leu Asp Val Trp Asn  Gly Gly His Ile His  Cys Leu Asn
    1280                 1285                 1290

Thr Leu  Tyr Asn Lys Asp Ala  Arg Asn Glu Thr Thr  Asp Cys Leu
    1295                 1300                 1305

Gln Asp  Ala Leu Phe Asn Pro  Glu Arg Arg Leu Glu  Ala Leu Lys
    1310                 1315                 1320

Asp Thr  Phe Asp Arg Phe Ile  Phe Tyr Val Pro Ser  Val Lys Val
    1325                 1330                 1335

Ala Glu  Pro Glu Leu Gln Val  Trp His Pro Pro Pro  Ser Lys Tyr
    1340                 1345                 1350

Trp Gly  Gln Lys His Glu Lys  Gln Leu Ile Gln Lys  Leu Phe Leu
    1355                 1360                 1365

Lys Pro  Ala Thr Pro Leu His  Ser Ile Ala Ser Ala  Met Val Thr
    1370                 1375                 1380

Gln Phe  Pro Asp Pro Arg Leu  Ile Gln Tyr Asp Cys  Gly Lys Leu
    1385                 1390                 1395

Gln Thr  Leu Asp Ile Leu Leu  Arg Lys Leu Lys Leu  Gly Ser His
    1400                 1405                 1410

Arg Val  Leu Ile Phe Thr Gln  Met Thr Lys Met Leu  Asp Val Leu
    1415                 1420                 1425

Glu Ala  Phe Leu Asn Tyr His  Gly His Ile Tyr Leu  Arg Leu Asp
    1430                 1435                 1440

Gly Thr  Thr Lys Val Asp Gln  Arg Gln Val Leu Met  Glu Arg Phe
    1445                 1450                 1455

Asn Gly  Asp Lys Arg Ile Phe  Ala Phe Ile Leu Ser  Thr Arg Ser
    1460                 1465                 1470

Gly Gly  Val Gly Val Asn Leu  Thr Gly Ala Asp Thr  Val Ile Phe
    1475                 1480                 1485

Tyr Asp  Ser Asp Trp Asn Pro  Thr Met Asp Ala Gln  Ala Gln Asp
    1490                 1495                 1500

Arg Cys  His Arg Ile Gly Gln  Thr Arg Asp Val His  Ile Tyr Arg
    1505                 1510                 1515

Leu Val  Ser Glu Arg Thr Ile  Glu Glu Asn Ile Leu  Lys Lys Ala
    1520                 1525                 1530

Asn Gln  Lys Arg Leu Leu Gly  Asp Leu Ala Ile Glu  Gly Gly Asn
    1535                 1540                 1545
```

```
Phe Thr  Thr Ala Tyr Phe Lys  Ser Ser Thr Ile Gln  Asp Leu Phe
    1550                 1555                 1560

Asn Ile  Asp Gln Asn Glu Glu  Ser Ala Ser Ala Arg  Met Ser Glu
    1565                 1570                 1575

Val Val  Glu Leu Arg Lys Glu  Arg Glu Lys Ala Leu  Ser Thr Asp
    1580                 1585                 1590

Leu Val  His Ser Ala Asp Asp  Lys Ala Thr Val Gly  Ala Leu Glu
    1595                 1600                 1605

Asn Ala  Phe Glu Ala Cys Glu  Asp Asp Gln Asp Val  Gln Ala Ala
    1610                 1615                 1620

Lys Thr  Ala Lys Ala Glu Ala  Val Ala Asp Leu Ala  Glu Phe Asp
    1625                 1630                 1635

Glu Asn  Ile Pro Leu Asp Asp  Gln Glu Lys Glu Pro  Glu Ile Ser
    1640                 1645                 1650

Lys Ala  Glu Gln Glu Ile Asn  Asn Ile Ile Glu Lys  Leu Thr Pro
    1655                 1660                 1665

Ile Glu  Lys Tyr Ala Met Asn  Phe Ile Glu Ala Thr  Glu Ser Ala
    1670                 1675                 1680

Trp Ser  Ala Glu Gln Leu Ala  Ala Ala Ala Arg Glu  Ile Glu Glu
    1685                 1690                 1695

Gln Lys  Lys Glu Trp Glu Gln  Asn Arg Leu Ala Ala  Met Arg Glu
    1700                 1705                 1710

Glu Glu  Glu Arg Arg Ala Arg  Glu Leu Glu Glu Glu  Ser Asp Ile
    1715                 1720                 1725

Ile Thr  Tyr Ser Arg Asp Asp  Ala Thr Asn Gln Val  Ser Ser Lys
    1730                 1735                 1740

Asn Lys  Lys Ile Asn Arg Tyr  Asn Lys Ile Leu Ser  Asn Lys Arg
    1745                 1750                 1755

Val Arg  Leu Lys Lys Asp Gly  Asp Glu Asp Val Glu  Lys Lys Asp
    1760                 1765                 1770

Asp Val  Glu Lys Lys Asp Gly  Val Glu Lys Arg Leu  Lys Lys Thr
    1775                 1780                 1785

Arg Thr  Arg Arg Leu Ser Gln  Lys Ser Lys Asp Val  Glu Val Glu
    1790                 1795                 1800

Glu Pro  Asp Ala Cys Glu Ser  Gln Glu Glu Ser Gln  Ile Asn Gly
    1805                 1810                 1815

Gly Asp  Thr Asp Asn Ser Asp  Ser Asp Ser Asp Ser  Asp Ser Glu
    1820                 1825                 1830

Ser Ser  Ser Ser Met Glu Ser  Lys Thr Thr Leu Asn  His Val Asp
    1835                 1840                 1845

Pro Asn  Ser Pro Arg Thr Arg  Ser Arg Gly Thr Val  Ala Ile Asn
    1850                 1855                 1860

Leu Trp  Thr Leu Asp Val Ser  Pro Ile Leu Pro Gly  Glu Lys Pro
    1865                 1870                 1875

Met Lys  Lys Tyr Gly Glu Asn  His Arg Lys Asn Ile  Lys Arg Val
    1880                 1885                 1890

Arg Ser  Val Ser Glu Asn Asp  Asn Asp Gly Asp Lys  Asp Gly Arg
    1895                 1900                 1905

Lys Arg  Leu Arg Arg Lys Tyr  Pro Thr Ser Leu Glu  Thr Ser Glu
    1910                 1915                 1920

Glu Glu  Asn Ser Asn Gln Ser  Arg Glu Lys Ser Thr  Lys Lys Arg
    1925                 1930                 1935

Ala Lys  Val Ala Pro Lys Gly  Lys Thr Cys Lys Val  Ile Leu Ser
```

-continued

```
    1940                1945                1950

Asn Ile  Leu Asn Asp Lys Arg  Phe Lys Val Asn Leu  Lys Glu Asp
    1955                1960                1965

Ile Glu  Ile Ser Val Ser Thr  Gln Ile Asn Glu Thr  Ser Thr Ser
    1970                1975                1980

Ser Asn  Gln Asn Gln Thr Lys  Asp Cys Glu Ser Ser  Gln His Glu
    1985                1990                1995

Asn Ser  Asn Leu Asp Glu Gln  Asn Asp Ser Leu Asp  Asn Thr Glu
    2000                2005                2010

Val Thr  Ser Ser Glu Leu Ser  Lys Leu Thr Gly Cys  Thr Glu Ile
    2015                2020                2025

Asp Asn  Asn Glu Ser Ser Lys  Gln Glu Asn Glu Glu  Leu Asp Glu
    2030                2035                2040

Ser Ile  Leu Glu Asp Lys Tyr  Asp Glu Asp Phe Ile  Thr Asn Lys
    2045                2050                2055

Asn Glu  Asp Ile Asp Glu Glu  Thr Leu Leu Glu Glu  Asp Asn Gln
    2060                2065                2070

Ile Glu  Gln Val Glu Asn Lys  Asn Ile Asp Ser Thr  Lys Asp Glu
    2075                2080                2085

Lys Gln  Gly Asp Asp Ser Asn  Val Ser Asp Val Gly  His Leu Ser
    2090                2095                2100

Lys Asp  Asn Asp Asn Glu Glu  Lys Met Glu Val Thr  Glu Ser Val
    2105                2110                2115

Asp Glu  Glu Asn Gly Asp Ile  Asn Lys Lys Val Asp  Glu Asp Glu
    2120                2125                2130

Ser Val  Lys Asp Lys Arg Glu  Arg Arg Lys Gly Asn  Glu Glu Asp
    2135                2140                2145

Asp Asn  Thr Asp Asn Glu Glu  Asn Ile Gln Lys Ser  Glu Asn Asp
    2150                2155                2160

Glu Gly  Asp Ile Lys Lys Gln  Gly Asn Gln Asp Glu  Glu Val Glu
    2165                2170                2175

Glu Lys  Thr Leu Gly Asn Ser  Thr Glu Ser Val Asn  Glu Ile Ala
    2180                2185                2190

Asn Glu  Ile Ser Arg Cys Lys  Pro Leu Asn Glu Gln  His Asn Glu
    2195                2200                2205

Leu Val  Asp Glu Val Val Asn  Asp Thr Ser Asn Met  Asp Glu Tyr
    2210                2215                2220

Ile Lys  Lys Ser Glu Asn Ser  Lys Val Val Glu Lys  Thr Ser Glu
    2225                2230                2235

Glu Ile  Leu Phe Asn Asp Arg  Gly Asn Gln Asp Ser  Ser Ser Gln
    2240                2245                2250

Asp Val  Lys Asp Glu Glu Ile  Ser Ser His Asn Arg  Gly Asp Glu
    2255                2260                2265

Lys Val  Ser Phe His Asp Arg  Ile Asp Lys Glu Val  Leu Pro Glu
    2270                2275                2280

Cys Arg  Lys Glu Glu Glu Lys  His Asn Arg Lys Asn  Glu Val Leu
    2285                2290                2295

Ser Gln  Thr Ile Lys Asp Glu  Glu Ala Gln Ser His  Asn Arg Lys
    2300                2305                2310

Asp Glu  Ser Gly Thr Phe Pro  Asn Val Ala Asp Ile  Glu Asn Arg
    2315                2320                2325

Leu Asn  Asn Lys Val Pro His  Val Asp Asn Gly His  Thr Glu Thr
    2330                2335                2340
```

```
Val Arg  Met Ser Lys Leu Val  Thr Ser Asn Arg Asn  Ala Asn Phe
    2345                2350                2355

Arg Ser  Pro Glu Thr Arg Arg  Ser Phe Arg Lys Cys  Gly Lys Ile
    2360                2365                2370

Ser Asn  Asn Gln Thr Leu Asp  Gly Trp Val Lys Arg  Ser Pro Val
    2375                2380                2385

Leu Pro  Val Glu Ala Ala Lys  Val Asn Asp Asn Ser  Lys Tyr Lys
    2390                2395                2400

Asn Val  Gly Ser Pro Glu Leu
    2405                2410


<210> SEQ ID NO 93
<211> LENGTH: 240
<212> TYPE: DNA
<213> ORGANISM: Artificial Sequence
<220> FEATURE:
<223> OTHER INFORMATION: SNF2-helicase degenerate dsRNA sequence
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 93

cgsythctyy tmacsggyac hcctctvcar aayaarctwc chgarytstg ggcbytdcth     60

aayttyytvc tbccstcbat yttyaarwsb tgytcbacdt tygarcartg gttcaaygcv    120

cchttygcha cmacbggmga raargtygar ytdaaygarg argaracvat yytkatyaty    180

mgdcgtytdc ayaargtyyt kcgwccktty ytvytnmgdc gnytvaaaaa rgargtmgar    240


<210> SEQ ID NO 94
<211> LENGTH: 27
<212> TYPE: DNA
<213> ORGANISM: Artificial Sequence
<220> FEATURE:
<223> OTHER INFORMATION: SNF2-helicase degenerate dsRNA sequence
<220> FEATURE:
<221> NAME/KEY: misc_feature
<222> LOCATION: (21)..(21)
<223> OTHER INFORMATION: n is a, c, g, or t

<400> SEQUENCE: 94

mghgcygtbt gyythatygg ngaycar                                         27


<210> SEQ ID NO 95
<211> LENGTH: 60
<212> TYPE: DNA
<213> ORGANISM: Artificial Sequence
<220> FEATURE:
<223> OTHER INFORMATION: SNF2-helicase degenerate dsRNA sequence

<400> SEQUENCE: 95

tayaarctyc tvytsacmgg machccgytb caraacaayc tmgargaryt rttycatytr     60


<210> SEQ ID NO 96
<211> LENGTH: 61
<212> TYPE: DNA
<213> ORGANISM: Artificial Sequence
<220> FEATURE:
<223> OTHER INFORMATION: SNF2-helicase degenerate dsRNA sequence

<400> SEQUENCE: 96
```

garttygaya cbaaycaymg rctkcthath acwggbacyc ckytvcaraa ywskytdaar 60
g 61

<210> SEQ ID NO 97
<211> LENGTH: 23
<212> TYPE: DNA
<213> ORGANISM: Artificial Sequence
<220> FEATURE:
<223> OTHER INFORMATION: Bromodomain degenerate dsRNA sequence

<400> SEQUENCE: 97
ytswsygaac crttyatgaa ryt 23

<210> SEQ ID NO 98
<211> LENGTH: 65
<212> TYPE: DNA
<213> ORGANISM: Artificial Sequence
<220> FEATURE:
<223> OTHER INFORMATION: HAND-SLIDE degenerate dsRNA sequence

<400> SEQUENCE: 98
gchgtvgatg cytayttymg vgargcwytv mgdgtytchg arccyaargc dccdaargch 60 cchmg 65

<210> SEQ ID NO 99
<211> LENGTH: 36
<212> TYPE: DNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (33)..(33)
<223> OTHER INFORMATION: n is a, c, g, or t

<400> SEQUENCE: 99
mghaartrbg ayatggavga rvvdccbaar ytngar 36

<210> SEQ ID NO 100
<211> LENGTH: 56
<212> TYPE: DNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (29)..(29)
<223> OTHER INFORMATION: n is a, c, g, or t

<400> SEQUENCE: 100
bhggdaarad dggrkkbryb ggmaaymwna chacdrtsta ykmhrtagar gaaaay 56

<210> SEQ ID NO 101
<211> LENGTH: 322
<212> TYPE: DNA
<213> ORGANISM: Diabrotica virgifera

<400> SEQUENCE: 101
aagaaggcat agaacagaaa gagagttggg cgaacgaata tctcagttca tttaaagtgg 60
ctagttatgt tacaaaagaa ggggaagttg aggaagaagt tgacactgag attattaaac 120
aagaagcgga aaataccgat ccggcctact ggatcaagct gcttagacat cattatgagc 180
aacaacagga agatatagct aggacgttag gaaaaggcaa aagagtgagg aaacaggtta 240
attataatga cggaggaatg acaactgaca cacgagaaga tacgacatgg caagaaaatc 300
tctctgatta ccattctgac tt 322

<210> SEQ ID NO 102
<211> LENGTH: 401
<212> TYPE: DNA
<213> ORGANISM: Diabrotica virgifera

<400> SEQUENCE: 102
tcacagtcga aacacccact gaatcagtct accaattcga aggagaagat tatcgtgaga 60
agcagaaaac catcggcttg agcaactgga tagaacctcc caaaagagaa aggaaggcca 120
actatgccgt cgatgcttac ttcagagaag ctttaagggt ttctgagcct aaagcgccta 180
aggctccaag accaccaaaa cagcccatcg tacaagattt ccagtttttc ccgccgagat 240
tattcgaact tttggaccag gagatctact tttacaggaa atctttggga tataaggttc 300
cgaaaaactt agaacttgga cctgacgcgt ccaagcaaca gaaagaagag caaagaaaaa 360
tagatgagtc agaaccgctc accgaagacg aacagcaaga a 401

<210> SEQ ID NO 103
<211> LENGTH: 271
<212> TYPE: DNA
<213> ORGANISM: Diabrotica virgifera

<400> SEQUENCE: 103
ttgctcaatc ctacatacac ttttaactcc ttcttgggtt ttagcccttt ctctacttca 60
attttcaatc ttctaagcaa gaatggtttt aatacagcat gcagcctctc caccatggag 120
ttgcctccca gacattgact ggtgttaaac caggcatcga aatcatcaga tgagttaaaa 180
acgtctggca gtaagaagtt gagaagagac cagagttcat gtaaattgtt ttgtaatgga 240
gtacctgtta gcagtagcct gttggtattc t 271

<210> SEQ ID NO 104
<211> LENGTH: 372
<212> TYPE: DNA
<213> ORGANISM: Diabrotica virgifera

<400> SEQUENCE: 104
gatcaaattc aagcaactag cgaaattgga aaaaaaatca gacgaagaac ttactgaata 60
ttacaaacat ttcgttatga tgtgcaagaa gcagacaggc atgaacatag aagacagcaa 120
ctatgacaat accatcgaac atatctcaga agaaaaggca cgaaggacat tggaaaggct 180
ggagctgttg tcgaggatca gagaagaaat tttaacccat cctaaactcg acgaaagatt 240
gagggtgtgc attacttcgg ctgatatgcc tgaatggtgg attgccggca aacacgacaa 300
ggatctcttg ttgggggtcg ccaaacatgg tttaggaaga accgactact accttctgaa 360
cgatcctgat ct 372

<210> SEQ ID NO 105
<211> LENGTH: 315
<212> TYPE: DNA
<213> ORGANISM: Diabrotica virgifera

<400> SEQUENCE: 105
tttgcttcct tctttcaact cgcgcagggg gcttgggcat taatttagct actgctgata 60
ctgtgataat ttttgattcg gactggaatc ctcaaaacga tcttcaagcg caggcaagag 120
ctcataggat cggtcaaaag aaccaagtca acatttatag gttagttact gctagatctg 180
tagaggaaga aattgtagaa agggcaaaac aaaaaatggt actggatcat cttgtaattc 240
agagaatgga cacgacggga agaaccgttt tggacaaaaa ggggtcttct aataataatc 300
cgtttaacaa agaag 315

<210> SEQ ID NO 106
<211> LENGTH: 449
<212> TYPE: DNA
<213> ORGANISM: Diabrotica virgifera

<400> SEQUENCE: 106
acttatctaa agggatgcta gctgagttcg atgtcatact cacaacgtat acgctggttg 60
gaaatagttc agaagagaga aaaatgttcc gagtgacaag gatgcattat gtaatcttcg 120
atgaagcaca tatgttgaaa aatatgaata ctcttcggta tgaaaattta attaagataa 180
acgctaaaca taggatactg ttaaccggca ctccgttaca aaataattta ttagaactaa 240
tgtcgctgtt gatatttgtg atgccgaata tattcgctga aaaaaggtgg acttgaaaaa 300
cttattccaa aaaaattcta aaaaagcaga agacgactct ctacctacct tcgaaaagga 360
gcaaattgaa caagccaaaa gaattatgaa acctttcctt ttgcgaagac tgaaatgtga 420
cgtccttcgg gatcttccca agaaaacgg 449

<210> SEQ ID NO 107
<211> LENGTH: 38
<212> TYPE: DNA
<213> ORGANISM: Artificial Sequence
<220> FEATURE:
<223> OTHER INFORMATION: Primer Mi2.T7.F

<400> SEQUENCE: 107
taatacgact cactataggg aagaaggcat agaacaga 38

<210> SEQ ID NO 108
<211> LENGTH: 39
<212> TYPE: DNA
<213> ORGANISM: Artificial Sequence
<220> FEATURE:
<223> OTHER INFORMATION: Primer Mi2.T7.R

<400> SEQUENCE: 108
taatacgact cactataggg tcagaatggt aatcagaga 39

<210> SEQ ID NO 109
<211> LENGTH: 38
<212> TYPE: DNA
<213> ORGANISM: Artificial Sequence
<220> FEATURE:
<223> OTHER INFORMATION: Primer ISWI30.T7.F

<400> SEQUENCE: 109
taatacgact cactataggg tgaatcagtc taccaatt 38

<210> SEQ ID NO 110
<211> LENGTH: 38
<212> TYPE: DNA
<213> ORGANISM: Artificial Sequence
<220> FEATURE:
<223> OTHER INFORMATION: Primer ISWI30.T7.R

<400> SEQUENCE: 110
taatacgact cactataggg ggttctgact catctatt 38

-continued

<210> SEQ ID NO 111
<211> LENGTH: 39
<212> TYPE: DNA
<213> ORGANISM: Artificial Sequence
<220> FEATURE:
<223> OTHER INFORMATION: Primer ISWI2.T7.F

<400> SEQUENCE: 111
taatacgact cactataggg ttgctcaatc ctacataca 39

<210> SEQ ID NO 112
<211> LENGTH: 38
<212> TYPE: DNA
<213> ORGANISM: Artificial Sequence
<220> FEATURE:
<223> OTHER INFORMATION: Primer ISWI2.T7.R

<400> SEQUENCE: 112
taatacgact cactataggg gaataccaac aggctact 38

<210> SEQ ID NO 113
<211> LENGTH: 38
<212> TYPE: DNA
<213> ORGANISM: Artificial Sequence
<220> FEATURE:
<223> OTHER INFORMATION: Primer KSMT.T7.F

<400> SEQUENCE: 113
taatacgact cactataggg gatcaaattc aagcaact 38

<210> SEQ ID NO 114
<211> LENGTH: 38
<212> TYPE: DNA
<213> ORGANISM: Artificial Sequence
<220> FEATURE:
<223> OTHER INFORMATION: Primer KSMT.T7.R

<400> SEQUENCE: 114
taatacgact cactataggg ttcttcctaa accatgtt 38

<210> SEQ ID NO 115
<211> LENGTH: 38
<212> TYPE: DNA
<213> ORGANISM: Artificial Sequence
<220> FEATURE:
<223> OTHER INFORMATION: Primer CHD1.T7.F

<400> SEQUENCE: 115
taatacgact cactataggg tttgcttcct tctttcaa 38

<210> SEQ ID NO 116
<211> LENGTH: 39
<212> TYPE: DNA
<213> ORGANISM: Artificial Sequence
<220> FEATURE:
<223> OTHER INFORMATION: Primer CHD1.T7.R

<400> SEQUENCE: 116
taatacgact cactataggg cttctttgtt aaacggatt 39

<210> SEQ ID NO 117
<211> LENGTH: 40
<212> TYPE: DNA
<213> ORGANISM: Artificial Sequence
<220> FEATURE:
<223> OTHER INFORMATION: Primer ETL1.T7.F

<400> SEQUENCE: 117
taatacgact cactataggg acttatctaa agggatgcta 40

<210> SEQ ID NO 118
<211> LENGTH: 38
<212> TYPE: DNA
<213> ORGANISM: Artificial Sequence
<220> FEATURE:
<223> OTHER INFORMATION: Primer ETL1.T7.R

<400> SEQUENCE: 118
taatacgact cactataggg gtagagagtc gtcttctg 38

<210> SEQ ID NO 119
<211> LENGTH: 18
<212> TYPE: DNA
<213> ORGANISM: Artificial Sequence
<220> FEATURE:
<223> OTHER INFORMATION: Primer Mi2.qPCR.F

<400> SEQUENCE: 119
agagtgagga aacaggtt 18

<210> SEQ ID NO 120
<211> LENGTH: 21
<212> TYPE: DNA
<213> ORGANISM: Artificial Sequence
<220> FEATURE:
<223> OTHER INFORMATION: Primer Mi2.qPCR.R

<400> SEQUENCE: 120
aagtcagaat ggtaatcaga g 21

<210> SEQ ID NO 121
<211> LENGTH: 20
<212> TYPE: DNA
<213> ORGANISM: Artificial Sequence
<220> FEATURE:
<223> OTHER INFORMATION: Primer Mi2.qPCR.F3

<400> SEQUENCE: 121
agttgggcga acgaatatct 20

<210> SEQ ID NO 122
<211> LENGTH: 20
<212> TYPE: DNA
<213> ORGANISM: Artificial Sequence
<220> FEATURE:
<223> OTHER INFORMATION: Primer Mi2.qPCR.R3

<400> SEQUENCE: 122
cggtattttc cgcttcttgt 20

<210> SEQ ID NO 123
<211> LENGTH: 22
<212> TYPE: DNA
<213> ORGANISM: Artificial Sequence
<220> FEATURE:
<223> OTHER INFORMATION: Primer ISWI30.qPCR.F

<400> SEQUENCE: 123
aggaaatctt tgggatataa gg 22

<210> SEQ ID NO 124

-continued

<211> LENGTH: 18
<212> TYPE: DNA
<213> ORGANISM: Artificial Sequence
<220> FEATURE:
<223> OTHER INFORMATION: Primer ISWI.qPCR.R

<400> SEQUENCE: 124
ttcttgctgt tcgtcttc 18

<210> SEQ ID NO 125
<211> LENGTH: 20
<212> TYPE: DNA
<213> ORGANISM: Artificial Sequence
<220> FEATURE:
<223> OTHER INFORMATION: Primer ISWI30.qPCR.F

<400> SEQUENCE: 125
tcacagtcga aacacccact 20

<210> SEQ ID NO 126
<211> LENGTH: 20
<212> TYPE: DNA
<213> ORGANISM: Artificial Sequence
<220> FEATURE:
<223> OTHER INFORMATION: Primer ISWI.qPCR.R

<400> SEQUENCE: 126
tggccttcct ttctcttttg 20

<210> SEQ ID NO 127
<211> LENGTH: 20
<212> TYPE: DNA
<213> ORGANISM: Artificial Sequence
<220> FEATURE:
<223> OTHER INFORMATION: Primer ISWI2.qPCR.F

<400> SEQUENCE: 127
gcagtaagaa gttgagaaga 20

<210> SEQ ID NO 128
<211> LENGTH: 19
<212> TYPE: DNA
<213> ORGANISM: Artificial Sequence
<220> FEATURE:
<223> OTHER INFORMATION: Primer ISWI2.qPCR.R

<400> SEQUENCE: 128
agaataccaa caggctact 19

<210> SEQ ID NO 129
<211> LENGTH: 18
<212> TYPE: DNA
<213> ORGANISM: Artificial Sequence
<220> FEATURE:
<223> OTHER INFORMATION: Primer KSMT.qPCR.F

<400> SEQUENCE: 129
cacgaaggac attggaaa 18

<210> SEQ ID NO 130
<211> LENGTH: 18
<212> TYPE: DNA
<213> ORGANISM: Artificial Sequence
<220> FEATURE:
<223> OTHER INFORMATION: Primer KSMT.qPCR.R

<400> SEQUENCE: 130
gcacaccctc aatctttc 18

<210> SEQ ID NO 131
<211> LENGTH: 24
<212> TYPE: DNA
<213> ORGANISM: Artificial Sequence
<220> FEATURE:
<223> OTHER INFORMATION: Primer CHD1.qPCR.F

<400> SEQUENCE: 131
ttataggtta gttactgcta gatc 24

<210> SEQ ID NO 132
<211> LENGTH: 18
<212> TYPE: DNA
<213> ORGANISM: Artificial Sequence
<220> FEATURE:
<223> OTHER INFORMATION: Primer CHD1.qPCR.R

<400> SEQUENCE: 132
tcgtgtccat tctctgaa 18

<210> SEQ ID NO 133
<211> LENGTH: 20
<212> TYPE: DNA
<213> ORGANISM: Artificial Sequence
<220> FEATURE:
<223> OTHER INFORMATION: Primer ETL1.qPCR.F

<400> SEQUENCE: 133
tgatatttgt gatgccgaat 20

<210> SEQ ID NO 134
<211> LENGTH: 18
<212> TYPE: DNA
<213> ORGANISM: Artificial Sequence
<220> FEATURE:
<223> OTHER INFORMATION: Primer ETL1.qPCR.R

<400> SEQUENCE: 134
agagtcgtct tctgcttt 18

<210> SEQ ID NO 135
<211> LENGTH: 4768
<212> TYPE: RNA
<213> ORGANISM: Diabrotica virgifera

<400> SEQUENCE: 135
caaguggcca uggcaugcca cagggucccc cuggacaacc aggucagcaa caccaaggcc 60
gaacugcuga uaauuuacau gccuuacaaa aagcaauaga uacaauggaa gaaaaaggua 120
ugcaagaaga ucagagguau ucacaguuac uggcguuacg ugcuagaucc aguggucaac 180
caucuaacgg aguucuuaca ccgcugcaaa ugaaucaacu uagaaaucaa auuauggcau 240
acaggugccu agcgaggagc caaccaauuc cuccuucaau aauguugggg cugcaaggaa 300
agaggccuga cgguucacca caguuuccua caccuccguc aaguccguuu caaccacaag 360
gaccuggugc acccccuggu ccggaacaac caccagcuaa ugcagaaaac guagcagagc 420
cagcagcacc aguaggaccg caaggugcac aaggaccucc uaaccaacag agagcucaaa 480
cuagccaguu aguccccaau aagcaaacuc guuucacuac caugcccaaa ccaucuggac 540
uagauccacu aguucuucuu caagagaggg aaacuagggu ggcagcuaga aucgcugcua 600

-continued

```
gaauagaaca auguaguaac uuaccuacca aucuuucaga caaaguccgc augcaagcac    660
agauagaauu gagagcuuug cggugccuua auuuccaaag gcaacuaaga agcgaaauuu    720
ugaacuguau uaggagagau auaacgcuug aaucugcugu aaauuuuaaa gcauauaaaa    780
gaacgaagcg acagggucua aaagaaucga gagcuacaga gaaguuagaa aaacaacaga    840
aguuagaagc agaaagaaag agaagacaga agaaccaaga auuuuugaau gcuguauuga    900
acaauggaaa agaauucaag gaauuccaca agcagaauca agcgaaauua gcuaagauua    960
auaaagcugu uauuaauuau cacgcuaaug cugaaagaga gcaaaagaaa gaagcagaaa   1020
ggagagagaa ggaacguaug aucagauuga uggcagaaga ugaagaaggu uauagacagu   1080
ugaucgauca aaagaaagac aaacgucuag cguucuugcu uucccaaaca gaugaauaua   1140
ucaguaacuu aacagagaug gugaaaaugc acaaagucga acaaaguaac aagaagcggg   1200
aagaagaacg acggaagaga aggcaagaca aaaugcagca gccugacagg aaagucacag   1260
uuaucgaaau ggcuacuggg aauaagguua guggagaaaa cgcuccgacu guccaggaac   1320
uuccugaaug guuacagacu cauccugguu gggagaugau agauacagaa gacgaggacg   1380
agaaugacga auauagaaug gacgauuaug aagaaaauaa ucaagucgau gcuacagaaa   1440
ucauucagaa agccaagguu gaggaugacg aauaucacaa gaaugccaca gaggaacaga   1500
cguacuacgg uauugcacau acagugagcg agucaguauc agaacaggcc uccauuauga   1560
uaaacgguga acugaaagag uaccagguca aaggacugga auggauggua uccuuguaca   1620
acaacaaucu uaaugguauc cuagcagacg agauggguuu ggguaagacu auucaaacca   1680
uuggccugau caccuacuug auggagaaaa aaaaguugaa ugggccauuu uugaucauug   1740
ugccguuauc cacuauaucu aauuggaugu uggaguucga aaaaugggcu ccuucuguug   1800
uggucgucuc cuacaaaggc ucaccugguc acaggaaauu gcuucagggu cagaugaagu   1860
cagcaaaauu caauguucuu cuuacuacuu augaauauau cauuaaagau aagggaauuc   1920
uuucaaaagu accguuuaag uauaugaucg uggacgaggg ucacagaaug aagaaccauc   1980
auugcaaguu gacccagacu uugaacacuc acuacgcagc uccuuuccgc cuucucuuaa   2040
ccgguacucc ucuacaaaac aaacuaccag aacugugggc guugcuuaac uucuuacuuc   2100
cgucuauuuu caagaguugu uccacuuucg agcaaugguu caacgccccu uucgcaacca   2160
cgggagaaaa gguugaacuu aacgaagaag aaaccauccu uaucauccga cgucuucaca   2220
aaguccugcg accuuuccuc uuaagacguc ucaaaaagga aguagagucu cagcuucccg   2280
acaaagucga auacauuauc aaaugcgaga uguccgguuu gcaaaaagug uuguaccaac   2340
acaugcagag caagggaguu cugcucaccg acgggtccga aaaggguaau aggggccgag   2400
guggagcuaa ggcuaucaug aauaccauca ugcaacugcg gaagcugugu aaucauccuu   2460
ucauguucca aaugaucgaa gaaaaguauu gugaauaugu aggcaugggu gggggacuca   2520
caucagggcc ggauauauac agaucuucug guaaauuuga acuucuggau cggguauugc   2580
caaagcucaa ggcgacugac cacagagucc uacuguucug ucaaaugacg acguugauga   2640
acaucaugga agacuacuuc auuuggagag guuacaaaua ucuucgucug gaugguaugg   2700
uaaaagcgga agaucgggcg gaacuacuca agaaguucaa ugacaaacaa agcgaauauu   2760
uuguguuucu auugucaaca agagcaggag gucuuggacu caacuugcaa agugcugaua   2820
cuguuaucau cuuugauucu gacuggaauc cucaccagga uuuacaagcu caagaucgug   2880
cccaucguau aggccagcaa aaugaaguca ggguccuacg uuuaaugaca guuaauucag   2940
uggaagaaag aaucuuagcu gcagcuaaau acaaacuuau aauggacgag aaaguaaucc   3000
```

aagcugguau guucgaucag aagucuacag gcucagagag acaucaguuu uugcagagua 3060
uuuuacacca ugacggaagc gacgaagaag aggaaaacga aguuccugau gacgaaacag 3120
ugaaccagau guuggcccga agggaaaacg aauuucagcu uuuccagaag auggaucagg 3180
aaagaaagga agaagaugaa aagaccggaa agucgcgacu uauucaagaa agcgaauugc 3240
ccgaauggcu guugaagcaa gacgaugaaa ucuacucgug gggccuugau gauccagaug 3300
cuguuuuagg aaggggguagu aggcaaagaa aagaaguuga uuauguugac agccugacgg 3360
agaaagagug gcuuaaggcu auugacgaag agggagaauu ugaggaagaa caagaaggug 3420
auaaagaagg ucucagaaag aaaagaggga ggaagaggaa gaagcgcgau gaugacgaag 3480
aggcaagcca aauuaagaga agaaaggugc aucuagccga gaucaagaug aagaaaaaga 3540
ugaagaggcu uauggaaguu guugugaacu acagggauag ggaugguaga guauugagcg 3600
aaccguuuau gaaacuucca ucaaagaagg aguuaccuga auauuacgau acgauuaaga 3660
aaccuauuga uauugaaaaa gucguugcca acguagaaga aggaaaauau uucacgaugc 3720
acgauuugga aagagauuuc gacuugcugu gccaaaacgc ccaacaauac aacgaagaag 3780
acuccaugau cuacgaggac agccucguuc uucgacaggu guuuagaagc gcgagggaaa 3840
agaucgacgg uaccucagac cacgacgaca acgccgaugg accggcggug gcucagauca 3900
aacgaccucg ugguagaccu cgaaaacaca agagacccga agagaucgag gccgaagcgg 3960
cggcucagaa agcuauggag gaggcaucga agcugagagc ucaagcugag gcggaagagc 4020
uuagaucuaa gguggaggag gcaucucaga gagccaaaga ggaagcgaaa gcaagggagg 4080
aagccaaagc uagggaagaa gccgaaaucg agaacaugga ggagauuccc acaagcacau 4140
gaucuauaga gcaaccggaa acaaaaaggc aaaaaagaaa uauuauauag aaaagaugua 4200
cauguucaau ggagauacau uuucgcugag uuacaacggg uaaugcuuuu acaacggaua 4260
uuuugacgua ugaauguuga cguucagaug aaguauauuu auaaaauaau ccagaccuuu 4320
acguuuuggu ugauuuguuu ucuguauugu ucaguuuauu gaacaaccau uaauagcagc 4380
uuaccuaaau gauuuagaaa agcaucugag uuauuuagau aaguuuugag auuauauuua 4440
uuaacuuuaa uauuacuauc uuuauuauag cauauuguaa uuauuuuuuc cuguccuucu 4500
uucguugugu gguagauaau ccgagaguca acaguuauaa gcaaaugaaa uucaguuaaa 4560
ccucaaaugu acaaaaugau caaauuaaug uuuacaauuu auuuuuuuac cacgcacauc 4620
cacuauuacu auugucaguc auugagauau cauuuuauau agcuccaugu cugucuuccu 4680
caauuuacag agaagcaauu agacaaguaa ugacauaaua uggugcugaa auaaugugcu 4740
ugauagugau guugaaaaag uaacuauu 4768

<210> SEQ ID NO 136
<211> LENGTH: 5147
<212> TYPE: RNA
<213> ORGANISM: Diabrotica virgifera

<400> SEQUENCE: 136
ucacgugccu ccacaaggcc auguuccucc acagggucac gugccuccac aaggccaugu 60
uccuccacag ggacaucuuc cuccacaggg ccauauucca ccacaggguc augguccaac 120
gcagggccac auaccuccuc aggggcaugu uccaccacaa ggacauauac cuccucaagg 180
gcaugcaccc ccacaaggac augcaccacc acaggggcau ccuggcguuc cuccugguca 240
ucagagucau ccucaagggc auccacaaac accagggcau ccuggaccug gacauauacc 300

-continued

```
accuggugga gcaaugcacc cagggcauua uccaaguggc cauggcaugc cacagggucc    360
cccuggacaa ccaggucagc aacaccaagg ccgaacugcu gauaauuuac augccuuaca    420
aaaagcaaua gauacaaugg aagaaaaagg uaugcaagaa gaucagaggu auucacaguu    480
acuggcguua cgugcuagau ccagugguca accaucuaac ggaguucuua caccgcugca    540
aaugaaucaa cuuagaaauc aaauuauggc auacaggugc cuagcgagga gccaaccaau    600
uccuccuuca auaaauguugg ggcugcaagg aaagaggccu gacgguucac cacaguuucc    660
uacaccuccg ucaaguccgu uucaaccaca aggaccuggu gcacccccug guccggaaca    720
accaccagcu aaugcagaaa acguagcaga gccagcagca ccaguaggac cgcaaggugc    780
acaaggaccu ccuaaccaac agagagcuca aacuagccag uuagucccca auaaagcaaac    840
ucguuucacu accaugccca aaccaucugg acuagaucca cuaguucuuc uucaagagag    900
ggaaacuagg guggcagcua gaaucgcugc uagaauagaa caauguagua acuuaccuac    960
caaucuuuca gacaaagucc gcaugcaagc acagauagaa uugagagcuu ugcggugccu   1020
caauuuccaa aggcaacuaa gaagcgaaau uuugaacugu auuaggagag auauaacgcu   1080
ugaaucugcu guaaauuuua aagcauauaa aagaacgaag cgacagggucuaaaagaauc   1140
gagagcuaca gagaaguuag aaaaacaaca gaaguuagaa gcagaaagaa agagaagaca   1200
gaagaaccaa gaauuuuuga augcuguauu gaacaaugga aaagaauuca aggaauucca   1260
caagcagaau caagcgaaau uagcuaagau uaauaaagcu guuauuaauu aucacgcuaa   1320
ugcugaaaga gagcaaaaga aagaagcaga aaggagagag aaggaacgua ugaucagauu   1380
gauggcagaa gaugaagaag guuauagaaa gcucauugau caaaagaaag acaaacgucu   1440
agcguucuug cuuucgcaaa cagaugagua uauaacuaac cucacggaga ugguaaagca   1500
acacaaguug gaacaaacca auaaaaagaa agaggaggaa aaacgcaaga agaagcagca   1560
gaaaaugcaa caaccagaua ggaaaguuac aguucuggaa acugcaacag guaaaaaagu   1620
aacaggagag gcugcuccua cacugcgaca aguucaagaa ugguuaaucc aacauccugg   1680
augggagaug gucgauacag augaugagga ugaugaaaac ggggagaaga gggaugauga   1740
cuaugaugaa aaucaagaag uggaugaugc aaaagaaguu auuaaaaaag cuaaaguuga   1800
agaugacgaa uaucacaaaa acacaaaaga agaacagacu uacuacagua uugcucacac   1860
uguucaugaa gugguaacag aacaagcauc cauucugguu aauggaaagc uuaaggaaua   1920
ucaaauuaga ggguuagaau ggauggugucuuuguacaau aacaaucuga augguauucu   1980
agcagaugag augggucuag guaaaaccau ucaaacgauu ggcuuguuga ccuauuugau   2040
ggaaaaaaag aagauaaaug gaccguuuuu gaucauagug ccacuuucaa ccauuucuaa   2100
uuggauguug gaauuucaaa agugggcccc uacuguaguu gucauuucau acaaaggcuc   2160
uccugugguu agaaaaguga uccagagcca guuaaaagcu gcuaaauuca augugcuucu   2220
cacuaccuac gaguacauua uuaaggacaa ggguguauua gcaaaaaucc cauuuaaaua   2280
uaugaucaua gaugagggucaucguaugaa aaaccaccac ugcaaauuga cucaaguccu   2340
gaauacgcac uauuuggcgc ccuacagacu ccugcuuacu gguacucccc uacaaaauaa   2400
auuaccagaa uuaugggccu uguugaauuu cuuguugccu ucgauuuuca agaguugcuc   2460
cacuuuugaa caaugguuca augcgccauu cgcaacaaca ggagaaaagg uugaguuaaa   2520
cgaagaagaa acuauccuua ucauccgucg ucuucacaaa guacucaggc cguuucuccu   2580
gagacgucuc aagaaagaag ucgaaucuca gcuuccagac aaaguggaau auaucauaaa   2640
gugugacaug ucgggccuac aaaagguucu cuaugcacac augcagagca agggugugu u   2700
```

acuuaccgau gguuccgaga agggcaguaa aggaagggga ucuaaggcac ugaugaacac 2760
cauuaugcag cugaggaaac ugugcaauca uccguuuaug uuccaaaaua ucgaagagaa 2820
auauugugau cauguuggua uugcuggugg agugguuucu ggacccgaca cuuauagggu 2880
aucugguaag uuugagcucu uggacagaau auugcccaaa augaaagcaa cuaaccauag 2940
gauucuucuu uucugucaaa ugacucaauu aaugaccauc auggaagauu aucuaaauug 3000
gagaggauuc aaauaucuuc gucuugaugg uacaaucaaa ucagaagauc gcggggaccu 3060
auuaucgaaa uuuaaugaua aaaauaguga auauuuuuug uuuuugcuau cuacacgggc 3120
uggaggucug ggacuuaauu ugcagacagc ugauacugug auuaucuucg auuccgauug 3180
gaauccucau caggauuuac aagcucagga ucgagcucau cguauuggac agcaaaauga 3240
gguccgaguu uugcguuuga ugacuguuaa cucuguugag gaacgaauuu uagcugcagc 3300
uaaauacaag cuuacuaugg acgaaaaggu cauucaagcu gguauguucg aucagaaguc 3360
uacgggaucu gaaaggcagc aguuucuuca gaguauuuua cacaaugaug guagugauga 3420
agaagaggaa aaugaagugc cugaugacga aaccgucaac caaaugauag cuaggacaga 3480
ggaugaguuu cagcucuucc aaaaaaugga uacggaaaga aaagaggaga augaaaaacu 3540
uggucagcau aaaaagucgc gauugguuca agaaugugaa cuuccggauu ggcugacaaa 3600
gccagaugaa gaugauggcu ggggugauga uuauacugaa gcgcuauugg gcagaggaac 3660
caggcagcga aaggaaguug auuaugcuga uaguuuaaca gaaaaggaau gguuaaaggc 3720
uaucgaugaa gacggagacu acgaugaaga agaagaggaa gaaaaaguac aaaagaagag 3780
ggguaggaag agaaggaagc gugacgauuc ugacgaugac accagcaguu cuacgagaag 3840
gcguaagcua ccccaaaguc agguagaagc uaggcuaaag agaaaaauga aaaaguugau 3900
gaacauaguu acaaauuaua aagacaggga uggacgacag cuuagcgauc aauucauuaa 3960
auugccucca aggaaagagu auccagacua uuauacuauu auuaaaaagc cuauagauau 4020
uagcaagaua uuaaauuaua uagaugaugg aaaguacucu gauuucuccg aucuggaacg 4080
agacuucaug cuucucugcc agaaugcuca aaucuauaac gaagaagcgu cguugauuca 4140
cgaagacagc aucguacugc agucggucuu uucgagugcc aagcagaaga ucgaagccuc 4200
cccggauucg gacgacgaaa aagaugacaa uaauuccgau guagaaacuc cuaagaauaa 4260
aaauaaaccu gguaaaggca agagacgacc cggcaggccu aggaggucgg cgaaaaaaua 4320
cauuucggac gacgaugacg acgacugaag aguuuaggug uaagagaaau gagaaugaaa 4380
uucuuauugc aaaaguugua cauaugaagg uguuguuauu cuuuaccaaa gcugguaaau 4440
guuugauuua aagggaaacu ggaacuuuuc ucuugguuuu agauaguacu auagauaggu 4500
uuugauaggg aauaacaggu ucaagauucg ccccaguuga aauuugcuua aaugaucaaa 4560
gaguacuuaa guauaaugaa ucacgauugu uuaaauuuua acuugcacuu agugacaaaa 4620
aaauaacagc uuauaaauaa auuuacguag caagaaugau ccuauugauu aagaaugaau 4680
gagccucucc aaagauaguc caaaaagugu uucagggguga aaaggaguug ugaaaaauac 4740
aagaugqucu gcuaagcaac cuucuuugua acaaaaauca uguuuuucca gaaauuuuuu 4800
uuuauuuuau uaauauaguc cucuuuuauc ucaauacaac gcgauuccag cgauuuucca 4860
aacuucuuua ugccgucgga auaaggcccc accuagauug gauccguauu ucuccuauca 4920
gauccgaucc gacgucggau ugaaagcaaa cucaagguau uaagguaugg cugcacuuac 4980
auuggauccc cauccuccga uccgauauag ggcgauugau aggagaagcu acagcagaga 5040

-continued

```
agcaguucga cgucggccga uaucggaucg gucuucucac uacaguguag gcacugcgcu   5100

uuaauaccuu cccuaauaac acuaaacauu ccauguaugu uccuaga                  5147


<210> SEQ ID NO 137
<211> LENGTH: 5134
<212> TYPE: RNA
<213> ORGANISM: Diabrotica virgifera

<400> SEQUENCE: 137

acaguuaaau auugaaaaug gccuggugUu uugauaaaac ggaagaggcg aauuucuagu     60

agcauuuuaa gguuucauuu gcauuuaaaa caaauucaug uauuauaaaa uguaggauac    120

guuuccucgu auccaucuac uuaauuuagg auaacaauaa agggugugag acaguuaaau    180

auugaaaaug gccagugcuu cauuauuacc caaaacuuuc acuucuauug guggcaaagc    240

ccuaccuacc aacucacaac aaaacauuca gucaaaauuu aaagagauua caguuccacc    300

aggaaauacu ccucaagaug uuaaagaagg ccccagucac caaucaaauc caaaccauuu    360

ggcuucucuu caaaaggcca uugaaacuau ggaagagaag ggcuuacaag cugauccuag    420

auauucacag uuacuugcau ugcgagcuag cauuccuggg gcagaagaaa augguucucc    480

cuucucaaac aaccaaauca agcaauuaag aaaccaaaua auggcuuaca gguguuuggc    540

aagaaaucaa ccuguuccaa acaauuuagu auuagguuug cauggaaaaa cuccugaaaa    600

aguuccacau auuguaccuc caccgcaacc ucaagaagua ccuaaugggg gcgauccagg    660

accuucaaca aguucugcug cugcuguagc uccuagaaca ccacaaaagc ugccagcaaa    720

accaauugag gcucagcuug ucaacagaga accaagaguc acuacuuuau cuaaaccauc    780

uuccauagac ccuguuguuc uauuacaaga acgagaaaac aggguagcag cucguauagc    840

agcgaggauu gaacaaguca guaaucugcc gacugauaug ucugaggcau uacguauucg    900

ggcacaaaua gaacucagag cuuugagaug ucuaaaccuc cagagacaac uucguaguga    960

gguuuugagc uguauucgac gggacacaac auuagaaaca gcaguaaaug uaaaagcguu   1020

uaaacggacc aaacgucaag gucuucgaga agcuagagca acagaaaaac uugagaaaca   1080

acaaaagcug gaagcagaga gaaagaaacg ccagaagaac caagaguucu uaaacaaugu   1140

gauggcacac gcuaaagauu ucaaagaauu ccacaggcag aaccaagcaa aacuuucuaa   1200

acuuaauaaa gcuauucuua cuuaucacgc uaaugcggag agagaacaaa agaaggaaca   1260

agagagaaga gaaaaggaac guaugaagaa auugauggca gaagaugaag aagguuauag   1320

acaguugauc gaucaaaaga aagacaaacg ucuagcguuc uugcuuucgc aaacagauga   1380

guauauaacu aaccucacgg agaugguaaa gcaacacaag uuggaacaaa ccaauaaaaa   1440

gaaagaggag gaaaaacgca agaagaagca gcagaaaaug caacaaccag auaggaaagu   1500

uacaguucug gaaacugcaa cagguaaaaa aguaacagga gaggcugcuc cuacacugcg   1560

acaaguucag gaaugguuaa uccaacaucc uggaugggag auggucgaua cagaugauga   1620

ggaugaugaa aacggggaga agagggauga ugacuaugau gaaaaucaag aaguggauga   1680

ugcaaaagaa guuauuaaaa aagcuaaagu ugaagaugac gaauaucaca aaaacacaaa   1740

agaagaacag acuuacuaca guauugcuca cacuguucau gaaguggUaa cagaacaagc   1800

auccauucug guuaauggaa agcuuaagga auaucaaauu agaggguuag aauggauggu   1860

gucuuuguac aauaacaauc ugaaugguau ucuagcagau gagaugggUc uagguaaaac   1920

cauucaaacg auuggcuugu ugaccuauuu gauggaaaaa aagaagauaa auggaccguu   1980

uuugaucaua gugccacuuu caaccauuuc uaauuggaug uuggaauuuc aaaagugggc   2040
```

cccuacugua guugucauuu cauacaaagg cucuccugug guuagaaaag ugauccagag 2100
ccaguuaaaa gcugcuaaau ucaaugugcu ucucacuacc uacgaguaca uuauuaagga 2160
caagggugua uuagcaaaaa ucccauuuaa auauaugauc auagaugagg gucaucguau 2220
gaaaaaccac cacugcaaau ugacucaagu ccugaauacg cacuauuugg cgcccuacag 2280
acuccugcuu acugguacuc cccuacaaaa uaaauuacca gaauuauggg ccuuguugaa 2340
uuucuuguug ccuucgauuu ucaagaguug cuccacuuuu gaacaauggu ucaaugcgcc 2400
auucgcaaca acaggagaaa agguugaguu aaacgaagaa gaaacuaucc uuaucauccg 2460
ucgucuucac aaaguacuca ggccguuucu ccugagacgu cucaagaaag aagucgaauc 2520
ucagcuucca gacaaagugg aauauaucau aaagugugac augucgggcc uacaaaaggu 2580
ucucuaugca cacaugcaga gcaagggugu guuacuuacc gaugguuccg agaagggcag 2640
uaaaggaagg ggaucuaagg cacugaugaa caccauuaug cagcugagga aacugugcaa 2700
ucauccguuu auguuccaaa auaucgaaga gaaauauugu gaucauguug guauugcugg 2760
uggaguggau ucuggacccg acacuuauag gguaucuggu aaguuugagc ucuuggacag 2820
aauauugccc aaaaugaaag caacuaacca uaggauucuu cuuuucuguc aaaugacuca 2880
auuaaugacc aucauggaag auuaucuaaa uuggagagga uucaaauauc uucgucuuga 2940
ugguacaauc aaaucagaag aucgcgggga ccuauuaucg aaauuuaaug auaaaaauag 3000
ugaauauuuu uuguuuuugc uaucuacacg ggcuggaggu cugggacuua auuugcagac 3060
agcugauacu gugauuaucu ucgauuccga uuggaauccu caucaggauu uacaagcuca 3120
ggaucgagcu caucguauug gacagcaaaa ugagguccga guuuugcguu ugaugacugu 3180
uaacucuguu gaggaacgaa uuuuagcugc agcuaaauac aagcuuacua uggacgaaaa 3240
ggucauucaa gcugguaugu ucgaucagaa gucuacaggc ucagagagac aucaguuuuu 3300
gcagaguauu uuacaccaug acggaagcga cgaagaagag gaaaacgaag uuccugauga 3360
cgaaacagug aaccagaugu uggcccgaag ggaaaacgaa uuucagcuuu uccagaagau 3420
ggaucaggaa agaaaggaag aagaugaaaa gaccggaaag ucgcgacuua uucaagaaag 3480
cgaauugccc gaauggcugu ugaagcaaga cgaugaaauc uacucguggg gccuugauga 3540
uccagaugcu guuuuaggaa gggguaguag gcaaagaaaa gaaguugauu auguugacag 3600
ccugacggag aaagaguggc uuaaggcuau ugacgaagag ggagaauuug aggaagaaca 3660
agaaggugau aaagaagguc ucagaaagaa aagagggagg aagaggaaga agcgcgauga 3720
ugacgaagag gcaagccaaa uuaagagaag aaaggugcau cuagccgaga ucaagaugaa 3780
gaaaaagaug aagaggcuua uggaaguugu ugugaacuac agggacaggg augguagagu 3840
auugagcgaa ccguuuauga aacuuccauc aaagaaggag uuaccugagu auuacgauac 3900
gauuaagaaa ccuauugaua uugaaaaagu cguugccaac guagaagaag gaaaauauuu 3960
cacgaugcac gauuuggaaa gagauuucga cuugcugugc caaaacgccc aacaauacaa 4020
cgaagaagac uccaugaucu acgaggacag ccucguucuu cgacaggugu uuagaagcgc 4080
gagggaaaag aucgacggua ccucagacca cgacgacaac gccgauggac cggcgguggc 4140
ucagaucaaa cgaccucgug guagaccucg aaaacacaag agacccgaag agaucgaggc 4200
cgaagcggcg gcucagaaag cuauggagga ggcaucgaag cugagagcuc aagcugaggc 4260
ggaagagcuu agaucuaagg uggaggaggc aucucagaga gccaaagagg aagcgaaagc 4320
aagggaggaa gccaaagcua gggaagaagc cgaaaucgag aacauggagg agauucccac 4380
aagcacauga ucuauagagc aaccggaaac aaaaaggcaa aaaagaaaua uuauauagaa 4440
aagauguaca uguucaaugg agauacauuu ucgccgaguu acaacgggua augcuuuuac 4500
aacggauauu uugacguaug aauguugacg uucagaugaa guauauuuau aaaauaaucc 4560
agaccuuuac guuuugguug auuuguuuuc uguauuguuc aguuuauuga acaaccauua 4620
auagcagcuu accuaaauga uuuagaaaag caucugaguu auuuagauaa guuuugagau 4680
uauauuuauu aacuuuaaua uuacuaucuu uauuauagca uauuguaauu auuuuuuccu 4740
guccuucuuu cguugugugg uagauaaucc gagagucaac aguuauaagc aaaugaaauu 4800
caguuaaacc ucaaauguac aaaaugauca aauuaauguu uacaauuuau uuuuuuacca 4860
cgcacauuca cuauuacuau ugucagucau ugagauauca uuuuauauag cuccaugucu 4920
gucuuccuca auuuacagag aagcaauuag acaaguaaug acauaaauag gugcugaaau 4980
aaugugcuug auagugaugu ucacaaagua acuauucguu acaaaguacu cguuacuuac 5040
aaauaccgaa acuaacgauu acuauacaga gaggcaaauc guuacuuuga uuacacugau 5100
uacuucguau caaucguauc agagcgagua acga 5134

<210> SEQ ID NO 138
<211> LENGTH: 538
<212> TYPE: RNA
<213> ORGANISM: Diabrotica virgifera

<400> SEQUENCE: 138
aguguauuag caaaaauccc auuuaaauau augaucauag augaggguca ucguaugaaa 60
aaccaccacu gcaaauugac ucaaguccug aauacgcacu auuuggcgcc cuacagacuc 120
cugcuuacug guacuccccu acaaaauaaa uuaccagaau uaugggccuu guugaauuuc 180
uuguugccuu cgauuuucaa gaguugcucc acuuuugaac aaugguucaa ugcgccauuc 240
gcaacaacag gagaaaaggu ugaguuaaac gaagaagaaa cuauccuuau cauccgucgu 300
cuucacaaag uacucaggcc guuucuccug agacgucuca agaaagaagu cgaaucucag 360
cuuccagaca aaguggaaua uaucauaaag ugugacaugu cgggccuaca aaagguucuc 420
uaugcacaca ugcagagcaa gggugugaua cuuaccgaug guuccgagaa gggcaguaaa 480
ggaaggggau cuaaggacaa cuagaugaac accauuaugc agcugaggaa acugugcu 538

<210> SEQ ID NO 139
<211> LENGTH: 352
<212> TYPE: RNA
<213> ORGANISM: Diabrotica virgifera

<400> SEQUENCE: 139
uugaacugua uuaggagaga uauaacgcuu gaaucugcug uaaauuuuaa agcauauaaa 60
agaacgaagc gacagggucu aaaagaaucg agagcuacag agaaguuaga aaaacaacag 120
aaguuagaag cagaaagaaa gagaagacag aagaaccaag aauuuuugaa ugcuguauug 180
aacaauggaa aagaauucaa ggaauuccac aagcagaauc aagcgaaauu agcuaagauu 240
aauaaagcug uuauuaauua ucacgcuaau gcugaaagag agcaaaagaa agaagcagaa 300
aggagagaga aggaacguau gaucagauug auggcagaag augaagaagg uu 352

<210> SEQ ID NO 140
<211> LENGTH: 459
<212> TYPE: RNA
<213> ORGANISM: Diabrotica virgifera

<400> SEQUENCE: 140
augaggguca ucguaugaaa aaccaccacu gcaaauugac ucaaguccug aauacgcacu 60
auuuggcgcc cuacagacuc cugcuuacug guacuccccu acaaaauaaa uuaccagaau 120
uaugggccuu guugaauuuc uuguugccuu cgauuuucaa gaguugcucc acuuuugaac 180
aaugguucaa ugcgccauuc gcaacaacag gagaaaaggu ugaguuaaac gaagaagaaa 240
cuauccuuau cauccgucgu cuucacaaag uacucaggcc guuucuccug agacgucuca 300
agaaagaagu cgaaucucag cuuccagaca aaguggaaua uaucauaaag ugugacaugu 360
cgggccuaca aaagguucuc uaugcacaca ugcagagcaa gggugugua cuuaccgaug 420 guuccgagaa gggcaguaaa ggaaggggau cuaaggaca 459

<210> SEQ ID NO 141
<211> LENGTH: 812
<212> TYPE: RNA
<213> ORGANISM: Artificial Sequence
<220> FEATURE:
<223> OTHER INFORMATION: Brahmav1 hpRNA

<400> SEQUENCE: 141
gcgcccuaca gacuccugcu uacugguacu ccccuacaaa auaaauuacc agaauuaugg 60
gccuuguuga auuucuuguu gccuucgauu uucaagaguu gcuccacuuu ugaacaaugg 120
uucaaugcgc cauucgcaac aacaggagaa aagguugagu uaaacgaaga agaaacuauc 180
cuuaucaucc gucgucuuca caaaguacuc aggccguuuc uccugagacg ucucaagaaa 240
gaagucgaau cucagcuucc agacaaagug gaauauauca uaaaguguga caugugacua 300
guaccgguug ggaaagguau guuucugcuu cuaccuuuga uauauauaua auaauuauca 360
cuaauuagua guaauauagu auuucaagua uuuuuuucaa aauaaaagaa uguaguauau 420
agcuauugcu uuucuguagu uuauaagugu guauauuuua auuuauaacu uuucuaauau 480
augaccaaaa cauggugaug ugcagguuga uccgcggaca ugucacacuu uaugauauau 540
uccacuuugu cuggaagcug agauucgacu ucuuucuuga gacgucucag gagaaacggc 600
cugaguacuu ugugaagacg acggaugaua aggauaguuu cuucuucguu uaacucaacc 660
uuuucuccug uuguugcgaa uggcgcauug aaccauuguu caaaagugga gcaacucuug 720
aaaaucgaag gcaacaagaa auucaacaag gcccauaauu cugguaauuu auuuuguagg 780
ggaguaccag uaagcaggag ucuguagggc gc 812

<210> SEQ ID NO 142
<211> LENGTH: 822
<212> TYPE: RNA
<213> ORGANISM: Artificial Sequence
<220> FEATURE:
<223> OTHER INFORMATION: Brahmav2 hpRNA

<400> SEQUENCE: 142
cauauaaaag aacgaagcga cagggucuaa aagaaucgag agcuacagag aaguuagaaa 60
aacaacagaa guuagaagca gaaagaaaga gaagacagaa gaaccaagaa uuuuugaaug 120
cuguauugaa caauggaaaa gaauucaagg aauuccacaa gcagaaucaa gcgaaauuag 180
cuaagauuaa uaaagcuguu auuaauuauc acgcuaaugc ugaaagagag caaaagaaag 240
aagcagaaag gagagagaag gaacguauga ucagauugau ggcagaagau gaagaagguu 300
gacuaguacc gguugggaaa gguauguuuc ugcuucuacc uuugauauau auauaauaau 360
uaucacuaau uaguaguaau auaguauuuc aaguauuuuu uucaaaauaa aagaauguag 420
uauauagcua uugcuuuucu guaguuuaua aguguguaua uuuuaauuua uaacuuuucu 480
aauauaugac caaaacaugg ugaugugcag guugauccgc ggaaccuucu ucaucuucug 540
ccaucaaucu gaucauacgu uccuucucuc uccuuucugc uucuuucuuu ugcucucuuu 600
cagcauuagc gugauaauua auaacagcuu uauuaaucuu agcuaauuuc gcuugauucu 660
gcuuguggaa uuccuugaau ucuuuuccau uguucaauac agcauucaaa aauucuuggu 720
ucuucugucu ucucuuucuu ucugcuucua acuucuguug uuuuucuaac uucucuguag 780
cucucgauuc uuuuagaccc ugucgcuucg uucuuuuaua ug 822

<210> SEQ ID NO 143
<211> LENGTH: 5146
<212> TYPE: RNA
<213> ORGANISM: Diabrotica virgifera

<400> SEQUENCE: 143
uugagaacga gaacacgaac gaguguaucg ucguguuucu uuuucuuugg uuauugugua 60
aauuaauuac aaacguguua aaauuuacuu aaaguuagug auuuguguau uuauaguuug 120
uaagugaugg caucagauga agaaguggag gauucuuucg ccggggagga agaugccccc 180
gacgauacgg cugaacaaau agauaacgau ccugauucug aagaugguguu uccuaaagga 240 ggggaagaag augaugauua ugaaccagaa gauuccagaa agaaaaagaa gggaaagaaa 300
agaaaagcca ggggagaaga aaagaaaggc aagaaaaaga agaaaaagcg aaagaaugau 360
aguggggaug aaagugacuu uggagaagau gauaauggag guggggacuc agauuaugca 420
agcaguagua aaagaggaag gaaaaagggu ucuacuaaac acucuucugc aucaucaaca 480
ccaacaccag cuagugacuc uggcacagga ggcaugccca ccaucgagca aguuuguuca 540
acauuugguu uaacugaugu cgagcuugac uauucagaug cugauaugca aaacuugacc 600
accuauaagu uguuccaaca gcaugugaga ccgcuccuug cuaaggaaaa uccaaagguu 660
ccuaugucaa aguugaugau guugguugcu gcaaaauggc gcgaauuuuc uaauucaaac 720
cccaaucugc aaagcgaaaa ugaaccgucu gcugcaacuu caaccacauc ugaagaaagu 780
uauccaaaaa cuaaucguuc gagagcaucc aaggaagcag cacaaaagau aguagaggcu 840
gacucugagc cauaugauga cgaauuugau gacgaagacg aggaggaaaa agaagagaaa 900
ggaaagaaaa aaaagaguaa uagaggaagg ccuaguaaaa agaaggcuac uaaaguacca 960
acuuuaaaga uuaaacuagg aaagaggaag cguggaaguu cggaugaaga gggcgaucuu 1020
aguggaggug gcucugaucg cgauucugau gcugaguuug agcagaugcu acaagaagcu 1080
gaagaaccaa aauccaacaa aucuaccacu ggugaagaau ccgcacagcc aucagaauca 1140
ccugcagaug aaaauccacc accaaaacgc aaagcgaaaa ccaaaauugg uugcaaaaca 1200
aagagaaaga agaaaacaaa gagugguaaa ccugaagaug aaaauuauga acaucaagau 1260
uacugcgagg uaugucaaca agguggagaa auuauccucu gugauacuug cccuagagcu 1320
uaccacuugg uuugccugga accugaauua gaagaagccc cugaaggaaa guggagaguugc 1380 ccucauugug agaaugaagg uccggcugaa caagaugaug acgagcauca agaauucugc 1440
aggguuugca aagauggugg cgaacuuuug uguugcgauu ccuguacauc ugcguaccac 1500
acgcacuguc uuaacccgcc acuucccgaa auaccugacg gcgauuggaa auguccuagg 1560
ugcgguuguc cgccucuugu gggcaaaguu gcgaaaauuc uuacguggaa auggguugau 1620
gauccuccua aaaagaagga caauggugaa gaggagccuc cuacacgaca uagagaguac 1680
uuuguuaagu ggcaugagcu aucauauugg cauuguaguu ggauaaccga gcuucaauug 1740

-continued

```
gauguauauc auccucucau guuucgaagu uauucaagaa agugggacau ggaagagccu   1800
ccuaaacuug aagaaccuau ggaugaagcu gacacuagau guagcagauu ccugaaaaug   1860
gguggaaaca acaacgacga ugaacucgaa gagaaguauu acagauacgg aauaaaacca   1920
gaauggcuaa uaguccaucg ugucaucaac caccguacga ugcgagacgg aagaacuuug   1980
uacuuaguaa aauggcgaga gcuaacuuac gaucaagcua ccugggaaga agauucugac   2040
gauaucccag cccuaaaguc ugccaucgaa uauuacacag auucaagagc ugcuaauuua   2100
uccggagcug gagguaagcu aaagaagaaa guuggaagga agccgaaagc uaaagaacuu   2160
aucgaugacg acgauagaaa cgguccucgc agauauacuc caccgccaga uaagcccugc   2220
agugaucuga agaagaaacu agacaaacaa cccucauauu uggacgagag uggauugcuu   2280
cacgaguacc aacuagaggg ucuuaacugg cuucguuauu cgugggccaa cgguauagac   2340
acuaucuuag ccgacgagau gggucucggu aaaaccauuc aaaccauugu cuucuuguau   2400
ucgcucuaca aggaagguca cugcaaaggu ccguuucuaa uuagaguccc acuuucaacg   2460
aucaucaauu gggagagaga auucgaaaau ugggcaccug auuuuuauug uauuacauau   2520
guuggugaca aggacugcag agccgugauu cgugagaacg aacucaguuu cgaagauggu   2580
gcugucagag gaggucgagc uucgagaauc agagccgguu ccaucaaguu uaacguuuug   2640
uugaccagcu acgaauuaau uucgaucgau ucggcauguc ucgguucuau cgaaugggcc   2700
guuuugguag ucgaugaagc ucauagauug aaaagcaauc aaucaaaauu cuucaaaauc   2760
uuaaacgcuu auaauauagc uuauaaacuc cucuugaccg gaacaccgcu ucaaaacaac   2820
cucgaagaau uguuccauuu guugaacuuc cucaacgguc agaaauucaa cgaucuccaa   2880
aacuuccaag ccgaauucgc cgacauuucg aaagaagacc aagugaagaa auugcacgag   2940
auguugggac cucauaugcu gcgucgucuc aaggccgaug ugcugaagag caugccuucg   3000
aaaucugaau uuaucgucag agucgaauua ucgcccaugc agaagaaaua uuauaaauau   3060
auuuugacga ggaacuuuga agcuuuaaau ccuaaaggag gcggacaguc gguaucuuua   3120
cuuaacauua ugauggaucu caagaaaugu ugcaaccauc ccuaucuuuu cccagccgcc   3180
ucggaagaag cuccgcuggg uccccauggu aauugggaug uaggucauuu gauuaaggcu   3240
ucaggaaagu ugguguuauu agcgaagaug uugaagaucc uuagagaaca gggucacaga   3300
guguugaucu ucucgcaaau gacgaagaug uuggauauaa uggaagauuu ucuugaagga   3360
gaaggguaua aauacgaacg uauugauggg gcuauuacug guaaucuccg ucaagaagcu   3420
aucgauaggu uuaacgcucc aggugcuccc caguuuguuu uccuuuuguc cacuaaagcu   3480
ggugguuugg gcaucaaucu ugcuacagca gauacuguaa ucaucuauga uuccgauugg   3540
aauccccaca augauauuca ggcauucucc agagcucauc guaucgguca agccaacaag   3600
gugaugaucu accguuuugu aacacguaac aguguggaag aacguguuac gcaaguagcc   3660
aagcggaaaa ugauguuaac ucacuuggua gucagaccug gaaugggcgg aaaaggugcc   3720
aacuuuacua agcaagaguu ggacgauauu cucagauucg guacugaaga auuguuuaaa   3780
gaaagugaag gcaaagaaga cgaagccauu cacuacgacg acaaagcugu gggagaauug   3840
cuggaucguu cuaaagaagg cauagaacag aaagagaguu gggcgaacga auaucucagu   3900
ucauuuaaag uggcuaguua uguuacaaaa gaaggggaag uugaggaaga aguugacacu   3960
gagauuauua aacaagaagc ggaaaauacc gauccggccu acuggaucaa gcugcuuaga   4020
caucauuaug agcaacaaca ggaagauaua gcuaggacgu uaggaaaagg caaaagagug   4080
```

```
aggaaacagg uuaauuauaa ugacggagga augacaacug acacacgaga agauacgaca   4140
uggcaagaaa aucucucuga uuaccauucu gacuuuucug cgggaucgga ugaggauaag   4200
gaagacgaua aggaagacga ugauucgaug agaagaacga cgccgauuua agcagaagga   4260
gucgaagaaa gauggaaagg aaagacgaga aggaucgucc uuuaccaccg uuacuagcca   4320
gaguuggcgg caauauugaa guacucgguu uuaaugccag gcagcguaaa gcguuccuua   4380
augcuauuau gcgcuacgga augccaccac aagacgcuuu caauucacag uggcuggua   4440
gagaucuucg aggaaaaucu gagaagauau ucaaggcuua cgugucucuc uuuaugaggc   4500
aucuuugcga accuggugca gauaaugcug auacguuugc ggacggugug ccgagggaag   4560
gacugaguag gcaacauguu uugacaagga uuggugugau gucacuuaua agaaagaagg   4620
uucaggaguu cgaacacauc aacggcgagu auagcaugcc ggaaguaauc aaaaagagca   4680
uuauggauca aaauaaaauc aaugccgccg gcaccgccac cacaagcgaa gcagaaacgc   4740
cuaaaagugc uacuaccagu acuagugcua cgccagcuac aagugcugcu cccagucccg   4800
cucccacaca aggagaagau aaagauaagg auaaagauuc cguucagagu gacgaaaaua   4860
aagauaaaga agugguuaau aaaacggaaa ccgaagauga agagaagaaa acgggagaau   4920
cuucaacaga aaagccgaaa acugaaccgg aagaagugaa agaagcuucu ccgaaaaccg   4980
aaauuccuga agcuaguucc gaagcugaua aaucugagau caaauccgaa gucgauaccu   5040
cgucuguaac cagcgaggaa aagaaagaag agaaagagga agaggccaaa aaagaagaac   5100
ccgaagagac caaaauggaa auacaggagg aggaacuugu uaaaga                  5146


<210> SEQ ID NO 144
<211> LENGTH: 3076
<212> TYPE: RNA
<213> ORGANISM: Diabrotica virgifera

<400> SEQUENCE: 144

agcggcggca gcacgcagca ggcaacacug gcaacagcag uuuuuuuaac gcgcgguggc     60
ugagaauuga gaaugcuguu guaaauuucu uuguuaauca aauaaaacuu uguuucaaca    120
uauugcaaaa uucaucuaaa cguucaacau gucacaaacu gaaggcucga cagaggcgag    180
cguaagugcc ucagaaccaa uggaagaagc agagaacucg gaauuggcuc aaaaugaaga    240
aucuucuuca gauacuaccu cuaaggguga agaguucgag gucaaagugg cuucugacag    300
aggaaaaaga uuugacuacu uguugaaaca gacugaaauc uuuucacauu uuaugaacca    360
aacaaaaucu cccaguaaac caaaaacugg gaggccuaaa aaagagaaga gugauacauc    420
ugauuuaaga caucguaaaa cugaacaaga agaagaugaa gaacuuuuag cagaaaccaa    480
ccuuaaaaca aagacuacaa cucguuuuga ugccucacca cccuacauca aacaugggga    540
aaugagagau uaucaagucc gugguuugaa cuggaugauu ucuuuguaug aacauggcau    600
caaugguauu uuagcagaug agaugggguu ggguaaaacu uuacaaacca uaucucugcu    660
uggauauaug aagcacuaua aaaguacacc ugguccucau auugucauug uuccuaaauc    720
uaccuuauca aacuggauga augaguucga gaaguggugu ccaaccuuga gagccguuug    780
ucucauuggu gaucaagagg cuaggagcuc auuuaucaga gauacgauga ugccuggga    840
augggauguu uguguaaccu cguacgaaau guguauuaaa gaaaaaucug uauuuaaaaa    900
guucaacugg agauauaugg ucauugacga agcucaucgu auaaaaaaug aaaaaucuaa    960
gcuuuccgaa auucucaggg aguucaagac uacuaacagg cuacugcuaa cagguacucc   1020
auuacaaaac aauuuacacg aacucugggc ucuucucaac uucuuacugc cagauguuuu   1080
```

caacucaucg gaugauuucg augccugguu caacaccagu caaugucugg gagacaacgc 1140
cuuggucgag agauugcaug cuguauuaaa accauucuug cuuagaagau ugaaagcuga 1200
aguggagaaa cggcuaaaac ccaagaagga guuaaaagug uauguaggau ugagcaagau 1260
gcaacgagaa ugguauacca aagugcugau gaaggauauu gauauaguga auggugcagg 1320
aaagguagaa aaaaugcgac uacagaauau ucucaugcag uuaagaaaau gcacaaauca 1380
ccccuaccuu uuugauggcg cugagcccgg accaccuuac acaaccgaug aacaucucgu 1440
guacaauugc gguaaaaugg uguugcugga uaaacugcuu cccaaauuga aggaacagga 1500
aucucgugua cuuaucuucu cucagaugac ccguauguug gauauacuug aagauuauug 1560
ucauuggcga caguaccaau auugucguuu ggauggucaa accccacacg aagacagaca 1620
gagacaaauc aacgaguaua acgaagacaa uagccaaaag uuuaucuuua uguugucaac 1680
uagagccggu ggauugggua ucaauuuggc cacagcugau guaguuauua uauaugauuc 1740
ggauuggaau ccccagaugg aucugcaagc cauggacaga gcgcauagaa uuggucagaa 1800
gaaacaaguc agaguuuuca gguuuauuac cgaaaacacu guggaagaaa aaaucgucga 1860
aagagcugaa guaaaauuac guuuagacaa auuaguuauc cagcaggguc guuuagccga 1920
uuccaaagca cagacucuaa acaaagacga aauguugaac augauccggc acggugccaa 1980
ccacguauuu gcuucuaagg auuccgaaau aacagaugaa gauaucgaua guauauugga 2040
aaagggagaa augaagaccg cucagcuagc ucagaagaug gaaaccaugg gcgaaucguc 2100
acuucgcaac uucacagucg aaacacccac ugaaucaguc uaccaauucg aaggagaaga 2160
uuaucgugag aagcagaaaa ccaucggcuu gagcaacugg auagaaccuc ccaaaagaga 2220
aaggaaggcc aacuaugccg ucgaugcuua cuucagagaa gcuuuaaggg uuucugagcc 2280
uaaagcgccu aaggcuccaa gaccaccaaa acagcccauc guacaagauu uccaguuuuu 2340
cccgccgaga uuauucgaac uuuuggacca ggagaucuac uuuuacagga aaucuuuggg 2400
auauaagguu ccgaaaaacu uagaacuugg accugacgcg uccaagcaac agaaagaaga 2460
gcaaagaaaa auagaugagu cagaaccgcu caccgaagac gaacagcaag aaaaagaaaa 2520
cuuguuaacg caagguuuca ccaauuggag uaaacgcgau uucaaucagu ucaucaaagc 2580
caacgagaaa uaugguaggg acgauauuga gaacaucgcc aaggauguug aaggcaaaac 2640
gccugaagaa guuauggaau auucugcggu guuuugggaa agaugucaug aauuacagga 2700
uauugauaga auaaauggccc agauugagag aggagaaacu aaaauacaaa gaagagcuag 2760
uauuaagaag gcacuugaug cuaaaauggc aagauaucgu gcaccauucc aucagcugag 2820
aauuucuuac ggcaccaaca aaggcaagaa cuacauggag gacgaagaca gguuuuuggu 2880
guguauguug cacaaguugg guuucgauag agaaaacguu uaugaagagu uaagagcagc 2940
uguacgugcg ucaccacaau ucagauuuga uugguucuua aaaucgagaa cugccaugga 3000
gcugcaaagg agaugcaaca cauugauaac guuaauagaa agagaaaaug cugaauugga 3060
ggaaagagaa aaaauu 3076

<210> SEQ ID NO 145
<211> LENGTH: 4137
<212> TYPE: RNA
<213> ORGANISM: Diabrotica virgifera

<400> SEQUENCE: 145
auggaaggcu cagagucgga aaauucagcu ucugguuccg guucagaaaa ugagagcaaa 60

-continued

```
agugauucca guaacaacuc uggaagcgcu ucugguaguu cuucuucgga cgguuccgau    120
acaggcgaag aaacuguaga aaauggaucg gccaauaaaa guaguaguaa aagugacgga    180
gaagaaguac uugaagaaag uaacgggugu agccaagauu caaacucuau accuccugcu    240
aguccagaua guucgaguaa auucgauacu accaaagauu uaaguucuga uaggaguucg    300
gaucccucua gcaucagacg aucaguuagg ucgcgaagag agccggaaag acuucagagu    360
aaagacagug auagggcuuc gagugauaaa agcaacaaaa gugcugaaga uuggaaauac    420
aaugacgcua guucgucaga gucugaacca gaaguaaaag aacgcccccc accuaguaaa    480
cgcguaggug ccagagcgcg aacgacugug auaaaaaaga aaaaguccaa gaaaagaagc    540
caauacaguu cagaagauga ggaaacgagc gacgaaagcg augaggauag uaggagagcu    600
guguccagaa ggaaggcuac uacaguuagu uacaaggaag aaagugagga ugagaaaacg    660
gauuccgagg auuugcuaga aguugauaau aaugaaccgg uagaaccugu cccggaagaa    720
aaaugugaaa caauagaaag aauuuuggca acgagaagag gaaaaauugg aguuaccgga    780
aacauuacua cagucuacua uguagaagaa aauggugauc cgaaugaagg aguugaugaa    840
aaggauuuag auaguacaga agaucaguau cuaaucaaau ggaaagauug ggcucauauu    900
cacaacacau gggaaucaga caaaaguuua cgagaacaga aaguaaaggg gaugaaaaaa    960
uuggaaaauu auaucaaaaa agaagucgaa auucaacagu ggcuuaaaua uucuacuccu   1020
gaggaugugg aauauuauga augucaaaug gaguuaucuc aggaucuuuu gaagaguuuc   1080
aacgaggucg agaggauaau agcaaaguac aauaagccug augggguaa agauuauuau   1140
auuaaauggc aaagucuucc auaugcugaa ucgacuuggg aagauucagu ucuaauucaa   1200
cgaaaauggc cugaccaaau aaaugaauuc gaagcuaggg agcaaucaag uaugacccca   1260
acgagacacu guaaaguacu caaacauaga cccaaauucc acgaagucaa gacccagccu   1320
gaauauauga ugggcaaaga acagacuuug auacugcgug auuaccaaau acauggucuc   1380
aacuggauga uacauuccug gucaaaagaa aacucuguua uauuagcaga cgagaugggg   1440
cucgguaaaa cgauucagac aauuugcuuu cuauacuauc ucuucaauac ucaccaccuc   1500
cacggaccau uuuugugugu ugugccccuu ucuacaauga cgucguggca gagggaaaug   1560
acacaguggg cacccgacuu gaacuuuguc acauacuugg gagauguuca guccagagau   1620
acgauucgcc aauaugaaug gugcuuugaa gggucaaaaa ggcuaaaguu caaugcaauu   1680
cucacaacgu augaaauugu uuugaaggau aaagcauuuu uaggaagucu cagcugggcu   1740
guguuacuag uagaugaagc ucacagguug aaaaacgaug auucuuuguu guacaaagcu   1800
uuaauggaau uugacacuaa ucacaggcuu cuuauuacug guacuccuuu acaaaauagu   1860
uuaaaagaac uuugggcgcu gcuacauuuu aucaugcccg cuaaguuuga aacaugggac   1920
gaauucaaaa gagaacacga aaacaccaca aacuccacaa acuauaccaa acuccacaaa   1980
caacuugaac cguuuauuuu aagacgggua aagaaagaug uagaaaaauc ucuccccgcu   2040
aaaguagaac aaauucuuag gguagagaug acgucuaucc agaaacaaua cuauaagugg   2100
auauuaacaa aaaauuauaa ugccuugaga agaggaguca aaggauccac aacaaccuuc   2160
uuaaaauauug ugauagaacu gaagaaaugu uguaaccauu cgucuuugau caagcccca   2220
gauauugaaa cacaauacaa ucaacacgac guuuugcagc aacuucucag agguucggga   2280
aaauuagugc uucuggauaa auugcuuauc cguuugcgca auacuggcca uagaguacua   2340
aucuucucgc agauggucccg gauguuggac auucuugccg aauauuugca gcuucgacau   2400
uucccguuuc agaggcuaga ugguggcauc aagggagagc ugcgacguca agccuuagau   2460
```

cauuucaaug cugaagggguc ucaagauuuu ugcuuccuuc uuucaacucg cgcagggggc 2520
uugggcauua auuuagcuac ugcugauacu gugauaauuu uugauucgga cuggaauccu 2580
caaaacgauc uucaagcgca ggcaagagcu cauaggaucg gucaaaagaa ccaagucaac 2640
auuuauaggu uaguuacugc uagaucugua gaggaagaaa uuguagaaag ggcaaaacaa 2700
aaaaugguac uggaucaucu uguaauucag agaauggaca cgacgggaag aaccguuuug 2760
gacaaaaagg ggucuucuaa uaauaauccg uuuaacaaag aagaucugac ggcgauuuug 2820
aaauuuggag cugaggaauu auuuaaagau gaagaugacg augaggaacc aaacugugau 2880
auugacgaaa uucuucgacg agcugagacc agagaugaag cuccuucauu gguuggagau 2940
gaacuacuuu cggcauuuaa aguagcaagu uucgccgcuu uugacgaaga ugccgagccc 3000
ucaccaguca acaauguugu uaacgacgau gaaaguaaag acugggauga aauuauucca 3060
gaaaaacuuc guaucaaggc agaggaagag gaaaagaaca aggaaaugga agaucuuuau 3120
cuuccuccgc gaagucgaaa aacucuucaa cagauuaauc aaucugaaag ugacggggaa 3180
gaaggcaaag guaggaagaa aacgaagaaa gauggagaug aaucgggagg uuccaguggc 3240
gaugaugaca cugacgagga aaaaccuaaa aaacgaggaa ggccaccagc aaaccccaga 3300
gaaaaguuca agaacuucac ugaugcugag auuagaaggu uuauaaaaag uuauaagaaa 3360
uuuaguggac ccuuaaagcg auuagaggca guugcuugug augcugaauu gcaagaaaaa 3420
ccauuagcug aguuacggaa auugggagaa cuucuucaug agaggugcag ggcauuuaug 3480
aaugaacaag cuaaagaaaa uacagagucu aacacucaag acgaacccaa aggucgcaaa 3540
agaggaccau cguuuaaaau uggaggagug ucuguaaaug ccaaaacgau gauggcuugu 3600
gaggaagagu uagaaccauu agaugaaguc auuccagcug auccaaauga acgauuacgu 3660
uggguuuuug auguaaaaac gaagucgucu cacuuugaug uggacugggg uauggaagag 3720
gacacuaagu uauugaaagg aauuuaucac uauggucuug gcucauggga gcaaauaaaa 3780
uuggauccau uauuaggcau uggugauaaa auuuuccuua auaaugaaga uaaaaagccg 3840
caggcuaaac aucuuuuauc aagagcagaa uacuuauuaa agauuaugaa aaagcaauua 3900
gaucuaaaga agggggguuca aaaaccaaaa agacagagga aaaaagaaca aaaaguucuu 3960
acuaaggaaa uuauugauga cgaugaaagc ucaaaugaug uuucaucauu accaaguucc 4020
gcuccaguua caguaucagu agcuccgguu guuaaaaagg uaaagaaaga agugaaaaaa 4080
gaaaaggagg auaaagaaga auccucgccc gagaaaaagg aaaaaaaaga aggauaa 4137

<210> SEQ ID NO 146
<211> LENGTH: 767
<212> TYPE: RNA
<213> ORGANISM: Diabrotica virgifera

<400> SEQUENCE: 146
uacgagaugu ucaucgguug uguaaggugg uccgggcuca gcgccaucaa aaagguaggg 60
gugauuggug cauuuucuca acugcaugaa aauauucugu agccgcauuu uugccaccug 120
ugcaccauuc aguauaucaa uauccuucau uagcacuuug guauuaccau ucucgcugca 180
uuuugcucaa uccuacauac acuuuuaacu ccuucuuggg uuuuagcccu uucucuacuu 240
caauuuucaa ucuucuaagc aagaauggau uuaauacagc augcagccuc uccaccaugg 300
aguugccucc cagacauuga cuggguguuaa accaggcauc gaaaucauca gaugaguuaa 360
aaacgucugg caguaagaag uugagaagag accagaguuc auguaaauug uuuuguaaug 420

-continued gaguaccugu uagcaguagc cuguugguau ucuugaauuc ccugagaauu ucggaaagcu 480
uagucuuuuu cauuuuuuau acgaugagcu ucaucaacga ccagauaucu ccacuugaac 540
uuuuuuaaua gagauuuuuc uuuaauacac auuucauacg agguuauaca gacaucccau 600
ucaccaggca ucaucguauc ucugauaauu gaguuccuag ccucuugauc gccaaugaga 660
caaacagcuc ucaagguugg acaccacugc uggaacucau ucauccaauu ugauaaggua 720
gauuuaggaa caacgacaaa uaugaggacc agguguacuu uuauagu 767

<210> SEQ ID NO 147
<211> LENGTH: 3074
<212> TYPE: RNA
<213> ORGANISM: Diabrotica virgifera

<400> SEQUENCE: 147
cuuuguuaau caaauaaaac uuuguuucaa cauauugcaa aauucaucua aacguucaac 60
augucacaaa cugaaggcuc gacagaggcg agcguaagug ccucagaacc aauggaagaa 120
gcagagaacu cggaauuggc ucaaaaugaa gaaucuucuu cagauacuac cucuaagggu 180
gaagaguucg aggucaaagu ggcuucugac agaggaaaaa gauuugacua cuuguugaaa 240
cagacugaaa ucuuuucaca uuuuaugaac caaacaaaau cucccaguaa accaaaaacu 300
gggaggccua aaaaagagaa gagugauaca ucugauuuaa gacaucguaa aacugaacaa 360
gaagaagaug aagaacuuuu agcagaaacc aaccuuaaaa caaagacuac aacucguuuu 420
gaugccucac cacccuacau caaacauggg gaaaugagag auuaucaagu ccgugguuug 480
aacuggauga uuucuuugua ugaacauggc aucaauggua uuuuagcaga ugagaugggu 540
uugguuaaaa cuuuacaaac cauaucucug cuuggauaua ugaagcacua uaaaaguaca 600
ccugguccuc auauugucau uguuccuaaa ucuaccuuau caaacuggau gaaugaguuc 660
gagaaguggu guccaaccuu gagagccguu ugucucauug gugaucaaga ggcuaggagc 720
ucauuuauca gagauacgau gaugccuggu gaaugggaug uuuguguaac cucguacgaa 780
auguguauua aagaaaaauc uguauuuaaa aaguucaacu ggagauauau ggucauugac 840
gaagcucauc guauaaaaaa ugaaaaaucu aagcuuuccg aaauucucag ggaguucaag 900
acuacuaaca ggcuacugcu aacagguacu ccauuacaaa acaauuuaca cgaacucugg 960
gcucuucuca acuucuuacu gccagauguu uucaacucau cggaugauuu cgaugccugg 1020
uucaacacca gucaaugucu gggagacaac gccuuggucg agagauugca ugcuguauua 1080
aaaccauucu ugcuuagaag auugaaagcu gaaguggaga aacggcuaaa acccaagaag 1140
gaguuaaaag uguauguagg auugagcaag augcaacgag aaugguauac caaagugcug 1200
augaaggaua uugauauagu gaauggugca ggaaagguag aaaaaaugcg acuacagaau 1260
auucucaugc aguuaagaaa augcacaaau caccccuacc uuuuugaugg cgcugagccc 1320
ggaccaccuu acacaaccga ugaacaucuc guguacaauu gcgguaaaau gguguugcug 1380
gauaaacugc uucccaaauu gaaggaacag gaaucucgug uacuuaucuu cucucagaug 1440
acccguaugu uggauauacu ugaagauuac ugucauuggc gacaguacca auauugucgu 1500
uuggaugguc aaaccccaca cgaagacaga cagagacaaa ucaacgagua uaacgaagac 1560
aauagccaaa aguuuaucuu uauguuguca acuagagccg guggauuggg uaucaauuug 1620
gccacagcug auguaguuau uauauaugau ucggauugga auccccagau ggaucugcaa 1680
gccauggaca gagcgcauag aauuggucag aagaaacaag ucagaguuuu cagguuuauu 1740
accgaaaaca cuguggaaga aaaaaucguc gaaagagcug aaguaaaauu acguuuagac 1800
aaauuaguua uccagcaggg ucguuuagcc gauuccaaag cacagacucu aaacaaagac 1860
gaaauguuga acaugauccg gcacggugcc aaccacguau uugcuucuaa ggauuccgaa 1920
auaacagaug aagauaucga uaguauauug gaaaagggag aaaugaagac cgcucagcua 1980
gcucagaaga uggaaaccau gggcgaaucg ucacuucgca acuucacagu cgaaacaccc 2040
acugaaucag ucuaccaauu cgaaggagaa gauuaucgug agaagcagaa aaccaucggc 2100
uugagcaacu ggauagaacc ucccaaaaga gaaaggaagg ccaacuaugc cgucgaugcu 2160
uacuucagag aagcuuuaag gguuucugag ccuaaagcgc cuaaggcucc aagaccacca 2220
aaacagccca ucguacaaga uuuccaguuu uucccgccga gauuauucga acuuuuggac 2280
caggagaucu acuuuuacag gaaaucuuug ggauauaagg uuccgaaaaa cuuagaacuu 2340
ggaccugacg cguccaagca acagaaagaa gagcaaagaa aaauagauga gucagaaccg 2400
cucaccgaag acgaacagca agaaaaagaa aacuuguuaa cgcaagguuu caccaauugg 2460
aguaaacgcg auuucaauca guucaucaaa gccaacgaga aauaugguag ggacgauauu 2520
gagaacaucg ccaaggaugu ugaaggcaaa acgccugaag aaguuaugga auauucugcg 2580
guguuuuggg aaagauguca ugaauuacag gauauugaua gaauaauggc ccagauugag 2640
agaggagaaa cuaaaauaca aagaagagcu aguauuaaga aggcacuuga ugcuaaaaug 2700
gcaagauauc gugcaccauu ccaucagcug agaauuucuu acggcaccaa caaaggcaag 2760
aacuacaugg aggacgaaga cagguuuuug guguguaugu ugcacaaguu ggguuucgau 2820
agagaaaacg uuuaugaaga guuaagagca gcuguacgug cgucaccaca auucagauuu 2880
gauugguucu uaaaaucgag aacugccaug gagcugcaaa ggagaugcaa cacauugaua 2940
acguuaauag aaagagaaaa ugcugaauug gaggaaagag aaaaaauuga uaaaaagaaa 3000
aaaguuucca aaucuucaaa ucuuggaggu auuccugccc aaaucagcuc gaaaucuuca 3060
cagaaacgga agaa 3074

<210> SEQ ID NO 148
<211> LENGTH: 4998
<212> TYPE: RNA
<213> ORGANISM: Diabrotica virgifera

<400> SEQUENCE: 148
uuucaaauaa aauuuguucc uugauaauaa aaaaacaaag aaaauggagg uuaaauccaau 60 aauuagaacu cgacauauug uaaaauuaau gaaaaauggc cgcaaaauau uauguacuaa 120
gauugcccug auucuacaau aucucgaguu aaaauuauug gauuaaaguu uaguaaacgu 180
cauuuuguuu guuuuuuguu caaggaacaa auuuuauuug aaaauucuuu uuaucucuuu 240
uaguuuacga acuagaaccu uauaaauaau ucaauuguuc agcagccaaa aauacauaaa 300
aaauuugaaa aggucacagu gucuagcuga ccccuagauu caguuuaaaa auuaaaaaua 360
uuauuaaucg ucgggauaau cguagaacga auaacuugaa uacugcgcgu uacuauuuac 420
auuagagccu agguuggugc caucugaagg uaacgggacc ggcaaaggcc uugaugguuu 480
gcgaggucgg uauguuccuc uagaaccggc guuugacggg ccaccugguu uuaaacgggg 540
ucugccagga ccccgccgca uugaugggu uugagcagua gaacugcuag cuugagcagc 600
uccagaaacu uccaaaaagc agugggacgg ugaugaaugc aucgaagcug cagacauagu 660
aguagaaucu ggagacgguu gauccguuaa aaagauacua ccaggucccg gugauguaga 720
gacagaagaa cuauuagaua ucuggcggcc aagcccuguc guacggcuuc gagauccucu 780

-continued aggccguccc cuucgagaug acccucuucc aggaagccuu gguuugacag uugugccgua 840
uacauuguau acaguauauu uauucguaau ugccgaauca gauucaucau uguaaauguc 900
uacgccauca ucuaucagaa ugucguuaga auugacacuu aauggacugu ugggcccacu 960
uucgacgaca guacuaguag cuucuucuaa uguaacugau uccaguuuag cuuuuuuggg 1020
uuccaugcca acugguauug ucuuauauug uaauuuucgu uuccugucua acucuucgga 1080
aguauuaucg auuuucaaau gauauuuuug uaccaauuca ucaucaucca acagcaagga 1140
caccacuucc uugggcuuga guguauccgg uuuaaaguua ccaccgcuaa ugaccaauuu 1200
uugaaucucg cucuuuucuc uagcccuuug uaagaugcgu ucuucaauag aaccuuuaca 1260
aauuaaucug uacaccguca ccugcuuggu cugacccaac cgaugggccc uguccauagc 1320
cugcuggucc acagucgggu uccaaucacu gucguagaaa auuacaguau cugcagcagu 1380
uaaauugaua ccaaguccac cagcucuugu cgacaguaga aaaacaaaaa ugucugcucu 1440
ggcuuggaaa ucagcaacca uaucccuucg uucugauauu uuugaugaac caucuaaccu 1500
cauauacuua ugaugccugu gccacaugua uucuucuaaa agaucaauca ucuuugucau 1560
cugcgaauau auuaaaacgc gauguccuuc cucuuugagu cuuuuaagga guccaucaag 1620
uaccgacagu uuuccagaau cgguaacuaa acucuccuua ucugguauca caauauucga 1680
aaaaccguua acaggucuca aauuaucaac ugcauuaaac ggucgaggau guaaaguuuc 1740
ugcugauuua uaauucaauu uauuguuggu cgcuuucgac caguaagaau uaagagaguu 1800
gaaacuaaau ucgucuagau gacgcuguag aucccacgcu gcucuacgag aauaacaaua 1860
uaagccgagu ggggccgccg auacccuagg cauacaauaa aaaagaaagg cgggaauuuc 1920
agucuuugua cauuggaaca ccugaguuaa ccucuuuaug uaaggaaaau cagucaauau 1980
auuuuguauc ugguucacuc uauggucauu aacucuuaaa agugcaucau uuccugcguu 2040
aaguucuuua guuuuuaauc uaauauuuuu auguucaaca guuucuggag uggaaugaaa 2100
cacaugaucg guaugugugu aaaacacucu auuuccuuug uuuuguucag uaaaaacuaa 2160
aucaccaaau acaucacuac uucgaaucug auauugauuu aaacggaaaa aauuccucaa 2220
cuguaauguc ggccguuuuc uaaaggauau gucccauagu uuucuauaau auaauauuuc 2280
auuggauuuu uggcauucgu aauaauguuu ccaccugugc aaaauauucc cuugaaauau 2340
ccuaaaaaca ucuucagcug auaaacccaa aaagugacaa aaauuaaaaa ugguugggaug 2400 caaaccaucu ugaauagcau cuuuuauguc uccugguuug aaaaugaagu guuuccuaau 2460
uuucuccauu aaaauuucuc gaacauugaa aucauaaauu ugauaaggaa cuguguacug 2520
caaagaacuu auucuaaugg gagauuuggc gucucuucuc ucaaaaaguu cgggaugguu 2580
gcaaaccuuu cuaaacugca ucaccaaauu caucaaauuu gaaguaaaau ucuuaucuac 2640
agugugagaa ucuccccgc caacugugua auucaagaga ucuucaauuu ugauuuuuug 2700
uuuuagagcc aaauacaaua aauucugucu uguggucagu ggacaguaga ccauuacuuc 2760
uauuuuauca gacaguucau uuucaacauc uuucuugauu cuccucaaca uaaaagguuu 2820
uaaaaucaua uguaaacgag auaaguguuu uucaucgaua ccaguuuugu uuucagcaug 2880
gcuuucaaug ucuuuugaaa accauucguu gaacuccuca ugugagucaa agaguguugg 2940
cauaauaaaa ugcaauaagg cccauagcuc cgccauacug uuuuguauug ggguaccacu 3000
caacaacaau cuguuccugc aacuaaaacc uaauagaguc uuccaucuca uugaacuagu 3060
acuuuugaua gccugugcuu caucuaguau cauguauugc cauuuuauuc uauuaaagua 3120
uuuuauaucu guuauaacua uuugguagga aguuaccaca augugaaaac uagcgucuuu 3180

-continued uguauacaug ucuuucaaau cccaaaacug ccuuaaaauu uuucuuucgu uuggauuucc 3240
ccaauagggc accacuuuaa aauccggcac aaacuuggcc acuucuugcu gccaauugug 3300
caggguugag gccggagaua uuaucaaaaa agggccccag acagaauauu uuucagcuau 3360
gugacaaaga aacgcaauac uuugaacagu uuugccuaga cccauuucau cagcuagaau 3420
accacugauu cccugagagu auaaaauugc caaccaauuc aucccucuua guugauaucc 3480
uuuuaauuug ccucuaaaca uauuagguug uggcuguuca cccucuccau ugggaaauuc 3540
auuaagacac gaauuggcuu guuggucaaa augucuaguc cuugcuuuuu cacucugaaa 3600
ugcaucuaau gcauucuuuu uggccauuuc cuucauacuu ucacuaucgu aaguaucaca 3660
acuuaauuuu auugaacuuu ccucgucuag cuggcuuaaa auuagcaacu guucuucagg 3720
agaagccugu cccaauuucu uggacaugaa augagcauac agcucagucu gaguaauaag 3780
aaaguuuaau uuccucuguu gucgcuuggc uucuaccaac ucguggucaa uuuuucuuug 3840
uucuucugcu ucuuucucua accguuucuu aacuucucua ucaaaacgcc gugagcguuu 3900
ccaguaagca auauucucac gugauaaccu cuucauccuc cauggcuguu cuuugacuau 3960
ucgagcgcuu uggagagcuu uuugacgugc auauuuaaca caaugugaug ccacucguuu 4020
gcacugcagu agcauuuccu uguguuuguu aauuuuugau cuauguugcu uuccaauuuc 4080
uuuuuugacu auauuaguaa auaauuuucg ccgcuuuaug gucaucauau cuucccauuu 4140
ccgucuggac ucuucaucuu ugaauuuuuu uguuuuuuuc uuugguauau gaaguccuaa 4200
aggaggagga gguagagacu gauuuggaau gacaagucca uauucagaug gcaaauacuu 4260
aucagcuaua ucgucgaugc uuuggaaauc cauuccauuu uggagauuca aaucuaaaca 4320
ugguucaucc gaaauagcau ccaaaauauc aggaugguau aguggagacu uaaaugaguc 4380
uucuauuuua auuuuauuuu ucuugacagg uacugguaga uuuuuuucua cauguggaua 4440
aagaucuacu gcacugauca auccagcucc auaguaugca uaauuaucaa aauucucuuu 4500
ucuuuuucuu aaggauuuuu gauaugaaug caaccucaua acaugcuuau auuguacauc 4560
auccggacua cuaucugaac uuucuuguag aacaucagca agccauuucc uccuaguuga 4620
aacaguuuua agauuguaau acucauuggu agagugaggu ucugaaucuu uuaaaauaga 4680
aucuauauug acaucacuca gauugcccau gccaucauca gaaucgucag agucgcuacu 4740
uaacuguaau ugguugugua caucucguaa aaacauauua gugucgacag cuugcucaac 4800
ucuucuuaca ugaacugguu uagcuguaua ugaucuauua guuugaucaa gguagcuguu 4860
gguggguaau auuuuguaug auuuaucccu gccguuccac auuuuuucua aauguaauaa 4920
acuguuuuca gaauaucuau auaaauuaag cuaauauaau uuuacauuac auuacauucu 4980
caauuaguuc auuuuuua 4998

<210> SEQ ID NO 149
<211> LENGTH: 8026
<212> TYPE: RNA
<213> ORGANISM: Diabrotica virgifera

<400> SEQUENCE: 149
cgucgcuaug ucauauaaga ccaaugcguc auuuuugcug aacgcguaaa auguagaaaa 60
caggucuauu uugcaaauuu uuaaguuacg uggacuaccu aauuguauau uaaacuauua 120
gaaagacgau aaucauauuu uuuacugcgg augauuaacc uuaaugugaa uauuuuguga 180
uaacaugaug agaauucgaa gaugagugac gaaacuccgg ggguagggca gggugcucug 240

-continued

```
cccccgagag agggccaaag ccuucgacuc cuugcagagc gcccuacuag uggugcuacg    300
guaaggguag cccagguugu ugguggucag uauguguuga caacacaauc acaugguaug    360
ccagcucuag cacagauugc ugcugggaau cccaacguca cucgucugau aagcaucagu    420
ccaacuagag guggacaauc guccccacua aggcccaguu uggccaauca gucgaucguu    480
aauguucuua ccaagucucg accaaauccu aauguacgcu uacaguuauu ucaauccggu    540
gagaguucug gaaacaaugu ccagcauagu ccccauucga gaucacucaa aaggccguug    600
ucuuccacgg gugaaaaaaa agauagcuac gcuucuaagc ugcaacaugu aaugaaccau    660
cgcauuguuc gcucaaaauu aaugaaagaa aaguauaaug aacaucuucu agaggccuau    720
uauuuagaga ccggaaauaa cauucuagau uuauaucaau uugccaaaag accuaaaacc    780
caagcguauc uagcuuaucu uaaggaacau gccaucgauc cucgagauua uccugaacuu    840
cagacuacaa caacuguuac uguaccgcaa acgacgccua auacaccaac ugcuaccucu    900
gucagcucuc ugcccgguau cucucauagu uacgccaucc agacuaccag uucuacugua    960
acgacaccag aaaguaacag uaacaccucu acgccgaaau caguaucugu caaagugaag   1020
ucuacaucac uuccgaauac uguuagucaa gagaugauug uagagaaggc gaaacaagaa   1080
gcguacgugg uccaacgaau agccgauuua cagaaggaag gaauaugguc ugaaaggaga   1140
cuucccaaag ugcaagagau gccucggccu aaagcgcauu gggacuuuuu gaucgaagaa   1200
auggucuggu uggcagcuga uuuugcgcag gaacgcaaau ggaagaaagc cgccgcgaaa   1260
aaaugugcca gaaugguaca gaaguauuuc caagacaagg cgcucgccgc ccaaaaagcg   1320
gaaaaggcuc acgaacaaaa ucuuagaagg auagccgcgu ucugugcaaa ggagauuaag   1380
aucuuuugga acaacgucga aaaacucguc gaguauaaac agaauacaau cuuggaggag   1440
aagcggaaaa aggcgcucga ucagcagcuu aguuuuaucg uggaucagac ugagaaguau   1500
ucgcaguugc uugccgaagg aaugaauaag accgcagaac agccuccuag uucagcgcca   1560
ucucgaucag ugucucgaac gcagucugau acagaauucg auccggaucu ucagagcgau   1620
gaagacgacg aagagaccau ugcucgagaa gaagcuuuag guaacgaagg acauaaagaa   1680
gaaaucgaag cgcuacagaa agaaucucag auggaauuag acgauuuacu agaggacgau   1740
uuccugaggg auuaccuuuu aaaucgagac acgauccgau ucagcgaauc cgaagauucg   1800
gacgaugaca cggacucgaa aaaagaaucu uucaaaggcg acaaagaaca gucugacgau   1860
ucugaaucuu cuaaagaaga agauacggaa gacgagagcg aagaugaauc uaugaagguu   1920
acugaaucgg uuguuaaaga agaacacgac gaguugaaaa uauuaguaga agauucucaa   1980
aaagagggag aaauuaagac ugaacaagau acaaaagacg accuuaucaa ugacgcagcu   2040
gcuauagcug aaaguaucca accuaaagga aacacccugu cuucuacuaa uguaucaaca   2100
aauauaccau uuuuauuaaa auauacgcua agagaauacc agcacaucgg uuuggauugg   2160
cugguaacua uguucgacag aaaacugaac gguauauuag cagaugaaau ggguuuaggc   2220
aaaacaauac aaacgauagc ucuucuagca cacuuggcgu gcgagaagga aaacuggggc   2280
ccccaucuga uaguaguccc cacuucugug augcugaauu gggaaaugga augcaaaaag   2340
uggugucc gg cuuuuaaaau ucuaacguau uacggaacgc agaaggaaag aaaauuuaaa   2400
cggauaggau ggacgaagcc uaacgcguuu cacauaugca uuacuucgua caagcuaguc   2460
auucaggacc accagaguuu caggaggaaa aaguggaagu aucugauacu ggacgaggcc   2520
caaaacauca agaauuucaa gucgcaacga uggcagcugu uguuaaauuu ucaaacucaa   2580
caacgucugc uguugacugg uacaccuuug cagaacaacc ucauggaauu guggucccuu   2640
```

augcauuuuu uaaugccgaa cguauuucag ucgcauagag aguucaaaga augguuuucg 2700
aauccgguga caggaaugau ugaaggaaau ucugaauaca acgaaaguau uaucaagaga 2760
cugcacaagg uauuaagacc auuucuucua aggcgguuga aaagcgaagu ggaaaaacaa 2820
augccaaaaa aguacgaaca cguggucaug uguaggcuau ccaaacgaca gagguauuug 2880
uaugaugacu acaugucccg agcaaaaacg agggaaacuu uaacuacugg aaaucuguug 2940
aguguuauaa augugcugau gcagcugagg aaagugugua aucauccgaa ucuauuugaa 3000
auuagaccaa cgacaucgcc uuuucagugu gacaacaucc ggcuucauau uccauccauu 3060
guauauucag cuuuagauua cgauccugau aagcacguga accuucaagc uuuaaaucuu 3120
cuacuaauca ugcaagaaau ccacuuuggu ucguaccagu guuaccggau gagacaauca 3180
agaaauucca agaaaauuuu cgaaauggaa acgaauucua gcaaaaaucc accaccuugu 3240
ccgccaugua aguuagccau gcgaguucua acagacaaac cuucagccac ugacgaaaag 3300
aaugagaaga aagacaugca agcuuuaagu cagccgccuc cauugcaagu uaaaggaaug 3360
agccagccua acaugaagau gaagguuucu ggagugcaau uuguuccaca gagcauacuu 3420
aaaucaauuc caguagugaa cauaucacaa ggggcuacag gucaaaucgg agcaccuguu 3480
agugugacau cuguauuaaa accacaagac aaaauaucug cuaguuuugc acagcuaguu 3540
caaacgucua cuggcaaaca cuuguuacua acgucgaauc ccaacauuac gacgagccca 3600
gugacaacua caacaccagg uggacaaaaa uugaccuucc uaucgaagca gcccguuucu 3660
acgauuggua augcgggcca ugcuguaacg aaagcuuaug ucaaauuuca guuaacgucu 3720
guuacgacag caucaacuuu cacaacaguu acgacaguca acuccaauac gauaucugua 3780
gcuaaaagug aagauaacaa agggaugcga augucuguug guaaugauua uauagguaaa 3840
cuuuauucua aacaaaauag ccuggacgug cgauggaaua gcggcgaaaa acauuuaggu 3900
uuaacaaaug aagacgaucc caaaggugaa cgaaagaaga gacuuucccu caugucacgc 3960
aucaacaaga uccguugcuc agcucuucca cuguacggcc gagauuucca agaagcuguc 4020
aaaauauaua cgccuaacca gcuggauguu uggaacgggg gucauauuca cugcuugaac 4080
acacuguaca auaaggaugc caggaaugaa acgacggauu gucuccaaga cgcguuguuu 4140
aauccugaaa gaagauugga agcucuaaaa gauacuuuug aucgauuuau auucuaugua 4200
ccuucuguga aaguggcgga acccgaacug caaguguggc auccuccacc gaguaaauau 4260
uggggccaaa aacacgagaa acaacuuaua cagaaacuau uccuaaaacc ugcaacaccu 4320
cuucauagua uagcaucugc aaugguaacg caguuuccag auccuaggcu uauucaauau 4380
gacuguggga aguuacaaac ucuggauaua cuauugagga aguuaaaacu gggaagucau 4440
cgaguauuga ucuucacgca gaugacgaaa auguuggaug uacuagaggc auuuuugaau 4500
uaccacgguc auauauaucu uagguuagau gguaccacaa aaguugauca aagacaagug 4560
uugauggaga gguucaacgg ugauaaacgu auuuucgcuu uuauuuuguc cacgcguucc 4620
gggggcgugg guguaaauuu aaccggagcg gauacuguga uauuuuauga uuccgauugg 4680
aauccaacua uggacgcgca agcgcaagau cguugucacc gaaucgguca aacgagagac 4740
guacacauuu acaggcuagu uagcgagcga acgauagagg agaauauauu gaagaaggcc 4800
aaucagaaac gauugcucgg agaucuggcg aucgaagggg guaauuucac aacggcguac 4860
uucaagaguu cgacgauuca ggacuuauuc aacauagacc aaaacgaaga aagcgcaucu 4920
gcccgaaugu cagaaguugu cgaacugaga aaagaaagag agaaggcccu cagcacagac 4980
cugguucauu cugcugacga uaaagccacc gucggugcuc ucgaaaaugc uuucgaagca 5040
ugcgaggacg accaggacgu ccaagccgcg aaaacggcca aagccgaagc uguugcagau 5100
cuugcagagu uugaugaaaa cauuccucug gaugaucaag agaaagaacc ugagaucagc 5160
aaggcggaac aggaaauuaa uaauauuaua gaaaaguuaa cucccauaga aaaauacgcc 5220
augaauuuca ucgaggcaac agaaucugcg uggucugcag aacagcuugc agcugcugca 5280
agagagaucg aagaacagaa aaaggaaugg gagcagaacc gucuggcggc gaugcgagaa 5340
gaggaggaac gucgugcucg agaguuagaa gaagaaucug auaucaucac guauucaaga 5400
gaugacgcca ccaaccaggu uagcucaaaa aacaaaaaaa ucaauaggua uaauaaaauu 5460
uuaaguaaua aaaggguuag gcucaaaaaa gauggagaug aagacguuga gaaaaaagau 5520
gacgucgaga aaaaagaugg aguugaaaaa agguugaaga agacuaggac acgaaggcug 5580
ucucaaaaaa gcaaagaugu agaggucgaa gaaccggaug cuugugaauc acaagaagaa 5640
ucucaaauua acggagggga uacggauaau agugauagug auucugauuc ugauagcgaa 5700
ucuucaucuu ccauggaauc uaaaacuacc uuaaaccacg uugauccaaa uucaccuaga 5760
acuaggucua ggggcacagu ggcuauuaac cuuuggacac ucgaugucag cccgauuuug 5820
ccuggagaaa aaccgaugaa aaaauacggg gagaaccaua gaaaaaauau uaagaggguu 5880
agaucugugu cugaaaacga uaacgaugga gauaaagacg guagaaagcg auugaggagg 5940
aaauacccca ccaguuuaga aacaucagaa gaagaaaaca guaaccaguc aagagaaaaa 6000
ucuacuaaga aacgugccaa gguagcaccc aaagggaaaa cuuguaaagu aauuuuaagu 6060
aauauacuga acgauaaacg auuuaaaguc aacuuaaaag aagacauuga gauuucagug 6120
agcacacaaa uuaaugagac uuccaccagc ucaaaccaga aucaaaccaa agauugcgag 6180
ucuagucaac augagaauag caauuuagau gaacagaaug auucucuuga caauacagaa 6240
guuaccucau ccgaacuuag uaaauuaacu gguuguacug aaauagauaa uaacgaaagu 6300
aguaaacagg aaaaugaaga auuagacgaa ucuauacucg aagauaaaua ugaugaagau 6360
uucauuacaa acaaaaauga agacauagau gaagaaacac uccuugaaga agauaaucag 6420
auagagcagg uugaaaauaa aaauauugau agcacgaaag augaaaaaca gggugaugac 6480
aguaauguuu cagauguagg ucauuuaagu aaagauaacg auaaugagga aaaaauggaa 6540
guaacagaaa guguugacga ggaaaauggu gauaucaaua agaaaguaga ugaagaugag 6600
agcguuaaag auaaaagaga aaggagaaaa gguaaugagg aagaugauaa uacagacaau 6660
gaagaaaaca uccaaaaguc agaaaaugau gagggcgaua uuaaaaagca aggaaaucaa 6720
gaugaagaag uagaagagaa aaccuuagga aauucuacug aaucaguuaa cgaaauagca 6780
aaugaaauaa guagaugcaa accuuuaaau gagcagcaca acgaauuggu agaugaagua 6840
guaaaugaca caaguaauau ggaugaauau auaaaaaaau cggaaaauuc caaaguugua 6900
gaaaagacaa gugaagaaau acuauucaac gauaggggaa aucaagauuc aucgucccag 6960
gauguaaaag augaagagau aucaucccac aacagaggag augaaaaggu gucauuccac 7020
gauaggauag auaaagaggu auuaccugaa uguaggaaag aggaagagaa acacaauaga 7080
aaaaaugaag uacuaucaca aacuauaaaa gaugaagagg cacagaccca caauaggaaa 7140
gaugaaucgg guacauuucc aaacguagca gauauagaaa auagacuuaa caacaaaguu 7200
ccucacgucg auaaugguca uaccgaaacg gucagaaugu cuaaauuggu aacgucuaau 7260
agaaaugcca auuucagguc uccugaaacg agaagaagcu ucagaaagug ugguaaaauu 7320
ucgaacaauc agacuuuaga cgguugggug aaacggucgc cuguauuacc ugucgaagcu 7380
gcuaaaguaa acgauaacuc aaaauauaaa aauguugguu cgcccgaguu auagggagau 7440
uugacugugg aaagaggaga aauuuaaaag uuuuugauag uuaaaaaagu guuuauugau 7500
caauguacac ugcaauaagg uaauaacuca aaaauaauuu auuucuuuac aguuuucuuc 7560
uucauccacu ccuggacaaa ggccucacga aguguuuuac aaguuucuuu gauaacgggu 7620
aaaaccaaaa aauaguaaag uucgcauaac cuucuggcua augucuaguc uuaggguuca 7680
agucgcgcaa gcgcccagac cgaccgcuuu acgugccuuc cgaaugacgg cggcggcuca 7740
gaacaauuuc uuaaugucag ugccaggaau cuaaccuaga uccucuagcu uguuaaguca 7800
guaauaaaca uuaguucaac ggacauauug ucacuuuauu gcgcaugcgu uuaucauuac 7860
ugagucuuga guucugccua gccguaccgu ugacauauuc guaaagauug uaguaauaag 7920
gcaugcauca gaucuuuaua gauuucaaac augcuuauga cucaguuaca auucguccaa 7980
gacuauggaa ugguauaguu gagcuggaca uaccuaagaa auuagc 8026

<210> SEQ ID NO 150
<211> LENGTH: 240
<212> TYPE: RNA
<213> ORGANISM: Artificial Sequence
<220> FEATURE:
<223> OTHER INFORMATION: SNF2/Helicase degenerate dsRNA sequence
<220> FEATURE:
<221> NAME/KEY: misc_feature
<222> LOCATION: (216)..(216)
<223> OTHER INFORMATION: n is a, c, g, or u
<220> FEATURE:
<221> NAME/KEY: misc_feature
<222> LOCATION: (222)..(222)
<223> OTHER INFORMATION: n is a, c, g, or u
<400> SEQUENCE: 150
cgsyuhcuyy umacsggyac hccucuvcar aayaarcuwc chgaryusug ggcbyudcuh 60
aayuuyyuvc ubccsucbau yuuyaarwsb ugyucbacdu uygarcarug guucaaygcv 120
cchuuygcha cmacbggmga raarguygar yudaaygarg argaracvau yyukauyauy 180
mgdcguyudc ayaarguyyu kcgwcckuuy yuvyunmgdc gnyuvaaaaa rgargumgar 240

<210> SEQ ID NO 151
<211> LENGTH: 27
<212> TYPE: RNA
<213> ORGANISM: Artificial Sequence
<220> FEATURE:
<223> OTHER INFORMATION: SNF2/Helicase degenerate dsRNA sequence
<220> FEATURE:
<221> NAME/KEY: misc_feature
<222> LOCATION: (21)..(21)
<223> OTHER INFORMATION: n is a, c, g, or u
<400> SEQUENCE: 151
mghgcygubu gyyuhauygg ngaycar 27

<210> SEQ ID NO 152
<211> LENGTH: 60
<212> TYPE: RNA
<213> ORGANISM: Artificial Sequence
<220> FEATURE:
<223> OTHER INFORMATION: SNF2/Helicase degenerate dsRNA sequence
<400> SEQUENCE: 152
uayaarcuyc uvyusacmgg machccgyub caraacaayc umgargaryu ruuycauyur 60

<210> SEQ ID NO 153

<211> LENGTH: 61
<212> TYPE: RNA
<213> ORGANISM: Artificial Sequence
<220> FEATURE:
<223> OTHER INFORMATION: SNF2/Helicase degenerate dsRNA sequence

<400> SEQUENCE: 153
garuuygaya cbaaycaymg rcukcuhauh acwggbacyc ckyuvcaraa ywskyudaar 60
g 61

<210> SEQ ID NO 154
<211> LENGTH: 23
<212> TYPE: RNA
<213> ORGANISM: Artificial Sequence
<220> FEATURE:
<223> OTHER INFORMATION: Bromodomain degenerate dsRNA sequence

<400> SEQUENCE: 154
yuswsygaac cruuyaugaa ryu 23

<210> SEQ ID NO 155
<211> LENGTH: 65
<212> TYPE: RNA
<213> ORGANISM: Artificial Sequence
<220> FEATURE:
<223> OTHER INFORMATION: HAND-SLIDE degenerate dsRNA sequence

<400> SEQUENCE: 155
gchguvgaug cyuayuuymg vgargcwyuv mgdguyuchg arccyaargc dccdaargch 60 cchmg 65

<210> SEQ ID NO 156
<211> LENGTH: 36
<212> TYPE: RNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (33)..(33)
<223> OTHER INFORMATION: n is a, c, g, or u

<400> SEQUENCE: 156
mghaarurbg ayauggavga rvvdccbaar yungar 36

<210> SEQ ID NO 157
<211> LENGTH: 56
<212> TYPE: RNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (29)..(29)
<223> OTHER INFORMATION: n is a, c, g, or u

<400> SEQUENCE: 157
bhggdaarad dggrkkbryb ggmaaymwna chacdrusua ykmhruagar gaaaay 56

<210> SEQ ID NO 158
<211> LENGTH: 322
<212> TYPE: RNA
<213> ORGANISM: Diabrotica virgifera

<400> SEQUENCE: 158
aagaaggcau agaacagaaa gagaguuggg cgaacgaaua ucucaguuca uuuaaagugg 60

```
cuaguuaugu uacaaaagaa ggggaaguug aggaagaagu ugacacugag auuauuaaac    120

aagaagcgga aaauaccgau ccggccuacu ggaucaagcu gcuuagacau cauuaugagc    180

aacaacagga agauauagcu aggacguuag gaaaaggcaa aagagugagg aaacagguua    240

auuauaauga cggaggaaug acaacugaca cacgagaaga uacgacaugg caagaaaauc    300

ucucugauua ccauucugac uu                                               322


<210> SEQ ID NO 159
<211> LENGTH: 401
<212> TYPE: RNA
<213> ORGANISM: Diabrotica virgifera

<400> SEQUENCE: 159

ucacagucga aacacccacu gaaucagucu accaauucga aggagaagau uaucgugaga     60

agcagaaaac caucggcuug agcaacugga uagaaccucc caaaagagaa aggaaggcca    120

acuaugccgu cgaugcuuac uucagagaag cuuuaagggu uucugagccu aaagcgccua    180

aggcuccaag accaccaaaa cagcccaucg uacaagauuu ccaguuuuuc ccgccgagau    240

uauucgaacu uuuggaccag gagaucuacu uuuacaggaa aucuuuggga uauaagguuc    300

cgaaaaacuu agaacuugga ccugacgcgu ccaagcaaca gaaagaagag caaagaaaaa    360

uagaugaguc agaaccgcuc accgaagacg aacagcaaga a                         401


<210> SEQ ID NO 160
<211> LENGTH: 271
<212> TYPE: RNA
<213> ORGANISM: Diabrotica virgifera

<400> SEQUENCE: 160

uugcucaauc cuacauacac uuuuaacucc uucuuggguu uuagcccuuu cucuacuuca     60

auuuucaauc uucuaagcaa gaaugguuuu aauacagcau gcagccucuc caccauggag    120

uugccuccca gacauugacu gguguuaaac caggcaucga aaucaucaga ugaguuaaaa    180

acgucuggca guaagaaguu gagaagagac cagaguucau guaaauuguu uuguaaugga    240

guaccuguua gcaguagccu guugguauuc u                                    271


<210> SEQ ID NO 161
<211> LENGTH: 372
<212> TYPE: RNA
<213> ORGANISM: Diabrotica virgifera

<400> SEQUENCE: 161

gaucaaauuc aagcaacuag cgaaauugga aaaaaaauca gacgaagaac uuacugaaua     60

uuacaaacau uucguuauga ugugcaagaa gcagacaggc augaacauag aagacagcaa    120

cuaugacaau accaucgaac auaucucaga agaaaaggca cgaaggacau uggaaaggcu    180

ggagcuguug ucgaggauca gagaagaaau uuuaacccau ccuaaacucg acgaaagauu    240

gagggugugc auuacuucgg cugauaugcc ugaauggugg auugccggca aacacgacaa    300

ggaucucuug uugggggucg ccaaacaugg uuuaggaaga accgacuacu accuucugaa    360

cgauccugau cu                                                          372


<210> SEQ ID NO 162
<211> LENGTH: 315
<212> TYPE: RNA
<213> ORGANISM: Diabrotica virgifera
```

<400> SEQUENCE: 162
uuugcuuccu ucuuucaacu cgcgcagggg gcuugggcau uaauuuagcu acugcugaua 60
cugugauaau uuuugauucg gacuggaauc cucaaaacga ucuucaagcg caggcaagag 120
cucauaggau cggucaaaag aaccaaguca acauuuauag guuaguuacu gcuagaucug 180
uagaggaaga aauuguagaa agggcaaaac aaaaaauggu acuggaucau cuuguaauuc 240
agagaaugga cacgacggga agaaccguuu uggacaaaaa ggggucuucu aauaauaauc 300
cguuuaacaa agaag 315

<210> SEQ ID NO 163
<211> LENGTH: 449
<212> TYPE: RNA
<213> ORGANISM: Diabrotica virgifera

<400> SEQUENCE: 163
acuuaucuaa agggaugcua gcugaguucg augucauacu cacaacguau acgcugguug 60
gaaauaguuc agaagagaga aaaauguucc gagugacaag gaugcauuau guaaucuucg 120
augaagcaca uauguugaaa aauaugaaua cucuucggua ugaaaauuua auuaagauaa 180
acgcuaaaca uaggauacug uuaaccggca cuccguuaca aaauaauuua uuagaacuaa 240
ugucgcuguu gauauuugug augccgaaua uauucgcuga aaaaaggugg acuugaaaaa 300
cuuauuccaa aaaaauucua aaaaagcaga agacgacucu cuaccuaccu ucgaaaagga 360
gcaaauugaa caagccaaaa gaauuaugaa accuuuccuu uugcgaagac ugaaauguga 420
cguccuucgg gaucuuccca agaaaacgg 449

<210> SEQ ID NO 164
<211> LENGTH: 4125
<212> TYPE: DNA
<213> ORGANISM: Diabrotica virgifera

<400> SEQUENCE: 164
atggcatcag atgaagaagt ggaggattct ttcgccgggg aggaagatgc ccccgacgat 60
acggctgaac aaatagataa cgatcctgat tctgaagatg gtgttcctaa aggaggggaa 120
gaagatgatg attatgaacc agaagattcc agaaagaaaa agaagggaaa gaaaagaaaa 180
gccaggggag aagaaaagaa aggcaagaaa aagaagaaaa agcgaaagaa tgatagtggg 240
gatgaaagtg actttggaga agatgataat ggaggtgggg actcagatta tgcaagcagt 300
agtaaaagag gaaggaaaaa gggttctact aaacactctt ctgcatcatc aacaccaaca 360
ccagctagtg actctggcac aggaggcatg cccaccatcg agcaagtttg ttcaacattt 420
ggtttaactg atgtcgagct tgactattca gatgctgata tgcaaaactt gaccacctat 480
aagttgttcc aacagcatgt gagaccgctc cttgctaagg aaaatccaaa ggttcctatg 540
tcaaagttga tgatgttggt tgctgcaaaa tggcgcgaat tttctaattc aaaccccaat 600
ctgcaaagcg aaaatgaacc gtctgctgca acttcaacca catctgaaga aagttatcca 660
aaaactaatc gttcgagagc atccaaggaa gcagcacaaa agatagtaga ggctgactct 720
gagccatatg atgacgaatt tgatgacgaa gacgaggagg aaaaagaaga gaaaggaaag 780
aaaaaaaaga gtaatagagg aaggcctagt aaaaagaagg ctactaaagt accaacttta 840
aagattaaac taggaaagag gaagcgtgga agttcggatg aagagggcga tcttagtgga 900
ggtggctctg atcgcgattc tgatgctgag tttgagcaga tgctacaaga agctgaagaa 960
ccaaaatcca acaaatctac cactggtgaa gaatccgcac agccatcaga atcacctgca 1020

-continued

```
gatgaaaatc caccaccaaa acgcaaagcg aaaaccaaaa ttggttgcaa aacaaagaga   1080
aagaagaaaa caaagagtgg taaacctgaa gatgaaaatt atgaacatca agattactgc   1140
gaggtatgtc aacaaggtgg agaaattatc ctctgtgata cttgccctag agcttaccac   1200
ttggtttgcc tggaacctga attagaagaa gcccctgaag gaaagtggag ttgccctcat   1260
tgtgagaatg aaggtccggc tgaacaagat gatgacgagc atcaagaatt ctgcagggtt   1320
tgcaaagatg gtggcgaact tttgtgttgc gattcctgta catctgcgta ccacacgcac   1380
tgtcttaacc cgccacttcc cgaaatacct gacggcgatt ggaaatgtcc taggtgcggt   1440
tgtccgcctc ttgtgggcaa agttgcgaaa attcttacgt ggaaatgggt tgatgatcct   1500
cctaaaaaga aggacaatgg tgaagaggag cctcctacac gacatagaga gtactttgtt   1560
aagtggcatg agctatcata ttggcattgt agttggataa ccgagcttca attggatgta   1620
tatcatcctc tcatgtttcg aagttattca agaaagtggg acatggaaga gcctcctaaa   1680
cttgaagaac ctatggatga agctgacact agatgtagca gattcctgaa aatgggtgga   1740
aacaacaacg acgatgaact cgaagagaag tattacagat acggaataaa accagaatgg   1800
ctaatagtcc atcgtgtcat caaccaccgt acgatgcgag acggaagaac tttgtactta   1860
gtaaaatggc gagagctaac ttacgatcaa gctacctggg aagaagattc tgacgatatc   1920
ccagccctaa agtctgccat cgaatattac acagattcaa gagctgctaa tttatccgga   1980
gctggaggta agctaaagaa gaaagttgga aggaagccga aagctaaaga acttatcgat   2040
gacgacgata gaaacggtcc tcgcagatat actccaccgc cagataagcc ctgcagtgat   2100
ctgaagaaga aactagacaa acaaccctca tatttggacg agagtggatt gcttcacgag   2160
taccaactag agggtcttaa ctggcttcgt tattcgtggg ccaacggtat agacactatc   2220
ttagccgacg agatgggtct cggtaaaacc attcaaacca ttgtcttctt gtattcgctc   2280
tacaaggaag gtcactgcaa aggtccgttt ctaattagtg tcccactttc aacgatcatc   2340
aattgggaga gagaattcga aaattgggca cctgattttt attgtattac atatgttggt   2400
gacaaggact gcagagccgt gattcgtgag aacgaactca gtttcgaaga tggtgctgtc   2460
agaggaggtc gagcttcgag aatcagagcc ggttccatca agtttaacgt tttgttgacc   2520
agctacgaat taatttcgat cgattcggca tgtctcggtt ctatcgaatg ggccgttttg   2580
gtagtcgatg aagctcatag attgaaaagc aatcaatcaa aattcttcaa aatcttaaac   2640
gcttataata tagcttataa actcctcttg accggaacac cgcttcaaaa caacctcgaa   2700
gaattgttcc atttgttgaa cttcctcaac ggtcagaaat tcaacgatct ccaaaacttc   2760
caagccgaat tcgccgacat ttcgaaagaa gaccaagtga agaaattgca cgagatgttg   2820
ggacctcata tgctgcgtcg tctcaaggcc gatgtgctga agagcatgcc ttcgaaatct   2880
gaatttatcg tcagagtcga attatcgccc atgcagaaga aatattataa atatattttg   2940
acgaggaact ttgaagcttt aaatcctaaa ggaggcggac agtcggtatc tttacttaac   3000
attatgatgg atctcaagaa atgttgcaac catccctatc ttttcccagc cgcctcggaa   3060
gaagctccgc tgggtcccca tggtaattgg gatgtaggtc atttgattaa ggcttcagga   3120
aagttggtgc tattagcgaa gatgttgaag atccttagag aacagggtca cagagtgttg   3180
atcttctcgc aaatgacgaa gatgttggat ataatggaag attttcttga aggagaaggg   3240
tataaatacg aacgtattga tggggctatt actggtaatc tccgtcaaga agctatcgat   3300
aggtttaacg ctccaggtgc tccccagttt gttttccttt tgtccactaa agctggtggt   3360
```

-continued

```
ttgggcatca atcttgctac agcagatact gtaatcatct atgattccga ttggaatccc   3420

cacaatgata ttcaggcatt ctccagagct catcgtatcg gtcaagccaa caaggtgatg   3480

atctaccgtt ttgtaacacg taacagtgtg gaagaacgtg ttacgcaagt agccaagcgg   3540

aaaatgatgt taactcactt ggtagtcaga cctggaatgg gcggaaaagg tgccaacttt   3600

actaagcaag agttggacga tattctcaga ttcggtactg aagaattgtt taaagaaagt   3660

gaaggcaaag aagacgaagc cattcactac gacgacaaag ctgtgggaga attgctggat   3720

cgttctaaag aaggcataga acagaaagag agttgggcga acgaatatct cagttcattt   3780

aaagtggcta gttatgttac aaaagaaggg gaagttgagg aagaagttga cactgagatt   3840

attaaacaag aagcggaaaa taccgatccg gcctactgga tcaagctgct tagacatcat   3900

tatgagcaac aacaggaaga tatagctagg acgttaggaa aaggcaaaag agtgaggaaa   3960

caggttaatt ataatgacgg aggaatgaca actgacacac gagaagatac gacatggcaa   4020

gaaaatctct ctgattacca ttctgacttt tctgcgggat cggatgagga taaggaagac   4080

gataaggaag acgatgattc gatgagaaga acgacgccga tttaa                  4125
```

<210> SEQ ID NO 165
<211> LENGTH: 2928
<212> TYPE: DNA
<213> ORGANISM: Diabrotica virgifera

<400> SEQUENCE: 165

```
atgtcacaaa ctgaaggctc gacagaggcg agcgtaagtg cctcagaacc aatggaagaa     60

gcagagaact cggaattggc tcaaaatgaa gaatcttctt cagatactac ctctaagggt    120

gaagagttcg aggtcaaagt ggcttctgac agaggaaaaa gatttgacta cttgttgaaa    180

cagactgaaa tcttttcaca ttttatgaac caaacaaaat ctcccagtaa accaaaaact    240

gggaggccta aaaaagagaa gagtgataca tctgatttaa gacatcgtaa aactgaacaa    300

gaagaagatg aagaactttt agcagaaacc aaccttaaaa caaagactac aactcgtttt    360

gatgcctcac caccctacat caaacatggg gaaatgagag attatcaagt ccgtggtttg    420

aactggatga tttctttgta tgaacatggc atcaatggta ttttagcaga tgagatgggt    480

ttgggtaaaa ctttacaaac catatctctg cttggatata tgaagcacta taaaagtaca    540

cctggtcctc atattgtcat tgttcctaaa tctaccttat caaactggat gaatgagttc    600

gagaagtggt gtccaacctt gagagccgtt tgtctcattg gtgatcaaga ggctaggagc    660

tcatttatca gagatacgat gatgcctggt gaatgggatg tttgtgtaac ctcgtacgaa    720

atgtgtatta aagaaaaatc tgtatttaaa aagttcaact ggagatatat ggtcattgac    780

gaagctcatc gtataaaaaa tgaaaaatct aagctttccg aaattctcag ggagttcaag    840

actactaaca ggctactgct aacaggtact ccattacaaa acaatttaca cgaactctgg    900

gctcttctca acttcttact gccagatgtt ttcaactcat cggatgattt cgatgcctgg    960

ttcaacacca gtcaatgtct gggagacaac gccttggtcg agagattgca tgctgtatta   1020

aaaccattct tgcttagaag attgaaagct gaagtggaga aacggctaaa acccaagaag   1080

gagttaaaag tgtatgtagg attgagcaag atgcaacgag aatggtatac caaagtgctg   1140

atgaaggata ttgatatagt gaatggtgca ggaaaggtag aaaaaatgcg actacagaat   1200

attctcatgc agttaagaaa atgcacaaat cacccctacc tttttgatgg cgctgagccc   1260

ggaccacctt acacaaccga tgaacatctc gtgtacaatt gcggtaaaat ggtgttgctg   1320

gataaactgc ttcccaaatt gaaggaacag gaatctcgtg tacttatctt ctctcagatg   1380
```

acccgtatgt tggatatact tgaagattat tgtcattggc gacagtacca atattgtcgt 1440
ttggatggtc aaaccccaca cgaagacaga cagagacaaa tcaacgagta taacgaagac 1500
aatagccaaa agtttatctt tatgttgtca actagagccg gtggattggg tatcaatttg 1560
gccacagctg atgtagttat tatatatgat tcggattgga atccccagat ggatctgcaa 1620
gccatggaca gagcgcatag aattggtcag aagaaacaag tcagagtttt caggtttatt 1680
accgaaaaca ctgtggaaga aaaaatcgtc gaaagagctg aagtaaaatt acgtttagac 1740
aaattagtta tccagcaggg tcgtttagcc gattccaaag cacagactct aaacaaagac 1800
gaaatgttga acatgatccg gcacggtgcc aaccacgtat ttgcttctaa ggattccgaa 1860
ataacagatg aagatatcga tagtatattg gaaaagggag aaatgaagac cgctcagcta 1920
gctcagaaga tggaaaccat gggcgaatcg tcacttcgca acttcacagt cgaaacaccc 1980
actgaatcag tctaccaatt cgaaggagaa gattatcgtg agaagcagaa aaccatcggc 2040
ttgagcaact ggatagaacc tcccaaaaga gaaaggaagg ccaactatgc cgtcgatgct 2100
tacttcagag aagctttaag ggtttctgag cctaaagcgc ctaaggctcc aagaccacca 2160
aaacagccca tcgtacaaga tttccagttt ttcccgccga gattattcga acttttggac 2220
caggagatct acttttacag gaaatctttg ggatataagg ttccgaaaaa cttagaactt 2280
ggacctgacg cgtccaagca acagaaagaa gagcaaagaa aaatagatga gtcagaaccg 2340
ctcaccgaag acgaacagca agaaaaagaa aacttgttaa cgcaaggttt caccaattgg 2400
agtaaacgcg atttcaatca gttcatcaaa gccaacgaga aatatggtag ggacgatatt 2460
gagaacatcg ccaaggatgt tgaaggcaaa acgcctgaag aagttatgga atattctgcg 2520
gtgttttggg aaagatgtca tgaattacag gatattgata gaataatggc ccagattgag 2580
agaggagaaa ctaaaataca aagaagagct agtattaaga aggcacttga tgctaaaatg 2640
gcaagatatc gtgcaccatt ccatcagctg agaatttctt acggcaccaa caaaggcaag 2700
aactacatgg aggacgaaga caggtttttg gtgtgtatgt tgcacaagtt gggtttcgat 2760
agagaaaacg tttatgaaga gttaagagca gctgtacgtg cgtcaccaca attcagattt 2820
gattggttct taaaatcgag aactgccatg gagctgcaaa ggagatgcaa cacattgata 2880
acgttaatag aaagagaaaa tgctgaattg gaggaaagag aaaaaatt 2928

<210> SEQ ID NO 166
<211> LENGTH: 330
<212> TYPE: DNA
<213> ORGANISM: Diabrotica virgifera

<400> SEQUENCE: 166
atgaaaaaga ctaagctttc cgaaattctc agggaattca agaataccaa caggctactg 60
ctaacaggta ctccattaca aaacaattta catgaactct ggtctcttct caacttctta 120
ctgccagacg tttttaactc atctgatgat ttcgatgcct ggtttaacac cagtcaatgt 180
ctgggaggca actccatggt ggagaggctg catgctgtat taaaaccatt cttgcttaga 240
agattgaaaa ttgaagtaga gaaagggcta aaacccaaga aggagttaaa agtgtatgta 300
ggattgagca aaatgcagcg agaatggtaa 330

<210> SEQ ID NO 167
<211> LENGTH: 4125
<212> TYPE: RNA
<213> ORGANISM: Diabrotica virgifera -continued

<400> SEQUENCE: 167

```
auggcaucag augaagaagu ggaggauucu uucgccgggg aggaagaugc ccccgacgau     60
acggcugaac aaauagauaa cgauccugau ucugaagaug guguuccuaa aggaggggaa    120
gaagaugaug auuaugaacc agaagauucc agaaagaaaa agaagggaaa gaaaagaaaa    180
gccaggggag aagaaaagaa aggcaagaaa aagaagaaaa agcgaaagaa ugauaguggg    240
gaugaaagug acuuuggaga agaugauaau ggaggugggg acucagauua ugcaagcagu    300
aguaaaagag gaaggaaaaa ggguucuacu aaacacucuu cugcaucauc aacaccaaca    360
ccagcuagug acucuggcac aggaggcaug cccaccaucg agcaaguuug uucaacauuu    420
gguuuaacug augucgagcu ugacuauuca gaugcugaua ugcaaaacuu gaccaccuau    480
aaguuguucc aacagcaugu gagaccgcuc cuugcuaagg aaaauccaaa gguuccuaug    540
ucaaaguuga ugauguuggu ugcugcaaaa uggcgcgaau uuucuaauuc aaaccccaau    600
cugcaaagcg aaaaugaacc gucugcugca acuucaacca caucugaaga aaguuaucca    660
aaaacuaauc guucgagagc auccaaggaa gcagcacaaa agauaguaga ggcugacucu    720
gagccauaug augacgaauu ugaugacgaa gacgaggagg aaaaagaaga gaaaggaaag    780
aaaaaaaaga guaauagagg aaggccuagu aaaaagaagg cuacuaaagu accaacuuua    840
aagauuaaac uaggaaagag gaagcgugga aguucggaug aagagggcga ucuuagugga    900
gguggcucug aucgcgauuc ugaugcugag uuugagcaga ugcuacaaga agcugaagaa    960
ccaaaaucca acaaaucuac cacuggugaa gaauccgcac agccaucaga aucaccugca   1020
gaugaaaauc caccaccaaa acgcaaagcg aaaaccaaaa uugguugcaa aacaaagaga   1080
aagaagaaaa caaagagugg uaaaccugaa gaugaaaauu augaacauca agauuacugc   1140
gagguauguc aacaaggugg agaaauuauc cucugugaua cuugcccuag agcuuaccac   1200
uugguuugcc uggaaccuga auuagaagaa gccccugaag gaaaguggag uugcccucau   1260
ugugagaaug aagguccggc ugaacaagau gaugacgagc aucaagaauu cugcaggguu   1320
ugcaaagaug guggcgaacu uuuguguugc gauuccugua caucugcgua ccacacgcac   1380
ugucuuaacc cgccacuucc cgaaauaccu gacggcgauu ggaaaugucc uaggugcggu   1440
uguccgccuc uugugggcaa aguugcgaaa auucuuacgu ggaaaugggu ugaugauccu   1500
ccuaaaaaga aggacaaugg ugaagaggag ccuccuacac gacauagaga guacuuuguu   1560
aaguggcaug agcuaucaua uuggcauugu aguuggauaa ccgagcuuca auuggaugua   1620
uaucauccuc ucauguuucg aaguuauuca agaaaguggg acauggaaga gccuccuaaa   1680
cuugaagaac cuauggauga agcugacacu agauguagca gauuccugaa aaugggugga   1740
aacaacaacg acgaugaacu cgaagagaag uauuacagau acggaauaaa accagaaugg   1800
cuaauagucc aucgugucau caaccaccgu acgaugcgag acggaagaac uuuguacuua   1860
guaaaauggc gagagcuaac uuacgaucaa gcuaccuggg aagaagauuc ugacgauauc   1920
ccagcccuaa agucugccau cgaauauuac acagauucaa gagcugcuaa uuuauccgga   1980
gcuggaggua agcuaaagaa gaaaguugga aggaagccga aagcuaaaga acuuaucgau   2040
gacgacgaua gaaacggucc ucgcagauau acuccaccgc cagauaagcc cugcagugau   2100
cugaagaaga aacuagacaa acaacccuca uauuuggacg agaguggauu gcuucacgag   2160
uaccaacuag agggucuuaa cuggcuucgu uauucguggg ccaacgguau agacacuauc   2220
uuagccgacg agaugggucu cgguaaaacc auucaaacca uugucuucuu guauucgcuc   2280
uacaaggaag gucacugcaa agguccguuu cuaauuagug ucccacuuuc aacgaucauc   2340
```

aauugggaga gagaauucga aaauugggca ccugauuuuu auuguauuac auauguuggu 2400
gacaaggacu gcagagccgu gauucgugag aacgaacuca guuucgaaga uggugcuguc 2460
agaggagguc gagcuucgag aaucagagcc gguuccauca aguuuaacgu uuuguugacc 2520
agcuacgaau uaauuucgau cgauucggca ugucucgguu cuaucgaaug ggccguuuug 2580
guagucgaug aagcucauag auugaaaagc aaucaaucaa aauucuucaa aaucuuaaac 2640
gcuuauaaua uagcuuauaa acuccucuug accggaacac cgcuucaaaa caaccucgaa 2700
gaauuguucc auuuguugaa cuuccucaac ggucagaaau ucaacgaucu ccaaaacuuc 2760
caagccgaau ucgccgacau uucgaaagaa gaccaaguga agaaauugca cgagauguug 2820
ggaccucaua ugcugcgucg ucucaaggcc gaugugcuga agagcaugcc uucgaaaucu 2880
gaauuuaucg ucagagucga auuaucgccc augcagaaga aauauuauaa auauauuuug 2940
acgaggaacu uugaagcuuu aaauccuaaa ggaggcggac agucgguauc uuuacuuaac 3000
auuaugaugg aucucaagaa auguugcaac caucccuauc uuuucccagc cgccucggaa 3060
gaagcuccgc ugggucccca ugguaauugg gauguagguc auuugauuaa ggcuucagga 3120
aaguuggugc uauuagcgaa gauguugaag auccuuagag aacaggguca cagaguguug 3180
aucuucucgc aaaugacgaa gauguuggau auaauggaag auuuucuuga aggagaaggg 3240
uauaaauacg aacguauuga uggggcuauu acugguaauc uccgucaaga agcuaucgau 3300
agguuuaacg cuccaggugc uccccaguuu guuuuccuuu uguccacuaa agcuggugu 3360 uugggcauca aucuugcuac agcagauacu guaaucaucu augauuccga uuggaauccc 3420
cacaaugaua uucaggcauu cuccagagcu caucguaucg gucaagccaa caaggugaug 3480
aucuaccguu uuguaacacg uaacagugug gaagaacgug uuacgcaagu agccaagcgg 3540
aaaaugaugu uaacucacuu gguagucaga ccuggaaugg gcggaaaagg ugccaacuuu 3600
acuaagcaag aguuggacga uauucucaga uucgguacug aagaauuguu uaaagaaagu 3660
gaaggcaaag aagacgaagc cauucacuac gacgacaaag cugugggaga auugcuggau 3720
cguucuaaag aaggcauaga acagaaagag aguugggcga acgaauaucu caguucauuu 3780
aaaguggcua guuauguuac aaaagaaggg gaaguugagg aagaaguuga cacugagauu 3840
auuaaacaag aagcggaaaa uaccgauccg gccuacugga ucaagcugcu uagacaucau 3900
uaugagcaac aacaggaaga uauagcuagg acguuaggaa aaggcaaaag agugaggaaa 3960
cagguuaauu auaaugacgg aggaaugaca acugacacac gagaagauac gacauggcaa 4020
gaaaaucucu cugauuacca uucugacuuu ucugcgggau cggaugagga uaaggaagac 4080
gauaaggaag acgaugauuc gaugagaaga acgacgccga uuuaa 4125

<210> SEQ ID NO 168
<211> LENGTH: 2928
<212> TYPE: RNA
<213> ORGANISM: Diabrotica virgifera

<400> SEQUENCE: 168
augucacaaa cugaaggcuc gacagaggcg agcguaagug ccucagaacc aauggaagaa 60
gcagagaacu cggaauuggc ucaaaaugaa gaaucuucuu cagauacuac cucuaagggu 120
gaagaguucg aggucaaagu ggcuucugac agaggaaaaa gauuugacua cuuguugaaa 180
cagacugaaa ucuuuucaca uuuuaugaac caaacaaaau cucccaguaa accaaaaacu 240
gggaggccua aaaaagagaa gagugauaca ucugauuuaa gacaucguaa aacugaacaa 300

-continued

```
gaagaagaug aagaacuuuu agcagaaacc aaccuuaaaa caaagacuac aacucguuuu    360
gaugccucac cacccuacau caaacauggg gaaaugagag auuaucaagu ccgugguuug    420
aacuggauga uuucuuugua ugaacauggc aucaauggua uuuuagcaga ugagaugggu    480
uuggguaaaa cuuuacaaac cauaucucug cuuggauaua ugaagcacua uaaaaguaca    540
ccugguccuc auauugucau uguuccuaaa ucuaccuuau caaacuggau gaaugaguuc    600
gagaaguggu guccaaccuu gagagccguu ugucucauug gugaucaaga ggcuaggagc    660
ucauuuauca gagauacgau gaugccuggu gaaugggaug uuuguguaac cucguacgaa    720
auguguauua aagaaaaauc uguauuuaaa aaguucaacu ggagauauau ggucauugac    780
gaagcucauc guauaaaaaa ugaaaaaucu aagcuuuccg aaauucucag ggaguucaag    840
acuacuaaca ggcuacugcu aacagguacu ccauuacaaa acaauuuaca cgaacucugg    900
gcucuucuca acuucuuacu gccagauguu uucaacucau cggaugauuu cgaugccugg    960
uucaacacca gucaaugucu gggagacaac gccuuggucg agagauugca ugcuguauua   1020
aaaccauucu ugcuuagaag auugaaagcu gaaguggaga aacggcuaaa acccaagaag   1080
gaguuaaaag uguauguagg auugagcaag augcaacgag aaugguauac caaagugcug   1140
augaaggaua uugauauagu gaauggugca ggaaagguag aaaaaaugcg acuacagaau   1200
auucucaugc aguuaagaaa augcacaaau caccccuacc uuuuugaugg cgcugagccc   1260
ggaccaccuu acacaaccga ugaacaucuc guguacaauu gcgguaaaau gguguugcug   1320
gauaaacugc uucccaaauu gaaggaacag gaaucucgug uacuuaucuu cucucagaug   1380
acccguaugu uggauauacu ugaagauuau ugucauuggc gacaguacca auauugucgu   1440
uuggaugguc aaaccccaca cgaagacaga cagagacaaa ucaacgagua uaacgaagac   1500
aauagccaaa aguuuaucuu uauguuguca acuagagccg guggauuggg uaucaauuug   1560
gccacagcug auguaguuau uauauaugau ucggauugga auccccagau ggaucugcaa   1620
gccauggaca gagcgcauag aauuggucag aagaaacaag ucagaguuuu cagguuuauu   1680
accgaaaaca cuguggaaga aaaaaucguc gaaagagcug aaguaaaauu acguuuagac   1740
aaauuaguua uccagcaggg ucguuuagcc gauuccaaag cacagacucu aaacaaagac   1800
gaaauguuga acaugauccg gcacggugcc aaccacguau uugcuucuaa ggauuccgaa   1860
auaacagaug aagauaucga uaguauauug gaaaagggag aaaugaagac cgcucagcua   1920
gcucagaaga uggaaaccau gggcgaaucg ucacuucgca acuucacagu cgaaacaccc   1980
acugaaucag ucuaccaauu cgaaggagaa gauuaucgug agaagcagaa aaccaucggc   2040
uugagcaacu ggauagaacc ucccaaaaga gaaaggaagg ccaacuaugc cgucgaugcu   2100
uacuucagag aagcuuuaag gguuucugag ccuaaagcgc cuaaggcucc aagaccacca   2160
aaacagccca ucguacaaga uuuccaguuu uucccgccga gauuauucga acuuuuggac   2220
caggagaucu acuuuuacag gaaaucuuug ggauauaagg uuccgaaaaa cuuagaacuu   2280
ggaccugacg cguccaagca acagaaagaa gagcaaagaa aaauagauga gucagaaccg   2340
cucaccgaag acgaacagca agaaaaagaa aacuuguuaa cgcaagguuu caccaauugg   2400
aguaaacgcg auuucaauca guucaucaaa gccaacgaga aauaugguag ggacgauauu   2460
gagaacaucg ccaaggaugu ugaaggcaaa acgccugaag aaguuaugga auauucugcg   2520
guguuuuggg aaagauguca ugaauuacag gauauugaua gaauaauggc ccagauugag   2580
agaggagaaa cuaaaauaca aagaagagcu aguauuaaga aggcacuuga ugcuaaaaug   2640
gcaagauauc gugcaccauu ccaucagcug agaauuucuu acggcaccaa caaaggcaag   2700
```

-continued

```
aacuacaugg aggacgaaga cagguuuuug guguguaugu ugcacaaguu ggguuucgau   2760

agagaaaacg uuuaugaaga guuaagagca gcuguacgug cgucaccaca auucagauuu   2820

gauugguucu uaaaaucgag aacugccaug gagcugcaaa ggagaugcaa cacauugaua   2880

acguuaauag aaagagaaaa ugcugaauug gaggaaagag aaaaaauu               2928


<210> SEQ ID NO 169
<211> LENGTH: 330
<212> TYPE: RNA
<213> ORGANISM: Diabrotica virgifera

<400> SEQUENCE: 169

augaaaaaga cuaagcuuuc cgaaauucuc agggaauuca agaauaccaa caggcuacug     60

cuaacaggua cuccauuaca aaacaauuua caugaacucu ggucucuucu caacuucuua    120

cugccagacg uuuuuaacuc aucugaugau uucgaugccu gguuuaacac cagucaaugu    180

cugggaggca acuccauggu ggagaggcug caugcuguau uaaaaccauu cuugcuuaga    240

agauugaaaa uugaaguaga gaaagggcua aaacccaaga aggaguuaaa aguguaugua    300

ggauugagca aaaugcagcg agaaugguaa                                    330


<210> SEQ ID NO 170
<211> LENGTH: 330
<212> TYPE: DNA
<213> ORGANISM: Diabrotica virgifera

<400> SEQUENCE: 170

ccattctcgc tgcattttgc tcaatcctac atacactttt aactccttct tgggttttag     60

ccctttctct acttcaattt tcaatcttct aagcaagaat ggttttaata cagcatgcag    120

cctctccacc atggagttgc ctcccagaca ttgactggtg ttaaaccagg catcgaaatc    180

atcagatgag ttaaaaacgt ctggcagtaa gaagttgaga agagaccaga gttcatgtaa    240

attgttttgt aatggagtac ctgttagcag tagcctgttg gtattcttga attccctgag    300

aatttcggaa agcttagtct tttcatttt                                     330


<210> SEQ ID NO 171
<211> LENGTH: 329
<212> TYPE: DNA
<213> ORGANISM: Diabrotica virgifera

<400> SEQUENCE: 171

ccattctcgt tgcatcttgc tcaatcctac atacactttt aactccttct tgggttttag     60

ccgtttctcc acttcagctt tcaatcttct aagcaagaat ggttttaata cagcatgcag    120

tctctcgacc aaggcgttgt ctcccagaca ttgactggtg ttgaaccagg catcgaaatc    180

atccgatgag ttgaaaacat ctggcagtaa gaagttgaga agagcccaga gttcgtgtaa    240

attgttttgt aatggagtac ctgttagcag tagcctgtta gtagtcttga actccctgag    300

aatttcggaa agcttagatt tttcatttt                                     329
```

PARENTAL RNAI SUPPRESSION OF CHROMATIN REMODELING GENES TO CONTROL COLEOPTERAN PESTS

CROSS REFERENCE TO RELATED APPLICATIONS

This application claims the benefit of the filing date of U.S. Provisional Patent Application No. 62/092,768, filed on Dec. 16, 2014, and U.S. Provisional Patent Application No. 62/170,076, filed on Jun. 2, 2015. Furthermore, this application is a continuation-in-part of U.S. patent application Ser. No. 13/646,485, filed on Oct. 5, 2012, and published on Apr. 11, 2013, as U.S. Patent Publication No US 2013/0091601 A1. U.S. patent application Ser. No. 13/646,485 claims the benefit of the filing date of U.S. Provisional Application No. 61/544,214, U.S. Provisional Application No. 61/544,227, and U.S. Provisional Application No. 61/544,217, all of which were filed on Oct. 6, 2011. The disclosures of each of the foregoing applications are hereby incorporated herein in their entirety by this reference.

FIELD OF THE DISCLOSURE

The present invention relates generally to genetic control of plant damage caused by coleopteran pests. In particular embodiments, the present disclosure relates to identification of target coding and non-coding polynucleotides, and the use of recombinant DNA technologies for post-transcriptionally repressing or inhibiting expression of target coding and non-coding polynucleotides in the cells of a coleopteran pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in the Americas: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella; D. speciosa* Germar; and *D. u. undecimpunctata* Mannerheim. The United States Department of Agriculture has estimated that corn rootworms cause $1 billion in lost revenue each year, including $800 million in yield loss and $200 million in treatment costs.

Both WCR and NCR are deposited in the soil as eggs during the summer. The insects remain in the egg stage throughout the winter. The eggs are oblong, white, and less than 0.004 inches in length. The larvae hatch in late May or early June, with the precise timing of egg hatching varying from year to year due to temperature differences and location. The newly hatched larvae are white worms that are less than 0.125 inches in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inches in length.

Corn rootworm larvae complete development on corn and several other species of grasses. Larvae reared on yellow foxtail emerge later and have a smaller head capsule size as adults compared to larvae reared on corn. Ellsbury et al. (2005) Environ. Entomol. 34:627-34. WCR adults feed on corn silk, pollen, and kernels on exposed ear tips. Adults will quickly shift to preferred silks and pollen when they become available. NCR adults also feed on reproductive tissues of the corn plant. WCR females typically mate once. Branson et al. (1977) Ann. Entom. Soc. America 70(4):506-8.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis* (Bt)), transgenic plants that express Bt toxins, or a combination thereof. Crop rotation suffers from the disadvantage of placing restrictions upon the use of farmland. Moreover, oviposition of some rootworm species may occur in crop fields other than corn or extended diapause results in egg hatching over multiple years, thereby mitigating the effectiveness of crop rotation practiced with corn and other crops.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of yield loss from the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to their toxicity to non-target species.

RNA interference (RNAi) is a process utilizing endogenous cellular pathways, whereby an interfering RNA (iRNA) molecule (e.g., a double stranded RNA (dsRNA) molecule) that is specific for all, or any portion of adequate size, of a target gene results in the degradation of the mRNA encoded thereby. In recent years, RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro ribonucleic acids (miRNAs) are structurally very similar molecules that are cleaved from precursor molecules containing a polynucleotide "loop" connecting the hybridized passenger and guide strands, and they may be similarly incorporated into RISC. Post-transcriptional gene silencing occurs when the guide strand binds specifically to a complementary mRNA molecule and induces cleavage by Argonaute, the catalytic component of the RISC complex. This process is known to spread systemically throughout some eukaryotic organisms despite initially limited concentrations of siRNA and/or miRNA, such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In insects, there are at least two DICER genes, where DICER1 facilitates miRNA-directed degradation by Argonaute1. Lee et al. (2004) Cell 117(1):69-81. DICER2 facilitates siRNA-directed degradation by Argonaute2.

U.S. Pat. No. 7,612,194 and U.S. Patent Publication Nos. 2007/0050860, 2010/0192265, and 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type Ht ATPase (V-ATPase) disclosed therein for the expression of anti-sense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midguts, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. 2007/0050860, 2010/0192265, and 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. 2007/0050860 and 2010/0192265, and 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA. U.S. Patent Application Publication No. U.S. 2013/040173 and PCT Application Publication No. WO 2013/169923 describes the use of a sequence derived from a *Diabrotica virgifera* Snf7 gene for RNA interference in maize. (Also disclosed in Bolognesi et al. (2012) PLoS ONE 7(10): e47534. doi:10.1371/journal.pone.0047534).

The overwhelming majority of sequences complementary to corn rootworm DNAs (such as the foregoing) do not provide a plant protective effect from species of corn rootworm when used as dsRNA or siRNA. For example, Baum et al. (2007) Nature Biotechnology 25:1322-1326, describe the effects of inhibiting several WCR gene targets by RNAi. These authors reported that 8 of the 26 target genes they tested were not able to provide experimentally significant coleopteran pest mortality at a very high iRNA (e.g., dsRNA) concentration of more than 520 ng/cm$^2$.

The authors of U.S. Pat. No. 7,612,194 and U.S. Patent Publication No. 2007/0050860 made the first report of in planta RNAi in corn plants targeting the western corn rootworm. Baum et al. (2007) Nat. Biotechnol. 25(11):1322-6. These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

Another potential application of RNAi for insect control involves parental RNAi (pRNAi). First described in *Caenorhabditis elegans*, pRNAi was identified by injection of dsRNA into the body cavity (or application of dsRNA via ingestion), causing gene inactivity in offspring embryos. Fire et al. (1998), supra; Timmons and Fire (1998) Nature 395(6705):854. A similar process was described in the model coleopteran, *Tribolium castaneum*, whereby female pupae injected with dsRNA corresponding to three unique genes that control segmentation during embryonic development resulted in knock down of zygotic genes in offspring embryos. Bucher et al. (2002) Curr. Biol. 12(3):R85-6. Nearly all of the offspring larvae in this study displayed gene-specific phenotypes one week after injection. Although injection of dsRNA for functional genomics studies has been successful in a variety of insects, uptake of dsRNA from the gut environment through oral exposure to dsRNA and subsequent down-regulation of essential genes is required in order for RNAi to be effective as a pest management tool. Auer and Frederick (2009) Trends Biotechnol. 27(11):644-51.

Parental RNAi has been used to describe the function of embryonic genes in a number of insect species, including the springtail, *Orchesella cincta* (Konopova and Akam (2014) Evodevo 5(1):2); the brown plant hopper, *Nilaparvata lugens*; the sawfly, *Athalia rosae* (Yoshiyama et al. (2013) J. Insect Physiol. 59(4):400-7); the German cockroach, *Blattella germanica* (Piulachs et al. (2010) Insect Biochem. Mol.

Biol. 40:468-75); and the pea aphid, *Acyrthosiphon pisum* (Mao et al. (2013) Arch Insect Biochem Physiol 84(4):209-21). The pRNAi response in all these instances was achieved by injection of dsRNA into the hemocoel of the parental female.

SUMMARY OF THE DISCLOSURE

Disclosed herein are nucleic acid molecules (e.g., target genes, DNAs, dsRNAs, siRNAs, shRNAs, miRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella; D. speciosa* Germar; and *D. u. undecimpunctata* Mannerheim. In particular examples, exemplary nucleic acid molecules are disclosed that may be homologous to at least a portion of one or more native nucleic acids in a coleopteran pest. In some embodiments, coleopteran pests are controlled by reducing the capacity of an existing generation to produce a subsequent generation of the pest. In certain examples, delivery of the nucleic acid molecules to coleopteran pests does not result in significant mortality to the pests, but reduces the number of viable progeny produced therefrom.

In these and further examples, the native nucleic acid may be a target gene, the product of which may be, for example and without limitation: involved in a metabolic process; involved in a reproductive process; and/or involved in embryonic and/or larval development. In some examples, post-transcriptional inhibition of the expression of a target gene by a nucleic acid molecule comprising a polynucleotide homologous thereto may result in reduced viability, growth, and/or reproduction of the coleopteran pest. In specific examples, a chromatin remodeling gene is selected as a target gene for post-transcriptional silencing. In particular examples, a target gene useful for post-transcriptional inhibition is the novel chromatin remodeling gene referred to herein as *Diabrotica brahma* (SEQ ID NO:1, SEQ ID NO:3, SEQ ID NO:5, and SEQ ID NO:7). In particular examples, a target gene useful for post-transcriptional inhibition is the novel chromatin remodeling gene referred to herein as *Diabrotica* mi-2 (SEQ ID NO:79 and SEQ ID NO:164). In particular examples, a target gene useful for post-transcriptional inhibition is the novel chromatin remodeling gene referred to herein as *Diabrotica* iswi-1 (SEQ ID NO:81 and SEQ ID NO:165). In particular examples, a target gene useful for post-transcriptional inhibition is the novel chromatin remodeling gene referred to herein as *Diabrotica* chd1 (SEQ ID NO:83). In particular examples, a target gene useful for post-transcriptional inhibition is the novel chromatin remodeling gene referred to herein as *Diabrotica* iswi-2 (SEQ ID NO:85 and SEQ ID NO:166). In particular examples, a target gene useful for post-transcriptional inhibition is the novel chromatin remodeling gene referred to herein as *Diabrotica* iswi30 (SEQ ID NO:87). In particular examples, a target gene useful for post-transcriptional inhibition is the novel chromatin remodeling gene referred to herein as *Diabrotica* ino80 (SEQ ID NO:89). In particular examples, a target gene useful for post-transcriptional inhibition is the novel chromatin remodeling gene referred to herein as *Diabrotica domino* (SEQ ID NO:91).

An isolated nucleic acid molecule comprising the polynucleotide of SEQ ID NO:1; the complement of SEQ ID NO:1; SEQ ID NO:3; the complement of SEQ ID NO:3; SEQ ID NO:5; the complement of SEQ ID NO:5; SEQ ID NO:7; the complement of SEQ ID NO:7; SEQ ID NO:79; the complement of SEQ ID NO:79; SEQ ID NO:81; the complement of SEQ ID NO:81; SEQ ID NO:83; the complement of SEQ ID NO:83; SEQ ID NO:85; the complement of SEQ ID NO:85; SEQ ID NO:87; the complement of SEQ ID NO:87; SEQ ID NO:89; the complement of SEQ ID NO:89; SEQ ID NO:91; the complement of SEQ ID NO:91; SEQ ID NO:164; the complement of SEQ ID NO:164; SEQ ID NO:165; the complement of SEQ ID NO:165; SEQ ID NO:166; the complement of SEQ ID NO:166; and/or fragments of any of the foregoing (e.g., SEQ ID NO:8, SEQ ID NO:10, and SEQ ID NOs:101-106) is therefore disclosed herein.

Also disclosed are nucleic acid molecules comprising a polynucleotide that encodes a polypeptide that is at least about 85% identical to an amino acid sequence within a target chromatin remodeling gene product (for example, the product of a *brahma*, mi-2, iswi-1, chd1, iswi-2, iswi30, ino80, or *domino* gene). For example, a nucleic acid molecule may comprise a polynucleotide encoding a polypeptide that is at least 85% identical to a polypeptide selected from the group consisting of SEQ ID NO:2, SEQ ID NO:4, SEQ ID NO:6, and SEQ ID NO:9 (*Diabrotica* BRAHMA); an amino acid sequence within a product of *Diabrotica brahma* (e.g., SEQ ID NO:9); SEQ ID NO:80 (*Diabrotica* MI-2); an amino acid sequence within a product of *Diabrotica* mi-2; SEQ ID NO:82 (*Diabrotica* ISWI-1); an amino acid sequence within a product of *Diabrotica* iswi-1; SEQ ID NO:84 (*Diabrotica* CHD1); an amino acid sequence within a product of *Diabrotica* chd1; SEQ ID NO:86 (*Diabrotica* ISWI-2); an amino acid sequence within a product of *Diabrotica* iswi-2; SEQ ID NO:88 (*Diabrotica* ISWI30); an amino acid sequence within a product of *Diabrotica* iswi30; SEQ ID NO:90 (*Diabrotica* IN080); an amino acid sequence within a product of *Diabrotica* ino80; SEQ ID NO:92 (*Diabrotica* DOMINO); and an amino acid sequence within a product of *Diabrotica* domino. Further disclosed are nucleic acid molecules comprising a polynucleotide that is the reverse complement of a polynucleotide that encodes a polypeptide at least 85% identical to an amino acid sequence within a target chromatin remodeling gene product.

Also disclosed are cDNA polynucleotides that may be used for the production of iRNA (e.g., dsRNA, siRNA, shRNA, miRNA, and hpRNA) molecules that are complementary to all or part of a coleopteran pest target gene, for example, a chromatin remodeling gene. In particular embodiments, dsRNAs, siRNAs, shRNAs, miRNAs, and/or hpRNAs may be produced in vitro or in vivo by a genetically-modified organism, such as a plant or bacterium. In particular examples, cDNA molecules are disclosed that may be used to produce iRNA molecules that are complementary to all or part of mRNA transcribed from *Diabrotica brahma* (SEQ ID NO:1, SEQ ID NO:3, SEQ ID NO:5, and SEQ ID NO:7); *Diabrotica* mi-2 (SEQ ID NO:79 and SEQ ID NO:164); *Diabrotica* iswi-1 (SEQ ID NO:81 and SEQ ID NO:165); *Diabrotica* chd1 (SEQ ID NO:83); *Diabrotica* iswi-2 (SEQ ID NO:85 and SEQ ID NO:166); *Diabrotica* iswi30 (SEQ ID NO:87); *Diabrotica* ino80 (SEQ ID NO:89); and/or *Diabrotica* domino (SEQ ID NO:91).

Further disclosed are means for inhibiting expression of an essential gene in a coleopteran pest, and means for protecting a plant from a coleopteran pest. A means for inhibiting expression of an essential gene in a coleopteran pest is a single- or double-stranded RNA molecule consisting of a polynucleotide selected from the group consisting of SEQ ID NO:141 and SEQ ID NO:142; and the complements thereof. Functional equivalents of means for inhibiting expression of an essential gene in a coleopteran pest include single- or double-stranded RNA molecules that are substantially homologous to all or part of mRNA transcribed from a WCR gene encoding a ATP-dependent remodeling enzyme, such as mRNAs comprising SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, or SEQ ID NO:166. A means for protecting a plant from a coleopteran pest is a DNA molecule comprising a polynucleotide encoding a means for inhibiting expression of an essential gene in a coleopteran pest operably linked to a promoter, wherein the DNA molecule is capable of being integrated into the genome of a maize plant.

Disclosed are methods for controlling a population of a coleopteran pest, comprising providing to a coleopteran pest an iRNA (e.g., dsRNA, siRNA, shRNA, miRNA, and hpRNA) molecule that functions upon being taken up by the pest to inhibit a biological function within the pest, wherein the iRNA molecule comprises all or part of (e.g., at least 15 contiguous nucleotides of) a polynucleotide selected from the group consisting of: SEQ ID NO:135; the complement of SEQ ID NO:135; SEQ ID NO:136; the complement of SEQ ID NO:136; SEQ ID NO:137; the complement of SEQ ID NO:137; SEQ ID NO:138; the complement of SEQ ID NO:138; SEQ ID NO:139; the complement of SEQ ID NO:139; SEQ ID NO:140; the complement of SEQ ID NO:140; SEQ ID NO:141; the complement of SEQ ID NO:141; SEQ ID NO:142; the complement of SEQ ID NO:142; SEQ ID NO:143; the complement of SEQ ID NO:143; SEQ ID NO:144; the complement of SEQ ID NO:144; SEQ ID NO:145; the complement of SEQ ID NO:145; SEQ ID NO:146; the complement of SEQ ID NO:146; SEQ ID NO:147; the complement of SEQ ID NO:147; SEQ ID NO:148; the complement of SEQ ID NO:148; SEQ ID NO:149; the complement of SEQ ID NO:149; SEQ ID NO:150; the complement of SEQ ID NO:150; SEQ ID NO:151; the complement of SEQ ID NO:151; SEQ ID NO:152; the complement of SEQ ID NO:152; SEQ ID NO:153; the complement of SEQ ID NO:153; SEQ ID NO:154; the complement of SEQ ID NO:154; SEQ ID NO:155; the complement of SEQ ID NO:155; SEQ ID NO:156; the complement of SEQ ID NO:156; SEQ ID NO:157; the complement of SEQ ID NO:157; SEQ ID NO:158; the complement of SEQ ID NO:158; SEQ ID NO:159 the complement of SEQ ID NO:159; SEQ ID NO:160; the complement of SEQ ID NO:160; SEQ ID NO:161; the complement of SEQ ID NO:161; SEQ ID NO:162; the complement of SEQ ID NO:162; SEQ ID NO:163; the complement of SEQ ID NO:163; SEQ ID NO:167; the complement of SEQ ID NO:167; SEQ ID NO:168; the complement of SEQ ID NO:168; SEQ ID NO:169; the complement of SEQ ID NO:169; a polynucleotide that hybridizes to a native coding polynucleotide of a *Diabrotica* organism (e.g., WCR) comprising all or part of any of SEQ ID NO:1, SEQ ID NO:3, SEQ ID NO:5, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166; and the complement of a polynucleotide that hybridizes to a native coding polynucleotide of a *Diabrotica* organism comprising all or part of any of SEQ ID NO:1, SEQ ID NO:3, SEQ ID NO:5, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166.

Also disclosed herein are methods wherein dsRNAs, siRNAs, shRNAs, miRNAs, and/or hpRNAs may be provided to a coleopteran pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by a coleopteran pest. Ingestion of dsRNAs, siRNA, shRNAs, miRNAs, and/or hpRNAs of the invention may then result in RNAi in the pest, which in turn may result in silencing of a gene essential for a metabolic process; a reproductive process; and/or larval development. Thus, methods are disclosed wherein nucleic acid molecules comprising exemplary polynucleotide(s) useful for parental control of coleopteran pests are provided to a coleopteran pest. In particular examples, the coleopteran pest controlled by use of nucleic acid molecules of the invention may be WCR, SCR, NCR, MCR, *D. balteata, D. undecimpunctata tenella, D. speciosa*, or *D. u. undecimpunctata*. In some examples, delivery of the nucleic acid molecules to coleopteran pests does not result in significant mortality to the pests, but reduces the number of viable progeny produced therefrom. In some examples, delivery of the nucleic acid molecules to a coleopteran pest results in significant mortality to the pests, and also reduces the number of viable progeny produced therefrom.

The foregoing and other features will become more apparent from the following Detailed Description of several embodiments, which proceeds with reference to the accompanying Figures.

BRIEF DESCRIPTION OF THE FIGURES

FIG. 3C; CHD subfamily II: Mi-2; FIG. 3D; CHD subfamily III: kismet, FIG. 3E; Other SNF2-containing proteins, FIG. 3F.

FIG. 4 includes an alignment of WCR iswi-2 dsRNA (query, SEQ ID NO:170) to iswi-1 transcript (subject, SEQ ID NO:171), showing 93% sequence identity. The alignment was performed using BLAST-2-Seq.

BRIEF DESCRIPTION OF THE SEQUENCE LISTING

Figure 1A:
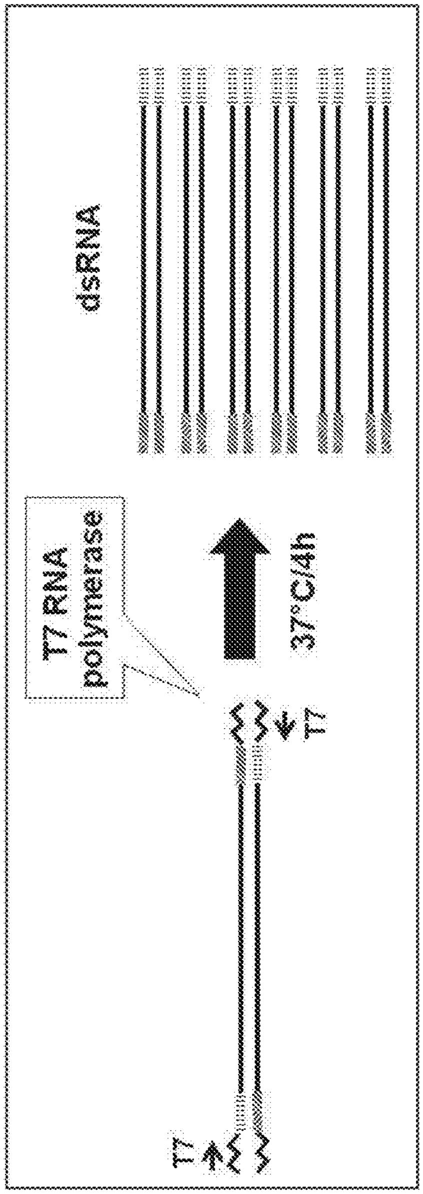
FIG. 1A includes a depiction of the strategy used to generate dsRNA from a single transcription template with a single pair of primers, and FIG. 1B includes a depiction of the strategy used to generate dsRNA from two transcription templates.

The nucleic acid sequences identified in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO:1 shows an exemplary *Diabrotica* chromatin remodeling gene DNA, referred to herein in some places as *brahma*-c4465 rc.

SEQ ID NO:2 shows the amino acid sequence of a *Diabrotica* BRAHMA polypeptide encoded by an exemplary *Diabrotica* chromatin remodeling gene DNA.

SEQ ID NO:3 shows a further exemplary *Diabrotica* chromatin remodeling gene DNA, referred to herein in some places as *brahma*-8089.

SEQ ID NO:4 shows the amino acid sequence of a further *Diabrotica* BRAHMA polypeptide encoded by an exemplary *Diabrotica* chromatin remodeling gene DNA.

SEQ ID NO:5 shows a further exemplary *Diabrotica* chromatin remodeling gene DNA, referred to herein in some places as *brahma*-525.

SEQ ID NO:6 shows the amino acid sequence of a further *Diabrotica* BRAHMA polypeptide encoded by an exemplary *Diabrotica* chromatin remodeling gene DNA.

SEQ ID NO:7 shows an exemplary *Diabrotica* chromatin remodeling gene DNA, referred to herein in some places as contig[000]_*brahma*_949-1126, containing "*brahma* variant 1" (or "*brahma* var 1").

SEQ ID NO:8 shows an exemplary *Diabrotica* chromatin remodeling gene DNA, referred to herein in some places as *brahma* reg-352.

SEQ ID NO:9 shows the amino acid sequence of a *Diabrotica* BRAHMA polypeptide encoded by an exemplary *Diabrotica* chromatin remodeling gene DNA.

SEQ ID NO:10 shows an exemplary *Diabrotica* chromatin remodeling gene DNA, referred to herein in some places as *brahma* variant 1 (or *brahma* var 1), which is used in some examples for the production of a dsRNA.

SEQ ID NO:11 shows a segment of an exemplary YFP gene, which is used in some examples for the production of a dsRNA.

SEQ ID NO:12 shows the nucleotide sequence of a T7 phage promoter.

SEQ ID NOs:13-20 show primers used to amplify gene regions of a *Diabrotica* brahma gene or a YFP gene.

SEQ ID NO:21 shows a DNA sequence of annexin region 1.

SEQ ID NO:22 shows a DNA sequence of annexin region 2.

SEQ ID NO:23 shows a DNA sequence of beta spectrin 2 region 1.

SEQ ID NO:24 shows a DNA sequence of beta spectrin 2 region 2.

SEQ ID NO:25 shows a DNA sequence of mtRP-L4 region 1.

SEQ ID NO:26 shows a DNA sequence of mtRP-L4 region 2.

SEQ ID NOs:27-52 show primers used to amplify gene regions of annexin, beta spectrin 2, mtRP-L4, and YFP for dsRNA synthesis.

SEQ ID NO:53 shows a segment of an exemplary GFP gene, which is used in some examples for the production of a dsRNA.

SEQ ID NOs:54 and 55 show primers used for PCR amplification of a GFP sequence, used in some examples for dsRNA production.

SEQ ID NO:56 shows an exemplary DNA comprising an ST-LS1 intron.

SEQ ID NO:57 shows an exemplary DNA encoding a *Diabrotica* chromatin remodeling gene-targetting hairpin-forming RNA; containing *brahma* v1 sense polynucleotides, a loop polynucleotide (underlined) including an intron, and *brahma* v1 antisense polynucleotide (bold font):

GCGCCCTACAGACTCCTGCTTACTGGTACTCCCCTACAAAATAAATTACC

AGAATTATGGGCCTTGTTGAATTTCTTGTTGCCTTCGATTTTCAAGAGTT

GCTCCACTTTTGAACAATGGTTCAATGCGCCATTCGCAACAACAGGAGAA

AAGGTTGAGTTAAACGAAGAAGAAACTATCCTTATCATCCGTCGTCTTCA

CAAAGTACTCAGGCCGTTTCTCCTGAGACGTCTCAAGAAAGAAGTCGAAT

CTCAGCTTCCAGACAAAGTGGAATATATCATAAAGTGTGACATGTGACTA

GTACCGGTTGGGAAAGGTATGTTTCTGCTTCTACCTTTGATATATATATA

ATAATTATCACTAATTAGTAGTAATATAGTATTTCAAGTATTTTTTTCAA

AATAAAAGAATGTAGTATATAGCTATTGCTTTTCTGTAGTTTATAAGTGT

GTATATTTTAATTTATAACTTTTCTAATATATGACCAAAACATGGTGATG

TGCAGGTTGATCCGCGGACATGTCACACTTTATGATATATTCCACTTTGT

CTGGAAGCTGAGATTCGACTTCTTTCTTGAGACGTCTCAGGAGAAACGGC

CTGAGTACTTTGTGAAGACGACGGATGATAAGGATAGTTTCTTCTTCGTT

TAACTCAACCTTTTCTCCTGTTGTTGCGAATGGCGCATTGAACCATTGTT

CAAAAGTGGAGCAACTCTTGAAAATCGAAGGCAACAAGAAATTCAACAAG

GCCCATAATTCTGGTAATTTATTTTGTAGGGGAGTACCAGTAAGCAGGAG

TCTGTAGGGCGC

SEQ ID NO:58 shows a further exemplary DNA encoding a *Diabrotica* chromatin remodeling gene-targetting hairpin-forming RNA; containing *brahma* v2 sense polynucleotides, a loop polynucleotide (underlined) including an intron, and *brahma* v2 antisense polynucleotide (bold font):

CATATAAAAGAACGAAGCGACAGGGTCTAAAAGAATCGAGAGCTACAGAG

AAGTTAGAAAAACAACAGAAGTTAGAAGCAGAAAGAAAGAGAAGACAGAA

GAACCAAGAATTTTTGAATGCTGTATTGAACAATGGAAAAGAATTCAAGG

-continued

AATTCCACAAGCAGAATCAAGCGAAATTAGCTAAGATTAATAAAGCTGTT

ATTAATTATCACGCTAATGCTGAAAGAGAGCAAAAGAAAGAAGCAGAAAG

GAGAGAGAAGGAACGTATGATCAGATTGATGGCAGAAGATGAAGAAGGTT

GACTAGTACCGGTTGGGAAAGGTATGTTTCTGCTTCTACCTTTGATATAT

ATATAATAATTATCACTAATTAGTAGTAATATAGTATTTCAAGTATTTTT

TTCAAAATAAAAGAATGTAGTATATAGCTATTGCTTTTCTGTAGTTTATA

AGTGTGTATATTTTAATTTATAACTTTTCTAATATATGACCAAAACATGG

TGATGTGCAGGTTGATCCGCGGAACCTTCTTCATCTTCTGCCATCAATCT

GATCATACGTTCCTTCTCTCTCCTTTCTGCTTCTTTCTTTTGCTCTCTTT

CAGCATTAGCGTGATAATTAATAACAGCTTTATTAATCTTAGCTAATTTC

GCTTGATTCTGCTTGTGGAATTCCTTGAATTCTTTTCCATTGTTCAATAC

AGCATTCAAAAATTCTTGGTTCTTCTGTCTTCTCTTTCTTTCTGCTTCTA

ACTTCTGTTGTTTTTCTAACTTCTCTGTAGCTCTCGATTCTTTTAGACCC

TGTCGCTTCGTTCTTTTATATG

SEQ ID NO:59 shows the nucleotide sequence of a T20VN primer oligonucleotide.

SEQ ID NOs:60-64 show primers and probes used for dsRNA transcript expression analyses.

SEQ ID NO:65 shows a nucleotide sequence of a portion of a SpecR coding region used for binary vector backbone detection.

SEQ ID NO:66 shows a nucleotide sequence of an AADJ coding region used for genomic copy number analysis.

SEQ ID NOs:67-78 show the nucleotide sequences of DNA oligonucleotides used for gene copy number determinations and binary vector backbone detection.

SEQ ID NO:79 shows a further exemplary *Diabrotica* chromatin remodeling gene DNA, referred to herein in some places as mi-2.

SEQ ID NO:80 shows the amino acid sequence of a *Diabrotica* MI-2 polypeptide encoded by an exemplary *Diabrotica* chromatin remodeling gene DNA.

SEQ ID NO:81 shows a further exemplary *Diabrotica* chromatin remodeling gene DNA, referred to herein in some places as iswi-1.

SEQ ID NO:82 shows the amino acid sequence of a *Diabrotica* ISWI-1 polypeptide encoded by an exemplary *Diabrotica* chromatin remodeling gene DNA.

SEQ ID NO:83 shows a further exemplary *Diabrotica* chromatin remodeling gene DNA, referred to herein in some places as chd1.

SEQ ID NO:84 shows the amino acid sequence of a *Diabrotica* CHD1 polypeptide encoded by an exemplary *Diabrotica* chromatin remodeling gene DNA.

SEQ ID NO:85 shows a further exemplary *Diabrotica* chromatin remodeling gene DNA, referred to herein in some places as iswi-2.

SEQ ID NO:86 shows the amino acid sequence of a *Diabrotica* ISWI-2 polypeptide encoded by an exemplary *Diabrotica* chromatin remodeling gene DNA.

SEQ ID NO:87 shows a further exemplary *Diabrotica* chromatin remodeling gene DNA, referred to herein in some places as iswi-30 or iswi-3.

SEQ ID NO:88 shows the amino acid sequence of a *Diabrotica* ISWI-30 (“ISWI-3”) polypeptide encoded by an exemplary *Diabrotica* chromatin remodeling gene DNA.

SEQ ID NO:89 shows a further exemplary *Diabrotica* chromatin remodeling gene DNA, referred to herein in some places as ino80.

SEQ ID NO:90 shows the amino acid sequence of a *Diabrotica* IN080 polypeptide encoded by an exemplary *Diabrotica* chromatin remodeling gene DNA.

SEQ ID NO:91 shows a further exemplary *Diabrotica* chromatin remodeling gene DNA, referred to herein in some places as *domino.*

SEQ ID NO:92 shows the amino acid sequence of a *Diabrotica* DOMINO polypeptide encoded by an exemplary *Diabrotica* chromatin remodeling gene DNA.

SEQ ID NOs:93-96 show exemplary DNAs encoding dsRNA sequences for targeting SNF2-Helicase regions of insect (e.g., *Diabrotica, Tribolium, Euschistus heros*, and *Drosophila melanogaster*) chromatin remodeling gene DNA.

SEQ ID NOs:97-100 show exemplary DNAs encoding dsRNA sequences for targeting chromatin remodeling domains (Chromodomain, Bromodomain, or HAND-SLIDE regions) of insect (e.g., *Diabrotica, Tribolium, Euschistus heros*, and *Drosophila melanogaster*) chromatin remodeling gene DNA.

SEQ ID NO:101 shows an exemplary *Diabrotica* chromatin remodeling gene DNA, referred to herein in some places as mi-2 region1 ("mi2_5146").

SEQ ID NO:102 shows an exemplary *Diabrotica* chromatin remodeling gene DNA, referred to herein in some places as iswi-30 region1 ("iswi_3074").

SEQ ID NO:103 shows an exemplary *Diabrotica* chromatin remodeling gene DNA, referred to herein in some places as iswi-2 region1 ("SNF2_c18929").

SEQ ID NO:104 shows an exemplary *Diabrotica* chromatin remodeling gene DNA, referred to herein in some places as KISMET_2388 region1.

SEQ ID NO:105 shows an exemplary *Diabrotica* chromatin remodeling gene DNA, referred to herein in some places as CHD1 region1 ("Helicase_16208").

SEQ ID NO:106 shows an exemplary *Diabrotica* chromatin remodeling gene DNA, referred to herein in some places as ETL1 region1 ("SWI_SNF_Irc2582").

SEQ ID NOs:107-134 show primers used to amplify gene regions of chromatin remodeling genes.

SEQ ID NOs:135-163 show exemplary RNAs transcribed from nucleic acids comprising exemplary chromatin remodeling gene polynucleotides and fragments thereof.

SEQ ID NO:164 shows the open reading frame of an exemplary *Diabrotica* mi-2 chromatin remodeling gene DNA.

SEQ ID NO:165 shows the open reading frame of an exemplary *Diabrotica* iswi-1 chromatin remodeling gene DNA.

SEQ ID NO:166 shows the open reading frame of an exemplary *Diabrotica* iswi-2 chromatin remodeling gene DNA.

SEQ ID NOs:167-169 show further exemplary RNAs transcribed from nucleic acids comprising exemplary chromatin remodeling gene polynucleotides and fragments thereof.

DETAILED DESCRIPTION

I. Overview of Several Embodiments

RNA interference (RNAi) was developed as a tool for insect pest management, using one of the most likely target pest species for transgenic plants that express dsRNA; the western corn rootworm. Thus far, most genes proposed as targets for RNAi in rootworm larvae do not achieve their purpose, and those useful targets that have been identified involve those that cause lethality in the larval stage. Herein, we describe RNAi-mediated knockdown of chromatin remodeling genes (e.g., *brahma*, mi-2, iswi-1, chd1, iswi-2, iswi30, ino80, and *domino*) in the western corn rootworm, which is shown to disrupt embryonic development when, for example, iRNA molecules are delivered via chromatin remodeling gene-targeting dsRNA fed to adult females. There was almost complete absence of hatching in the eggs collected from females exposed to chromatin remodeling gene-targeting dsRNA. In embodiments herein, the ability to deliver chromatin remodeling gene-targeting dsRNA by feeding to adult insects confers a pRNAi effect that is very useful for insect (e.g., coleopteran) pest management. Furthermore, the potential to affect multiple target sequences in both larval and adult rootworms may increase opportunities to develop sustainable approaches to insect pest management involving RNAi technologies.

Disclosed herein are methods and compositions for genetic control of coleopteran pest infestations. Methods for identifying one or more gene(s) essential to the life cycle of a coleopteran pest (e.g., gene(s) essential for normal reproductive capacity and/or embryonic and/or larval development) for use as a target gene for RNAi-mediated control of a coleopteran pest population are also provided. DNA plasmid vectors encoding an RNA molecule may be designed to suppress one or more target gene(s) essential for growth, survival, development, and/or reproduction. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in a coleopteran pest. In these and further embodiments, a coleopteran pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Some embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of a coleopteran pest. Disclosed is a set of isolated and purified nucleic acid molecules comprising a polynucleotide, for example, as set forth in SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; and fragments thereof. In some embodiments, a stabilized dsRNA molecule may be expressed from these polynucleotides, fragments thereof, or a gene comprising one of these polynucleotides, for the post-transcriptional silencing or inhibition of a target gene. In certain embodiments, isolated and purified nucleic acid molecules comprise all or part of any of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164, SEQ ID NO:165; and SEQ ID NO:166.

Some embodiments involve a recombinant host cell (e.g., a plant cell) having in its genome at least one recombinant DNA encoding at least one iRNA (e.g., dsRNA) molecule(s). In particular embodiments, the dsRNA molecule(s) may be produced when ingested by a coleopteran pest to post-transcriptionally silence or inhibit the expression of a target gene in the pest or progeny of the pest. The recombinant DNA may comprise, for example, any of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166; fragments of any of SEQ ID NO:1, SEQ ID NO:3, SEQ ID NO:5, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166 (e.g., SEQ ID NO:8, SEQ ID NO:10, and SEQ ID NOs:101-106); and a polynucleotide consisting of a partial sequence of a gene comprising one of SEQ ID NO:1, SEQ ID NO:3, SEQ ID NO:5, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166, and/or complements thereof.

Some embodiments involve a recombinant host cell having in its genome a recombinant DNA encoding at least one iRNA (e.g., dsRNA) molecule(s) comprising all or part of any of SEQ ID NOs:139-142 and 167-169 (e.g., at least one polynucleotide selected from the group consisting of SEQ ID NOs:143-146); all or part of SEQ ID NO:147 (e.g., SEQ ID NO:162); all or part of SEQ ID NO:148; all or part of SEQ ID NO:149 (e.g., SEQ ID NO:166); all or part of SEQ ID NO:150; all or part of SEQ ID NO:151 (e.g., SEQ ID NO:163); all or part of SEQ ID NO:152; all or part of SEQ ID NO:153; all or part of SEQ ID NO:167; all or part of SEQ ID NO:168; and all or part of SEQ ID NO:169. When ingested by a coleopteran pest, the iRNA molecule(s) may silence or inhibit the expression of a target chromatin remodeling gene (e.g., a DNA comprising all or part of a polynucleotide selected from the group consisting of SEQ ID NO:1; SEQ ID NO:3; SEQ ID NO:5; SEQ ID NO:7; SEQ ID NO:79; SEQ ID NO:81; SEQ ID NO:86; SEQ ID NO:88; SEQ ID NO:90; SEQ ID NO:92; SEQ ID NO:94, SEQ ID NO:164, SEQ ID NO:165, and SEQ ID NO:166) in the pest or progeny of the pest, and thereby result in cessation of reproduction in the pest, and/or growth, development, and/or feeding in progeny of the pest.

In some embodiments, a recombinant host cell having in its genome at least one recombinant DNA encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA(s). In particular embodiments, an RNA molecule capable of forming a dsRNA molecule may be expressed in a transgenic plant cell. Therefore, in these and other embodiments, a dsRNA molecule may be isolated from a transgenic plant cell. In particular embodiments, the transgenic plant is a plant selected from the group comprising corn (*Zea mays*) and plants of the family Poaceae.

Some embodiments involve a method for modulating the expression of a target gene in a coleopteran pest cell. In these and other embodiments, a nucleic acid molecule may be provided, wherein the nucleic acid molecule comprises a polynucleotide encoding an RNA molecule capable of forming a dsRNA molecule. In particular embodiments, a polynucleotide encoding an RNA molecule capable of forming a dsRNA molecule may be operatively linked to a promoter, and may also be operatively linked to a transcription termination sequence. In particular embodiments, a method for modulating the expression of a target gene in a coleopteran pest cell may comprise: (a) transforming a plant cell with a vector comprising a polynucleotide encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the polynucleotide of the vector. A plant may be regenerated from a plant cell that has the vector integrated in its genome and comprises the dsRNA molecule encoded by the polynucleotide of the vector.

Also disclosed is a transgenic plant comprising a vector having a polynucleotide encoding an RNA molecule capable of forming a dsRNA molecule integrated in its genome, wherein the transgenic plant comprises the dsRNA molecule encoded by the polynucleotide of the vector. In particular embodiments, expression of an RNA molecule capable of forming a dsRNA molecule in the plant is sufficient to modulate the expression of a target gene in a cell of a coleopteran pest that contacts the transformed plant or plant cell (for example, by feeding on the transformed plant, a part of the plant (e.g., root) or plant cell) or in a cell of a progeny of the coleopteran pest that contacts the transformed plant or plant cell (for example, by parental transmission), such that reproduction of the pest is inhibited. Transgenic plants disclosed herein may display tolerance and/or protection from coleopteran pest infestations. Particular transgenic plants may display protection and/or enhanced protection from one or more coleopteran pest(s) selected from the group consisting of: WCR; NCR; SCR; MCR; *D. balteata* LeConte; *D. speciosa* Germar; *D. u. tenella*; and *D. u. undecimpunctata* Mannerheim.

Also disclosed herein are methods for delivery of control agents, such as an iRNA molecule, to a coleopteran pest. Such control agents may cause, directly or indirectly, an impairment in the ability of a coleopteran pest population to feed, grow or otherwise cause damage in a host. In some embodiments, a method is provided comprising delivery of a stabilized dsRNA molecule to a coleopteran pest to suppress at least one target gene in the pest or its progeny, thereby causing parental RNAi and reducing or eliminating plant damage in a pest host. In some embodiments, a method of inhibiting expression of a target gene in a coleopteran pest may result in cessation of reproduction in the pest, and/or growth, development, and/or feeding in progeny of the pest. In some embodiments, the method may significantly reduce the size of a subsequent pest generation in an infestation, without directly resulting in mortality in the pest(s) that contact the iRNA molecule. In some embodiments, the method may significantly reduce the size of a subsequent pest generation in an infestation, while also resulting in mortality in the pest(s) that contact the iRNA molecule.

In some embodiments, compositions (e.g., a topical composition) are provided that comprise an iRNA (e.g., dsRNA) molecule for use with plants, animals, and/or the environment of a plant or animal to achieve the elimination or reduction of a coleopteran pest infestation. In some embodiments, compositions are provided that include a prokaryote comprising a DNA encoding an iRNA molecule; for example, a transformed bacterial cell. In particular examples, such a transformed bacterial cell may be utilized as a conventional pesticide formulation. In particular embodiments, the composition may be a nutritional composition or resource, or food source, to be fed to the coleopteran pest. Some embodiments comprise making the nutritional composition or food source available to the pest. Ingestion of a composition comprising iRNA molecules may result in the uptake of the molecules by one or more cells of the coleopteran pest, which may in turn result in the inhibition of expression of at least one target gene in cell(s) of the pest or its progeny. Ingestion of or damage to a plant or plant cell by a coleopteran pest infestation may be limited or eliminated in or on any host tissue or environment in which the pest is present by providing one or more compositions comprising an iRNA molecule in the host of the pest.

The compositions and methods disclosed herein may be used together in combinations with other methods and compositions for controlling damage by coleopteran pests. For example, an iRNA molecule as described herein for protecting plants from coleopteran pests may be used in a method comprising the additional use of one or more chemical agents effective against a coleopteran pest, biopesticides effective against a coleopteran pest, crop rotation, recombinant genetic techniques that exhibit features different from the features of RNAi-mediated methods and RNAi compositions (e.g., recombinant production of proteins in plants that are harmful to a coleopteran pest (e.g., Bt toxins)), and/or recombinant expression of non-parental iRNA molecules (e.g., lethal iRNA molecules that result in the cessation of growth, development, and/or feeding in the coleopteran pest that ingests the iRNA molecule).

II. Abbreviations dsRNA double-stranded ribonucleic acid
GI growth inhibition
GFP green fluorescent protein
NCBI National Center for Biotechnology Information
gDNA genomic deoxyribonucleic acid
iRNA inhibitory ribonucleic acid
ISWI Imitation SWI/imitation switch
ORF open reading frame
RNAi ribonucleic acid interference
miRNA micro ribonucleic acid
siRNA small inhibitory ribonucleic acid
hpRNA hairpin ribonucleic acid
shRNA short hairpin ribonucleic acid
pRNAi parental RNA interference
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR Polymerase chain reaction
qPCR quantitative polymerase chain reaction
RISC RNA-induced Silencing Complex
RH relative humidity
SCR southern corn rootworm (*Diabrotica undecimpunctata howardi* Barber)
SEM standard error of the mean
YFP yellow fluorescent protein

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to pest insects of the order Coleoptera, including pest insects in the genus *Diabrotica*, which feed upon agricultural crops and crop products, including corn and other true grasses. In particular examples, a coleopteran pest is selected from a list comprising *D. v. virgifera* LeConte (WCR); *D. barberi* Smith and Lawrence (NCR); *D. u. howardi* (SCR); *D. v. zeae* (MCR); *D. balteata LeConte; D. u. tenella; D. speciosa* Germar; and *D. u. undecimpunctata* Mannerheim.

Contact (with an organism): As used herein, the term "contact with" or "uptake by" an organism (e.g., a coleopteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize). The terms "corn plant" and "maize" are used interchangeably herein.

Expression: As used herein, "expression" of a coding polynucleotide (for example, a gene or a transgene) refers to the process by which the coded information of a nucleic acid transcriptional unit (including, e.g., gDNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Inhibition: As used herein, the term "inhibition," when used to describe an effect on a coding polynucleotide (for example, a gene), refers to a measurable decrease in the cellular level of mRNA transcribed from the coding polynucleotide and/or peptide, polypeptide, or protein product of the coding polynucleotide. In some examples, expression of a coding polynucleotide may be inhibited such that expression is approximately eliminated. "Specific inhibition" refers to the inhibition of a target coding polynucleotide without consequently affecting expression of other coding polynucleotides (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, gDNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleic acid molecule refers to a polynucleotide having nucleobases that may form base pairs with the nucleobases of the nucleic acid molecule (i.e., A-T/U, and G-C).

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG   polynucleotide

TACTACTAC   "complement" of the polynucleotide

CATCATCAT   "reverse complement" of the
            polynucleotide
```

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over a region comprising the complementary and reverse complementary polynucleotides.

"Nucleic acid molecules" include all polynucleotides, for example: single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), shRNA (small hairpin RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, gDNA, and DNA-RNA hybrids. The terms "polynucleotide" and "nucleic acid," and "fragments" thereof will be understood by those in the art as a term that includes both gDNAs, ribosomal RNAs, transfer RNAs, messenger RNAs, operons, and smaller engineered polynucleotides that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleic acid, they may be used as probes for detecting DNA or RNA. Oligonucleotides composed of DNA (oligodeoxyribonucleotides) may be used in PCR, a technique for the amplification of DNAs. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding polynucleotide," "structural polynucleotide," or "structural nucleic acid molecule" refers to a polynucleotide that is ultimately translated into a polypeptide, via transcription and mRNA, when placed under the control of appropriate regulatory elements. With respect to RNA, the term "coding polynucleotide" refers to a polynucleotide that is translated into a peptide, polypeptide, or protein. The boundaries of a coding polynucleotide are determined by a translation start codon at the 5'-terminus and a translation stop codon at the 3'-terminus. Coding polynucleotides include, but are not limited to: gDNA; cDNA; EST; and recombinant polynucleotides.

As used herein, "transcribed non-coding polynucleotide" refers to segments of mRNA molecules such as 5'UTR, 3'UTR and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18 S rRNA, 23 S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "linker" in a nucleic acid and which is transcribed into an RNA molecule.

Lethal RNA interference: As used herein, the term "lethal RNA interference" refers to RNA interference that results in death or a reduction in viability of the subject individual to which, for example, a dsRNA, miRNA, siRNA, shRNA, and/or hpRNA is delivered.

Parental RNA interference: As used herein, the term "parental RNA interference" (pRNAi) refers to a RNA interference phenotype that is observable in progeny of the subject (e.g., a coleopteran pest) to which, for example, a dsRNA, miRNA, siRNA, shRNA, and/or hpRNA is delivered. In some embodiments, pRNAi comprises the delivery of a dsRNA to a coleopteran pest, wherein the pest is thereby rendered less able to produce viable offspring. A nucleic acid that initiates pRNAi may or may not increase the incidence of mortality in a population into which the nucleic acid is delivered. In certain examples, the nucleic acid that initiates pRNAi does not increase the incidence of mortality in the population into which the nucleic acid is delivered. For example, a population of coleopteran pests may be fed one or more nucleic acids that initiate pRNAi, wherein the pests survive and mate but produce eggs that are less able to hatch viable progeny than eggs produced by pests of the same species that are not fed the nucleic acid(s). In one mechanism of pRNAi, parental RNAi delivered to a female is able to knock down zygotic gene expression in offspring embryos of the female. Bucher et al. (2002) Curr. Biol. 12(3):R85-6.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell, such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome," as it applies to bacteria, refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acids with even greater sequence similarity to the sequences of the reference polynucleotides will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleobases of the two nucleic acid molecules. The two molecules are then able to form hydrogen bonds with corresponding bases on the opposite strand to form a duplex molecule that, if it is sufficiently stable, is detectable using methods well known in the art. A polynucleotide need not be 100% complementary to its target nucleic acid to be specifically hybridizable. However, the amount of complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acids. Generally, the temperature of hybridization and the ionic strength (especially the $Na^{+}$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual, 2nd* ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 20% mismatch between the sequence of the hybridization molecule and a homologous polynucleotide within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects polynucleotides that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects polynucleotides that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (polynucleotides that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a nucleic acid, refers to a polynucleotide having contiguous nucleobases that hybridize under stringent conditions to the reference nucleic acid. For example, nucleic acids that are substantially homologous to a reference nucleic acid of any of SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:86, SEQ ID NO:88, SEQ ID NO:90, SEQ ID NO:92, SEQ ID NO:94, SEQ ID NO:104, SEQ ID NO:105, SEQ ID NO:106, SEQ ID NO:108, SEQ ID NO:164, SEQ ID NO:165, and SEQ ID NO:166 are those nucleic acids that hybridize under stringent conditions (e.g., the Moderate Stringency conditions set forth, supra) to the reference nucleic acid of SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:86, SEQ ID NO:88, SEQ ID NO:90, SEQ ID NO:92, SEQ ID NO:94, SEQ ID NO:104, SEQ ID NO:105, SEQ ID NO:106, SEQ ID NO:108, SEQ ID NO:164, SEQ ID NO:165, and/or SEQ ID NO:166. Substantially homologous polynucleotides may have at least 80% sequence identity. For example, substantially homologous polynucleotides may have from about 80% to 100% sequence identity, such as 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target polynucleotides under conditions where specific binding is desired, for example, under stringent hybridization conditions.

As used herein, the term "ortholog" refers to a gene in two or more species that has evolved from a common ancestral nucleic acid, and may retain the same function in the two or more species.

As used herein, two nucleic acid molecules are said to exhibit "complete complementarity" when every nucleotide of a polynucleotide read in the 5' to 3' direction is complementary to every nucleotide of the other polynucleotide when read in the 3' to 5' direction. A polynucleotide that is complementary to a reference polynucleotide will exhibit a sequence identical to the reverse complement of the reference polynucleotide. These terms and descriptions are well defined in the art and are easily understood by those of ordinary skill in the art.

Operably linked: A first polynucleotide is operably linked with a second polynucleotide when the first polynucleotide is in a functional relationship with the second polynucleotide. When recombinantly produced, operably linked polynucleotides are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory genetic element and a coding polynucleotide, means that the regulatory element affects the expression of the linked coding polynucleotide. "Regulatory elements," or "control elements," refer to polynucleotides that influence the timing and level/amount of transcription, RNA processing or stability, or translation of the associated coding polynucleotide. Regulatory elements may include promoters; translation leaders; introns; enhancers; stem-loop structures; repressor binding polynucleotides; polynucleotides with a termination sequence; polynucleotides with a polyadenylation recognition sequence; etc. Particular regulatory elements may be located upstream and/or downstream of a coding polynucleotide operably linked thereto. Also, particular regulatory elements operably linked to a coding polynucleotide may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding polynucleotide for expression in a cell, or a promoter may be operably linked to a polynucleotide encoding a signal peptide which may be operably linked to a coding polynucleotide for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, Xba1/NcoI fragment 5' to the *Brassica napus* ALS3 structural gene (or a polynucleotide similar to said Xba1/NcoI fragment) (International PCT Publication No. WO96/30530).

Additionally, any tissue-specific or tissue-preferred promoter may be utilized in some embodiments of the invention. Plants transformed with a nucleic acid molecule comprising a coding polynucleotide operably linked to a tissue-specific promoter may produce the product of the coding polynucleotide exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid. In some examples, a transgene may be a DNA that encodes one or both strand(s) of an RNA capable of forming a dsRNA molecule that comprises a polynucleotide that is complementary to a nucleic acid molecule found in a coleopteran pest. In further examples, a transgene may be an antisense polynucleotide, wherein expression of the antisense polynucleotide inhibits expression of a target nucleic acid, thereby producing a parental RNAi phenotype. In still further examples, a transgene may be a gene (e.g., a herbicide-tolerance gene, a gene encoding an industrially or pharmaceutically useful compound, or a gene encoding a desirable agricultural trait). In these and other examples, a transgene may contain regulatory elements operably linked to a coding polynucleotide of the transgene (e.g., a promoter).

Vector: A nucleic acid molecule as introduced into a cell, for example, to produce a transformed cell. A vector may include genetic elements that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of the coleopteran pests that are injurious to that crop growing at the same time and under the same conditions, which are targeted by the compositions and methods herein.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran Pest Polynucleotide

A. Overview

Described herein are nucleic acid molecules useful for the control of coleopteran pests. Described nucleic acid molecules include target polynucleotides (e.g., native genes, and non-coding polynucleotides), dsRNAs, siRNAs, shRNAs, hpRNAs, and miRNAs. For example, dsRNA, siRNA, miRNA, shRNA, and/or hpRNA molecules are described in some embodiments that may be specifically complementary to all or part of one or more native nucleic acids in a coleopteran pest. In these and further embodiments, the native nucleic acid(s) may be one or more target gene(s), the product of which may be, for example and without limitation: involved in a reproductive process or involved in larval development. Nucleic acid molecules described herein, when introduced into a cell (e.g., through parental transmission) comprising at least one native nucleic acid(s) to which the nucleic acid molecules are specifically complementary, may initiate RNAi in the cell, and consequently reduce or eliminate expression of the native nucleic acid(s). In some examples, reduction or elimination of the expression of a target gene by a nucleic acid molecule specifically complementary thereto may result in reduction or cessation of reproduction in the coleopteran pest, and/or growth, development, and/or feeding in progeny of the pest. These methods may significantly reduce the size of a subsequent pest generation in an infestation, for example, without directly resulting in mortality in the pest(s) that contact the iRNA molecule.

In some embodiments, at least one target gene in a coleopteran pest may be selected, wherein the target gene comprises a chromatin remodeling polynucleotide (e.g., a gene). In particular examples, such a chromatin remodeling gene in a coleopteran pest is selected, wherein the target gene comprises a polynucleotide selected from among *Diabrotica brahma* (SEQ ID NO:1, SEQ ID NO:3, SEQ ID NO:5, and SEQ ID NO:7); *Diabrotica* mi-2 (SEQ ID NO:79 and SEQ ID NO:164); *Diabrotica* iswi-1 (SEQ ID NO:81 and SEQ ID NO:165); *Diabrotica* chd1 (SEQ ID NO:83); *Diabrotica* iswi-2 (SEQ ID NO:85 and SEQ ID NO:166); *Diabrotica* iswi30 (SEQ ID NO:87); *Diabrotica* ino80 (SEQ ID NO:89); and *Diabrotica domino* (SEQ ID NO:91). For example, a target gene in certain embodiments comprises a chromatin remodeling polynucleotide selected from among SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and fragments of any of the foregoing (e.g., SEQ ID NO:8, SEQ ID NO:10, and SEQ ID NOs:101-106).

In some embodiments, a chromatin remodeling polynucleotide encodes a member of the group of "ATP-dependent remodeling enzymes," a class of ATPases that contain a SNF2 domain (sucrose non-fermenting, originally identified in *Saccharomyces cerevisiae*). ATP-dependent remodeling enzymes include, for example and without limitation, *BRAHMA* and its orthologs; MI-2 and its orthologs; ISWI-1 and its orthologs; CHD1 and its orthologs; ISWI-2 and its orthologs; ISWI30 and its orthologs; IN080 and its orthologs; and DOMINO and its orthologs. Chromatin remodelers (e.g., ATP-dependent remodeling enzymes) exert lasting epigenetic effects by mobilizing nucleosomes and thus changing the access of the transcriptional machinery to DNA.

ATP-dependent remodeling enzymes share the same functional domains and sequence-level conservation. In Pfam (pfam.sanger.ac.uk) searches, ATP-dependent remodeling enzymes can be identified by a combination of SNF2 family N-terminal and Helicase conserved C-terminal (SNF2-Helicase) domains. Thus, RNAi target sites can be designed within the conserved SNF2 family N-terminal and Helicase C-terminal domains (here referred to as SNF2-Helicase) that are common to all chromatin remodelers, as well as chromatin binding or other functional domains that are conserved within each family, which include but are not limited to bromodomain, chromodomain, and HAND-SLIDE domains.

In some embodiments, a target gene may be a nucleic acid molecule comprising a polynucleotide that can be reverse translated in silico to a polypeptide comprising a contiguous amino acid sequence that is at least about 85% identical (e.g., at least 84%, 85%, about 90%, about 95%, about 96%, about 97%, about 98%, about 99%, about 100%, or 100% identical) to the amino acid sequence of a protein product of a chromatin remodeling gene. A target gene may be any nucleic acid in a coleopteran pest, the post-transcriptional inhibition of which has a deleterious effect on the capacity of the pest to produce viable offspring, for example, to provide a protective benefit against the pest to a plant. In particular examples, a target gene is a nucleic acid molecule comprising a polynucleotide that can be reverse translated in silico to a polypeptide comprising a contiguous amino acid sequence that is at least about 85% identical, about 90% identical, about 95% identical, about 96% identical, about 97% identical, about 98% identical, about 99% identical, about 100% identical, or 100% identical to the amino acid sequence that is the in silico translation product of a *brahma*, mi-2, iswi-1, chd1, iswi-2, iswi30, ino80, or *domino* gene. Examples of such translation products include, for example and without limitation: SEQ ID NO:2; SEQ ID NO:4; SEQ ID NO:6; SEQ ID NO:9; SEQ ID NO:80; SEQ ID NO:82; SEQ ID NO:84; SEQ ID NO:86; SEQ ID NO:88; SEQ ID NO:90; and SEQ ID NO:92.

Provided in some embodiments are DNAs, the expression of which results in an RNA molecule comprising a polynucleotide that is specifically complementary to all or part of a native RNA molecule that is encoded by a coding polynucleotide in a coleopteran pest. In some embodiments, after ingestion of the expressed RNA molecule by a coleopteran pest, down-regulation of the coding polynucleotide in cells of the pest, or in cells of progeny of the pest, may be obtained. In particular embodiments, down-regulation of the coding polynucleotide in cells of the coleopteran pest may result in reduction or cessation of reproduction and/or proliferation in the pest, and/or growth, development, and/or feeding in progeny of the pest.

In some embodiments, target polynucleotides include transcribed non-coding RNAs, such as 5'UTRs; 3'UTRs; spliced leaders; introns; outrons (e.g., 5'UTR RNA subsequently modified in trans splicing); donatrons (e.g., non-coding RNA required to provide donor sequences for trans splicing); and other non-coding transcribed RNA of target coleopteran pest genes. Such polynucleotides may be derived from both mono-cistronic and poly-cistronic genes.

Thus, also described herein in connection with some embodiments are iRNA molecules (e.g., dsRNAs, siRNAs, miRNAs, shRNAs, and hpRNAs) that comprise at least one polynucleotide that is specifically complementary to all or part of a target nucleic acid in a coleopteran pest. In some embodiments an iRNA molecule may comprise polynucleotide(s) that are complementary to all or part of a plurality of target nucleic acids; for example, 2, 3, 4, 5, 6, 7, 8, 9, 10, or more target nucleic acids. In particular embodiments, an iRNA molecule may be produced in vitro or in vivo by a genetically-modified organism, such as a plant or bacterium. Also disclosed are cDNAs that may be used for the production of dsRNA molecules, siRNA molecules, miRNA molecules, shRNA molecules, and/or hpRNA molecules that are specifically complementary to all or part of a target nucleic acid in a coleopteran pest. Further described are recombinant DNA constructs for use in achieving stable transformation of particular host targets. Transformed host targets may express effective levels of dsRNA, siRNA, miRNA, shRNA, and/or hpRNA molecules from the recombinant DNA constructs. Therefore, also described is a plant transformation vector comprising at least one polynucleotide operably linked to a heterologous promoter functional in a plant cell, wherein expression of the polynucleotide(s) results in an RNA molecule comprising a string of contiguous nucleobases that are specifically complementary to all or part of a target nucleic acid in a coleopteran pest.

In particular examples, nucleic acid molecules useful for the control of coleopteran pests may include: all or part of a native nucleic acid isolated from *Diabrotica* comprising a chromatin remodeling gene polynucleotide (e.g., any of SEQ ID NO:1; SEQ ID NO:3; SEQ ID NO:5; SEQ ID NO:7; SEQ ID NO:8; SEQ ID NO:10; SEQ ID NO:79; SEQ ID NO:81; SEQ ID NO:83; SEQ ID NO:85; SEQ ID NO:87; SEQ ID NO:89; SEQ ID NO:91; SEQ ID NO:101; SEQ ID NO:102; SEQ ID NO:103; SEQ ID NO:104; SEQ ID NO:105; SEQ ID NO:106; SEQ ID NO:164; SEQ ID NO:165; and SEQ ID NO:166); DNAs that when expressed result in an RNA molecule comprising a polynucleotide that is specifically complementary to all or part of a native RNA molecule that is encoded by chromatin remodeling gene; iRNA molecules (e.g., dsRNAs, siRNAs, miRNAs, shRNAs, and hpRNAs) that comprise at least one polynucleotide that is specifically complementary to all or part of an RNA molecule encoded by a chromatin remodeling gene; cDNAs that may be used for the production of dsRNA molecules, siRNA molecules, miRNA molecules, shRNA molecules, and/or hpRNA molecules that are specifically complementary to all or part of an RNA molecule encoded by a chromatin remodeling gene; and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA, shRNA, and hpRNA) molecules that inhibit target gene expression in a cell, tissue, or organ of a coleopteran pest; and DNA molecules capable of being expressed as an iRNA molecule in a cell or microorganism to inhibit target gene expression in a cell, tissue, or organ of a coleopteran pest.

Some embodiments of the invention provide an isolated nucleic acid molecule comprising at least one (e.g., one, two, three, or more) polynucleotide(s) selected from the group consisting of: SEQ ID NOs:1, 3, 5, and 7; the complement of any of SEQ ID NOs:1, 3, 5, and 7; a fragment of at least 15 contiguous nucleotides (e.g., at least 19 contiguous nucleotides) of any of SEQ ID NOs:1, 3, 5, and 7 (e.g., SEQ ID NO:8 and SEQ ID NO:10); the complement of a fragment of at least 15 contiguous nucleotides of any of SEQ ID NOs:1, 3, 5, and 7; a native coding polynucleotide of a *Diabrotica* organism (e.g., WCR) comprising any of SEQ ID NOs:1, 3, 5, and 7; the complement of a native coding polynucleotide of a *Diabrotica* organism comprising any of SEQ ID NOs:1, 3, 5, and 7; a fragment of at least 15 contiguous nucleotides of a native coding polynucleotide of a *Diabrotica* organism comprising any of SEQ ID NOs:1, 3, 5, and 7; and the complement of a fragment of at least 15 contiguous nucleotides of a native coding polynucleotide of a *Diabrotica* organism comprising any of SEQ ID NOs:1, 3, 5, and 7. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:79; SEQ ID NO:164; the complement of SEQ ID NO:79; the complement of SEQ ID NO:164; a fragment of at least 15 contiguous nucleotides (e.g., at least 19 contiguous nucleotides) of SEQ ID NO:79 or SEQ ID NO:164 (e.g., SEQ ID NO:104); the complement of a fragment of at least 15 contiguous nucleotides of SEQ ID NO:79 or SEQ ID NO:164; a native coding polynucleotide of a *Diabrotica* organism (e.g., WCR) comprising SEQ ID NO:79 or SEQ ID NO:164; the complement of a native coding polynucleotide of a *Diabrotica* organism comprising SEQ ID NO:79; a fragment of at least 15 contiguous nucleotides of a native coding polynucleotide of a *Diabrotica* organism comprising SEQ ID NO:79 or SEQ ID NO:164; and the complement of a fragment of at least 15 contiguous nucleotides of a native coding polynucleotide of a *Diabrotica* organism comprising SEQ ID NO:79 or SEQ ID NO:164. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:81; SEQ ID NO:165; the complement of SEQ ID NO:81; the complement of SEQ ID NO:165; a fragment of at least 15 contiguous nucleotides (e.g., at least 19 contiguous nucleotides) of SEQ ID NO:81 or SEQ ID NO:165; the complement of a fragment of at least 15 contiguous nucleotides of SEQ ID NO:81 or SEQ ID NO:165; a native coding polynucleotide of a *Diabrotica* organism (e.g., WCR) comprising SEQ ID NO:81 or SEQ ID NO:165; the complement of a native coding polynucleotide of a *Diabrotica* organism comprising SEQ ID NO:81 or SEQ ID NO:165; a fragment of at least 15 contiguous nucleotides of a native coding polynucleotide of a *Diabrotica* organism comprising SEQ ID NO:81 or SEQ ID NO:165; and the complement of a fragment of at least 15 contiguous nucleotides of a native coding polynucleotide of a *Diabrotica* organism comprising SEQ ID NO:81 or SEQ ID NO:165. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:83; the complement of SEQ ID NO:83; a fragment of at least 15 contiguous nucleotides (e.g., at least 19 contiguous nucleotides) of SEQ ID NO:83 (e.g., SEQ ID NO:105); the complement of a fragment of at least 15 contiguous nucleotides of SEQ ID NO:83; a native coding polynucleotide of a *Diabrotica* organism (e.g., WCR) comprising SEQ ID NO:83; the complement of a native coding polynucleotide of a *Diabrotica* organism comprising SEQ ID NO:83; a fragment of at least 15 contiguous nucleotides of a native coding polynucleotide of a *Diabrotica* organism comprising SEQ ID NO:83; and the complement of a fragment of at least 15 contiguous nucleotides of a native coding polynucleotide of a *Diabrotica* organism comprising SEQ ID NO:83. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:85; SEQ ID NO:166; the complement of SEQ ID NO:85; the complement of SEQ ID NO:166; a fragment of at least 15 contiguous nucleotides (e.g., at least 19 contiguous nucleotides) of SEQ ID NO:85 or SEQ ID NO:166 (e.g., SEQ ID NO:103); the complement of a fragment of at least 15 contiguous nucleotides of SEQ ID NO:85 or SEQ ID NO:166; a native coding polynucleotide of a *Diabrotica* organism (e.g., WCR) comprising SEQ ID NO:85 or SEQ ID NO:166; the complement of a native coding polynucleotide of a *Diabrotica* organism comprising SEQ ID NO:85 or SEQ ID NO:166; a fragment of at least 15 contiguous nucleotides of a native coding polynucleotide of a *Diabrotica* organism comprising SEQ ID NO:85 or SEQ ID NO:166; and the complement of a fragment of at least 15 contiguous nucleotides of a native coding polynucleotide of a *Diabrotica* organism comprising SEQ ID NO:85 or SEQ ID NO:166. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:87; the complement of SEQ ID NO:87; a fragment of at least 15 contiguous nucleotides (e.g., at least 19 contiguous nucleotides) of SEQ ID NO:87 (e.g., SEQ ID NO:102); the complement of a fragment of at least 15 contiguous nucleotides of SEQ ID NO:87; a native coding polynucleotide of a *Diabrotica* organism (e.g., WCR) comprising SEQ ID NO:87; the complement of a native coding polynucleotide of a *Diabrotica* organism comprising SEQ ID NO:87; a fragment of at least 15 contiguous nucleotides of a native coding polynucleotide of a *Diabrotica* organism comprising SEQ ID NO:87; and the complement of a fragment of at least 15 contiguous nucleotides of a native coding polynucleotide of a *Diabrotica* organism comprising SEQ ID NO:87. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:89; the complement of SEQ ID NO:89; a fragment of at least 15 contiguous nucleotides (e.g., at least 19 contiguous nucleotides) of SEQ ID NO:89; the complement of a fragment of at least 15 contiguous nucleotides of SEQ ID NO:89; a native coding polynucleotide of a *Diabrotica* organism (e.g., WCR) comprising SEQ ID NO:89; the complement of a native coding polynucleotide of a *Diabrotica* organism comprising SEQ ID NO:89; a fragment of at least 15 contiguous nucleotides of a native coding polynucleotide of a *Diabrotica* organism comprising SEQ ID NO:89; and the complement of a fragment of at least 15 contiguous nucleotides of a native coding polynucleotide of a *Diabrotica* organism comprising SEQ ID NO:89. In particular embodiments, contact with or uptake by a coleopteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:91; the complement of SEQ ID NO:91; a fragment of at least 15 contiguous nucleotides (e.g., at least 19 contiguous nucleotides) of SEQ ID NO:91; the complement of a fragment of at least 15 contiguous nucleotides of SEQ ID NO:91; a native coding polynucleotide of a *Diabrotica* organism (e.g., WCR) comprising SEQ ID NO:91; the complement of a native coding polynucleotide of a *Diabrotica* organism comprising SEQ ID NO:91; a fragment of at least 15 contiguous nucleotides of a native coding polynucleotide of a *Diabrotica* organism comprising SEQ ID NO:91; and the complement of a fragment of at least 15 contiguous nucleotides of a native coding polynucleotide of a *Diabrotica* organism comprising SEQ ID NO:91. In particular embodiments, contact with or uptake by a coleopteran pest of the isolated polynucleotide inhibits the growth, development, reproduction and/or feeding of the pest.

In some embodiments, an isolated nucleic acid molecule of the invention may comprise at least one (e.g., one, two, three, or more) polynucleotide(s) selected from the group consisting of: SEQ ID NO:139; the complement of SEQ ID NO:139; SEQ ID NO:140; the complement of SEQ ID NO:140; SEQ ID NO:141; the complement of SEQ ID NO:141; SEQ ID NO:142; the complement of SEQ ID NO:142; SEQ ID NO:143; the complement of SEQ ID NO:143; SEQ ID NO:144; the complement of SEQ ID NO:144; SEQ ID NO:145; the complement of SEQ ID NO:145; SEQ ID NO:146; the complement of SEQ ID NO:146; SEQ ID NO:147; the complement of SEQ ID NO:147; SEQ ID NO:148; the complement of SEQ ID NO:148; SEQ ID NO:149; the complement of SEQ ID NO:149; SEQ ID NO:150; the complement of SEQ ID NO:150; SEQ ID NO:151; the complement of SEQ ID NO:151; SEQ ID NO:152; the complement of SEQ ID NO:152; SEQ ID NO:153; the complement of SEQ ID NO:153; SEQ ID NO:154; the complement of SEQ ID NO:154; SEQ ID NO:155; the complement of SEQ ID NO:155; SEQ ID NO:156; the complement of SEQ ID NO:156; SEQ ID NO:157; the complement of SEQ ID NO:157; SEQ ID NO:158; the complement of SEQ ID NO:158; SEQ ID NO:159; the complement of SEQ ID NO:159; SEQ ID NO:160; the complement of SEQ ID NO:160; SEQ ID NO:161; the complement of SEQ ID NO:161; SEQ ID NO:162; the complement of SEQ ID NO:162; SEQ ID NO:163; the complement of SEQ ID NO:163; SEQ ID NO:167; the complement of SEQ ID NO:167; SEQ ID NO:168; the complement of SEQ ID NO:168; SEQ ID NO:169; the complement of SEQ ID NO:169; a native polyribonucleotide transcribed in a *Diabrotica* organism from a gene comprising SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:83, SEQ ID NO:85, SEQ ID NO:87, SEQ ID NO:89, SEQ ID NO:91, SEQ ID NO:101, SEQ ID NO:102, SEQ ID NO:103, SEQ ID NO:104, SEQ ID NO:105, SEQ ID NO:106, SEQ ID NO:164, SEQ ID NO:165, or SEQ ID NO:166; the complement of a native polyribonucleotide transcribed in a *Diabrotica* organism from a gene comprising SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:83, SEQ ID NO:85, SEQ ID NO:87, SEQ ID NO:89, SEQ ID NO:91, SEQ ID NO:101, SEQ ID NO:102, SEQ ID NO:103, SEQ ID NO:104, SEQ ID NO:105, SEQ ID NO:106, SEQ ID NO:164, SEQ ID NO:165, or SEQ ID NO:166; a fragment of at least 15 contiguous nucleotides of a native polyribonucleotide transcribed in a *Diabrotica* organism from a gene comprising SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:83, SEQ ID NO:85, SEQ ID NO:87, SEQ ID NO:89, SEQ ID NO:91, SEQ ID NO:101, SEQ ID NO:102, SEQ ID NO:103, SEQ ID NO:104, SEQ ID NO:105, SEQ ID NO:106, SEQ ID NO:164, SEQ ID NO:165, or SEQ ID NO:166; and the complement of a fragment of at least 15 contiguous nucleotides of a native polyribonucleotide transcribed in a *Diabrotica* organism from a gene comprising SEQ ID NO:1, SEQ ID NO:3, SEQ ID NO:5, SEQ ID NO:7, SEQ ID NO:8, SEQ ID NO:10, SEQ ID NO:79, SEQ ID NO:81, SEQ ID NO:83, SEQ ID NO:85, SEQ ID NO:87, SEQ ID NO:89, SEQ ID NO:91, SEQ ID NO:101, SEQ ID NO:102, SEQ ID NO:103, SEQ ID NO:104, SEQ ID NO:105, SEQ ID NO:106, SEQ ID NO:164, SEQ ID NO:165, or SEQ ID NO:166. In particular embodiments, contact with or uptake by a coleopteran pest of the isolated polynucleotide inhibits the growth, development, reproduction and/or feeding of the pest. In some embodiments, contact with or uptake by the insect occurs via feeding on plant material or bait comprising the iRNA. In some embodiments, contact with or uptake by the insect occurs via spraying of a plant comprising the insect with a composition comprising the iRNA.

In some embodiments, a nucleic acid molecule of the invention may comprise at least one (e.g., one, two, three, or more) DNA(s) capable of being expressed as an iRNA molecule in a cell or microorganism to inhibit target gene expression in a cell, tissue, or organ of a coleopteran pest. Such DNA(s) may be operably linked to a promoter that functions in a cell comprising the DNA molecule to initiate or enhance the transcription of the encoded RNA capable of forming a dsRNA molecule(s). In one embodiment, the at least one (e.g., one, two, three, or more) DNA(s) may be derived from the polynucleotide of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, or SEQ ID NO:166. Derivatives of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166 includes fragments of these polynucleotides. In some embodiments, such a fragment may comprise, for example, at least about 15 contiguous nucleotides of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166, or a complement thereof. In some examples, such a fragment may comprise, for example, at least 19 contiguous nucleotides (e.g., 19, 20, 21, 22, 23, 24, 25, 26, 27, 28, 29, or 30 contiguous nucleotides) of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166, or a complement thereof.

Some embodiments comprise introducing partially- or fully-stabilized dsRNA molecules into a coleopteran pest to inhibit expression of a target gene in a cell, tissue, or organ of the coleopteran pest. When expressed as an iRNA molecule (e.g., dsRNA, siRNA, miRNA, shRNA, and hpRNA) and taken up by a coleopteran pest, polynucleotides comprising one or more fragments of any of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and the complements thereof, may cause one or more of death, developmental arrest, growth inhibition, change in sex ratio, reduction in brood size, cessation of infection, and/or cessation of feeding by a coleopteran pest. In particular examples, polynucleotides comprising one or more fragments (e.g., polynucleotides including about 15 to about 300 nucleotides) of any of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and the complements thereof, cause a reduction in the capacity of an existing generation of the pest to produce a subsequent generation of the pest.

In certain embodiments, dsRNA molecules provided by the invention comprise polynucleotides complementary to a transcript from a target gene comprising SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, and/or polynucleotides complementary to a fragment of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, the inhibition of which target gene in a coleopteran pest results in the reduction or removal of a polypeptide or polynucleotide agent that is essential for the pest's or the pest's progeny's growth, development, or other biological function. A selected polynucleotide may exhibit from about 80% to about 100% sequence identity to SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, a contiguous fragment of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, or the complement of either of the foregoing. For example, a selected polynucleotide may exhibit 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, a contiguous fragment of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91, SEQ ID NO:164, SEQ ID NO:165, and/or SEQ ID NO:166, or the complement of any of the foregoing.

In some embodiments, a DNA molecule capable of being expressed as an iRNA molecule in a cell or microorganism to inhibit target gene expression may comprise a single polynucleotide that is specifically complementary to all or part of a native polynucleotide found in one or more target coleopteran pest species, or the DNA molecule can be constructed as a chimera from a plurality of such specifically complementary polynucleotides.

In some embodiments, a nucleic acid molecule may comprise a first and a second polynucleotide separated by a "linker." A linker may be a region comprising any sequence of nucleotides that facilitates secondary structure formation between the first and second polynucleotides, where this is desired. In one embodiment, the linker is part of a sense or antisense coding polynucleotide for mRNA. The linker may alternatively comprise any combination of nucleotides or homologues thereof that are capable of being linked covalently to a nucleic acid molecule. In some examples, the linker may comprise an intron (e.g., as ST-LS1 intron).

For example, in some embodiments, the DNA molecule may comprise a polynucleotide coding for one or more different RNA molecules, wherein each of the different RNA molecules comprises a first polynucleotide and a second polynucleotide, wherein the first and second polynucleotides are complementary to each other. The first and second polynucleotides may be connected within an RNA molecule by a linker. The linker may constitute part of the first polynucleotide or the second polynucleotide. Expression of an RNA molecule comprising the first and second nucleotide polynucleotides may lead to the formation of a dsRNA molecule of the present invention, by specific intramolecular base-pairing of the first and second nucleotide polynucleotides. The first polynucleotide or the second polynucleotide may be substantially identical to a polynucleotide native to a coleopteran pest (e.g., a target gene, or transcribed non-coding polynucleotide), a derivative thereof, or a complementary polynucleotide thereto.

dsRNA nucleic acid molecules comprise double strands of polymerized ribonucleotides, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNAs transcribed from a target gene, and both RNA molecules are subsequently degraded by an inherent cellular RNA-degrading mechanism. This process may result in the effective degradation or removal of the RNA encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in coleopteran pests.

In some embodiments, a nucleic acid molecule of the invention may include at least one non-naturally occurring polynucleotide that can be transcribed into a single-stranded RNA molecule capable of forming a dsRNA molecule in vivo through intermolecular hybridization. Such dsRNAs typically self-assemble, and can be provided in the nutrition source of a coleopteran pest to achieve the post-transcriptional inhibition of a target gene. In these and further embodiments, a nucleic acid molecule of the invention may comprise two different non-naturally occurring polynucleotides, each of which is specifically complementary to a different target gene in a coleopteran pest. When such a nucleic acid molecule is provided as a dsRNA molecule to a coleopteran pest, the dsRNA molecule inhibits the expression of at least two different target genes in the pest.

C. Obtaining Nucleic Acid Molecules

A variety of polynucleotides in coleopteran pests may be used as targets for the design of nucleic acid molecules of the invention, such as iRNAs and DNA molecules encoding iRNAs. Selection of native polynucleotides is not, however, a straight-forward process. Only a small number of native polynucleotides in the coleopteran pest will be effective targets. For example, it cannot be predicted with certainty whether a particular native polynucleotide can be effectively down-regulated by nucleic acid molecules of the invention, or whether down-regulation of a particular native polynucleotide will have a detrimental effect on the growth, viability, proliferation, and/or reproduction of the coleopteran pest. The vast majority of native coleopteran pest polynucleotides, such as ESTs isolated therefrom (e.g., the coleopteran pest polynucleotides listed in U.S. Pat. No. 7,612,194), do not have a detrimental effect on the growth, viability, proliferation, and/or reproduction of the pest. Neither is it predictable which of the native polynucleotides that may have a detrimental effect on a coleopteran pest are able to be used in recombinant techniques for expressing nucleic acid molecules complementary to such native polynucleotides in a host plant and providing the detrimental effect on the pest upon feeding without causing harm to the host plant.

In some embodiments, nucleic acid molecules of the invention (e.g., dsRNA molecules to be provided in the host plant of a coleopteran pest) are selected to target cDNAs that encode proteins or parts of proteins essential for coleopteran pest reproduction and/or development, such as polypeptides involved in metabolic or catabolic biochemical pathways, cell division, reproduction, energy metabolism, embryonic development, larval development, transcriptional regulation, and the like. As described herein, ingestion of compositions by a target organism containing one or more dsRNAs, at least one segment of which is specifically complementary to at least a substantially identical segment of RNA produced in the cells of the target pest organism, can result in failure or reduction of the capacity to mate, oviposit, or produce viable progeny. A polynucleotide, either DNA or RNA, derived from a coleopteran pest can be used to construct plant cells resistant to infestation by the pests. The host plant of the coleopteran pest (e.g., *Z. mays*), for example, can be transformed to contain one or more of the polynucleotides derived from the coleopteran pest as provided herein. The polynucleotide transformed into the host may encode one or more RNAs that form into a dsRNA structure in the cells or biological fluids within the transformed host, thus making the dsRNA available if/when the pest forms a nutritional relationship with the transgenic host. This may result in the suppression of expression of one or more genes in the cells of the pest, and ultimately inhibition of reproduction and/or development.

Thus, in some embodiments, a gene is targeted that is essentially involved in the growth, development and reproduction of a coleopteran pest. Other target genes for use in the present invention may include, for example, those that play important roles in coleopteran pest viability, movement, migration, growth, development, infectivity, and establishment of feeding sites. A target gene may therefore be a housekeeping gene or a transcription factor. Additionally, a native coleopteran pest polynucleotide for use in the present invention may also be derived from a homolog (e.g., an ortholog), of a plant, viral, bacterial or insect gene, the function of which is known to those of skill in the art, and the polynucleotide of which is specifically hybridizable with a target gene in the genome of the target coleopteran pest. Methods of identifying a homolog of a gene with a known nucleotide sequence by hybridization are known to those of skill in the art.

In some embodiments, the invention provides methods for obtaining a nucleic acid molecule comprising a polynucleotide for producing an iRNA (e.g., dsRNA, siRNA, miRNA, shRNA, and hpRNA) molecule. One such embodiment comprises: (a) analyzing one or more target gene(s) for their expression, function, and phenotype upon dsRNA-mediated gene suppression in a coleopteran pest; (b) probing a cDNA or gDNA library with a probe comprising all or a portion of a polynucleotide or a homolog thereof from a targeted coleopteran pest that displays an altered (e.g., reduced) reproduction or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA or a homolog thereof; and (f) chemically synthesizing all or a substantial portion of a gene, or an siRNA, miRNA, hpRNA, mRNA, shRNA, or dsRNA.

In further embodiments, a method for obtaining a nucleic acid fragment comprising a polynucleotide for producing a substantial portion of an iRNA (e.g., dsRNA, siRNA, miRNA, shRNA, and hpRNA) molecule includes: (a) synthesizing first and second oligonucleotide primers specifically complementary to a portion of a native polynucleotide from a targeted coleopteran pest; and (b) amplifying a cDNA or gDNA insert present in a cloning vector using the first and second oligonucleotide primers of step (a), wherein the amplified nucleic acid molecule comprises a substantial portion of a siRNA, miRNA, hpRNA, mRNA, shRNA, or dsRNA molecule.

Nucleic acids of the invention can be isolated, amplified, or produced by a number of approaches. For example, an iRNA (e.g., dsRNA, siRNA, miRNA, shRNA, and hpRNA) molecule may be obtained by PCR amplification of a target polynucleotide (e.g., a target gene or a target transcribed non-coding polynucleotide) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a polynucleotide encoding the RNA, dsRNA, siRNA, miRNA, shRNA, or hpRNA molecule. RNA may also be produced by partial or total organic synthesis; any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of polynucleotides are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a polynucleotide that, upon expression to RNA and ingestion by a coleopteran pest, achieves suppression of a target gene in a cell, tissue, or organ of the pest. Thus, some embodiments provide a recombinant nucleic acid molecule comprising a polynucleotide capable of being expressed as an iRNA (e.g., dsRNA, siRNA, miRNA, shRNA, and hpRNA) molecule in a plant cell to inhibit target gene expression in a coleopteran pest. In order to initiate or enhance expression, such recombinant nucleic acid molecules may comprise one or more regulatory elements, which regulatory elements may be operably linked to the polynucleotide capable of being expressed as an iRNA. Methods to express a gene suppression molecule in plants are known, and may be used to express a polynucleotide of the present invention. See, e.g., International PCT Publication No. WO06/073727; and U.S. Patent Publication No. 2006/0200878 A1).

In specific embodiments, a recombinant DNA molecule of the invention may comprise a polynucleotide encoding an RNA that may form a dsRNA molecule. Such recombinant DNA molecules may encode RNAs that may form dsRNA molecules capable of inhibiting the expression of endogenous target gene(s) in a coleopteran pest cell upon ingestion. In many embodiments, a transcribed RNA may form a dsRNA molecule that may be provided in a stabilized form; e.g., as a hairpin and stem and loop structure.

In some embodiments, one strand of a dsRNA molecule may be formed by transcription from a polynucleotide which is substantially homologous to the RNA encoded by a polynucleotide selected from the group consisting of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166; the complement of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; a fragment of at least 15 contiguous nucleotides of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; the complement of a fragment of at least 15 contiguous nucleotides of SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; a native coding polynucleotide of a *Diabrotica* organism (e.g., WCR) comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; the complement of a native coding polynucleotide of a *Diabrotica* organism comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; a fragment of at least 15 contiguous nucleotides of a native coding polynucleotide of a *Diabrotica* organism comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166; and the complement of a fragment of at least 15 contiguous nucleotides of a native coding polynucleotide of a *Diabrotica* organism comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, or SEQ ID NO:166.

In particular embodiments, a recombinant DNA molecule encoding an RNA that may form a dsRNA molecule may comprise a coding region wherein at least two polynucleotides are arranged such that one polynucleotide is in a sense orientation, and the other polynucleotide is in an antisense orientation, relative to at least one promoter, wherein the sense polynucleotide and the antisense polynucleotide are linked or connected by a linker of, for example, from about five (~5) to about one thousand (~1000) nucleotides. The linker may form a loop between the sense and anti sense polynucleotides. The sense polynucleotide or the antisense polynucleotide may be substantially homologous to an RNA encoded by a target gene (e.g., a chromatin remodeling gene comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166) or fragment thereof. In some embodiments, however, a recombinant DNA molecule may encode an RNA that may form a dsRNA molecule without a linker. In embodiments, a sense coding polynucleotide and an anti sense coding polynucleotide may be different lengths.

Polynucleotides identified as having a deleterious effect on coleopteran pests or a plant-protective effect with regard to coleopteran pests may be readily incorporated into expressed dsRNA molecules through the creation of appropriate expression cassettes in a recombinant nucleic acid molecule of the invention. For example, such polynucleotides may be expressed as a hairpin with stem and loop structure by taking a first segment corresponding to an RNA encoded by a target gene polynucleotide (e.g., a chromatin remodeling gene comprising SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166, and fragments thereof); linking this polynucleotide to a second segment linker region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms comprising the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran pest polynucleotide is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve coleopteran pest-protective levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acids of the invention can, for example, be suitably inserted into a vector under the control of a suitable promoter that functions in one or more hosts to drive expression of a linked coding polynucleotide or other DNA element. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart protection from a coleopteran pest to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a polynucleotide that is substantially homologous and specifically hybridizable to a corresponding transcribed polynucleotide within a coleopteran pest that may cause damage to the host plant species. The coleopteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran pests that infest the transgenic host plant. In some embodiments, suppression of expression of the target gene in the target coleopteran pest may result in the plant being tolerant to attack by the pest.

In order to enable delivery of iRNA molecules to a coleopteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a polynucleotide of the invention operably linked to one or more regulatory elements, such as a heterologous promoter element that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked coding polynucleotides exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a polynucleotide or fragment for coleopteran pest control according to the invention may be cloned between two root-specific promoters oriented in opposite transcriptional directions relative to the polynucleotide or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran pest so that suppression of target gene expression is achieved.

Additional regulatory elements that may optionally be operably linked to a nucleic acid molecule of interest include 5'UTRs located between a promoter element and a coding polynucleotide that function as a translation leader element. The translation leader element is present in the fully-processed mRNA, and it may affect processing of the primary transcript, and/or RNA stability. Examples of translation leader elements include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank™ Accession No. V00087; and Bevan et al. (1983) Nature 304:184-7).

Additional regulatory elements that may optionally be operably linked to a nucleic acid molecule of interest also include 3' non-translated elements, 3' transcription termination regions, or polyadenylation regions. These are genetic elements located downstream of a polynucleotide, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation element can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum*

RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory elements operatively linked to one or more polynucleotides of the present invention. When expressed, the one or more polynucleotides result in one or more RNA molecule(s) comprising a polynucleotide that is specifically complementary to all or part of a native RNA molecule in a coleopteran pest. Thus, the polynucleotide(s) may comprise a segment encoding all or part of a polyribonucleotide present within a targeted coleopteran pest RNA transcript, and may comprise inverted repeats of all or a part of a targeted pest transcript. A plant transformation vector may contain polynucleotides specifically complementary to more than one target polynucleotide, thus allowing production of more than one dsRNA for inhibiting expression of two or more genes in cells of one or more populations or species of target coleopteran pests. Segments of polynucleotides specifically complementary to polynucleotides present in different genes can be combined into a single composite nucleic acid molecule for expression in a transgenic plant. Such segments may be contiguous or separated by a linker.

In some embodiments, a plasmid of the present invention already containing at least one polynucleotide(s) of the invention can be modified by the sequential insertion of additional polynucleotide(s) in the same plasmid, wherein the additional polynucleotide(s) are operably linked to the same regulatory elements as the original at least one polynucleotide(s). In some embodiments, a nucleic acid molecule may be designed for the inhibition of multiple target genes. In some embodiments, the multiple genes to be inhibited can be obtained from the same coleopteran pest species, which may enhance the effectiveness of the nucleic acid molecule. In other embodiments, the genes can be derived from different insect (e.g., coleopteran) pests, which may broaden the range of pests against which the agent(s) is/are effective. When multiple genes are targeted for suppression or a combination of expression and suppression, a polycistronic DNA element can be engineered.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate tolerance; a nitrilase gene which confers resistance to bromoxynil; a mutant acetolactate synthase (ALS) gene which confers imidazolinone or sulfonylurea tolerance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708; and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ *Stadler Genetics Symposium*, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acids encoding one or more iRNA molecules in the genome of the transgenic plant.

The most widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border elements. The T-region may also contain a selectable marker for efficient recovery of transgenic cells and plants, and a multiple cloning site for inserting polynucleotides for transfer such as a dsRNA encoding nucleic acid.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA encoding one or more iRNA molecules that inhibit target gene expression in a coleopteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of gDNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to gDNA derived from any plant species (e.g., *Z. mays*) or tissue type, including cell cultures.

A transgenic plant formed using *Agrobacterium*-dependent transformation methods typically contains a single recombinant DNA inserted into one chromosome. The polynucleotide of the single recombinant DNA is referred to as a "transgenic event" or "integration event". Such transgenic plants are heterozygous for the inserted exogenous polynucleotide. In some embodiments, a transgenic plant homozygous with respect to a transgene may be obtained by sexually mating (selfing) an independent segregant transgenic plant that contains a single exogenous gene to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have a coleopteran pest-protective effect. The iRNA molecules (e.g., dsRNA molecules) may be expressed from multiple nucleic acids introduced in different transformation events, or from a single nucleic acid introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple polynucleotides that are each homologous to different loci within one or more coleopteran pests (for example, the loci defined by SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166), both in different populations of the same species of coleopteran pest, or in different species of coleopteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a polynucleotide that encodes an iRNA molecule may be introduced into a first plant line that is amenable to transformation to produce a transgenic plant, which transgenic plant may be crossed with a second plant line to introgress the polynucleotide that encodes the iRNA molecule into the second plant line.

The invention also includes commodity products containing one or more of the polynucleotides of the present invention. Particular embodiments include commodity products produced from a recombinant plant or seed containing one or more of the polynucleotides of the present invention. A commodity product containing one or more of the polynucleotides of the present invention is intended to include, but not be limited to, meals, oils, crushed or whole grains or seeds of a plant, or any food product comprising any meal, oil, or crushed or whole grain of a recombinant plant or seed containing one or more of the polynucleotides of the present invention. The detection of one or more of the polynucleotides of the present invention in one or more commodity or commodity products contemplated herein is de facto evidence that the commodity or commodity product is produced from a transgenic plant designed to express one or more of the polynucleotides of the present invention for the purpose of controlling plant pests using dsRNA-mediated gene suppression methods.

In some aspects, seeds and commodity products produced by transgenic plants derived from transformed plant cells are included, wherein the seeds or commodity products comprise a detectable amount of a nucleic acid of the invention. In some embodiments, such commodity products may be produced, for example, by obtaining transgenic plants and preparing food or feed from them. Commodity products comprising one or more of the polynucleotides of the invention includes, for example and without limitation: meals, oils, crushed or whole grains or seeds of a plant, and any food product comprising any meal, oil, or crushed or whole grain of a recombinant plant or seed comprising one or more of the nucleic acids of the invention. The detection of one or more of the polynucleotides of the invention in one or more commodity or commodity products is de facto evidence that the commodity or commodity product is produced from a transgenic plant designed to express one or more of the iRNA molecules of the invention for the purpose of controlling coleopteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran pest other than the ones defined by SEQ ID NO:1, SEQ ID NO:3, SEQ ID NO:5, SEQ ID NO:7, SEQ ID NO:79, SEQ ID NO:81, SEQ ID NO:83, SEQ ID NO:85, SEQ ID NO:87, SEQ ID NO:89, SEQ ID NO:91, SEQ ID NO:164, SEQ ID NO:165, and SEQ ID NO:166; a transgenic event from which is transcribed an iRNA molecule targeting a gene in an organism other than a coleopteran pest (e.g., a plant-parasitic nematode); a gene encoding an insecticidal protein (e.g., a *Bacillus thuringiensis* insecticidal protein); a herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, polynucleotides encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran Pest

A. Overview

In some embodiments of the invention, at least one nucleic acid molecule useful for the control of coleopteran pests may be provided to a coleopteran pest, wherein the nucleic acid molecule leads to RNAi-mediated gene silencing in the pest. In particular embodiments, an iRNA molecule (e.g., dsRNA, siRNA, miRNA, shRNA, and hpRNA) may be provided to the coleopteran pest. In some embodiments, a nucleic acid molecule useful for the control of coleopteran pests may be provided to a pest by contacting the nucleic acid molecule with the pest. In these and further embodiments, a nucleic acid molecule useful for the control of coleopteran pests may be provided in a feeding substrate of the pest, for example, a nutritional composition. In these and further embodiments, a nucleic acid molecule useful for the control of a coleopteran pest may be provided through ingestion of plant material comprising the nucleic acid molecule that is ingested by the pest. In certain embodiments, the nucleic acid molecule is present in plant material through expression of a recombinant nucleic acid introduced into the plant material, for example, by transformation of a plant cell with a vector comprising the recombinant nucleic acid and regeneration of a plant material or whole plant from the transformed plant cell.

B. RNAi-Mediated Target Gene Suppression

In embodiments, the invention provides iRNA molecules (e.g., dsRNA, siRNA, miRNA, shRNA, and hpRNA) that may be designed to target essential native polynucleotides (e.g., essential genes) in the transcriptome of a coleopteran (e.g., WCR or NCR) pest, for example by designing an iRNA molecule that comprises at least one strand comprising a polynucleotide that is specifically complementary to the target polynucleotide. The sequence of an iRNA molecule so designed may be identical to that of the target polynucleotide, or may incorporate mismatches that do not prevent specific hybridization between the iRNA molecule and its target polynucleotide.

iRNA molecules of the invention may be used in methods for gene suppression in a coleopteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding polynucleotide including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary polynucleotide of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a polynucleotide, which polynucleotide may be expressed in vitro to produce an iRNA molecule that is substantially homologous to a nucleic acid molecule encoded by a polynucleotide within the genome of a coleopteran pest. In certain embodiments, the in vitro transcribed iRNA molecule may be a stabilized dsRNA molecule that comprises a stem-loop structure. After a coleopteran pest contacts the in vitro transcribed iRNA molecule, post-transcriptional inhibition of a target gene in the pest (for example, an essential gene) may occur.

In some embodiments of the invention, expression of an iRNA from a nucleic acid molecule comprising at least 15 contiguous nucleotides (e.g., at least 19 contiguous nucleotides) of a polynucleotide are used in a method for post-transcriptional inhibition of a target gene in a coleopteran pest, wherein the polynucleotide is selected from the group consisting of: SEQ ID NO:1; the complement of SEQ ID NO:1; SEQ ID NO:3; the complement of SEQ ID NO:3; SEQ ID NO:5; the complement of SEQ ID NO:5; SEQ ID NO:7; the complement of SEQ ID NO:7; SEQ ID NO:79; the complement of SEQ ID NO:79; SEQ ID NO:81; the complement of SEQ ID NO:81; SEQ ID NO:83; the complement of SEQ ID NO:83; SEQ ID NO:85; the complement of SEQ ID NO:85; SEQ ID NO:87; the complement of SEQ ID NO:87; SEQ ID NO:89; the complement of SEQ ID NO:89; SEQ ID NO:91; the complement of SEQ ID NO:91; SEQ ID NO:164; the complement of SEQ ID NO:164; SEQ ID NO:165; the complement of SEQ ID NO:165; SEQ ID NO:166, the complement of SEQ ID NO:166; a fragment of at least 15 contiguous nucleotides of SEQ ID NO:1; the complement of a fragment of at least 15 contiguous nucleotides of SEQ ID NO:1; a fragment of at least 15 contiguous nucleotides of SEQ ID NO:3; the complement of a fragment of at least 15 contiguous nucleotides of SEQ ID NO:3; a fragment of at least 15 contiguous nucleotides of SEQ ID NO:5; the complement of a fragment of at least 15 contiguous nucleotides of SEQ ID NO:5; a fragment of at least 15 contiguous nucleotides of SEQ ID NO:7; the complement of a fragment of at least 15 contiguous nucleotides of SEQ ID NO:7; a fragment of at least 15 contiguous nucleotides of SEQ ID NO:79; the complement of a fragment of at least 15 contiguous nucleotides of SEQ ID NO:79; a fragment of at least 15 contiguous nucleotides of SEQ ID NO:81; the complement of a fragment of at least 15 contiguous nucleotides of SEQ ID NO:81; a fragment of at least 15 contiguous nucleotides of SEQ ID NO:83; the complement of a fragment of at least 15 contiguous nucleotides of SEQ ID NO:83; a fragment of at least 15 contiguous nucleotides of SEQ ID NO:85; the complement of a fragment of at least 15 contiguous nucleotides of SEQ ID NO:85; a fragment of at least 15 contiguous nucleotides of SEQ ID NO:87; the complement of a fragment of at least 15 contiguous nucleotides of SEQ ID NO:87; a fragment of at least 15 contiguous nucleotides of SEQ ID NO:89; the complement of a fragment of at least 15 contiguous nucleotides of SEQ ID NO:89; a fragment of at least 15 contiguous nucleotides of SEQ ID NO:91; the complement of a fragment of at least 15 contiguous nucleotides of SEQ ID NO:91; a fragment of at least 15 contiguous nucleotides of SEQ ID NO:164; the complement of a fragment of at least 15 contiguous nucleotides of SEQ ID NO:164; a fragment of at least 15 contiguous nucleotides of SEQ ID NO:165; the complement of a fragment of at least 15 contiguous nucleotides of SEQ ID NO:165; a fragment of at least 15 contiguous nucleotides of SEQ ID NO:166; the complement of a fragment of at least 15 contiguous nucleotides of SEQ ID NO:166; a native coding polynucleotide of a *Diabrotica* organism comprising SEQ ID NO:1; the complement of a native coding polynucleotide of a *Diabrotica* organism comprising SEQ ID NO:1; a native coding polynucleotide of a *Diabrotica* organism comprising SEQ ID NO:3; the complement of a native coding polynucleotide of a *Diabrotica* organism comprising SEQ ID NO:3; a native coding polynucleotide of a *Diabrotica* organism comprising SEQ ID NO:5; the complement of a native coding polynucleotide of a *Diabrotica* organism comprising SEQ ID NO:5; a native coding polynucleotide of a *Diabrotica* organism comprising SEQ ID NO:7; the complement of a native coding polynucleotide of a *Diabrotica* organism comprising SEQ ID NO:7; a native coding polynucleotide of a *Diabrotica* organism comprising SEQ ID NO:79; the complement of a native coding polynucleotide of a *Diabrotica* organism comprising SEQ ID NO:79; a native coding polynucleotide of a *Diabrotica* organism comprising SEQ ID NO:81; the complement of a native coding polynucleotide of a *Diabrotica* organism comprising SEQ ID NO:81; a native coding polynucleotide of a *Diabrotica* organism comprising SEQ ID NO:83; the complement of a native coding polynucleotide of a *Diabrotica* organism comprising SEQ ID NO:83; a native coding polynucleotide of a *Diabrotica* organism comprising SEQ ID NO:85; the complement of a native coding polynucleotide of a *Diabrotica* organism comprising SEQ ID NO:85; a native coding polynucleotide of a *Diabrotica* organism comprising SEQ ID NO:87; the complement of a native coding polynucleotide of a *Diabrotica* organism comprising SEQ ID NO:87; a native coding polynucleotide of a *Diabrotica* organism comprising SEQ ID NO:89; the complement of a native coding polynucleotide of a *Diabrotica* organism comprising SEQ ID NO:89; a native coding polynucleotide of a *Diabrotica* organism comprising SEQ ID NO:91; the complement of a native coding polynucleotide of a *Diabrotica* organism comprising SEQ ID NO:91; a native coding polynucleotide of a *Diabrotica* organism comprising SEQ ID NO:164; the complement of a native coding polynucleotide of a *Diabrotica* organism comprising SEQ ID NO:164; a native coding polynucleotide of a *Diabrotica* organism comprising SEQ ID NO:165; the complement of a native coding polynucleotide of a *Diabrotica* organism comprising SEQ ID NO:165; a native coding polynucleotide of a *Diabrotica* organism comprising SEQ ID NO:166; the complement of a native coding polynucleotide of a *Diabrotica* organism comprising SEQ ID NO:166; a fragment of at least 15 contiguous nucleotides of a native coding polynucleotide of a *Diabrotica* organism comprising SEQ ID NO:1; the complement of a fragment of at least 15 contiguous nucleotides of a native coding polynucleotide of a *Diabrotica* organism comprising SEQ ID NO:1; a fragment of at least 15 contiguous nucleotides of a native coding polynucleotide of a *Diabrotica* organism comprising SEQ ID NO:3; the complement of a fragment of at least 15 contiguous nucleotides of a native coding polynucleotide of a *Diabrotica* organism comprising SEQ ID NO:3; a fragment of at least 15 contiguous nucleotides of a native coding polynucleotide of a *Diabrotica* organism comprising SEQ ID NO:5; the complement of a fragment of at least 15 contiguous nucleotides of a native coding polynucleotide of a *Diabrotica* organism comprising SEQ ID NO:5; a fragment of at least 15 contiguous nucleotides of a native coding polynucleotide of a *Diabrotica* organism comprising SEQ ID NO:7; the complement of a fragment of at least 15 contiguous nucleotides of a native coding polynucleotide of a *Diabrotica* organism comprising SEQ ID NO:7; a fragment of at least 15 contiguous nucleotides of a native coding polynucleotide of a *Diabrotica* organism comprising SEQ ID NO:79; the complement of a fragment of at least 15 contiguous nucleotides of a native coding polynucleotide of a *Diabrotica* organism comprising SEQ ID NO:79; a fragment of at least 15 contiguous nucleotides of a native coding polynucleotide of a *Diabrotica* organism comprising SEQ ID NO:81; the complement of a fragment of at least 15 contiguous nucleotides of a native coding polynucleotide of a *Diabrotica* organism comprising SEQ ID NO:81; a fragment of at least 15 contiguous nucleotides of a native coding polynucleotide of a *Diabrotica* organism comprising SEQ ID NO:83; the complement of a fragment of at least 15 contiguous nucleotides of a native coding polynucleotide of a *Diabrotica* organism comprising SEQ ID NO:83; a fragment of at least 15 contiguous nucleotides of a native coding polynucleotide of a *Diabrotica* organism comprising SEQ ID NO:85; the complement of a fragment of at least 15 contiguous nucleotides of a native coding polynucleotide of a *Diabrotica* organism comprising SEQ ID NO:85; a fragment of at least 15 contiguous nucleotides of a native coding polynucleotide of a *Diabrotica* organism comprising SEQ ID NO:87; the complement of a fragment of at least 15 contiguous nucleotides of a native coding polynucleotide of a *Diabrotica* organism comprising SEQ ID NO:87; a fragment of at least 15 contiguous nucleotides of a native coding polynucleotide of a *Diabrotica* organism comprising SEQ ID NO:89; the complement of a fragment of at least 15 contiguous nucleotides of a native coding polynucleotide of a *Diabrotica* organism comprising SEQ ID NO:89; a fragment of at least 15 contiguous nucleotides of a native coding polynucleotide of a *Diabrotica* organism comprising SEQ ID NO:91; and the complement of a fragment of at least 15 contiguous nucleotides of a native coding polynucleotide of a *Diabrotica* organism comprising SEQ ID NO:91; a fragment of at least 15 contiguous nucleotides of a native coding polynucleotide of a *Diabrotica* organism comprising SEQ ID NO:164; the complement of a fragment of at least 15 contiguous nucleotides of a native coding polynucleotide of a *Diabrotica* organism comprising SEQ ID NO:164; a fragment of at least 15 contiguous nucleotides of a native coding polynucleotide of a *Diabrotica* organism comprising SEQ ID NO:165; the complement of a fragment of at least 15 contiguous nucleotides of a native coding polynucleotide of a *Diabrotica* organism comprising SEQ ID NO:165; a fragment of at least 15 contiguous nucleotides of a native coding polynucleotide of a *Diabrotica* organism comprising SEQ ID NO:166; and the complement of a fragment of at least 15 contiguous nucleotides of a native coding polynucleotide of a *Diabrotica* organism comprising SEQ ID NO:166. In certain embodiments, expression of a nucleic acid molecule that is at least about 80% identical (e.g., 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

It is an important feature of some embodiments herein that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., polynucleotides substantially homologous to the iRNA molecule(s) are targeted for genetic inhibition. In some embodiments, an RNA molecule comprising a polynucleotide with a nucleotide sequence that is identical to that of a portion of a target gene may be used for inhibition. In these and further embodiments, an RNA molecule comprising a polynucleotide with one or more insertion, deletion, and/or point mutations relative to a target polynucleotide may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length polynucleotide exhibiting a greater homology compensates for a longer, less homologous polynucleotide. The length of the polynucleotide of a duplex region of a dsRNA molecule that is identical to a portion of a target gene transcript may be at least about 25, 50, 100, 200, 300, 400, 500, or at least about 1000 bases. In some embodiments, a polynucleotide of greater than 20-100 nucleotides may be used; for example, a polynucleotide of 100-200 or 300-500 nucleotides may be used. In particular embodiments, a polynucleotide of greater than about 200-300 nucleotides may be used. In particular embodiments, a polynucleotide of greater than about 500-1000 nucleotides may be used, depending on the size of the target gene.

In certain embodiments, expression of a target gene in a coleopteran pest may be inhibited by at least 10%; at least 33%; at least 50%; or at least 80% within a cell of the pest, such that a significant inhibition takes place. Significant inhibition refers to inhibition over a threshold that results in a detectable phenotype (e.g., cessation of reproduction, feeding, development, etc.), or a detectable decrease in RNA and/or gene product corresponding to the target gene being inhibited. Although in certain embodiments of the invention inhibition occurs in substantially all cells of the pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA or the complement thereof to effect what is referred to as "promoter trans suppression." Gene suppression may be effective against target genes in a coleopteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary polynucleotides in the cells of the coleopteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of IRNA Molecules Provided to a Coleopteran Pest

Expression of iRNA molecules for RNAi-mediated gene inhibition in a coleopteran pest may be carried out in any one of many in vitro or in vivo formats. The iRNA molecules may then be provided to a coleopteran pest, for example, by contacting the iRNA molecules with the pest, or by causing the pest to ingest or otherwise internalize the iRNA molecules. Some embodiments of the invention include transformed host plants of a coleopteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran pest during feeding, the pest may ingest iRNA molecules expressed in the transgenic plants or cells. The polynucleotides of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran pest comprises providing in the tissue of the host of the pest a gene-suppressive amount of at least one dsRNA molecule formed following transcription of a polynucleotide as described herein, at least one segment of which is complementary to an mRNA within the cells of the coleopteran pest. A dsRNA molecule, including its modified form such as an siRNA, miRNA, shRNA, or hpRNA molecule, ingested by a coleopteran pest in accordance with the invention may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a chromatin remodeling gene DNA molecule, for example, comprising a polynucleotide selected from the group consisting of SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; and SEQ ID NO:166. Isolated and substantially purified nucleic acid molecules including, but not limited to, non-naturally occurring polynucleotides and recombinant DNA constructs for providing dsRNA molecules of the present invention are therefore provided, which suppress or inhibit the expression of an endogenous coding polynucleotide or a target coding polynucleotide in the coleopteran pest when introduced thereto.

Particular embodiments provide a delivery system for the delivery of iRNA molecules for the post-transcriptional inhibition of one or more target gene(s) in a coleopteran plant pest and control of a population of the plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acids encoding a particular iRNA molecule may be produced by employing recombinant DNA technologies (which basic technologies are well-known in the art) to construct a plant transformation vector comprising a polynucleotide encoding an iRNA molecule of the invention (e.g., a stabilized dsRNA molecule); to transform a plant cell or plant; and to generate the transgenic plant cell or the transgenic plant that contains the transcribed iRNA molecule.

To impart protection from coleopteran pests to a transgenic plant, a recombinant DNA molecule may, for example, be transcribed into an iRNA molecule, such as a dsRNA molecule, a siRNA molecule, a miRNA molecule, a shRNA molecule, or a hpRNA molecule. In some embodiments, an RNA molecule transcribed from a recombinant DNA molecule may form a dsRNA molecule within the tissues or fluids of the recombinant plant. Such a dsRNA molecule may be comprised in part of a polynucleotide that is identical to a corresponding polynucleotide transcribed from a DNA within a coleopteran pest of a type that may infest the host plant. Expression of a target gene within the coleopteran pest is suppressed by the dsRNA molecule, and the suppression of expression of the target gene in the coleopteran pest results in the transgenic plant being resistant to the pest. The modulatory effects of dsRNA molecules have been shown to be applicable to a variety of genes expressed in pests, including, for example, endogenous genes responsible for cell division, chromosomal remodeling, and cellular metabolism or cellular transformation, including housekeeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a polynucleotide for use in producing iRNA molecules may be operably linked to one or more promoter elements functional in a plant host cell. The promoter may be an endogenous promoter, normally resident in the host genome. The polynucleotide of the present invention, under the control of an operably linked promoter element, may further be flanked by additional elements that advantageously affect its transcription and/or the stability of a resulting transcript. Such elements may be located upstream of the operably linked promoter, downstream of the 3' end of the expression construct, and may occur both upstream of the promoter and downstream of the 3' end of the expression construct.

In embodiments, suppression of a target gene (e.g., a chromatin remodeling gene) results in a parental RNAi phenotype; a phenotype that is observable in progeny of the subject (e.g., a coleopteran pest) contacted with the iRNA molecule. In some embodiments, the pRNAi phenotype comprises the pest being rendered less able to produce viable offspring. In particular examples of pRNAi, a nucleic acid that initiates pRNAi does not increase the incidence of mortality in a population into which the nucleic acid is delivered. In other examples of pRNAi, a nucleic acid that initiates pRNAi also increases the incidence of mortality in a population into which the nucleic acid is delivered.

In some embodiments, a population of coleopteran pests is contacted with an iRNA molecule, thereby resulting in pRNAi, wherein the pests survive and mate but produce eggs that are less able to hatch viable progeny than eggs produced by pests of the same species that are not provided the nucleic acid(s). In some examples, such pests do not oviposit eggs or produce fewer eggs than what is observable in pests of the same species that are not contacted with the iRNA molecule. In some examples, the eggs oviposited by such pests do not hatch or hatch at a rate that is significantly less than what is observable in pests of the same species that are not contacted with the iRNA molecule. In some examples, the larvae that hatch from eggs oviposited by such pests are not viable or are less viable than what is observable in pests of the same species that are not contacted with the iRNA molecule.

Transgenic crops that produce substances that provide protection from insect feeding are vulnerable to adaptation by the target insect pest population reducing the durability of the benefits of the insect protection substance(s). Traditionally, delays in insect pest adaptation to transgenic crops are achieved by (1) the planting of "refuges" (crops that do not contain the pesticidal substances, and therefore allow survival of insects that are susceptible to the pesticidal substance(s)); and/or (2) combining insecticidal substances with multiple modes of action against the target pests, so that individuals that are resistant to one mode of action are killed by a second mode of action.

In some examples, iRNA molecules (e.g., expressed from a transgene in a host plant) represent new modes of action for combining with *Bacillus thuringiensis* insecticidal protein technology and/or lethal RNAi technology in Insect Resistance Management gene pyramids to mitigate against the development of insect populations resistant to either of these control technologies.

Parental RNAi may result in some embodiments in a type of pest control that is different from the control obtained by lethal RNAi, and which may be combined with lethal RNAi to result in synergistic pest control. Thus, in particular embodiments, iRNA molecules for the post-transcriptional inhibition of one or more target gene(s) in a coleopteran plant pest can be combined with other iRNA molecules to provide redundant RNAi targeting and synergistic RNAi effects.

Parental RNAi (pRNAi) that causes egg mortality or loss of egg viability has the potential to bring further durability benefits to transgenic crops that use RNAi and other mechanisms for insect protection. pRNAi prevents exposed insects from producing progeny, and therefore from passing on to the next generation any alleles they carry that confer resistance to the pesticidal substance(s). pRNAi is particularly useful in extending the durability of insect-protected transgenic crops when it is combined with one or more additional pesticidal substances that provide protection from the same pest populations. Such additional pesticidal substances may in some embodiments include, for example, dsRNA; larval-active dsRNA; insecticidal proteins (such as those derived from *Bacillus thuringiensis* or other organisms); and other insecticidal substances. This benefit arises because insects that are resistant to the pesticidal substances occur as a higher proportion of the population in the transgenic crop than in the refuge crop. If a ratio of resistance alleles to susceptible alleles that are passed on to the next generation is lower in the presence of pRNAi than in the absence of pRNAi, the evolution of resistance will be delayed.

For example, pRNAi may not reduce the number of individuals in a first pest generation that are inflicting damage on a plant expressing an iRNA molecule. However, the ability of such pests to sustain an infestation through subsequent generations may be reduced. Conversely, lethal RNAi may kill pests that already are infesting the plant. When pRNAi is combined with lethal RNAi, pests that are contacted with a parental iRNA molecule may breed with pests from outside the system that have not been contacted with the iRNA, however, the progeny of such a mating may be non-viable or less viable, and thus may be unable to infest the plant. At the same time, pests that are contacted with a lethal iRNA molecule may be directly affected. The combination of these two effects may be synergistic; i.e., the combined pRNAi and lethal RNAi effect may be greater than the sum of the pRNAi and lethal RNAi effects independently. pRNAi may be combined with lethal RNAi, for example, by providing a plant that expresses both lethal and parental iRNA molecules; by providing in the same location a first plant that expresses lethal iRNA molecules and a second plant that expresses parental iRNA molecules; and/or by contacting female and/or male pests with the pRNAi molecule, and subsequently releasing the contacted pests into the plant environment, such that they can mate unproductively with the plant pests.

Some embodiments provide methods for reducing the damage to a host plant (e.g., a corn plant) caused by a coleopteran pest that feeds on the plant, wherein the method comprises providing in the host plant a transformed plant cell expressing at least one nucleic acid molecule of the invention, wherein the nucleic acid molecule(s) functions upon being taken up by the pest(s) to inhibit the expression of a target polynucleotide within the pest(s), which inhibition of expression results in reduced reproduction, for example, in addition to mortality and/or reduced growth of the pest(s), thereby reducing the damage to the host plant caused by the pest. In some embodiments, the nucleic acid molecule(s) comprise dsRNA molecules. In these and further embodiments, the nucleic acid molecule(s) comprise dsRNA molecules that each comprise more than one polynucleotide that is specifically hybridizable to a nucleic acid molecule expressed in a coleopteran pest cell. In some embodiments, the nucleic acid molecule(s) consist of one polynucleotide that is specifically hybridizable to a nucleic acid molecule expressed in a coleopteran pest cell.

In some embodiments, a method for increasing the yield of a corn crop is provided, wherein the method comprises introducing into a corn plant at least one nucleic acid molecule of the invention; and cultivating the corn plant to allow the expression of an iRNA molecule comprising the nucleic acid, wherein expression of an iRNA molecule comprising the nucleic acid inhibits coleopteran pest damage and/or growth, thereby reducing or eliminating a loss of yield due to coleopteran pest infestation. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a coleopteran pest cell. In some embodiments, the nucleic acid molecule(s) consists of one polynucleotide that is specifically hybridizable to a nucleic acid molecule expressed in a coleopteran pest cell.

In some embodiments, a method for increasing the yield of a plant crop is provided, wherein the method comprises introducing into a female coleopteran pest (e.g, by injection, by ingestion, by spraying, and by expression from a DNA) at least one nucleic acid molecule of the invention; and releasing the female pest into the crop, wherein mating pairs including the female pest are unable or less able to produce viable offspring, thereby reducing or eliminating a loss of yield due to coleopteran pest infestation. In particular embodiments, such a method provides control of subsequent generations of the pest. In similar embodiments, the method comprises introducing the nucleic acid molecule of the invention into a male coleopteran pest, and releasing the male pest into the crop (e.g., wherein pRNAi male pests produce less sperm than untreated controls). For example, given that WCR females typically mate only once, these pRNAi female and/or males can be used in competition to overwhelm native WCR insects for mates. In some embodiments, the nucleic acid molecule is a DNA molecule that is expressed to produce an iRNA molecule. In some embodiments, the nucleic acid molecule is a dsRNA molecule. In these and further embodiments, the nucleic acid molecule(s) comprise dsRNA molecules that each comprise more than one polynucleotide that is specifically hybridizable to a nucleic acid molecule expressed in a coleopteran pest cell. In some embodiments, the nucleic acid molecule(s) consists of one polynucleotide that is specifically hybridizable to a nucleic acid molecule expressed in a coleopteran pest cell.

In some embodiments, a method for modulating the expression of a target gene in a coleopteran pest is provided, the method comprising: transforming a plant cell with a vector comprising a polynucleotide encoding at least one iRNA molecule of the invention, wherein the polynucleotide is operatively-linked to a promoter and a transcription termination element; culturing the transformed plant cell under conditions sufficient to allow for development of a plant cell culture including a plurality of transformed plant cells; selecting for transformed plant cells that have integrated the polynucleotide into their genomes; screening the transformed plant cells for expression of an iRNA molecule encoded by the integrated polynucleotide; selecting a transgenic plant cell that expresses the iRNA molecule; and feeding the selected transgenic plant cell to the coleopteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a coleopteran pest cell. In some embodiments, the nucleic acid molecule(s) consists of one polynucleotide that is specifically hybridizable to a nucleic acid molecule expressed in a coleopteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to coleopteran pests. For example, the iRNA molecules of the invention may be directly introduced into the cells of a pest(s). Methods for introduction may include direct mixing of iRNA into the diet of the coleopteran pest (e.g., by mixing with plant tissue from a host for the pest), as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran pests known to infest the plant. iRNA molecules produced by chemical or enzymatic synthesis may also be formulated in a manner consistent with common agricultural practices, and used as spray-on or bait products for controlling plant damage by a coleopteran pest. The formulations may include the appropriate adjuvants (e.g., stickers and wetters) required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1: Materials and Methods

Sample Preparation and Bioassays for *Diabrotica* Larval Feeding Assays.

The template preparation for dsRNA including RNA extraction, cDNA synthesis, and PCR with T7-containing primers is included in Example 4. Samples were tested for activity in bioassays conducted with neonates on artificial insect diet. WCR eggs were obtained from CROP CHARACTERISTICS, INC (Farmington, Minn.).

The bioassays were conducted in 128-well plastic trays specifically designed for insect bioassays (C-D INTERNATIONAL, Pitman, N.J.). Each well contained approximately 1.0 mL of a diet designed for growth of coleopteran insects. A 60 μL aliquot of dsRNA sample was delivered by pipette onto the 1.5 $cm^2$ diet surface of each well (40 $\mu L/cm^2$). dsRNA sample concentrations were calculated as the amount of dsRNA per square centimeter ($ng/cm^2$) of surface area in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which time the total number of insects exposed to each sample, the number of dead insects, and the weight of surviving insects were recorded. Percent mortality, average live weights, and growth inhibition were calculated for each treatment. Stunting was defined as a decrease in average live weights. Growth inhibition (GI) was calculated as follows:

GI=[1−(TWIT/TNIT)/(TWIBC/TNIBC)], where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

The $GI_{50}$ is determined to be the concentration of sample in the diet at which the GI value is 50%. The $LC_{50}$ (50% Lethal Concentration) is recorded as the concentration of sample in the diet at which 50% of test insects are killed. Statistical analysis was done using JMP™ software (SAS, Cary, N.C.).

Example 2: Identification of Candidate Target Genes from *Diabrotica*

Insects from multiple stages of WCR (*Diabrotica virgifera virgifera* LeConte) development were selected for pooled transcriptome analysis to provide candidate target gene sequences for control by RNAi transgenic plant insect protection technology.

In one exemplification, total RNA was isolated from about 0.9 gm whole first-instar WCR larvae; (4 to 5 days post-hatch; held at 16° C.), and purified using the following phenol/TRI REAGENT™-based method (MOLECULAR RESEARCH CENTER, Cincinnati, Ohio).

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 μL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 gm of larvae yielded over 1 mg of total RNA, with an $A_{260}/A_{280}$ ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA; 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNaseAway™ (INVITROGEN INC., Carlsbad, Calif.). Two μL of RNA sample were mixed with 8 μL of TE buffer (10 mM Tris HCl pH 7.0; 1 mM EDTA) and 10 μL of RNA sample buffer (NOVAGEN® Catalog No 70606; EMD4 Bioscience, Gibbstown, N.J.). The sample was heated at 70° C. for 3 min, cooled to room temperature, and 5 μL (containing 1 μg to 2 μg RNA) were loaded per well. Commercially available RNA molecular weight markers were simultaneously run in separate wells for molecular size comparison. The gel was run at 60 volts for 2 hr.

A normalized cDNA library was prepared from the total RNA of whole larvae by a commercial service provider (EUROFINS MWG Operon, Huntsville, Ala.), using random priming. The normalized larval cDNA library was sequenced at ½ plate scale by GS FLX 454 Titanium™ series chemistry at EUROFINS MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were selected using information regarding lethal effects of particular genes in other insects such as *Drosophila* and *Tribolium*. For example, the *brahma* gene (ATP-dependent helicase brm) was selected based on the genetic analysis of the *Drosophila brahma* gene. Brizuela et al. (1994) Genet. 137:803-13. Once the sequence was identified, existing transcriptome sequences were searched using a stand-alone BLAST algorithm to identify western corn rootworm sequences that exhibited significant similarity to the *brahma* gene. More complete characterization of the western corn rootworm *brahma*-like sequences revealed a number of domains characteristic of chromatin remodeling proteins. Therefore, a search was completed on existing transcriptome resources for sequences with similar domains and activity. These genes (mi-2, iswi-1, iswi-2, iswi-3, chd1, ino80, and *domino*) were hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production as described below.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit available in the *Diabrotica* sequences to the non-*Diabrotica* candidate gene sequence. In most cases, *Tribolium* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, SEQUENCHER™ v4.9 (GENE CODES CORPORATION, Ann Arbor, Mich.) was used to assemble the sequences into longer contigs.

Additional transcriptome sequencing of *D. v. virgifera* has been previously described. Eyun et al. (2014) PLoS One 9(4):e94052. In another exemplification, using Illumina™ paired-end as well as 454 Titanium sequencing technologies, a total of ~700 gigabases were sequenced from cDNA prepared from eggs (15,162,017 Illumina™ paired-end reads after filtering), neonates (721,697,288 Illumina™ paired-end reads after filtering), and midguts of third instar larvae (44,852,488 Illumina™ paired-end reads and 415,742 Roche 454 reads, both after filtering). De novo transcriptome assembly was performed using Trinity (Grabherr et al. (2011) Nat. Biotechnol. 29(7):644-52) for each of three samples as well as for the pooled dataset. The pooled assembly resulted in 163,871 contigs with an average length of 914 bp. The amino acid sequence of *BRAHMA* was used as a query sequence to search the rootworm transcriptome and genome database (unpublished) with tBLASTN using a cut-off E value of $10^{-5}$. The deduced amino acid sequences were aligned with ClustalX™ and edited with GeneDoc™ software.

A candidate target gene was identified that may lead to coleopteran pest mortality or inhibition of growth, development, or reproduction in WCR, including *brahma* transcript SEQ ID NO:1 (with subsequence SEQ ID NO:8); *brahma* transcript SEQ ID NO:3 (with subsequences SEQ ID NO:8 and SEQ ID NO:10); *brahma* transcript SEQ ID NO:5 (with subsequence SEQ ID NO:10); *brahma* transcript SEQ ID NO:7 (with subsequence SEQ ID NO:10); mi-2 transcript SEQ ID NO:79 (with subsequence SEQ ID NO:104); mi-2 open reading frame SEQ ID NO:164; iswi-1 transcript SEQ ID NO:81; iswi-1 open reading frame SEQ ID NO:165; chd1 transcript SEQ ID NO:83 (with subsequence SEQ ID NO:105); iswi-2 transcript SEQ ID NO:85 (with subsequence SEQ ID NO:103); iswi-2 open reading frame SEQ ID NO:166; iswi30 transcript SEQ ID NO:87 (with subsequence SEQ ID NO:102); ino80 transcript SEQ ID NO:89; and *domino* transcript SEQ ID NO:91. These genes encode SNF2-type chromatin remodeler proteins, which are subunits of the chromatin remodeling complexes that play global roles in mobilizing nucleosomes. See, for example, Brizuela et al. (supra); Kal et al. (2000) Genes Devel. 14:1058-71; and Tamkun et al. (1992) Cell 68:561-72. Although they share a SNF2-Helicase domain, most chromatin remodelers within each species have non-redundant functions that are conferred by the additional domains they comprise. These characteristics present chromatin remodeling ATPases as attractive targets for multi-generational/parental RNAi.

Figure 2:
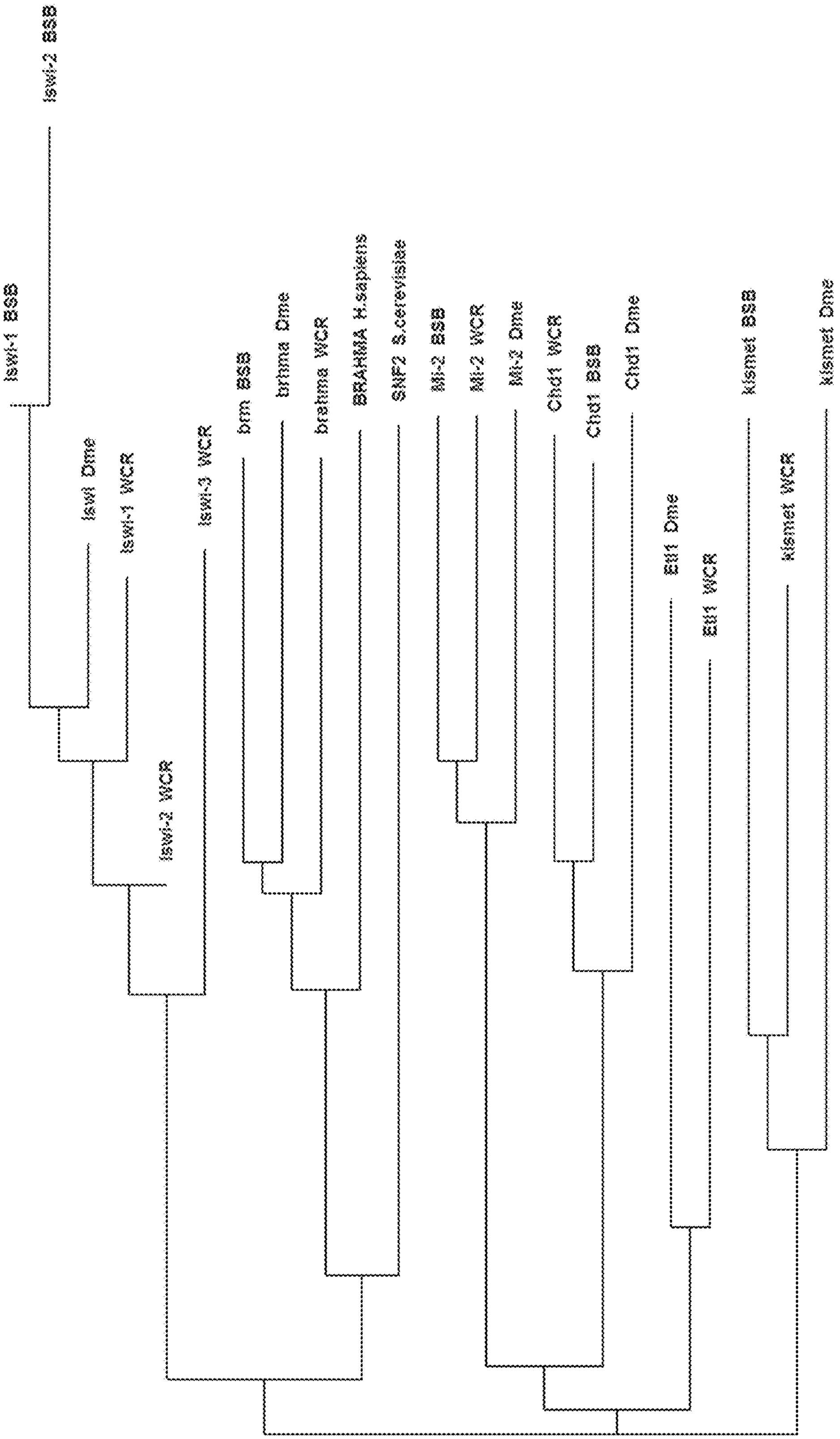
FIG. 2 includes a phylogenetic tree representation of ClustalW alignment of ATP-dependent remodelers from *Diabrotica virgifera virgifera* (WCR), *Euschistus heros* (BSB), *Drosophila*, human *BRAHMA* and *S. cerevisiae* SNF2. The alignment was performed in Clustal X 2.1, a windows interface for the ClustalW multiple sequence alignment program. The phylogram was rendered in TreeView (Win16) 1.40 software.
Figure 3A:
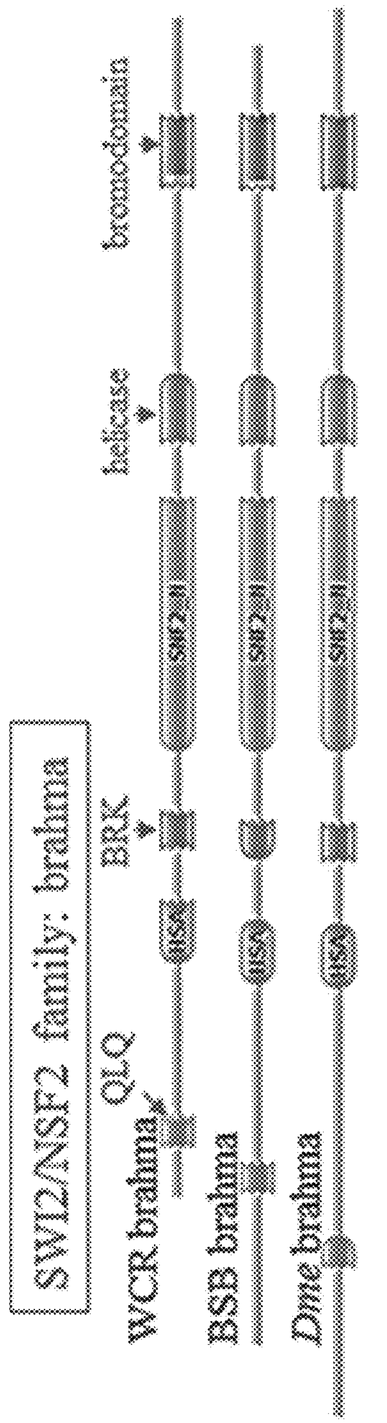
FIGS. 3A-3F include representations of the domain architecture of ATP-dependent chromatin remodeling enzymes of *Diabrotica virgifera virgifera* (WCR), *Euschistus heros* (BSB) and *Drosophila melanogaster* (Dme). The graphical representation is of Pfam output, with domains shaded and labeled. The proteins are organized by families and aligned with respect to SNF2 domain. "Squiggly" lines represent truncation/discontinuity for representation purposes. The protein families include SWI2NSF2*: brahma*, FIG. 3A; ISWI: Iswi, FIG. 3B; CHD subfamily I: Chd1.

The SWI2/SNF2 (mating type switch/sucrose non-fermenting) family of the ATP-dependent remodeling enzymes contains a bromodomain, which binds acetylated histones. While yeasts and vertebrates contain several SWI2/SNF2 proteins, only one SWI2/SNF2 protein, *BRAHMA*, has been identified in *Drosophila. BRAHMA* is well-conserved, and yet distinct, from other insect SNF2-containing proteins, with the putative WCR ortholog clustering closely to other chromatin remodeling complexes on a phylogenetic tree. FIG. 2. The human *BRAHMA*(BRM) as well as the *Saccharomyces cerevisiae* SNF2 protein cluster together with insect BRAHMAs. Furthermore, the WCR and *Euschistus heros* (BSB) orthologs of the *Drosophila* BRAHMA maintain overall protein domain conservation including the SNF2 ATPase/helicase, the bromodomain as well as additional domains: conserved Gln, Leu, Gln motif domain (QLQ), DNA-binding HSA domain, and BRK (*brahma* and kismet) domain. FIG. 3A.

*BRAHMA* is known to incorporate into BAP (*Brahma* Associated Proteins) and PBAP (Polybromo-associated BAP) chromatin remodeling complexes. The loss of *Drosophila brahma* impairs overall transcription by RNA polymerase II (Pol II), suggesting a broad function for the *BRAHMA* complexes. In *Drosophila*, the maternal contribution of *brahma* is needed for early embryogenesis, while the zygotic *brahma* expression is necessary for late embryonic development. In addition to embryogenesis, *Drosophila brahma* is involved in gametogenesis.

The ISWI (Imitation SWI/imitation switch) family is defined by histone-biding domain that comprises the HAND, SANT, and SLIDE domains in a HAND-SANT-SLIDE architecture. In *Drosophila*, the ISWI family of ATP-dependent remodeling enzymes has only one member, ISWI. The *Drosophila* ISWI can confer multiple functions by integrating into various complexes that include ATP-dependent chromatin assembly and remodeling factor (ACF), nucleosome remodeling factor (NURF), and chromatin accessibility complex (CHRAC). Loss of ISWI in *Drosophila* results in dramatic chromosome condensation defects.

Figure 3B:
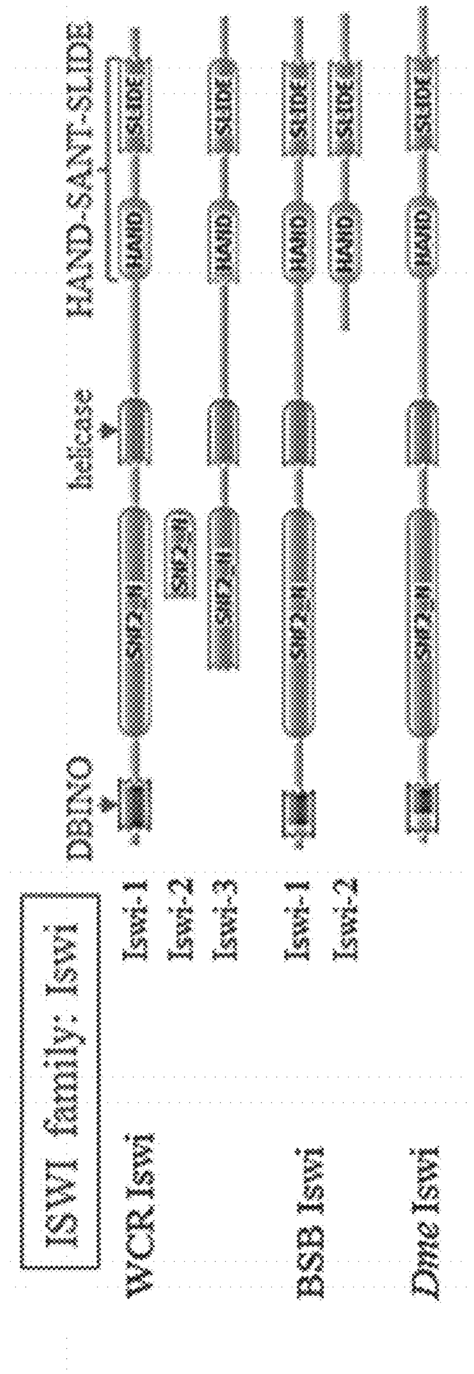

Disclosed herein are iswi orthologs in WCR, and additional iswi homologs with partial sequences. The complete WCR ISWI proteins contain the SNF2 ATPase/helicase, HAND-SANT-SLIDE (identified as HAND and SLIDE by Pfam) and DNA-binding domain (DBINO). FIG. 3B. The partial sequence of WCR ISWI, ISWI-2, consists of only SNF2 domain. FIG. 3B. This sequence has high homology to the other ISWI proteins; 91% identity to WCR ISWI-1 over the entire length of ISWI-2, and 93% identity over the region of a dsRNA targeted against iswi-2. FIG. 3B; FIG. 4. Thus, the parental RNAi effect of WCR iswi-2 can be attributed to the function of complete iswi-2 sequence, or to the ability of iswi-2-targeted dsRNA (FIG. 4) to "knock down" iswi-1. Table

TABLE 1

Effect of dsRNA from brahma-like sequences on total number of WCR egg produced and egg viability after 11 days of ingestion on artificial diet. Means were separated using Dunnett's test.

| Rep | iswi-1 | iswi-2 | chd1 | mi-2 | kis | etl1 | Water | GFP |
|---|---|---|---|---|---|---|---|---|
| | Total number of eggs | | | | | | | |
| 1 | 131.60 | 55.80 | 106.00 | 41.50 | 211.33 | 63.80 | 72 | 202.60 |
| 2 | 39.60 | 114.83 | 112.67 | 63.80 | 140.67 | 135.17 | 273.17 | 213.83 |

TABLE 1-continued

Effect of dsRNA from brahma-like sequences on total number of WCR egg produced and egg viability after 11 days of ingestion on artificial diet. Means were separated using Dunnett's test.

| Rep | iswi-1 | iswi-2 | chd1 | mi-2 | kis | etl1 | Water | GFP |
|---|---|---|---|---|---|---|---|---|
| 3 | 12.40 | 211.20 | 171.60 | 34.00 | 119.00 | 55.67 | 104.60 | 139.50 |
| Average | 61.20* | 127.28 | 130.09 | 46.43* | 157.00 | 84.88 | 149.92 | 185.31 |
| SEM† | 36.07 | 45.29 | 20.84 | 8.95 | 27.88 | 25.25 | 62.34 | 23.13 |
| | Percent egg hatch | | | | | | | |
| 1 | 0.00 | 0.00 | 16.77 | 0.00 | 21.55 | 41.54 | — | 18.54 |
| 2 | 3.34 | 0.00 | 23.40 | 0.00 | 50.52 | 58.75 | 46.17 | 39.42 |
| 3 | 0.00 | 0.62 | 34.20 | 0.00 | 26.44 | 20.69 | 23.62 | 36.08 |
| Average | 1.11* | 0.21* | 24.79 | 0.00* | 32.84 | 40.33 | 34.90 | 31.35 |
| SEM† | 1.11 | 0.21 | 5.08 | 0.00 | 8.95 | 11.00 | 9.20 | 6.47 |

*Indicates significance at p-value <0.05.
†SEM—Standard Error of the Mean.

Figure 3C:
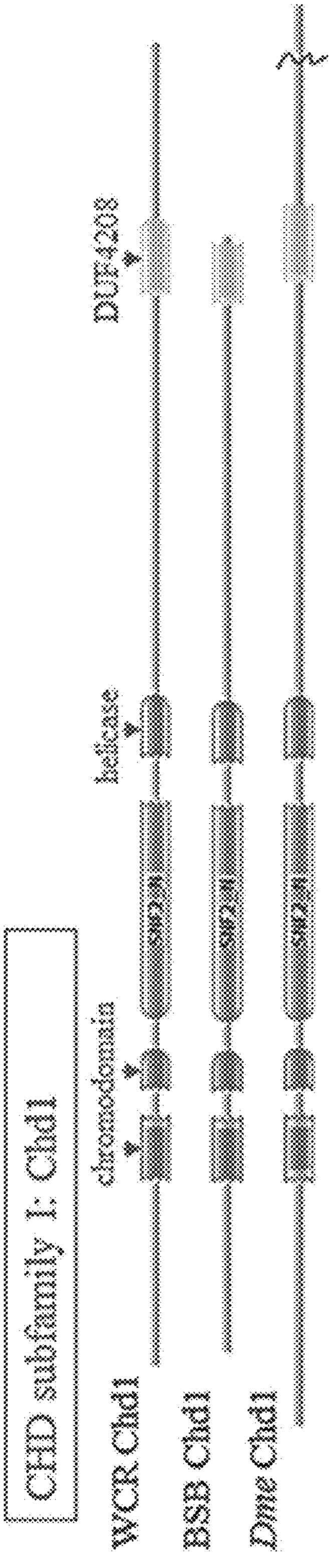

Proteins of the CHD (chromodomain helicase DNA-binding) family of ATP-dependent remodeling enzymes contain two amino-terminal chromodomains [chromatin organization modifier]. FIG. 3C. The *Drosophila* CHD proteins include CHD1, MI-2, CHD3, and KISMET. The CHD family is further subdivided into three subfamilies, herein referred to as subfamilies I, II, and III. The *Drosophila* CHD1 belongs to CHD subfamily I, which has a C-terminal DNA-binding domain. FIG. 3C (DUF4208). In *Drosophila*, CHD1 protein shows similar distribution patterns to *BRAHMA*, yet chd1 mutant flies are viable. Interestingly, the *Drosophila* chd1 is needed for gametogenesis. WCR females subjected to chd1 RNAi show a decrease in offspring viability. Table 1.

Figure 3D:
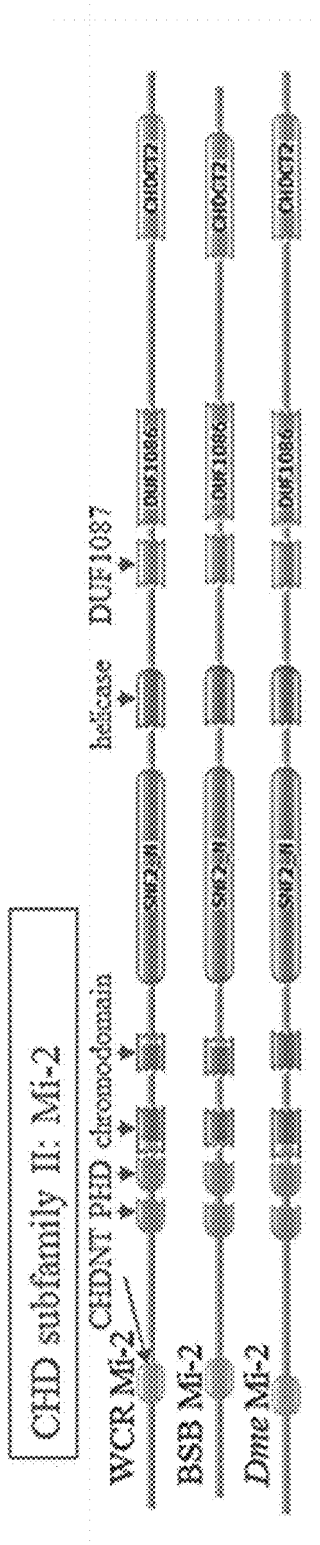

MI-2 and CHD3 belong to subfamily II. Enzymes of the CHD subfamily II have no DNA-binding domain, but have Zn-finger-like domains called PHD (plant homeodomain) fingers. The WCR ortholog of MI-2 mirrors the *Drosophila* domain arrangement, and includes the SNF2 ATPase/helicase domain, the double chromodomain, PHD fingers, and CHDNT domain that is associated with PHD finger-containing chromodomain helicases, as well as other conserved domains of unknown functions, DUF1087 and DUF1086. FIG. 3D. The *Drosophila* MI-2 is known to associate with the NuRD (Nucleosome Remodeling Deacetylase) and dMec (*Drosophila* MEP-1 containing complex) complexes. Maternal expression of mi-2 is necessary for gametogenesis. Mi-2 RNAi-treated female WCR produce no viable eggs. Table 1.

Figure 3E:
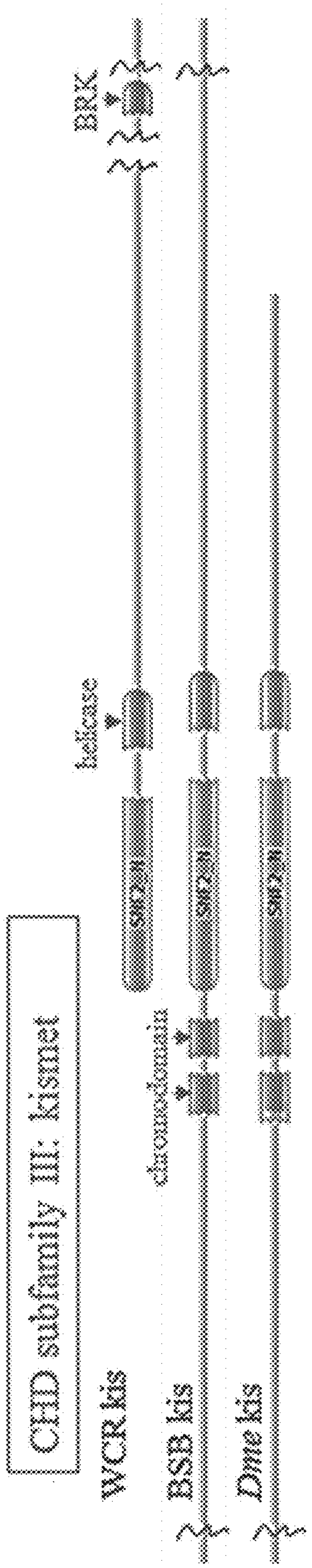

The third subfamily of CHD proteins is represented by KISMET in *Drosophila*; in humans this subfamily comprises CHD5-98. Like other CHD proteins, KISMET contains an SNF2 domain and a chromodomain. FIG. 3E. Unlike other CHD subfamilies, KISMET has characteristics of both CHD and SWI2/SNF2 proteins, in that it has a BRK domain that is common to both *BRAHMA* and KISMET. Although BRK is a well-established feature of *Drosophila* KISMET, a standard Pfam analysis did not identify this domain in *Drosophila*. FIG. 3E. Loss of either maternal or zygotic function of kismet causes defects during *Drosophila* embryogenesis and the insects die during early larval stages, while oogenesis is unaffected. The putative WCR ortholog of the *Drosophila* kismet produces no oviposition or hatch defects in response to parental RNAi. Table 1.

Figure 3F:
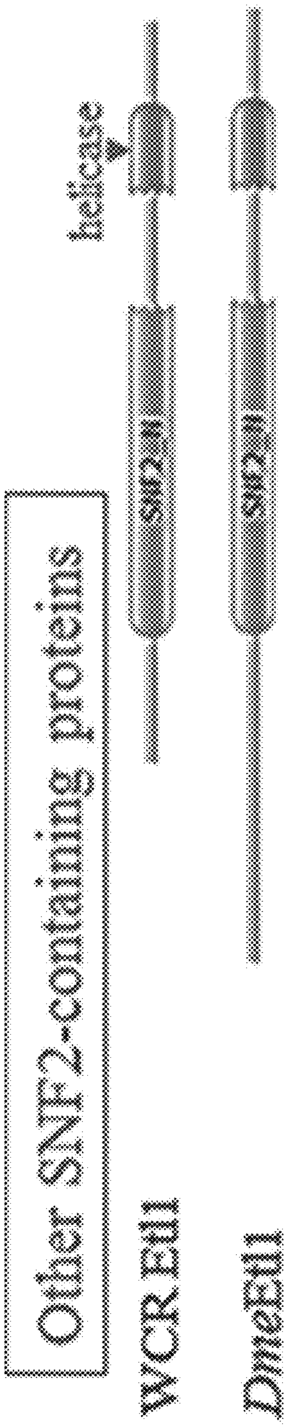

Additional SNF2-containing genes are present in *Drosophila*; the functions of most of these have not been defined. For example, the WCR transcriptome contains an etl1-like transcript. FIG. 3F. The Etl1 (Enhancer Trap Locus 1) SNF2-containing gene was first described in mice. The mouse etl1 has been described as having developmental effects, but being nonessential. Parental RNAi that targets WCR etl1 shows no oviposition or egg viability defects. Table 1.

The identified polynucleotides and their encoded polypeptides are novel. The sequences are not provided in public databases, and are not disclosed in WO/2011/025860; U.S. Patent Application No. 20070124836; U.S. Patent Application No. 20090306189; U.S. Patent Application No. US20070050860; U.S. Patent Application No. 20100192265; or U.S. Pat. No. 7,612,194. The *Diabrotica brahma* (SEQ ID NO:1) is somewhat (72% identity) related to a fragment of a sequence from *Metaseiulus occidentalis* (GENBANK Accession No. XM_003742362.1). The closest homolog of the *Diabrotica* BRAHMA amino acid sequence (SEQ ID NO:2) is a *Dendroctonus ponderosae* protein having GENBANK Accession No. ENN80791.1 (86% similar; 75% identical over the homology region). The *Diabrotica brahma* (SEQ ID NO:3 and SEQ ID NO:5) are somewhat (74% identity) related to a fragment of a sequence from *Nasonia vitripennis* (GENBANK Accession No. XM_001607119.3). The closest homolog of the *Diabrotica* BRAHMA amino acid sequence (SEQ ID NO:4) is a *Dendroctonus ponderosae* protein having GENBANK Accession No. ENN80791.1 (86% similar; 78% identical over the homology region). The closest homolog of the *Diabrotica* BRAHMA amino acid sequence (SEQ ID NO:6) is a *Dendroctonus ponderosae* protein having GENBANK Accession No. ENN80791.1 (86% similar; 75% identical over the homology region). There was no significant homologous nucleotide sequence found with a search in GENBANK for *Diabrotica brahma* (SEQ ID NO:7). There was no significant homologous nucleotide sequence found with a search in GENBANK for *Diabrotica brahma* (SEQ ID NO:8). The closest homolog of the *Diabrotica* BRAHMA amino acid sequence (SEQ ID NO:9) is a *Dendroctonus ponderosae* protein having GENBANK Accession No. ENN80791.1 (95% similar; 92% identical over the homology region). The *Diabrotica* mi-2 (SEQ ID NO:79) is somewhat (72% identity) related to a fragment of a sequence from *Aedes aegypti* (GENBANK Accession No. XM_001663273.1). The closest homolog of the *Diabrotica* MI-2 amino acid sequence (SEQ ID NO:80) is a *Tribolium castaneum* protein having GENBANK Accession No. XP_001812556.1 (85% similar; 77% identical over the homology region). The *Diabrotica* iswi-1 (SEQ ID NO:81) is somewhat (73% identity) related to a fragment of a sequence from *Python bivittatus* (GENBANK Accession No. XM_007428840.1). The closest homolog of the *Diabrotica* ISWI-1 amino acid sequence (SEQ ID NO:82) is a *Dendroctonus ponderosae* protein having GENBANK Accession No. ENN80673 0.1 (95% similar; 89% identical over the homology region). The *Diabrotica* chd1 (SEQ ID NO:83) is somewhat (74% identity) related to a fragment of a sequence from *Pediculus humanus corporis* (GENBANK Accession No. XM_002428164.1). The closest homolog of the *Diabrotica* CHD-1 amino acid sequence (SEQ ID NO:84) is a *Tribolium castaneum* protein having GENBANK Accession No. XP_970343.3 (82% similar; 73% identical over the homology region). The *Diabrotica* iswi-2 (SEQ ID NO:85) is somewhat (75% identity) related to a fragment of a sequence from *Tetrapisispora blattae* (GENBANK Accession No. XM_004179654.1). The closest homolog of the *Diabrotica* ISWI-2 amino acid sequence (SEQ ID NO:86) is a *Dendroctonus ponderosae* protein having GENBANK Accession No. ERL83291.1 (95% similar; 88% identical over the homology region). The *Diabrotica* iswi-30 (SEQ ID NO:87) is somewhat (73% identity) related to a fragment of a sequence from *Python bivittatus* (GENBANK Accession No. XM_007428840.1). The closest homolog of the *Diabrotica* ISWI-30 amino acid sequence (SEQ ID NO:88) is a *Dendroctonus ponderosae* protein having GENBANK Accession No. ENN80673.1 (95% similar; 89% identical over the homology region). The *Diabrotica* ino80 (SEQ ID NO:89) is somewhat (77% identity) related to a fragment of a sequence from *Bos mutus* (GENBANK Accession No. XM_005903961.1). The *Diabrotica domino* (SEQ ID NO:91) is somewhat (76% identity) related to a fragment of a sequence from *Acyrthosiphon pisum* (GENBANK Accession No. XM_008181422.1).

Full-length or partial clones of sequences of *Diabrotica* candidate chromatin remodelers containing SNF2 genes were used to generate PCR amplicons for dsRNA synthesis. dsRNA was also amplified from a DNA clone comprising the coding region for a yellow fluorescent protein (YFP) (SEQ ID NO:11; Shagin et al. (2004) Mol. Biol. Evol. 21:841-850).

Example 3: Amplification of Target Genes from *Diabrotica*

Primers were designed to amplify portions of coding regions of each target gene by PCR. See Table 2. Where appropriate, a T7 phage promoter sequence (TAATACGACTCACTATAGGG (SEQ ID NO:12)) was incorporated into the 5' ends of the amplified sense or antisense strands. See Table 2. Total RNA was extracted from WCR, and first-strand cDNA was used as template for PCR reactions using opposing primers positioned to amplify all or part of the native target gene sequence.

TABLE 2

Primers and Primer Pairs used to amplify portions of coding regions of exemplary chromatin remodelers containing SNF2 target genes and YFP target genes.

| | Gene (Region) | Primer_ID | Sequence |
|---|---|---|---|
| Pair 1 | brahma-Var2 | BrahmaR2_FT7 | TTAATACGACTCACTATAGGGAGAATGAGGGTCATCGTATGAAAAACC (SEQ ID NO: 13) |
| | | BrahmaR2_R | TGTCCTTAGATCCCCTTCCTTTAC (SEQ ID NO: 14) |
| Pair 2 | brahma-Var2 | BrahmaR2_F | ATGAGGGTCATCGTATGAAAAACC (SEQ ID NO: 15) |
| | | BrahmaR2_RT7 | TTAATACGACTCACTATAGGGAGATGTCCTTAGATCCCCTTCCTTTAC (SEQ ID NO: 16) |
| Pair 3 | brahma Reg-352 | Brahma352_FT7 | TAATACGACTCACTATAGGGAACCTTCTTCATCTTCTG (SEQ ID NO: 17) |
| | | Brahma352_RT7 | TAATACGACTCACTATAGGGTTGAACTGTATTAGGAGAG (SEQ ID NO: 18) |
| Pair 4 | mi-2 | Mi2.T7.F | TAATACGACTCACTATAGGGAAGAAGGCATAGAACAGA (SEQ ID NO: 107) |
| | | Mi2.T7.R | TAATACGACTCACTATAGGGTCAGAATGGTAATCAGAGA (SEQ ID NO: 108) |
| Pair 5 | iswi-30 | ISWI30.T7.F | TAATACGACTCACTATAGGGTGAATCAGTCTACCAATT (SEQ ID NO: 109) |
| | | ISWI30.T7.R | TAATACGACTCACTATAGGGGGTTCTGACTCATCTATT (SEQ ID NO: 110) |
| Pair 6 | iswi-2 | ISWI2.T7.F | TAATACGACTCACTATAGGGTTGCTCAATCCTACATACA (SEQ ID NO: 111) |
| | | ISWI2.T7.R | TAATACGACTCACTATAGGGGAATACCAACAGGCTACT (SEQ ID NO: 112) |
| Pair 7 | ksmt | KSMT.T7.F | TAATACGACTCACTATAGGGGATCAAATTCAAGCAACT (SEQ ID NO: 113) |
| | | KSMT.T7.R | TAATACGACTCACTATAGGGTTCTTCCTAAACCATGTT (SEQ ID NO: 114) |
| Pair 8 | chd1 | CHD1.T7.F | TAATACGACTCACTATAGGGTTTGCTTCCTTCTTTCAA (SEQ ID NO: 115) |
| | | CHD1.T7.R | TAATACGACTCACTATAGGGCTTCTTTGTTAAACGGATT (SEQ ID NO: 116) |

TABLE 2-continued

Primers and Primer Pairs used to amplify portions of coding regions of exemplary chromatin remodelers containing SNF2 target genes and YFP target genes.

| | Gene (Region) | Primer_ID | Sequence |
|---|---|---|---|
| Pair 9 | etl1 | ETL1.T7.F | TAATACGACTCACTATAGGGACTTATCTAAAGGGATGCTA (SEQ ID NO: 117) |
| | | ETL1.T7.R | TAATACGACTCACTATAGGGGTAGAGAGTCGTCTTCTG (SEQ ID NO: 118) |
| Pair 10 | YFP | YFP-F_T7 | TTAATACGACTCACTATAGGGAGACACCATGGGCTCCAGCGGCGCCC (SEQ ID NO: 19) |
| | | YFP-R_T7 | TTAATACGACTCACTATAGGGAGAAGATCTTGAAGGCGCTCTTCAGG (SEQ ID NO: 20) |
| Pair 11 | GFP | GFP-F_T7 | TAATACGACTCACTATAGGGGGTGATGCTACATACGGAAAG (SEQ ID NO: 54) |
| | | GFP-R_T7 | TAATACGACTCACTATAGGGTTGTTTGTCTCCGTGAT (SEQ ID NO: 55) |

Example 4: RNAi Constructs

Template Preparation by PCR and dsRNA Synthesis.

Figure 1B:
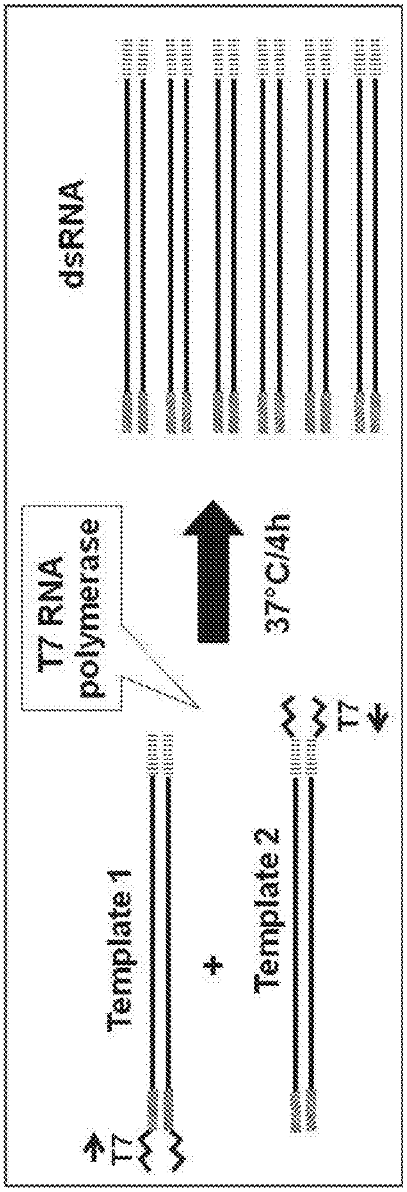

The strategies used to provide specific templates for chromatin remodelers containing SNF2 target gene dsRNA production are shown in FIG. 1A and FIG. 1B. Template DNAs intended for use in dsRNA synthesis were prepared by PCR using Primer Pair 1 and Primer Pair 2 respectively (Table 2) and (as PCR template) first-strand cDNA prepared from total RNA. For the selected target gene regions, two separate PCR amplifications were performed. FIGS. 1A and 1B. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. FIGS. 1A and 1B.

For the YFP negative control, a single PCR amplification was performed. FIG. 1B. The PCR amplification introduced a T7 promoter sequence at the 5' ends of the amplified sense and antisense strands. The two PCR amplified fragments for each region of the target genes were then mixed in approximately equal amounts, and the mixture was used as transcription template for dsRNA production. FIG. 1B. dsRNA for the negative control YFP coding region (SEQ ID NO:11) was produced using Primer Pair 10 (Table 2) and a DNA clone of the YFP coding region as template. A GFP negative control was amplified from the pIZT/V5-His expression vector (Invitrogen) using Primer Pair 11 (Table 2). The PCR product amplified for chromatin remodelers containing SNF2 target genes and GFP were used as a template for in vitro synthesis of dsRNAs using the MEGAscript high-yield transcription kit (Applied Biosystems Inc., Foster City, Calif.). The synthesized dsRNAs were purified using the RNeasy Mini kit (Qiagen, Valencia, Calif.) or an AMBION® MEGAscript® RNAi kit essentially as prescribed by the manufacturer's instructions. dsRNA preparations were quantified using a NANODROP™ 8000 spectrophotometer (THERMO SCIENTIFIC, Wilmington, Del.) or equivalent means and analyzed by gel electrophoresis to determine purity.

Example 5: Screening of Candidate Target Genes in *Diabrotica* Larvae

Replicated bioassays demonstrated that ingestion of synthetic dsRNA preparations derived from the *brahma*-Var1 target gene sequence identified in EXAMPLE 2 caused mortality and growth inhibition of western corn rootworm larvae when administered to WCR in diet-based assays. Table 3 and Table 4.

TABLE 3

Results of diet-based feeding bioassays of WCR larvae following 9-day exposure to a single dose of dsRNAs. ANOVA analysis found some significance differences in Mean % Mortality (Mort.). Means were separated using the Tukey-Kramer test.

| Sample Name | Dose ($ng/cm^2$) | No. Rows (Replications) | *Mean % Mortality +/− SEM | *Mean GI +/− SEM |
|---|---|---|---|---|
| brahma-Var1 | 500 | 4 | 52.62 ± 7.84 (A) | 0.10 ± 0.42 (A) |
| brahma Reg-352 | 500 | 5 | 39.76 ± 16.72 (AB) | 0.54 ± 0.19 (AB) |
| TE buffer** | 0 | 9 | 12.56 ± 3.70 (BC) | 0.00 ± 0.00 (AB) |
| Water | 0 | 9 | 11.45 ± 4.08 (BC) | 0.01 ± 0.01 (AB) |
| YFP dsRNA*** | 500 | 9 | 10.09 ± 4.16 (C) | −0.15 ± 0.19 (B) |

*SEM = Standard Error of the Mean. Letters in parentheses designate statistical levels. Levels not connected by same letter are significantly different ($p < 0.05$).

**TE = Tris HCl (1 mM) plus EDTA (1 mM) buffer, pH7.2.

***YFP = Yellow Fluorescent Protein

TABLE 4

Results of diet-based feeding bioassays of WCR larvae following 9-day exposure to a range of doses of dsRNAs.

| Sample Name | LC$_{50}$ (ng/cm$^2$) | LC$_{50}$ Range (ng/cm$^2$) |
|---|---|---|
| brahma-Var1 | 839 | 432-1000+ |

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,614,924, which discloses 9,112 sequences. However, it was determined that many genes suggested to have utility for RNAi-mediated insect control are not efficacious in controlling *Diabrotica*. It was also determined that *brahma*-Var1 provided surprising and unexpected control of *Diabrotica*, compared to other genes suggested to have utility for RNAi-mediated insect control.

For example, Annexin, Beta Spectrin 2, and mtRP-L4 were each suggested in U.S. Pat. No. 7,614,924 to be efficacious in RNAi-mediated insect control. SEQ ID NO:21 is the DNA sequence of Annexin Region 1 and SEQ ID NO:22 is the DNA sequence of Annexin Region 2. SEQ ID NO:23 is the DNA sequence of Beta Spectrin 2 Region 1 and SEQ ID NO:24 is the DNA sequence of Beta Spectrin 2 Region 2. SEQ ID NO:25 is the DNA sequence of mtRP-L4 Region 1 and SEQ ID NO:26 is the DNA sequence of mtRP-L4 Region 2.

Each of the aforementioned sequences was used to produce dsRNA by the dual Primer Pair methods of EXAMPLE 4 (FIGS. 1A and 1B), and the dsRNAs were each tested by the diet-based bioassay methods described above. A YFP sequence (SEQ ID NO:11) was also used to produce dsRNA as a negative control. Table 5 lists the sequences of the primers used to produce the Annexin, Beta Spectrin 2, mtRP-L4, and YFP dsRNA molecules. Table 6 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, YFP dsRNA, or water.

TABLE 5

Primers and Primer Pairs used to amplify portions of coding regions of genes.

| | Gene Region | Primer ID | Sequence |
|---|---|---|---|
| Pair 12 | Annexin Region 1 | Ann-F1_T7 | TTAATACGACTCACTATAGGGAGAGCTCCAACAGTGG TTCCTTATC (SEQ ID NO: 17) |
| | Annexin Region 1 | Ann-R1 | CTAATAATTCTTTTTTAATGTTCCTGAGG (SEQ ID NO: 18) |
| Pair 13 | Annexin Region 1 | Ann-F1 | GCTCCAACAGTGGTTCCTTATC (SEQ ID NO: 19) |
| | Annexin Region 1 | Ann-R1_T7 | TTAATACGACTCACTATAGGGAGACTAATAATTCTTT TTTAATGTTCCTGAGG (SEQ ID NO: 20) |
| Pair 14 | Annexin Region 2 | Ann-F2_T7 | TTAATACGACTCACTATAGGGAGATTGTTACAAGCTG GAGAACTTCTC (SEQ ID NO: 21) |
| | Annexin Region 2 | Ann-R2 | CTTAACCAACAACGGCTAATAAGG (SEQ ID NO: 22) |
| Pair 15 | Annexin Region 2 | Ann-F2 | TTGTTACAAGCTGGAGAACTTCTC (SEQ ID NO: 23) |
| | Annexin Region 2 | Ann-R2T7 | TTAATACGACTCACTATAGGGAGACTTAACCAACAAC GGCTAATAAGG (SEQ ID NO: 24) |
| Pair 16 | Beta-Spect2 Region 1 | Betasp2-F1_T7 | TTAATACGACTCACTATAGGGAGAAGATGTTGGCTGC ATCTAGAGAA (SEQ ID NO: 25) |
| | Beta-Spect2 Region 1 | Betasp2-R1 | GTCCATTCGTCCATCCACTGCA (SEQ ID NO: 26) |
| Pair 17 | Beta-Spect2 Region 1 | Betasp2-F1 | AGATGTTGGCTGCATCTAGAGAA (SEQ ID NO: 27) |
| | Beta-Spect2 Region 1 | Betasp2-R1_T7 | TTAATACGACTCACTATAGGGAGAGTCCATTCGTCCA TCCACTGCA (SEQ ID NO: 28) |
| Pair 18 | Beta-Spect2 Region 2 | Betasp2-F2_T7 | TTAATACGACTCACTATAGGGAGAGCAGATGAACACC AGCGAGAAA (SEQ ID NO: 29) |
| | Beta-Spect2 Region 2 | Betasp2-R2 | CTGGGCAGCTTCTTGTTTCCTC (SEQ ID NO: 30) |
| Pair 19 | Beta-Spect2 Region 2 | Betasp2-F2 | GCAGATGAACACCAGCGAGAAA (SEQ ID NO: 31) |
| | Beta-Spect2 Region 2 | Betasp2-R2_T7 | TTAATACGACTCACTATAGGGAGACTGGGCAGCTTCT TGTTTCCTC (SEQ ID NO: 32) |
| Pair 20 | mtRP-L4 Region 1 | L4-F1_T7 | TTAATACGACTCACTATAGGGAGAAGTGAAATGTTAG CAAATATAACATCC (SEQ ID NO: 33) |
| | mtRP-L4 Region 1 | L4-R1 | ACCTCTCACTTCAAATCTTGACTTTG (SEQ ID NO: 34) |

TABLE 5-continued

| Primers and Primer Pairs used to amplify portions of coding regions of genes. | | | |
|---|---|---|---|
| | Gene Region | Primer ID | Sequence |
| Pair 21 | mtRP-L4 Region 1 | L4-F1 | AGTGAAATGTTAGCAAATATAACATCC (SEQ ID NO: 35) |
| | mtRP-L4 Region 1 | L4-R1_T7 | TTAATACGACTCACTATAGGGAGAACCTCTCACTTCA AATCTTGACTTTG (SEQ ID NO: 36) |
| Pair 22 | mtRP-L4 Region 2 | L4-F2_T7 | TTAATACGACTCACTATAGGGAGACAAAGTCAAGATT TGAAGTGAGAGGT (SEQ ID NO: 37) |
| | mtRP-L4 Region2 | L4-R2 | CTACAAATAAAACAAGAAGGACCCC (SEQ ID NO: 38) |
| Pair 23 | mtRP-L4 Region 2 | L4-F2 | CAAAGTCAAGATTTGAAGTGAGAGGT (SEQ ID NO: 39) |
| | mtRP-L4 Region 2 | L4-R2_T7 | TTAATACGACTCACTATAGGGAGACTACAAATAAAAC AAGAAGGACCCC (SEQ ID NO: 40) |
| Pair 24 | YFP | YFP-F_T7 | TTAATACGACTCACTATAGGGAGACACCATGGGCTCC AGCGGCGCCC (SEQ ID NO: 41) |
| | YFP | YFP-R | AGATCTTGAAGGCGCTCTTCAGG (SEQ ID NO: 42) |
| Pair 25 | YFP | YFP-F | CACCATGGGCTCCAGCGGCGCCC (SEQ ID NO: 43) |
| | YFP | YFP-R_T7 | TTAATACGACTCACTATAGGGAGAAGATCTTGAAGGC GCTCTTCAGG (SEQ ID NO: 44) |

TABLE 6

Results of diet feeding assays obtained with western corn rootworm larvae.

| Gene Name | Dose ($ng/cm^2$) | Mean weight per insect (mg) | Mean % Mortality | Mean Growth Inhibition |
|---|---|---|---|---|
| annexin-region 1 | 1000 | 0.545 | 0 | −0.262 |
| annexin-region 2 | 1000 | 0.565 | 0 | −0.301 |
| beta spectrin2 region 1 | 1000 | 0.340 | 12 | −0.014 |
| beta spectrin2 region 2 | 1000 | 0.465 | 18 | −0.367 |
| mtRP-L4 region 1 | 1000 | 0.305 | 4 | −0.168 |
| mtRP-L4 region 2 | 1000 | 0.305 | 7 | −0.180 |
| TE buffer | 0 | 0.430 | 13 | 0.000 |
| Water | 0 | 0.535 | 12 | 0.000 |
| YFP | 1000 | 0.480 | 9 | −0.386 |

Example 6: Sample Preparation and Bioassays for *Diabrotica* Adult Feeding Assays Parental RNA interference (RNAi) in western corn rootworms was conducted by feeding dsRNA corresponding to the segments of chromatin remodelers containing SNF2 target gene sequence to gravid adult females. Adult rootworms (<48 hr after emergence) were obtained from CROP CHARACTERISTICS, Inc. (Farmington, Minn.). Adults were reared at 23±1° C., relative humidity of >75%, and Light:Dark periods of 8 hr:16 hr for all bioassays. The insect rearing diet was adapted from Branson and Jackson (1988, J. Kansas Entomol. Soc. 61:353-35). Dry ingredients were added (48 gm/100 mL) to a solution comprising double distilled water with 2.9% agar and 5.6 mL of glycerol. In addition, 0.5 mL of a mixture comprising 47% propionic acid and 6% phosphoric acid solutions was added per 100 mL of diet to inhibit microbial growth. The agar was dissolved in boiling water and the dry ingredients, glycerol, and propionic acid/phosphoric acid solution were added, mixed thoroughly, and poured to a depth of approximately 2 mm. Solidified diet plugs (about 4 mm in diameter by 2 mm height; 25.12 $mm^3$) were cut from the diet with a No. 1 cork borer. Six adult males and females (24 to 48 hrs old) were maintained on untreated artificial diet and were allowed to mate for 4 days in 16 well trays (5.1 cm long×3.8 cm wide×2.9 high) with vented lids.

On day five, males were removed from the container, and females were fed on artificial diet plugs surface treated with 3 μL gene-specific SNF2 dsRNA representing the different chromatin remodelers (2 μg/diet plug; approximately 79.6 $ng/mm^3$). Control treatments consisted of gravid females exposed to diet treated with the same concentration of GFP dsRNA (SEQ ID NO:53) or the same volume of water. GFP dsRNA was produced as described above using opposing primers having a T7 promoter sequence at their 5' ends (SEQ ID NOs:54 and 55). Fresh artificial diet treated with dsRNA was provided every other day throughout the experiment. On day 11, females were transferred to oviposition cages (7.5 cm×5.5 cm×5.5 cm) (ShowMan box, Althor Products, Wilton, Conn.) containing autoclaved silty clay loam soil sifted through a 60-mesh sieve (Jackson (1986) *Rearing and handling of Diabrotica virgifera and Diabrotica undecimpunctata howardi*. Pages 25 to 47 in J. L. Krysan and T. A. Miller, eds. *Methods for the study of pest Diabrotica*. Springer-Verlag, New York). Females were allowed to oviposit for four days and the eggs were incubated in soil within the oviposition boxes for 10 days at 27° C. and then removed by washing the oviposition soil through a 60-mesh sieve. Eggs were treated with a solution of formaldehyde (500 μL formaldehyde in 5 mL double distilled water) and methyl-(butycarbamoy)-2-benzimidazole carbamate (0.025 g in 50 mL double distilled water) to prevent fungal growth. Females removed from the oviposition boxes and subsamples of eggs from each treatment were flash frozen in liquid nitrogen for subsequent expression analyses by quantitative RT-PCR (See EXAMPLE 7). The dishes were photographed with Dino-Lite Pro digital microscope (Torrance, Calif.) and total eggs counted using the cell counter function of Image J software (Schneider et al. (2012) Nat. Methods 9:671-5). Harvested eggs were held in Petri dishes on moistened filter paper at 28° C. and monitored for 15 days to determine egg viability. Six replications, each comprising three to six females, were run on separate days. The number of larvae hatching from each treatment was recorded daily until no further hatching was observed.

Ingestion of *brahma* Reg-352 dsRNA molecules by adult WCR females was demonstrated to a have surprising, dramatic and reproducible effect on egg viability. The mated females exposed to *brahma* dsRNA produced a lower number of eggs to females exposed to untreated diet or diet treated with GFP dsRNA. Table 7. However, eggs collected from females that were exposed to *brahma* dsRNA were not viable. Table 7. Eggs collected from adult females exposed to *brahma* dsRNA did not hatch. Ingestion of *brahma* Reg-352 dsRNA molecules by adult WCR females was demonstrated to have dramatic and reproducible effects on both egg production and viability.

TABLE 7

Effect of brahma dsRNA on WCR egg production and egg viability after 11 days of ingestion on treated artificial diet. Means were separated using Dunnett's test.

| | brahma Reg-352 dsRNA | GFP dsRNA | Water |
|---|---|---|---|
| | Eggs per female | | |
| Rep1 | 49 | 44.5 | 108 |
| Rep2 | 67 | 61.7 | 103 |
| Rep3 | 31.3 | 137 | 79.5 |
| Averages† | 49.1 ± 10.3 | 81.1 ± 28.4 | 96.9 ± 8.8 |
| | Percent egg hatch | | |
| Rep1 | 0 | 41.9 | 56 |
| Rep2 | 0 | 71.1 | 67.3 |
| Rep3 | 0 | 53.3 | 42 |
| Averages† | 0** | 55.4 ± 8.5 | 55.1 ± 7.3 |

†±SEM—Standard Error of the Mean.
**Indicates significance at p-value < 0.05.

Ingestion of mi-2 (SEQ ID NO:101), iswi-30 (SEQ ID NO:102), and iswi-2 (SEQ ID NO:103) dsRNA molecules by adult WCR females was demonstrated to a have surprising, dramatic and reproducible effect on egg viability. The mated females exposed to iswi-30 and mi-2 dsRNA produced a lower number of eggs to females exposed to untreated diet or diet treated with GFP dsRNA. Table 8 and Table 9. However, eggs collected from females that were exposed to mi-2, iswi-30, and iswi-2 dsRNA were not viable. Table 8 and Table 9. Adult females exposed to mi-2 dsRNA had no eggs hatch.

TABLE 8

Effect of dsRNA from target gene sequences and controls on WCR egg production and egg viability after 11 days of ingestion on artificial diet. Means were separated using Dunnett's test.

Eggs per Female

| Rep | chd1 | ksmt | iswi-2 | etl1 | iswi | mi-2 | Water | GFP |
|---|---|---|---|---|---|---|---|---|
| 1 | 41.75 | 77.33 | 25.4 | 32.5 | 16.6 | 11.17 | | 85.2 |
| 2 | 47.00 | 47.83 | 40.33 | 80 | 65.8 | 25 | 89.17 | 52 |
| 3 | 69.6 | 73.75 | 64.6 | 29 | 0.4 | 41.75 | 50.8 | 48.5 |
| Average | 52.78 | 66.31 | 43.44 | 47.17 | 27.6 | 25.97 | 69.98 | 61.9 |
| SEM† | 8.54 | 9.29 | 11.42 | 16.45 | 19.67 | 8.84 | 15.66 | 11.69 |
| p-value | 0.32 | 0.829 | 0.133 | 0.192 | 0.02** | 0.02** | | 0.636 |

**Indicates significance at p-value ≤0.05.
†SEM—Standard Error of the Mean.

TABLE 9

Effect of iswi-30 dsRNA (7 replications) and mi-2 dsRNA (6 replications) from target gene sequences and controls on WCR egg production and egg viability after 11 days of ingestion on artificial diet. A total of 7 replications (consisting of 35 females) were completed for the GFP and water controls. Means were separated using Dunnett's test.

| | iswi-30 | mi-2 | Water | GFP |
|---|---|---|---|---|
| | Eggs per Female | | | |
| Average | 32.52 | 26.26 | 71.33 | 66.87 |
| SEM† | 16.11 | 4.40 | 10.46 | 7.85 |
| p-value | 0.0044** | 0.0014** | | 0.9525 |
| | Percent Hatch | | | |
| Rep | | | | |
| Average | 0.562 | 0 | 60.782 | 58.123 |
| SEM† | 0.471 | 0 | 8.835 | 10.391 |
| p-value | 0.003** | 0.0037** | | 0.767 |

**Indicates significance at p-value ≤ 0.05.
†SEM—Standard Error of the Mean.

Figure 5A:
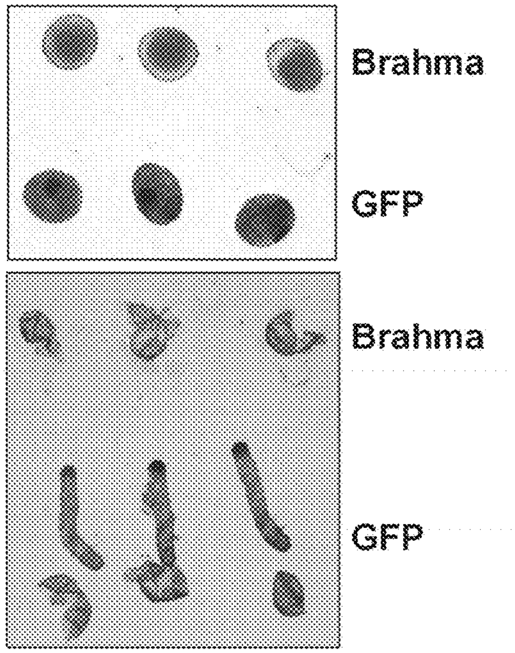
FIG. 5A includes representative photographs of WCR eggs dissected to examine embryonic development under different experimental conditions. Eggs that were oviposited by females treated with GFP dsRNA show normal development. Eggs oviposited by females treated with *brahma*, iswi-30, and mi-2 dsRNA (FIG. 5B-5D) show no embryonic or larval development.
Figure 5B:
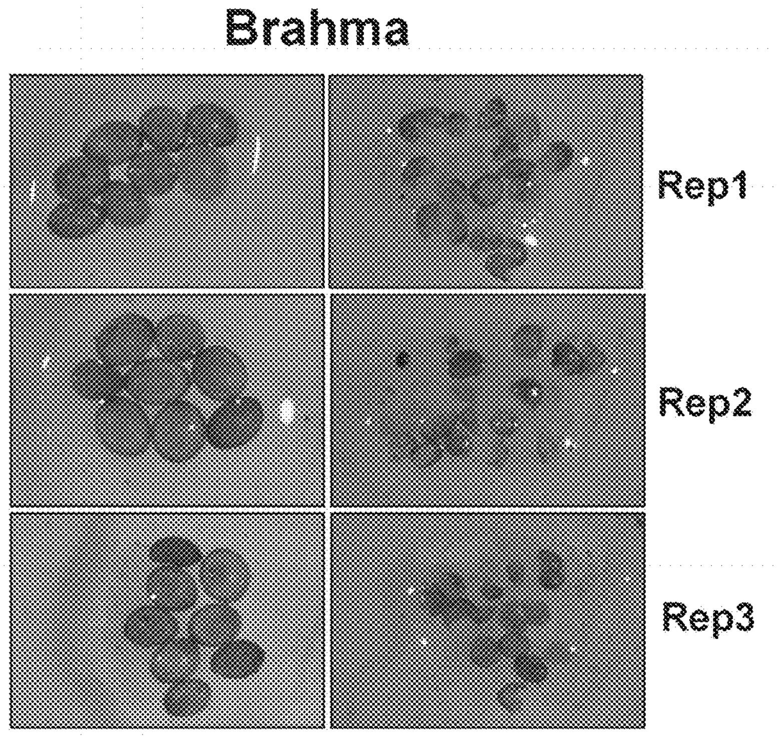
Figure 5C:
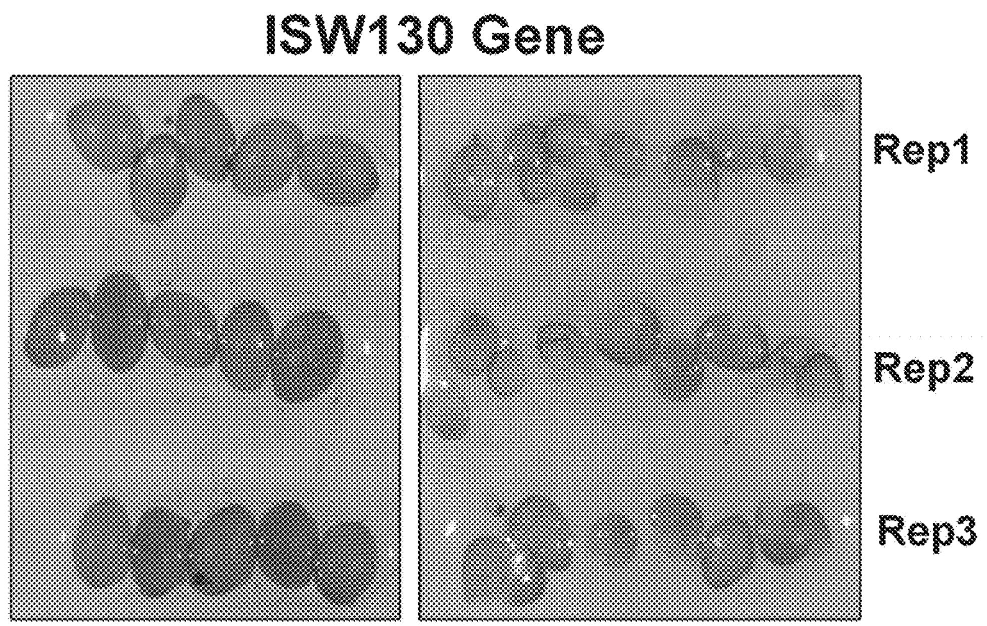
Figure 5D:
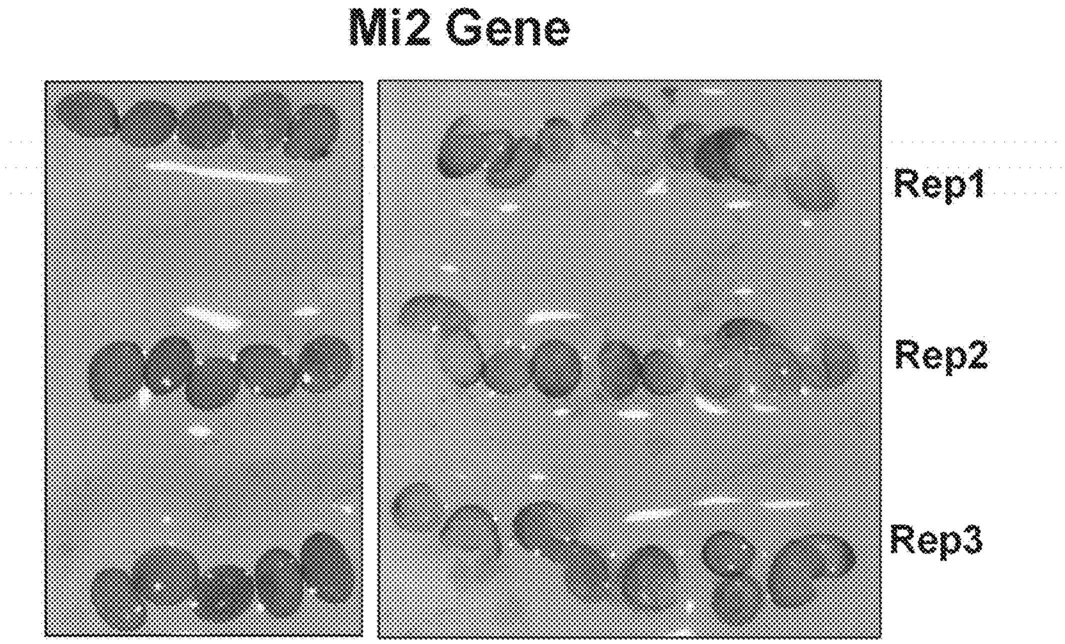

Unhatched eggs were dissected to examine embryonic development and to determine phenotypic responses of parental RNAi (pRNAi). The eggs deposited by WCR females treated with GFP dsRNA showed normal development. FIG. 5A. In contrast, eggs deposited by females treated with *brahma* Reg-352, mi-2 and iswi-30 dsRNA showed no embryonic development within the egg and, when dissected, had no indications of larval development. FIGS. 5B-5D. It is thus an unexpected and surprising finding of this invention that ingestion of *brahma*, mi-2, and iswi-30 dsRNA has a lethal or growth inhibitory effect on WCR eggs and larvae. It is further surprising and unexpected that *brahma*, mi-2, and iswi-30 dsRNA ingestion by gravid adult WCR females dramatically impacts egg production and egg viability, while having no discernible effect on the adult females themselves.

*Brahma* and its orthologs, as well as mi-2 and other chromatin remodelers and their orthologs, share the same functional domains and sequence-level conservation. RNAi target sites were designed within the conserved SNF2 family N-terminal and Helicase C-terminal domains (here referred to as SNF2-Helicase) that are common to all chromatin remodelers, as well as chromatin binding and other functional domains that are conserved within each family (including bromodomain, chromodomain, and HAND-SLIDE domains). RNAi target sequences that are common to *Diabrotica virgifera virgifera, Euchistus heros, Tribolium cas-*

*taneum*, and *Drosophila melanogaster* were designed. The DNA nucleotides and RNAi nucleotides are listed according to the standard IUPAC code:

A=Adenine
C=Cytosine
G=Guanine
T=Thymine
R=A or G
Y=C or T
S=G or C
W=A or T
K=G or T
M=A or C
B=C or G or T
D=A or G or T
H=A or C or T
V=A or C or G
N=A or C or G or T dsRNA encoding sequences targeting SNF2-Helicase regions (SEQ ID NOs:93-96) and chromatin remodeling domains (SEQ ID NOs:97-101) were designed by aligning the amino acid sequences for each target protein from four species, *Diabrotica virgifera virgifera, Euchistus heros, Tribolium castaneum*, and *Drosophila melanogaster*, using Vector NTI Align X (Invitrogen, Grand Island, N.Y.). Highly homologous regions of the amino acid sequence containing at least 8 amino acids within the SNF2 domain or chromatin remodeling domain specific to each target protein were selected. The corresponding nucleotide sequence for each species from each target was then aligned using the Align X program. Where there was a misalignment across the four species the nucleotides were replaced with nucleotides as shown above. Finally, the sequence was aligned against the nucleotide sequence from *Apis melifera* to determine if the sequence would also target that species. If the sequence could also target the protein from *A. melifera* either new regions were chosen or the sequence was shortened to at least 21 bases, which did not target *A. melifera* proteins.

Ingestion of dsRNA molecules encoding sequences targeting SNF2-Helicase regions (SEQ ID NOs:93-96) and chromatin remodeling domains (SEQ ID NOs:97-101) by adult WCR females is demonstrated to a have surprising, dramatic and reproducible effect on egg viability. The mated females exposed to dsRNA produce a lower number of eggs than females exposed to untreated diet or diet treated with GFP dsRNA.

The foregoing results clearly document the systemic nature of RNAi in western corn rootworm larvae and adults, and the potential to achieve a parental effect where genes associated with zygotic and/or embryonic development are knocked down in the eggs of females that are exposed to dsRNA. Importantly, this is the first report of a pRNAi response to ingested dsRNA in western corn rootworms. A systemic response is indicated based on the observation of knock down in tissues other than the alimentary canal where exposure and uptake of dsRNA is occurring. Because insects in general, and rootworms specifically, lack the RNA-dependent RNA polymerase that has been associated with systemic response in plants and nematodes, our results confirm that the dsRNA can be taken up by gut tissue and translocated to other tissues (e.g., developing ovarioles).

The ability to knock down the expression of genes involved with embryonic development such that the eggs do not hatch, offers a unique opportunity to achieve and improve control of western corn rootworms. Because adults readily feed on above-ground reproductive tissues (such as silks and tassels), adult rootworms can be exposed to iRNA control agents by transgenic expression of dsRNA to achieve root protection in the subsequent generation by preventing eggs from hatching. Delivery of the dsRNA through transgenic expression of dsRNA in corn plants, or by contact with surface-applied iRNAs, provides an important stacking partner for other transgenic approaches that target larvae directly and enhance the overall durability of pest management strategies.

Example 7: Real-Time PCR Analysis

Total RNA was isolated from the whole bodies of adult females, males, larvae, and eggs using RNeasy mini Kit (Qiagen, Valencia, Calif.) following the manufacturer's recommendations. Before the initiation of the transcription reaction, the total RNA was treated with DNase to remove any gDNA using Quantitech reverse transcription kit (Qiagen, Valencia, Calif.). Total RNA (500 ng) was used to synthesize first strand cDNA as a template for real-time quantitative PCR (qPCR). The RNA was quantified spectrophotometrically at 260 nm and purity evaluated by agarose gel electrophoresis. Primers used for qPCR analysis were designed using Beacon designer software (Premier Biosoft International, Palo Alto, Calif.). The efficiencies of primer pairs were evaluated using 5 fold serial dilutions (1:1/5:1/25:1/125:1/625) in triplicate. Amplification efficiencies were higher than 96.1% for all the qPCR primer pairs used in this study. All primer combinations used in this study showed a linear correlation between the amount of cDNA template and the amount of PCR product. All correlation coefficients were larger than 0.99. The 7500 Fast System SDS v2.0.6 Software (Applied Biosystems) was used to determine the slope, correlation coefficients, and efficiencies. Three biological replications, each with two technical replications were used for qPCR analysis. qPCR was performed using SYBR green kit (Applied Biosystems Inc., Foster City, Calif.) and 7500 Fast System real-time PCR detection system (Applied Biosystems Inc., Foster City, Calif.). qPCR cycling parameters included 40 cycles each consisting of 95° C. for 3 sec, 58° C. for 30 sec, as described in the manufacturer's protocol (Applied Biosystems Inc., Foster City, Calif.). At the end of each PCR reaction, a melt curve was generated to confirm a single peak and rule out the possibility of primer-dimer and non-specific product formation. Relative quantification of the transcripts were calculated using the comparative $2^{-\Delta\Delta CT}$ method and were normalized to ft-actin.

Figure 6A:
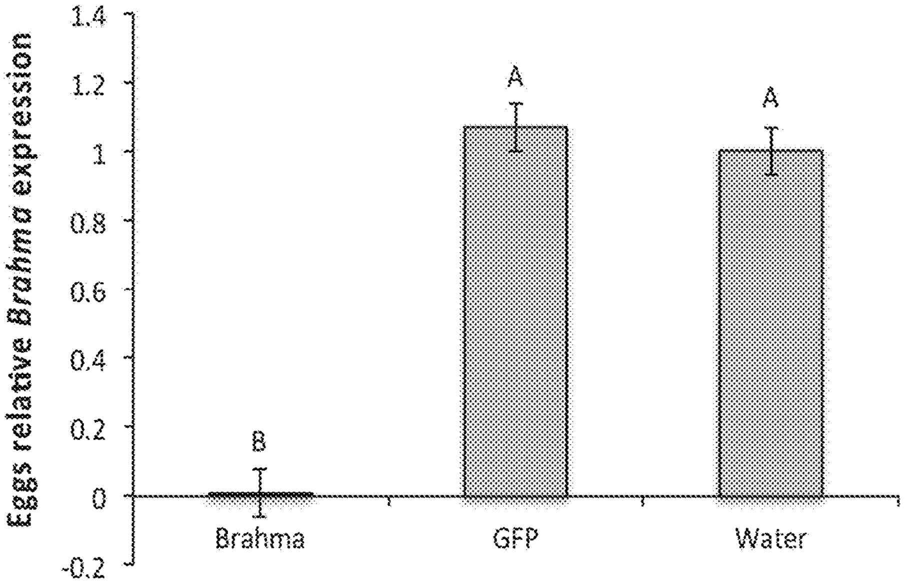
FIG. 6A includes a summary of data showing the relative expression of *brahma* in eggs collected from WCR females exposed to dsRNA in a treated artificial diet, relative to GFP and water controls. Also shown is the relative expression of *brahma* (FIG. 6B), mi-2 (FIG. 6C), and iswi30 (FIG. 6D) in adult females exposed to dsRNA in a treated artificial diet, relative to GFP and water controls. Bars followed by the same letter are not significantly different (P>0.05; N=3 biological replications of 10 eggs, larvae, or adults; replication with 2 technical replications/sample).
Figure 6B:
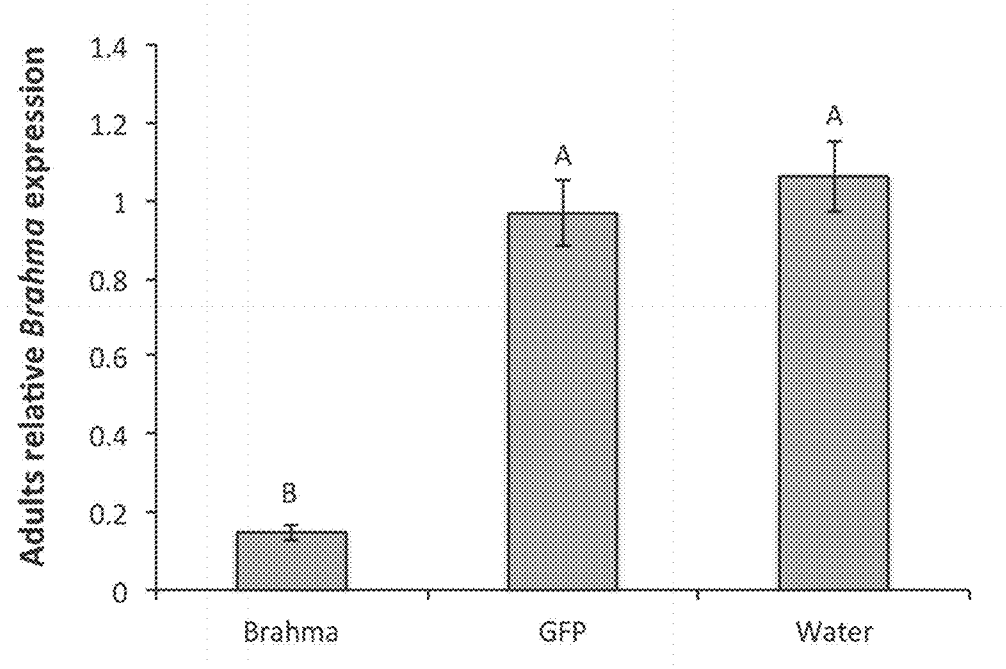
Figure 6C:
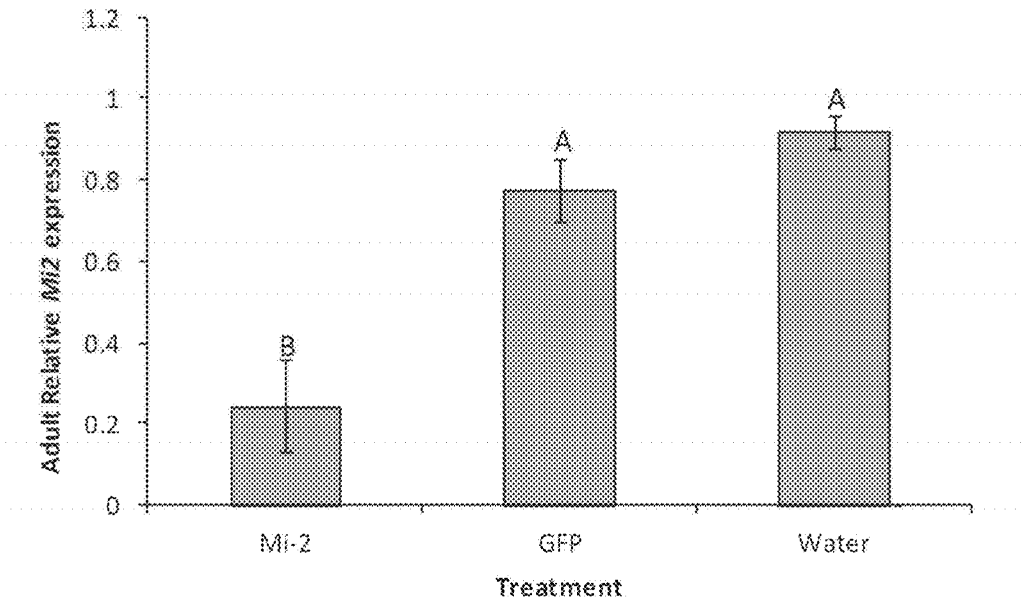
Figure 6D:
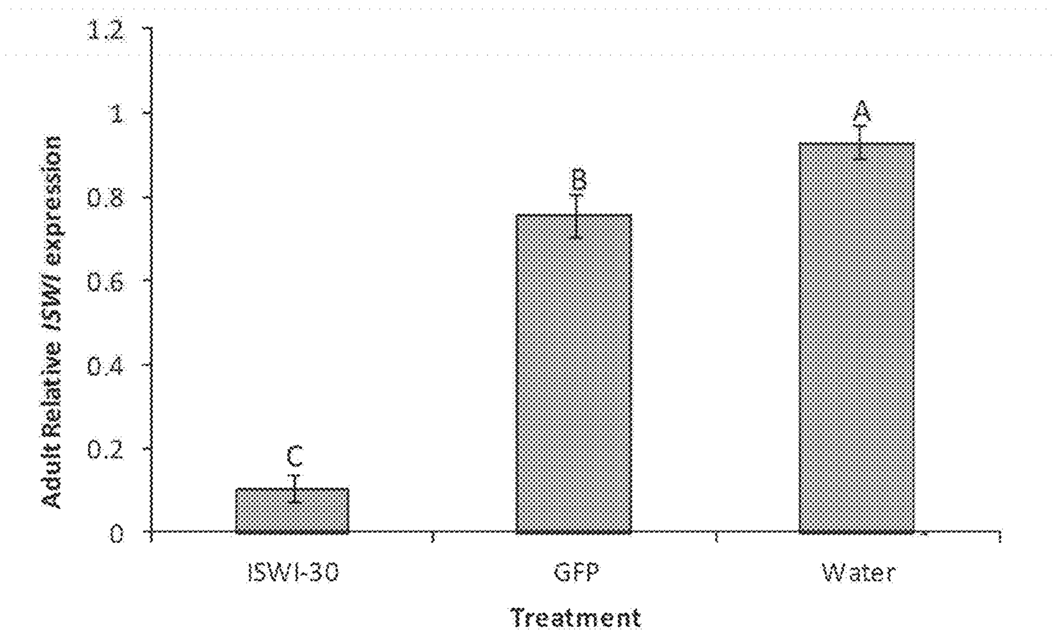

FIG. 6A shows the relative expression of *brahma* in eggs collected from females exposed to dsRNA in treated artificial diet relative to GFP and water controls. FIG. 6B shows the relative expression of *brahma* in adult females exposed to dsRNA in treated artificial diet relative to GFP and water controls. There is a reduction in transcript levels in female adults and eggs. FIG. 6C shows the relative expression of mi-2 in adult females exposed to dsRNA in treated artificial diet relative to GFP and water controls. FIG. 6D. Relative expression of iswi-30 in adult females exposed to dsRNA in treated artificial diet relative to GFP and water controls.

Example 8: Construction of Plant Transformation Vectors

Entry vectors harboring a target gene construct for dsRNA hairpin formation comprising segments of *brahma*-c4465 rc (SEQ ID NO:1), *brahma*-8089 (SEQ ID NO:3), *brahma*-525 (SEQ ID NO:5), Contig[0001]_*brahma*_949-1126 (SEQ ID NO:7), mi-2 (SEQ ID NO:79), iswi-1 (SEQ ID NO:81), chd1 (SEQ ID NO:83), iswi-2 (SEQ ID NO:85), iswi30 (SEQ ID NO:87), ino80 (SEQ ID NO:89), *domino* (SEQ ID NO:91), mi-2 (SEQ ID NO:164), iswi-1 (SEQ ID NO:165), and/or iswi-2 (SEQ ID NO:166) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientation to one another, the two segments being separated by an ST-LS1 intron sequence (SEQ ID NO:56; Vancanneyt et al. (1990) Mol. Gen. Genet. 220:245-50). Thus, the primary mRNA transcript contains the two *brahma* gene segment sequences as large inverted repeats of one another, separated by the intron sequence. A copy of a maize ubiquitin 1 promoter (U.S. Pat. No. 5,510,474) is used to drive production of the primary mRNA hairpin transcript, and a fragment comprising a 3' untranslated region from a maize peroxidase 5 gene (ZmPer5 3'UTR v2; U.S. Pat. No. 6,699,984) is used to terminate transcription of the hairpin-RNA-expressing gene.

An entry vector comprises a *brahma* v1 hairpin-RNA construct (SEQ ID NO:57) that comprises a segment of *brahma*-8089 (SEQ ID NO:3) and *brahma*-525 (SEQ ID NO:5).

An entry vector comprises a *brahma* v2 hairpin-RNA construct (SEQ ID NO:58) that comprises a segment of *brahma*-c4465 rc (SEQ ID NO:1) and *brahma*-8089 (SEQ ID NO:3) distinct from that above.

Entry vectors described above are used in standard GATEWAY® recombination reactions with a typical binary destination vector to produce *brahma* hairpin RNA expression transformation vectors for *Agrobacterium*-mediated maize embryo transformations.

A negative control binary vector, which comprises a gene that expresses a YFP hairpin dsRNA, is constructed by means of standard GATEWAY® recombination reactions with a typical binary destination vector and entry vector. An entry vector comprises a YFP hairpin sequence (SEQ ID NO:138) under the expression control of a maize ubiquitin 1 promoter (as above) and a fragment comprising a 3' untranslated region from a maize peroxidase 5 gene (as above).

A binary destination vector comprises a herbicide tolerance gene (aryloxyalknoate dioxygenase; AAD-1 v3) (U.S. Pat. No. 7,838,733, and Wright et al. (2010) Proc. Natl. Acad. Sci. U.S.A. 107:20240-5) under the regulation of a sugarcane bacilliform badnavirus (ScBV) promoter (Schenk et al. (1999) Plant Molec. Biol. 39:1221-30). A synthetic 5'UTR sequence, comprised of sequences from a Maize Streak Virus (MSV) coat protein gene 5'UTR and intron 6 from a maize Alcohol Dehydrogenase 1 (ADH1) gene, is positioned between the 3' end of the SCBV promoter segment and the start codon of the AAD-1 coding region. A fragment comprising a 3' untranslated region from a maize lipase gene (ZmLip 3'UTR; U.S. Pat. No. 7,179,902) is used to terminate transcription of the AAD-1 mRNA.

A further negative control binary vector, which comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter (as above) and a fragment comprising a 3' untranslated region from a maize lipase gene (ZmLip 3'UTR; as above). An entry vector comprises a YFP coding region under the expression control of a maize ubiquitin 1 promoter (as above) and a fragment comprising a 3' untranslated region from a maize peroxidase 5 gene (as above).

SEQ ID NO:57 presents a *brahma* v1 hairpin-forming sequence.

SEQ ID NO:58 presents a *brahma* v2 hairpin-forming sequence.

Example 9: Transgenic Maize Tissues Comprising Insecticidal dsRNAs

*Agrobacterium*-mediated Transformation.

Transgenic maize cells, tissues, and plants that produce one or more insecticidal dsRNA molecules (for example, at least one dsRNA molecule including a dsRNA molecule targeting a gene comprising segments of *brahma*-c4465 rc (SEQ ID NO:1), *brahma*-8089 (SEQ ID NO:3), *brahma*-525 (SEQ ID NO:5), Contig[0001]_*brahma*_949-1126 (SEQ ID NO:7), mi-2 (SEQ ID NO:79 and SEQ ID NO:164), iswi-ID NO:81 and SEQ ID NO:165), chd1 (SEQ ID NO:83), iswi-2 (SEQ ID NO:85 and SEQ ID NO:166), iswi30 (SEQ ID NO:87), ino80 (SEQ ID NO:89), and/or *domino* (SEQ ID NO:91) through expression of a chimeric gene stably integrated into the plant genome are produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues are selected by their ability to grow on Haloxyfop-containing medium and are screened for dsRNA production, as appropriate. Portions of such transformed tissue cultures may be presented to neonate corn rootworm larvae for bioassay, essentially as described in EXAMPLE 1.

*Agrobacterium* Culture Initiation.

Glycerol stocks of *Agrobacterium* strain DAt13192 cells (WO 2012/016222A2) harboring a binary transformation vector as described above (EXAMPLE 7) are streaked on AB minimal medium plates (Watson et al. (1975) J. Bacteriol. 123:255-264) containing appropriate antibiotics and are grown at 20° C. for 3 days. The cultures are then streaked onto YEP plates (gm/L: yeast extract, 10; Peptone, 10; NaCl 5) containing the same antibiotics and were incubated at 20° C. for 1 day.

*Agrobacterium* Culture.

On the day of an experiment, a stock solution of Inoculation Medium and acetosyringone is prepared in a volume appropriate to the number of constructs in the experiment and pipetted into a sterile, disposable, 250 mL flask. Inoculation Medium (Frame et al. (2011) *Genetic Transformation Using Maize Immature Zygotic Embryos*. IN *Plant Embryo Culture Methods and Protocols: Methods in Molecular Biology*. T. A. Thorpe and E. C. Yeung, (Eds), Springer Science and Business Media, LLC. pp 327-341) contained: 2.2 gm/L MS salts; 1×ISU Modified MS Vitamins (Frame et al. (2011)) 68.4 gm/L sucrose; 36 gm/L glucose; 115 mg/L L-proline; and 100 mg/L myo-inositol; at pH 5.4.) Acetosyringone is added to the flask containing Inoculation Medium to a final concentration of 200 μM from a 1 M stock solution in 100% dimethyl sulfoxide and the solution is thoroughly mixed.

For each construct, 1 or 2 inoculating loops-full of *Agrobacterium* from the YEP plate are suspended in 15 mL of the Inoculation Medium/acetosyringone stock solution in a sterile, disposable, 50 mL centrifuge tube, and the optical density of the solution at 550 nm ($OD_{550}$) is measured in a spectrophotometer. The suspension is then diluted to $OD_{550}$ of 0.3 to 0.4 using additional Inoculation Medium/acetosyringone mixture. The tube of *Agrobacterium* suspension is then placed horizontally on a platform shaker set at about 75 rpm at room temperature and shaken for 1 to 4 hours while embryo dissection is performed.

Ear Sterilization and Embryo Isolation.

Maize immature embryos are obtained from plants of *Zea mays* inbred line B104 (Hallauer et al. (1997) Crop Science 37:1405-1406) grown in the greenhouse and self- or sib-pollinated to produce ears. The ears are harvested approximately 10 to 12 days post-pollination. On the experimental day, de-husked ears are surface-sterilized by immersion in a 20% solution of commercial bleach (ULTRA CLOROX® GERMICIDAL BLEACH, 6.15% sodium hypochlorite; with two drops of TWEEN 20) and shaken for 20 to 30 min, followed by three rinses in sterile deionized water in a laminar flow hood. Immature zygotic embryos (1.8 to 2.2 mm long) are aseptically dissected from each ear and randomly distributed into microcentrifuge tubes containing 2.0 mL of a suspension of appropriate *Agrobacterium* cells in liquid Inoculation Medium with 200 μM acetosyringone, into which 2 μL of 10% BREAK-THRU® 5233 surfactant (EVONIK INDUSTRIES; Essen, Germany) had been added. For a given set of experiments, embryos from pooled ears are used for each transformation.

*Agrobacterium* Co-Cultivation.

Following isolation, the embryos are placed on a rocker platform for 5 minutes. The contents of the tube are then poured onto a plate of Co-cultivation Medium, which contains 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 200 μM acetosyringone in DMSO; and 3 gm/L GELZAN™, at pH 5.8. The liquid *Agrobacterium* suspension is removed with a sterile, disposable, transfer pipette. The embryos are then oriented with the scutellum facing up using sterile forceps with the aid of a microscope. The plate is closed, sealed with 3M™ MICROPORE™ medical tape, and placed in an incubator at 25° C. with continuous light at approximately 60 μmol $m^{-2}s^{-1}$ of Photosynthetically Active Radiation (PAR).

Callus Selection and Regeneration of Transgenic Events.

Following the Co-Cultivation period, embryos are transferred to Resting Medium, which is composed of 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino)ethanesulfonic acid monohydrate; PHYTOTECHNOLOGIES LABR.; Lenexa, Kans.); 250 mg/L Carbenicillin; and 2.3 gm/L GELZAN™; at pH 5.8. No more than 36 embryos are moved to each plate. The plates are placed in a clear plastic box and incubated at 27° C. with continuous light at approximately 50 μmol $m^{-2}s^{-1}$ PAR for 7 to 10 days. Callused embryos are then transferred (<18/plate) onto Selection Medium I, which is comprised of Resting Medium (above) with 100 nM R-Haloxyfop acid (0.0362 mg/L; for selection of calli harboring the AAD-1 gene). The plates are returned to clear boxes and incubated at 27° C. with continuous light at approximately 50 μmol $m^{-2}s^{-1}$ PAR for 7 days. Callused embryos are then transferred (<12/plate) to Selection Medium II, which is comprised of Resting Medium (above) with 500 nM R-Haloxyfop acid (0.181 mg/L). The plates are returned to clear boxes and incubated at 27° C. with continuous light at approximately 50 μmol $m^{-2}s^{-1}$ PAR for 14 days. This selection step allows transgenic callus to further proliferate and differentiate.

Proliferating, embryogenic calli are transferred (<9/plate) to Pre-Regeneration medium. Pre-Regeneration Medium contains 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 0.181 mg/L Haloxyfop acid; at pH 5.8. The plates are stored in clear boxes and incubated at 27° C. with continuous light at approximately 50 μmol $m^{-2}s^{-1}$ PAR for 7 days. Regenerating calli are then transferred (<6/plate) to Regeneration Medium in PHYTATRAYS™ (SIGMA-ALDRICH) and incubated at 28° C. with 16 hours light/8 hours dark per day (at approximately 160 μmol $m^{-2}s^{-1}$ PAR) for 14 days or until shoots and roots develop. Regeneration Medium contains 4.33 gm/L MS salts; 1×ISU Modified MS Vitamins; 60 gm/L sucrose; 100 mg/L myo-inositol; 125 mg/L Carbenicillin; 3 gm/L GELLAN™ gum; and 0.181 mg/L R-Haloxyfop acid; at pH 5.8. Small shoots with primary roots are then isolated and transferred to Elongation Medium without selection. Elongation Medium contains 4.33 gm/L MS salts; 1×ISU Modified MS Vitamins; 30 gm/L sucrose; and 3.5 gm/L GELRITE™: at pH 5.8.

Transformed plant shoots selected by their ability to grow on medium containing Haloxyfop are transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON™ growth chamber (27° C. day/24° C. night, 16-hour photoperiod, 50-70% RH, 200 μmol $m^{-2}s^{-1}$ PAR). In some instances, putative transgenic plantlets are analyzed for transgene relative copy number by quantitative real-time PCR assays using primers designed to detect the AAD1 herbicide tolerance gene integrated into the maize genome. Further, RNA qPCR assays are used to detect the presence of the linker sequence in expressed dsRNAs of putative transformants. Selected transformed plantlets are then moved into a greenhouse for further growth and testing.

Transfer and Establishment of $T_0$ Plants in the Greenhouse for Bioassay and Seed Production.

When plants reach the V3-V4 stage, they are transplanted into IE CUSTOM BLEND (PROFILE/METRO MIX 160) soil mixture and grown to flowering in the greenhouse (Light Exposure Type: Photo or Assimilation; High Light Limit: 1200 PAR; 16-hour day length; 27° C. day/24° C. night).

Plants to be used for insect bioassays are transplanted from small pots to TINUS™ 350-4 ROOTRAINERS® (SPENCER-LEMAIRE INDUSTRIES; Acheson, Alberta, Canada;) (one plant per event per ROOTRAINER®). Approximately four days after transplanting to ROOTRAINERS®, plants are used in bioassays.

Plants of the $T_1$ generation are obtained by pollinating the silks of $T_0$ transgenic plants with pollen collected from plants of non-transgenic elite inbred line B104 or other appropriate pollen donors, and planting the resultant seeds. Reciprocal crosses are performed when possible.

Example 10: Adult *Diabrotica* Plant Feeding Bioassay

Transgenic corn foliage (V3-4) expressing dsRNA for parental RNAi targets and GFP controls is lyophilized and ground to a fine powder with mortar and pestle and sieved through a 600 μM screen in order to achieve a uniform particle size prior to incorporation into artificial diet. The artificial diet is the same diet described previously for parental RNAi experiments except that the amount of water is doubled (20 mL $ddH_2O$, 0.40 g agar, 6.0 g diet mix, 700 μL glycerol, 27.5 μL mold inhibitor). Prior to solidification, lyophilized corn leaf tissue is incorporated into the diet at a rate of 40 mg/ml of diet and mixed thoroughly. The diet is then poured onto the surface of a plastic petri dish to a depth of approximately 4 mm and allowed to solidify. Diet plugs are cut from the diet and used to expose western corn rootworm adults using the same methods described previously for parental RNAi experiments.

For plant feeding bioassays pRNAi $T_0$ or $T_1$ events are grown in the greenhouse until the plants produce cobs, tassel and silk. A total of 25 newly emerged rootworm adults are released on each plant, and the entire plant is covered to prevent adults from escaping. Two weeks after release, female adults are recovered from each plant and maintained in the laboratory for egg collection. Depending on the parental RNAi target and expected phenotype, parameters such as number of eggs per female, percent egg hatch and larval mortality are recorded and compared with control plants.

Example 11: *Diabrotica* Larval Root-Feeding Bioassay of Transgenic Maize

Insect Bioassays.

Bioactivity of dsRNA of the subject invention produced in plant cells is demonstrated by bioassay methods. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples.

Insect Bioassays with Transgenic Maize Events.

Two western corn rootworm larvae (1 to 3 days old) hatched from washed eggs are selected and placed into each well of the bioassay tray. The wells are then covered with a “PULL N' PEEL” tab cover (BIO-CV-16, BIO-SERV) and placed in a 28° C. incubator with an 18 hr/6 hr light/dark cycle. Nine days after the initial infestation, the larvae are assessed for mortality, which is calculated as the percentage of dead insects out of the total number of insects in each treatment. The insect samples are frozen at −20° C. for two days, then the insect larvae from each treatment are pooled and weighed. The percent of growth inhibition is calculated as the mean weight of the experimental treatments divided by the mean of the average weight of two control well treatments. The data are expressed as a Percent Growth Inhibition (of the Negative Controls). Mean weights that exceed the control mean weight are normalized to zero.

Insect Bioassays in the Greenhouse.

Western corn rootworm (WCR, *Diabrotica virgifera virgifera* LeConte) eggs are received in soil from CROP CHARACTERISTICS (Farmington, Minn.). WCR eggs are incubated at 28° C. for 10 to 11 days. Eggs are washed from the soil, placed into a 0.15% agar solution, and the concentration is adjusted to approximately 75 to 100 eggs per 0.25 mL aliquot. A hatch plate is set up in a Petri dish with an aliquot of egg suspension to monitor hatch rates.

The soil around the maize plants growing in ROOTRANERS® is infested with 150 to 200 WCR eggs. The insects are allowed to feed for 2 weeks, after which time a “Root Rating” is given to each plant. A Node-Injury Scale is utilized for grading, essentially according to Oleson et al. (2005) J. Econ. Entomol. 98:1-8. Plants which pass this bioassay are transplanted to 5-gallon pots for seed production. Transplants are treated with insecticide to prevent further rootworm damage and insect release in the greenhouses. Plants are hand pollinated for seed production. Seeds produced by these plants are saved for evaluation at the $T_1$ and subsequent generations of plants.

Greenhouse bioassays include two kinds of negative control plants. Transgenic negative control plants are generated by transformation with vectors harboring genes designed to produce a yellow fluorescent protein (YFP) or a YFP hairpin dsRNA (See EXAMPLE 4). Non-transformed negative control plants are grown from seeds of line B104. Bioassays are conducted on two separate dates, with negative controls included in each set of plant materials.

Example 12: Molecular Analyses of Transgenic Maize Tissues

Molecular analyses (e.g., RNA qPCR) of maize tissues are performed on samples from leaves and roots that are collected from greenhouse grown plants on the same days that root feeding damage is assessed.

Results of RNA qPCR assays for the Per5 3'UTR are used to validate expression of hairpin transgenes. (A low level of Per5 3'UTR detection is expected in non-transformed maize plants, since there is usually expression of the endogenous Per5 gene in maize tissues.) Results of RNA qPCR assay for intervening sequence between repeat sequences (which is integral to the formation of dsRNA hairpin molecules) in expressed RNAs are used to validate the presence of hairpin transcripts. Transgene RNA expression levels are measured relative to the RNA levels of an endogenous maize gene.

DNA qPCR analyses to detect a portion of the AAD1 coding region in gDNA are used to estimate transgene insertion copy number. Samples for these analyses are collected from plants grown in environmental chambers. Results are compared to DNA qPCR results of assays designed to detect a portion of a single-copy native gene, and simple events (having one or two copies of the transgenes) are advanced for further studies in the greenhouse.

Additionally, qPCR assays designed to detect a portion of the spectinomycin-resistance gene (SpecR; harbored on the binary vector plasmids outside of the T-DNA) are used to determine if the transgenic plants contain extraneous integrated plasmid backbone sequences.

Hairpin RNA Transcript Expression Level: Per 5 3'UTR qPCR

Callus Cell Events. or transgenic plants are analyzed by real time quantitative PCR (qPCR) of the Per 5 3'UTR sequence to determine the relative expression level of the full length hairpin transcript, as compared to the transcript level of an internal maize gene (for example, GENBANK Accession No. BT069734), which encodes a TIP41-like protein (i.e. a maize homolog of GENBANK Accession No. AT4G34270; having a tBLASTX score of 74% identity). RNA is isolated using an RNAEASY™ 96 kit (QIAGEN, Valencia, Calif.). Following elution, the total RNA is subjected to a DNAse1 treatment according to the kit's suggested protocol. The RNA is then quantified on a NANO- DROP 8000 spectrophotometer (THERMO SCIENTIFIC) and concentration is normalized to 25 ng/µL. First strand cDNA is prepared using a HIGH CAPACITY cDNA SYNTHESIS KIT (INVITROGEN) in a 10 µL reaction volume with 5 µL denatured RNA, substantially according to the manufacturer's recommended protocol. The protocol is modified slightly to include the addition of 10 µL of 100 µM T20VN oligonucleotide (IDT) (TTTTTTTTTTTTTTTTTTTTVN, SEQ ID NO:59. where V is A, C, or G, and N is A, C, G, or T;) into the 1 mL tube of random primer stock mix, in order to prepare a working stock of combined random primers and oligo dT.

Following cDNA synthesis, samples are diluted 1:3 with nuclease-free water, and stored at −20° C. until assayed.

Separate real-time PCR assays for the Per5 3' UTR and TIP41-like transcript are performed on a LIGHTCYCLER™ 480 (ROCHE DIAGNOSTICS, Indianapolis, Ind.) in 10 reaction volumes. For the Per5 3'UTR assay, reactions are run with Primers P5U76S (F) (SEQ ID NO:60) and P5U76A (R) (SEQ ID NO:61), and a ROCHE UNIVERSAL PROBE™ (UPL76; Catalog No. 4889960001; labeled with FAM). For the TIP41-like reference gene assay, primers TIPmxF (SEQ ID NO:62) and TIPmxR (SEQ ID NO:63), and Probe HXTIP (SEQ ID NO:64) labeled with HEX (hexachlorofluorescein) are used.

All assays include negative controls of no-template (mix only). For standard curves, a blank (water in source well) is also included in the source plate to check for sample cross-contamination. Primer and probe sequences are set forth in Table 10. Reaction components recipes for detection of the various transcripts are disclosed in Table 11, and PCR reactions conditions are summarized in Table 12. The FAM (6-Carboxy Fluorescein Amidite) fluorescent moiety is excited at 465 nm and fluorescence is measured at 510 nm; the corresponding values for the HEX (hexachlorofluorescein) fluorescent moiety are 533 nm and 580 nm.

TABLE 11-continued

PCR reaction recipes for transcript detection.

| Component | Per5 3'UTR | TIP-like Gene |
|---|---|---|
| | Final Concentration | |
| Roche UPL76 (FAM) | 0.2 µM | 0 |
| HEXtipZM F | 0 | 0.4 µM |
| HEXtipZM R | 0 | 0.4 µM |
| HEXtipZMP (HEX) | 0 | 0.2 µM |
| cDNA (2.0 µL) | NA | NA |
| Water | To 10 µL | To 10 µL |

TABLE 12

Thermocycler conditions for RNA qPCR.

Per5 3'UTR and TIP41-like Gene Detection

| Process | Temp. | Time | No. Cycles |
|---|---|---|---|
| Target Activation | 95° C. | 10 min | 1 |
| Denature | 95° C. | 10 sec | 40 |
| Extend | 60° C. | 40 sec | |
| Acquire FAM or HEX | 72° C. | 1 sec | |
| Cool | 40° C. | 10 sec | 1 |

Data are analyzed using LIGHTCYCLER™ Software v1.5 by relative quantification using a second derivative max algorithm for calculation of Cq values according to the supplier's recommendations. For expression analyses, expression values are calculated using the ΔΔCt method (i.e., 2-(Cq TARGET-Cq REF)), which relies on the comparison of differences of Cq values between two targets, with the base value of 2 being selected under the assumption that, for optimized PCR reactions, the product doubles every cycle.

TABLE 10

Oligonucleotide sequences used for molecular analyses of transcript levels in transgenic maize.

| Target | Oligonucleotide | SEQ ID NO. | Sequence |
|---|---|---|---|
| Per5 3'UTR | P5U76S (F) | 60 | TTGTGATGTTGGTGGCGTAT |
| Per5 3'UTR | P5U76A (R) | 61 | TGTTAAATAAAACCCCAAAGATCG |
| Per5 3'UTR | Roche UPL76 (FAM-Probe) | NAv** | Roche Diagnostics Catalog Number 488996001 |
| TIP41 | TIPmxF | 62 | TGAGGGTAATGCCAACTGGTT |
| TIP41 | TIPmxR | 63 | GCAATGTAACCGAGTGTCTCTCAA |
| TIP41 | HXTIP (HEX-Probe) | 64 | TTTTTGGCTTAGAGTTGATGGTGTACTGATGA |

*TIP41-like protein.
**NAv Sequence Not Available from the supplier.

TABLE 11

PCR reaction recipes for transcript detection.

| Component | Per5 3'UTR | TIP-like Gene |
|---|---|---|
| | Final Concentration | |
| Roche Buffer | 1× | 1× |
| P5U76S (F) | 0.4 µM | 0 |
| P5U76A (R) | 0.4 µM | 0 |

Hairpin Transcript Size and Integrity: Northern Blot Assay.

In some instances, additional molecular characterization of the transgenic plants is obtained by the use of Northern Blot (RNA blot) analysis to determine the molecular size of the *brahma* hairpin RNA in transgenic plants expressing a *brahma* hairpin dsRNA.

All materials and equipment are treated with RNaseZAP (AMBION/INVITROGEN) before use. Tissue samples (100 mg to 500 mg) are collected in 2 mL SAFELOCK EPPENDORF tubes, disrupted with a KLECKO™ tissue pulverizer (GARCIA MANUFACTURING, Visalia, Calif.) with three tungsten beads in 1 mL of TRIZOL (INVITROGEN) for 5 min, then incubated at room temperature (RT) for 10 min. Optionally, the samples are centrifuged for 10 min at 4° C. at 11,000 rpm and the supernatant is transferred into a fresh 2 mL SAFELOCK EPPENDORF tube. After 200 μL chloroform are added to the homogenate, the tube is mixed by inversion for 2 to 5 min, incubated at RT for 10 minutes, and centrifuged at 12,000×g for 15 min at 4° C. The top phase is transferred into a sterile 1.5 mL EPPENDORF tube, 600 μL of 100% isopropanol are added, followed by incubation at RT for 10 min to 2 hr, and then centrifuged at 12,000×g for 10 min at 4° C. to 25° C. The supernatant is discarded and the RNA pellet is washed twice with 1 mL 70% ethanol, with centrifugation at 7,500×g for 10 min at 4° C. to 25° C. between washes. The ethanol is discarded and the pellet is briefly air dried for 3 to 5 min before resuspending in 50 μL of nuclease-free water.

Total RNA is quantified using the NANODROP8000® (THERMO-FISHER) and samples are normalized to 5 μg/10 μL. 10 μL of glyoxal (AMBION/INVITROGEN) are then added to each sample. Five to 14 ng of DIG RNA standard marker mix (ROCHE APPLIED SCIENCE, Indianapolis, Ind.) are dispensed and added to an equal volume of glyoxal. Samples and marker RNAs are denatured at 50° C. for 45 min and stored on ice until loading on a 1.25% SEAKEM GOLD agarose (LONZA, Allendale, N.J.) gel in NORTHERNMAX 10× glyoxal running buffer (AMBION/INVITROGEN). RNAs are separated by electrophoresis at 65 volts/30 mA for 2 hours and 15 minutes.

Following electrophoresis, the gel is rinsed in 2×SSC for 5 min and imaged on a GEL DOC station (BIORAD, Hercules, Calif.), then the RNA is passively transferred to a nylon membrane (MILLIPORE) overnight at RT, using 10×SSC as the transfer buffer (20×SSC consists of 3 M sodium chloride and 300 mM trisodium citrate, pH 7.0). Following the transfer, the membrane is rinsed in 2×SSC for 5 minutes, the RNA is UV-crosslinked to the membrane (AGILENT/STRATAGENE), and the membrane is allowed to dry at room temperature for up to 2 days.

The membrane is prehybridized in ULTRAHYB buffer (AMBION/INVITROGEN) for 1 to 2 hr. The probe consists of a PCR amplified product containing the sequence of interest, (for example, the antisense sequence portion of SEQ ID NO:57 or SEQ ID NO:58, as appropriate) labeled with digoxigenin by means of a ROCHE APPLIED SCIENCE DIG procedure. Hybridization in recommended buffer is overnight at a temperature of 60° C. in hybridization tubes. Following hybridization, the blot is subjected to DIG washes, wrapped, exposed to film for 1 to 30 minutes, then the film is developed, all by methods recommended by the supplier of the DIG kit.

Transgene Copy Number Determination.

Maize leaf pieces approximately equivalent to 2 leaf punches are collected in 96-well collection plates (QIAGEN). Tissue disruption is performed with a KLECKO™ tissue pulverizer (GARCIA MANUFACTURING, Visalia, Calif.) in BIOSPRINT96 AP1 lysis buffer (supplied with a BIOSPRINT96 PLANT KIT; QIAGEN) with one stainless steel bead. Following tissue maceration, gDNA is isolated in high throughput format using a BIOSPRINT96 PLANT KIT and a BIOSPRINT96 extraction robot. gDNA is diluted 2:3 DNA:water prior to setting up the qPCR reaction.

qPCR Analysis.

Transgene detection by hydrolysis probe assay is performed by real-time PCR using a LIGHTCYCLER®480 system. Oligonucleotides to be used in hydrolysis probe assays to detect the linker sequence (e.g. ST-LS1; SEQ ID NO:56), or to detect a portion of the SpecR gene (i.e. the spectinomycin resistance gene borne on the binary vector plasmids; SEQ ID NO:65; SPC1 oligonucleotides in Table 13), are designed using LIGHTCYCLER® PROBE DESIGN SOFTWARE 2.0. Further, oligonucleotides to be used in hydrolysis probe assays to detect a segment of the AAD-1 herbicide tolerance gene (SEQ ID NO:66; GAAD1 oligonucleotides in Table 13) are designed using PRIMER EXPRESS software (APPLIED BIOSYSTEMS). Table 13 shows the sequences of the primers and probes. Assays are multiplexed with reagents for an endogenous maize chromosomal gene (Invertase; GENBANK Accession No: U16123; referred to herein as IVR1), which serves as an internal reference sequence to ensure gDNA was present in each assay. For amplification, LIGHTCYCLER®480 PROBES MASTER mix (ROCHE APPLIED SCIENCE) is prepared at 1× final concentration in a 10 μL volume multiplex reaction containing 0.4 μM of each primer and 0.2 μM of each probe (Table 14). A two-step amplification reaction is performed as outlined in Table 15. Fluorophore activation and emission for the FAM- and HEX-labeled probes are as described above; CY5 conjugates are excited maximally at 650 nm and fluoresce maximally at 670 nm.

Cp scores (the point at which the fluorescence signal crosses the background threshold) are determined from the real time PCR data using the fit points algorithm (LIGHTCYCLER® SOFTWARE release 1.5) and the Relative Quant module (based on the ΔΔCt method). Data are handled as described previously (above; RNA qPCR).

TABLE 13

Sequences of primers and probes (with fluorescent conjugate) used for gene copy number determinations and binary vector plasmid backbone detection.

| Name | SEQ ID NO: | Sequence |
|---|---|---|
| ST-LS1-F | 67 | GTATGTTTCTGCTTCTACCTTTGAT |
| ST-LS1-R | 68 | CCATGTTTTGGTCATATATTAGAAAAGTT |
| ST-LS1-P (FAM) | 69 | AGTAATATAGTATTTCAAGTATTTTTTTC AAAAT |
| GAAD1-F | 70 | TGTTCGGTTCCCTCTACCAA |
| GAAD1-R | 71 | CAACATCCATCACCTTGACTGA |
| GAAD1-P (FAM) | 72 | CACAGAACCGTCGCTTCAGCAACA |
| IVR1-F | 73 | TGGCGGACGACGACTTGT |
| IVR1-R | 74 | AAAGTTTGGAGGCTGCCGT |
| IVR1-P (HEX) | 75 | CGAGCAGACCGCCGTGTACTTCTACC |
| SPC1A | 76 | CTTAGCTGGATAACGCCAC |
| SPC1S | 77 | GACCGTAAGGCTTGATGAA |
| TQSPEC (CY5*) | 78 | CGAGATTCTCCGCGCTGTAGA |

CY5 = Cyanine-5

TABLE 14

Reaction components for gene copy number analyses and plasmid backbone detection.

| Component | Amt. (μL) | Stock | Final Concentration |
|---|---|---|---|
| 2× Buffer | 5.0 | 2× | 1× |
| Appropriate Forward Primer | 0.4 | 10 μM | 0.4 |
| Appropriate Reverse Primer | 0.4 | 10 μM | 0.4 |
| Appropriate Probe | 0.4 | 5 μM | 0.2 |
| IVR1-Forward Primer | 0.4 | 10 μM | 0.4 |
| IVR1-Reverse Primer | 0.4 | 10 μM | 0.4 |
| IVR1-Probe | 0.4 | 5 μM | 0.2 |
| $H_2O$ | 0.6 | NA* | NA |
| gDNA | 2.0 | ND** | ND |
| Total | 10.0 | | |

*NA = Not Applicable
**ND = Not Determined

TABLE 15

Thermocycler conditions for DNA qPCR. Genomic copy number analyses

| Process | Temp. | Time | No. Cycles |
|---|---|---|---|
| Target Activation | 95° C. | 10 min | 1 |
| Denature | 95° C. | 10 sec | 40 |
| Extend & Acquire FAM, HEX, or CY5 | 60° C. | 40 sec | |
| Cool | 40° C. | 10 sec | 1 |

Example 13: Transgenic *Zea mays* Comprising Coleopteran Pest Sequences

Ten to 20 transgenic $T_0$ *Zea mays* plants are generated as described in EXAMPLE 8. A further 10-20 $T_1$ *Zea mays* independent lines expressing hairpin dsRNA for an RNAi construct are obtained for corn rootworm challenge. DNAs expressing hairpin dsRNA forming polynucleotides may be derived from a sequence as set forth in SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and fragments of the foregoing (e.g., SEQ ID NO:8, SEQ ID NO:10, and SEQ ID NOs:101-106). Additional hairpin dsRNAs may be derived, for example, from coleopteran pest sequences such as, for example, Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), RPS6 (U.S. Patent Application Publication No. 2013/0097730), *Brahma* (USSN), and Kruppel (USSN). These are confirmed through RT-PCR or other molecular analysis methods. Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, reproduction, and viability of feeding coleopteran pests.

In planta delivery of dsRNA, siRNA or miRNA corresponding to target genes and the subsequent uptake by coleopteran pests through feeding results in down-regulation of the target genes in the coleopteran pest through RNA-mediated gene silencing. When the function of a target gene is important at one or more stages of development, the growth, development, and reproduction of the coleopteran pest is affected, and in the case of at least one of WCR, NCR, SCR, MCR, *D. balteata* LeConte, *D. u. tenella*, and *D. u. undecimpunctata* Mannerheim, leads to failure to successfully infest, feed, develop, and/or reproduce, or leads to death of the coleopteran pest. The choice of target genes and the successful application of RNAi is then used to control coleopteran pests.

Phenotypic Comparison of Transgenic RNAi Lines and Nontransformed *Zea mays.*

Target coleopteran pest genes or sequences selected for creating hairpin dsRNA have no similarity to any known plant gene sequence. Hence it is not expected that the production or the activation of (systemic) RNAi by constructs targeting these coleopteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 14: Transgenic *Zea mays* Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is secondarily transformed via *Agrobacterium* or WHISKERS™ methodologies (See Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and fragments of any of the foregoing (e.g., SEQ ID NO:8, SEQ ID NO:10, and SEQ ID NOs:101-106)).

Plant transformation plasmid vectors prepared essentially as described in EXAMPLE 7 are delivered via *Agrobacterium* or WHISKERS™-mediated transformation methods into maize suspension cells or immature maize embryos obtained from a transgenic Hi II or B104 *Zea mays* plant comprising a heterologous coding sequence in its genome that is transcribed into an iRNA molecule that targets an organism other than a coleopteran pest.

Example 15: Transgenic *Zea mays* Comprising an RNAi Construct and Additional Coleopteran Pest Control Sequences A transgenic *Zea mays* plant comprising a heterologous coding sequence in its genome that is transcribed into an iRNA molecule that targets a coleopteran pest organism (for example, at least one dsRNA molecule including a dsRNA molecule targeting a gene comprising SEQ ID NO:1; SEQ ID NO:3; SEQ ID NO:5; SEQ ID NO:7; SEQ ID NO:79; SEQ ID NO:81; SEQ ID NO:83; SEQ ID NO:85; SEQ ID NO:87; SEQ ID NO:89; SEQ ID NO:91; SEQ ID NO:164; SEQ ID NO:165; SEQ ID NO:166; and fragments of any of the foregoing (e.g., SEQ ID NO:8, SEQ ID NO:10, and SEQ ID NOs: 101-106)) is secondarily transformed via *Agrobacterium* or WHISKERS™ methodologies (see Petolino and Arnold (2009) Methods Mol. Biol. 526:59-67) to produce one or more insecticidal protein molecules, for example, Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C insecticidal proteins. Plant transformation plasmid vectors prepared essentially as described in EXAMPLE 7 are delivered via *Agrobacterium* or WHISKERS™-mediated transformation methods into maize suspension cells or immature maize embryos obtained from a transgenic B104 *Zea mays* plant comprising a heterologous coding sequence in its genome that is transcribed into an iRNA molecule that targets a coleopteran pest organism. Doubly-transformed plants are obtained that produce iRNA molecules and insecticidal proteins for control of coleopteran pests.

Example 16: pRNAi-Mediated Insect Protection

Parental RNAi that causes egg mortality or loss of egg viability brings further durability benefits to transgenic crops that use RNAi and other mechanisms for insect protection. A basic two-patch model was used to demonstrate this utility.

One patch contained a transgenic crop expressing insecticidal ingredients, and the second patch contained a refuge crop not expressing insecticidal ingredients. Eggs were oviposited in the two-modeled patches according to their relative proportions. In this example, the transgenic patch represented 95% of the landscape, and the refuge patch represented 5%. The transgenic crop expressed an insecticidal protein active against corn rootworm larvae.

Corn rootworm resistance to the insecticidal protein was modeled as monogenic, with two possible alleles; one (S) conferring susceptibility, and the other (R) conferring resistance. The insecticidal protein was modeled to cause 97% mortality of homozygous susceptible (SS) corn rootworm larvae that feed on it. There was assumed to be no mortality of corn rootworm larvae that are homozygous for the resistance allele (RR). Resistance to the insecticidal protein was assumed to be incompletely recessive, whereby the functional dominance is 0.3 (there is 67.9% mortality of larvae that are heterozygous (RS) for resistance to the protein that feed on the transgenic crop).

The transgenic crop also expressed parentally active dsRNA that, through RNA-interference (pRNAi), causes the eggs of adult female corn rootworms that are exposed to the transgenic crop to be non-viable. Corn rootworm resistance to the pRNAi was also considered to be monogenic with two possible alleles; one (X) conferring susceptibility of the adult female to RNAi, and the other (Y) conferring resistance of the adult female to RNAi. Assuming a high level of exposure to the dsRNAs, the pRNAi was modeled to cause 99.9% of eggs produced by a homozygous susceptible (XX) female to be non-viable. The model assumed that pRNAi has no effect on the viability of eggs produced by homozygous resistant (YY) females. Resistance to the dsRNA was assumed to be recessive, whereby the functional dominance is 0.01 (98.9% of eggs produced by a female that is heterozygous (XY) for resistance to dsRNA are non-viable).

In the model, there was random mating among surviving adults and random oviposition across the two patches in accordance with their relative proportions. The genotypic frequencies of viable offspring followed Mendelian genetics for a two-locus genetic system.

The effect of pRNAi required the adult females to feed on plant tissue expressing parental active dsRNA. The interference with egg development may be lower for adult females emerging from the refuge crop than from the transgenic crop; corn rootworm adults are expected to feed more extensively in the patch in which they emerged following larval development. Therefore, the relative magnitude of the pRNAi effect on female corn rootworm adults emerging from the refuge patch was varied, with the proportion of the pRNAi effect ranging from 0 (no effect of pRNAi on adult females emerging from the refuge patch) to 1 (same effect of pRNAi on adult females emerging from the refuge patch as on adult females emerging from the transgenic patch).

This model could be easily adjusted to demonstrate the situation when the effect of pRNAi is also or alternatively achieved by feeding of adult males on plant tissue expressing parental active dsRNA.

Figure 7:
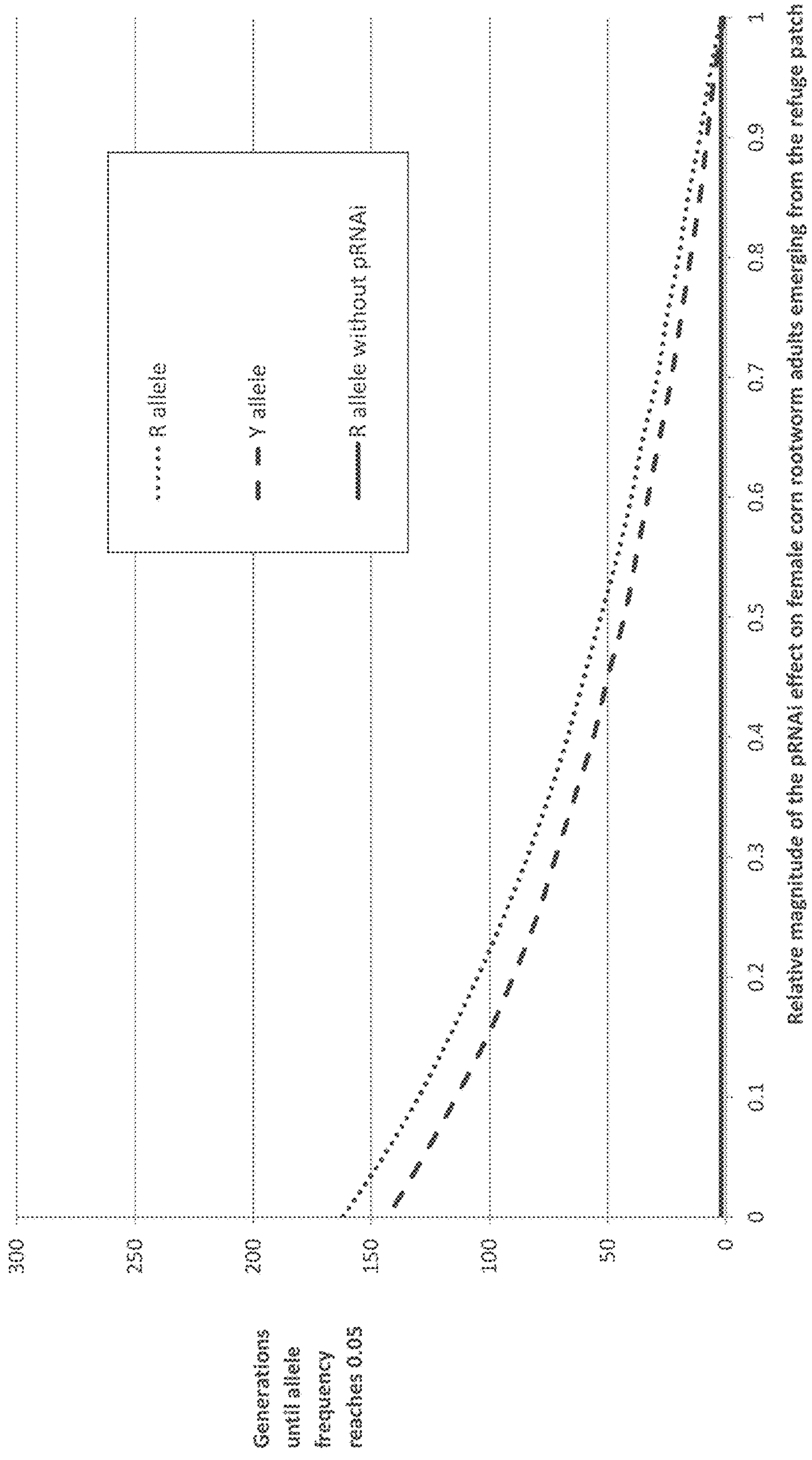
FIG. 7 includes a summary of modeling data showing the relative magnitude of the pRNAi effect on female WCR adults emerging from a "refuge patch" (i.e., that did not express insecticidal iRNAs or recombinant proteins in a transgenic crop) on the rate of increase in allele frequencies for resistance to an insecticidal protein (R) and RNAi (Y) when non-refuge plants express the insecticidal protein and parental active iRNA.

Frequencies of the two resistance alleles were calculated across generations. The initial frequencies of both of the resistance alleles (R and Y) were assumed to be 0.005. Results were presented as the number of insect generations for the frequencies of each of the resistance alleles to reach 0.05. To examine the resistance delay caused by the pRNAi, simulations that included pRNAi were compared to simulations that did not include pRNAi, but were identical in every other way. FIG. 7.

Figure 8:
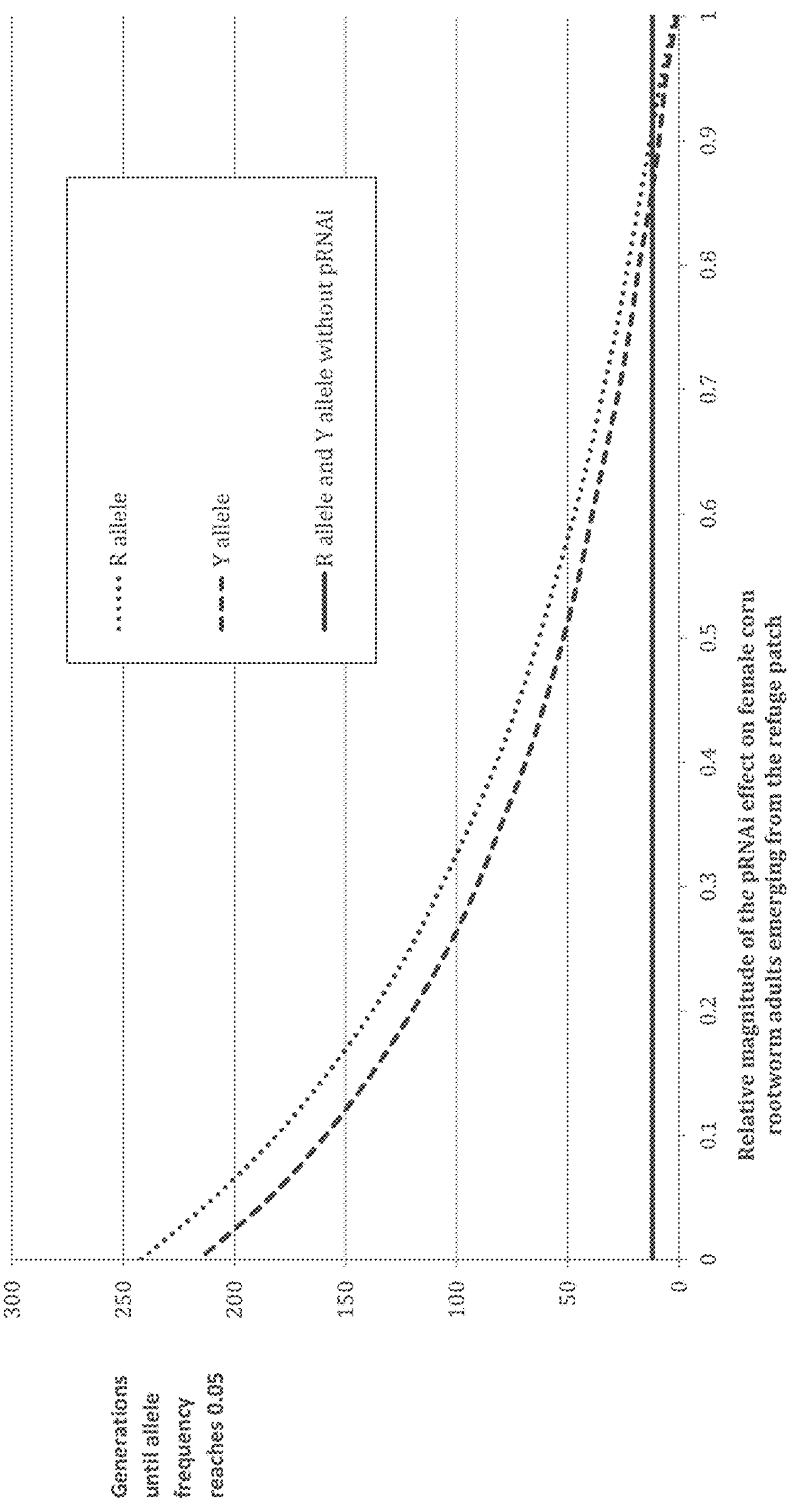
FIG. 8 includes a summary of modeling data showing the relative magnitude of the pRNAi effect on female WCR adults emerging from a "refuge patch" (i.e., that did not express insecticidal iRNAs or recombinant proteins in a transgenic crop of plants comprising corn rootworm larval-active interfering dsRNA in combination with the corn rootworm-active insecticidal protein in the transgenic crop) on the rate of increase in allele frequencies for resistance to an insecticidal protein (R) and RNAi (Y) when non-refuge plants express the insecticidal protein and both larval active and parental active iRNA molecules.

The model was also modified to include corn rootworm larval-active interfering dsRNA in combination with the corn rootworm-active insecticidal protein in the transgenic crop. Therein, the larval RNAi was assigned an effect of 97% larval mortality for homozygous RNAi-susceptible corn rootworm larvae (genotype XX), and no effect on corn rootworm larvae that are homozygous RNAi-resistant (YY). There was 67.9% mortality of corn rootworm larvae that were heterozygous for RNAi-resistance (XY). It was assumed that the same mechanism of resistance applied to both larval active RNAi and pRNAi in corn rootworms. As before, the pRNAi effect on adult females emerging from the refuge patch relative to the effect on adult females emerging from the transgenic patch was varied from 0 to 1. As before, to examine the resistance delay caused by the pRNAi, simulations that included pRNAi were compared to simulations that did not include pRNAi, but were identical in every other way (including larval RNAi). FIG. 8.

A clear resistance management benefit of pRNAi was observed when the magnitude of the pRNAi effect on egg viability for female corn rootworm adults emerging from the refuge patch was reduced compared with magnitude of the effect for adults emerging from the transgenic patch. The transgenic crops that produced parental active dsRNA in addition to an insecticidal protein were much more durable compared with transgenic crops that produced only an insecticidal protein. Similarly, transgenic crops that produced parental active dsRNA in addition to both an insecticidal protein and a larval active dsRNA were much more durable compared with transgenic crops that produced only an insecticidal protein and a larval active dsRNA. In the latter case, the durability benefit applied to both the insecticidal protein and the insecticidal interfering dsRNA.

Example 17: Parental RNAi Effects on WCR Males

Newly emerged virgin WCR males received from CROP CHARACTERISTICS (Farmington, Minn.) were exposed to artificial diet treated with dsRNA for pRNAi (*brahma*) for 7 days with continuous dsRNA feeding. The surviving males were then paired with virgin females and allowed to mate for 4 days. Females were isolated into oviposition chambers and maintained on untreated diet to determine if mating was successful, based on egg viability. In addition, the females were dissected to determine the presence of spermatophores after 10 days of oviposition. Controls of GFP dsRNA and water were included.

Three replicates of 10 males and 10 females per treatment per replication were performed. Replicates were completed with newly emerged adults on 3 different days. Each treatment per replicate contained 10 males per treatment per replication and were placed in one well of a tray. Each well included 12 diet plugs treated with water or dsRNA (GFP or *brahma*). Each diet plug was treated with 2 μg dsRNA in 3 μL water. Trays were transferred to a growth chamber with a temperature of 23±1° C., relative humidity >80%, and L:D 16:8. Males were transferred to new trays with 12 treated diet plugs in each well on days 3, 5, and 7. On day 7, three males per replication per treatment were flash frozen for qPCR analysis, as described in EXAMPLE 7. On day 8, ten females and ten treated males were placed together in a container to allow mating. Each container included 22 untreated diet plugs. Insects were transferred to new trays with 22 untreated diet plugs on day 10. Males were removed on day 12 and used to measure sperm viability using fluorescent staining techniques. Females were transferred to a new tray with 12 untreated diet plugs every other day until day 22. On day 16, females were transferred to egg cages containing autoclaved soil for oviposition. On day 22, all females were removed from the soil cages and frozen to check for the presence of spermatophores. The soil cages were transferred to a new growth chamber with a temperature of 27±1° C., relative humidity >80%, and 24 h dark. On day 28, the soil was washed using a sieve #60 to collect eggs from each cage. Eggs were treated with a solution of formaldehyde (500 μL formaldehyde in 5 mL double distilled water) and methyl-(butycarbamoy)-2-benzimidazole carbamate (0.025 g in 50 mL double distilled water) to prevent fungal contamination, and were placed in small petri dishes containing filter paper. Photographs were taken of each petri dish for egg counting using the cell counter function of the ImageJ Software (Schneider et al. (2012) Nat. Methods 9:671-5). Petri dishes with eggs were transferred to a small growth chamber with a temperature of 27±1° C., relative humidity >80%, and 24 h dark. Larval hatch was monitored daily from days 29-42.

Sperm Viability.

Virgin western corn rootworm males were exposed to artificial diet treated with dsRNA for 7 days with the parental RNAi gene *brahma*. Treated diet was provided every other day. Four males per treatment per replication were used to test for sperm viability using a fluorescent technique to discriminate between living and dead sperm as described by Collins and Donoghue (1999). The Live Dead Sperm Viability Kit™ (Life Technologies, Carlsbad Calif.) contains SYBR 14, a membrane-permeant nucleic acid stain, and propidium iodine, which stains dead cells.

WCR males were anesthetized on ice, testes and seminal vesicles were dissected, placed in 10 μL buffer (HEPES 10 mM, NaCl 150 mM, BSA 10%, pH 7.4,) and crushed with an autoclaved toothpick. Sperm viability was immediately assessed using the Live Dead Sperm Viability Kit™. A 1 μL volume of SYBR 14 (0.1 mM in DMSO) was added and incubated at room temperature for 10 minutes, followed by addition of 1 μL propidium iodine (2.4 mM), and incubated again at room temperature for 10 minutes. A 10 μL volume of sperm stained solution was transferred to a glass microslide and covered with a cover slip. Samples were evaluated using a Nikon™ Eclipse 90i microscope with a Nikon A1 confocal and MS-Elements Software. Samples were visualized at 10× with 488 excitation, a 500-550 nm band pass for live sperm (SYBR 14) and 663-738 nm band pass for dead sperm (propidium iodine) simultaneously. Digital images were recorded for five fields of view per sample. The number of live (green) and dead (red) sperm was evaluated using the cell counter function of ImageJ Software (Schneider et al. (2012) Nat. Methods 9:671-5)).

Males fed *brahma* dsRNA for 7 days produced less total sperm, less live sperm, and less dead sperm than males ingesting GFP dsRNA or water alone. Table 16. The average number of live sperm was significantly different between the treatments. There was no statistical difference in percent egg hatch from females that had mated with males that had ingested dsRNA treatments. Table 17.

TABLE 16

Effect of brahma dsRNA on WCR adult male sperm production and viability after 7 days of ingestion on treated artificial diet. Means were separated using Dunnett's test.

| Treatment | Average dead sperm ± SEM† | Average live sperm ± SEM† | Average total sperm ± SEM† |
|---|---|---|---|
| brahma | 46.89 ± 8.83** | 121.88 ± 15.43** | 152.29 ± 24.78** |
| GFP | 74.79 ± 14.17 | 222.74 ± 38.89* | 288.73 ± 43.18** |
| Water | 68.5 ± 12.26 | 164.7 ± 31.87 | 233.2 ± 22.33 |

†SEM—Standard Error of the Mean.

*Indicates significance at p-value ≤ 0.1.

**Indicates significance at p-value ≤ 0.05.

TABLE 17

Effect of brahma dsRNA on WCR egg production and egg viability after 7 days of ingestion dsRNA treated artificial diet by males only. Means were separated using Dunnett's test.

| | Egg numbers per female beetle | | | Percent egg hatch | | |
|---|---|---|---|---|---|---|
| | brahma Reg352 dsRNA | GFP dsRNA | Water | brahma Reg352 dsRNA | GFP dsRNA | Water |
| Average | 61.55* | 58.08 | 38.52 | 62.85 | 82.93 | 76.24 |
| SEM† | 21.46 | 11.38 | 15.94 | 12.83 | 2.56 | 5.31 |

*Indicates significance at p-value ≤0.1.
†SEM—Standard error of the mean.

Virgin males were treated as described above except that the exposure to dsRNA was increased to a total of 6 times. Males were transferred to new trays with 12 treated diet plugs in each well on days 3, 5, 7, 9, and 11. The surviving males were then paired with virgin females and allowed to mate for 4 days. Females were isolated into oviposition chambers and maintained on untreated diet to determine if mating was successful based on egg viability.

TABLE 18

Effect of brahma dsRNA on WCR egg production and egg viability after 7 days of ingestion dsRNA treated artificial diet by males only. Means were separated using Dunnett's test.

| | Egg numbers per female beetle | | | Percent egg hatch | | |
|---|---|---|---|---|---|---|
| | brahma Reg352 dsRNA | GFP dsRNA | Water | brahma Reg352 dsRNA | GFP dsRNA | Water |
| Average | 61.01 | 61.20 | 51.14 | 22.27* | 32.80 | 35.41 |
| SEM† | 5.99 | 14.83 | 8.28 | 3.99 | 6.89 | 7.5 |

*Indicates significance at p-value ≤0.1.
†SEM—Standard error of the mean.

Relative expression in males was determined as described in Example 7.

TABLE 19

Relative expression of brahma in adult males exposed to dsRNA in treated artificial diet relative to GFP and water controls. There is a reduction in transcript levels in male adults. Means were separated using Dunnett's test.

| Treatment | Relative expression | SEM† | p-value |
|---|---|---|---|
| brahma | 0.138 | 0.028 | <0.0001 |
| GFP | 0.964 | 0.132 | 0.836 |
| Water | 1.023 | 0.075 | |

†SEM—Standard error of the mean.

Example 18: Effective Concentration

Mated females were exposed to 4 exposure conditions of *brahma* dsRNA to determine the effective concentrations. Newly emerged (<48 hours) adult males and females were obtained from CROP CHARACTERISTICS (Farmington, Minn.). Treatments included 2, 0.2, 0.02, and 0.002 μg *brahma* dsRNA per diet plug. GFP at 2 μg and water served as the controls. Ten males and 10 females were placed together in one well containing 20 pellets of untreated artificial diet. Trays were transferred to a growth chamber and maintained at 23±1° C., relative humidity >80%, and 16:8 L:D photoperiod. Males were removed from the experiment on day 5. Freshly treated diet was provided every other day until day 13. On day 14 females were transferred to egg cages containing autoclaved soil and new treated artificial diet was provided (11 plugs per cage). Egg cages were placed back in the growth chamber. On day 16 new treated diet was provided as described above. All females were removed from the soil cages on day 18 and flash frozen for qPCR. Soil cages were transferred to a new growth chamber with a temperature of 27±1° C., relative humidity >80% and 24 h dark. On day 24 the soil was washed using a #60 sieve to collect eggs from each cage. Eggs were treated with a solution of formaldehyde (500 μl formaldehyde in 5 ml of double distilled water) and methyl-(butycarbamoy)-2-benzimidazole carbamate (0.025 g in 50 ml of double distilled water) to prevent fungal contamination and placed in small petri dishes containing filter paper. Photographs were taken of each petri dish for egg counting using the cell counter function of Image J software (Schneider et al. (2012) Nat. Methods 9:671-5). Petri dishes with eggs were transferred to a small growth chamber with a temperature of 27±1° C., relative humidity >80%, and 24 h dark. Larval hatching was monitored daily through 15 days. Larvae were counted and removed from the Petri dish each day.

There was significantly reduced egg hatch at the 2 and 0.2 μg/diet plug treatments (Table 20), but there was no difference in the number of eggs oviposited per female between any of the doses tested and the controls.

TABLE 20

Effect of brahma dsRNA concentrations on WCR egg production and egg viability after ingestion of treated artificial diet. Means were separated using Dunnett's test.

| | Dose | Avg. no. eggs per female beetle | | Percent egg hatch | |
|---|---|---|---|---|---|
| Treatment | (μg) | Average | SEM† | Average | SEM† |
| brahma Reg352 dsRNA | 2 | 23.22 | 5.96 | 0.23** | 0.25 |
| brahma Reg352 dsRNA | 0.2 | 80.05 | 9.86 | 7.09** | 4.45 |
| brahma Reg352 dsRNA | 0.02 | 76.85 | 17.51 | 29.03 | 10.71 |
| brahma Reg352 dsRNA | 0.002 | 71.16 | 18.9 | 45.26 | 4.01 |
| GFP dsRNA | 2 | 64.87 | 28.64 | 32.58 | 10 |
| Water | 0 | 70.71 | 20.18 | 39.41 | 3.92 |

†SEM—Standard Error of the Mean.
**Indicates significance at (p-value < 0.05).

Example 19: Timing of Exposure

Figure 9A:
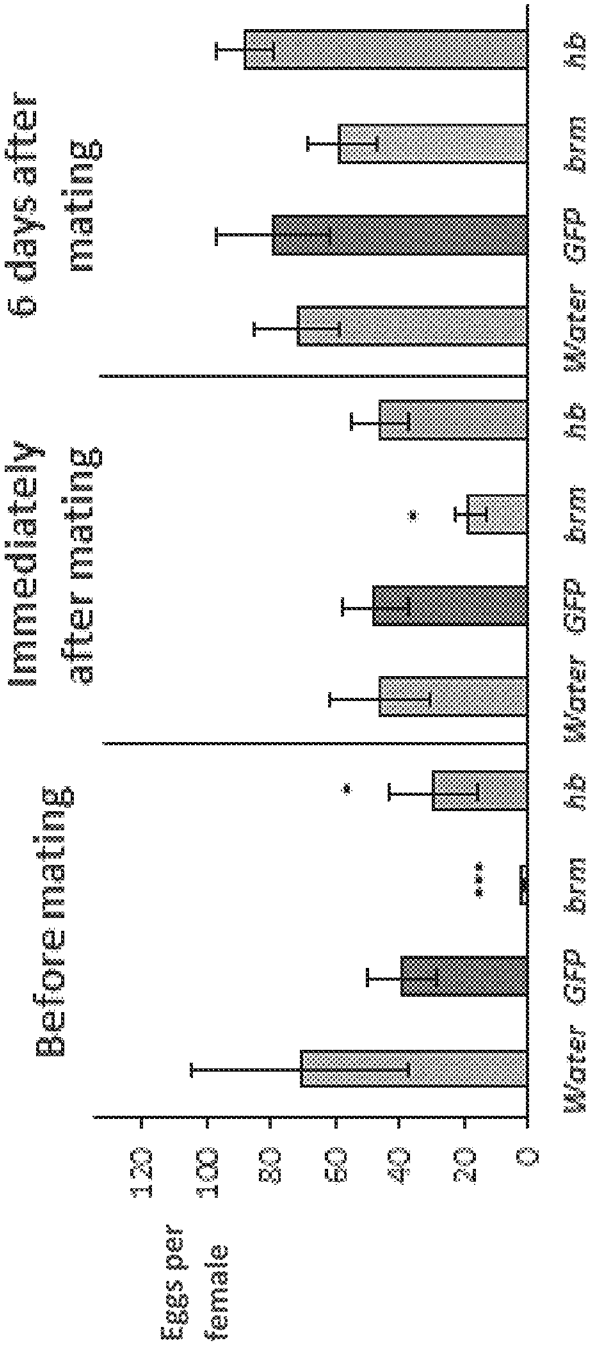
FIG. 9A illustrates a summary of data showing the number of eggs recovered per female and FIG. 9B illustrated results of the percent total larvae that hatched, respectively, after exposure to 2 μg of *brahma* or GFP dsRNA six times before mating, immediately after mating, and six days after mating. Comparisons performed with Dunnett's test, * indicates significance at p<0.1,  indicates significance at p<0.05, * indicates significance at p<0.001.
Figure 9B:
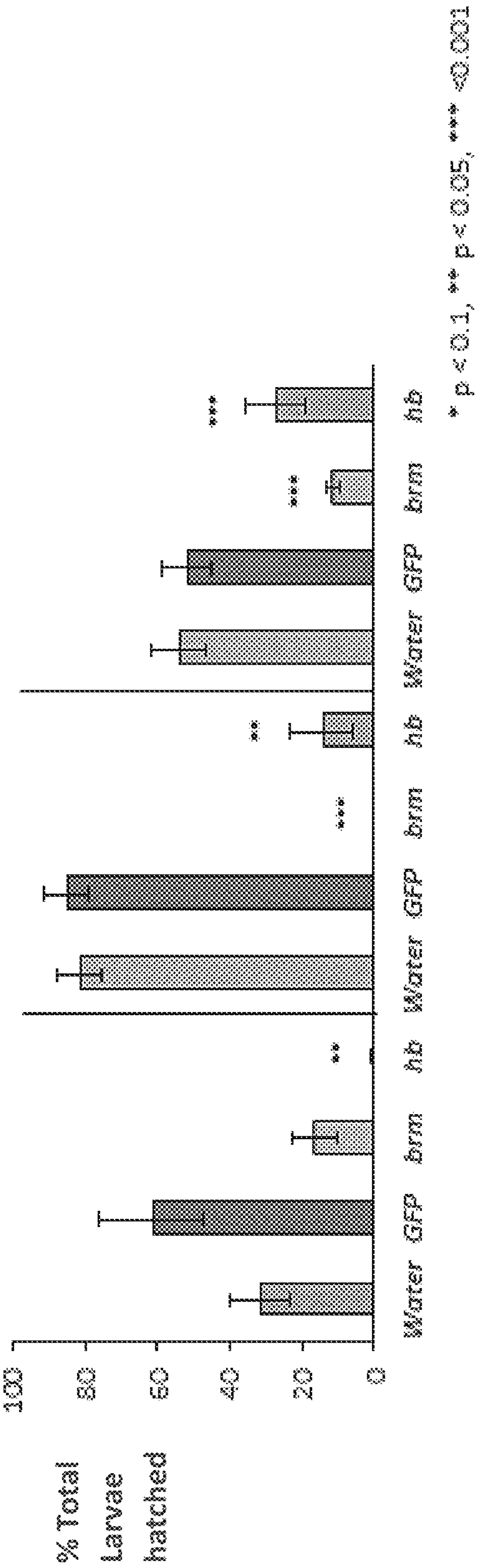
Figure 10:
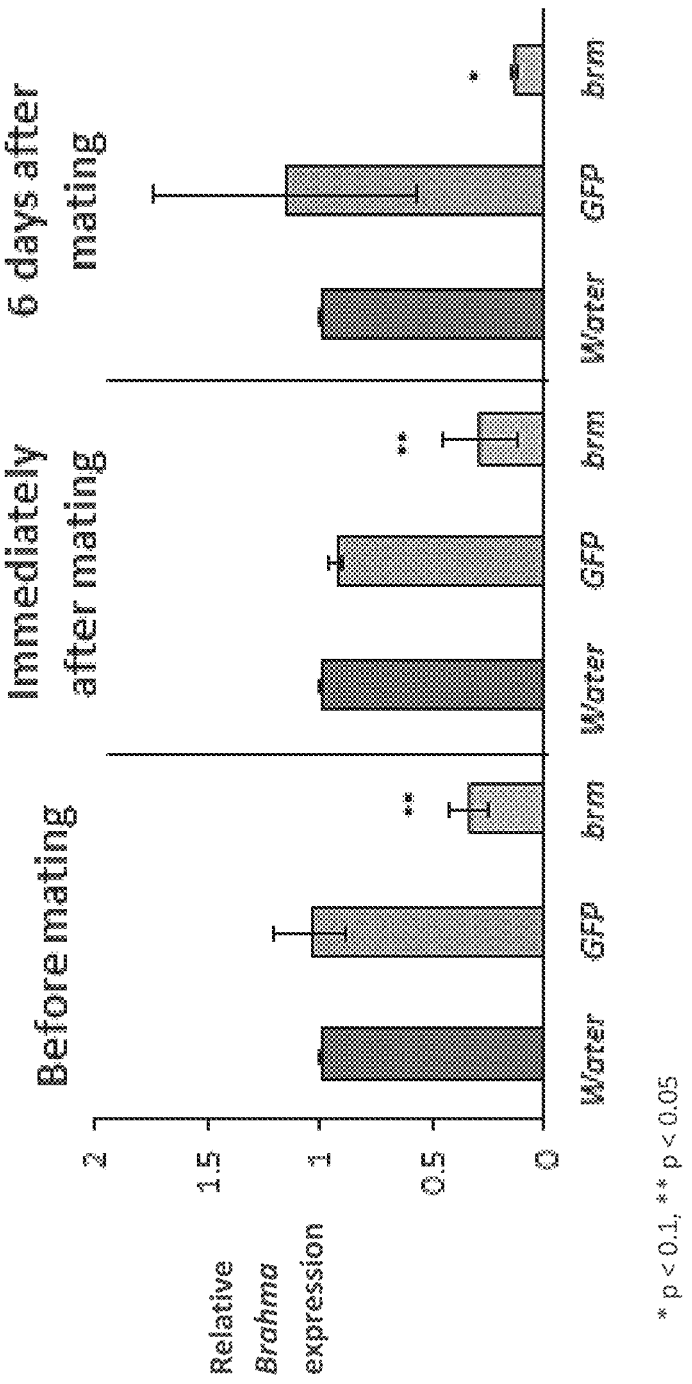
FIG. 10 illustrates a summary of data showing the relative *brahma* expression measured after exposure to 2 μg of *brahma* or GFP dsRNA six times before mating, immediately after mating, and six days after mating. Comparisons performed with Dunnett's test, * indicates significance at p<0.1,  indicates significance at p<0.05, * indicates significance at p<0.001.

Females were exposed 6 times to 2 μg of *brahma* dsRNA starting at three different times to determine the timing of exposure necessary to generate a parental RNAi effect. Females were exposed to dsRNA 6 times before mating, 6 times immediately after mating, and 6 days after mating. Three replications of 10 females and 10 males per replication were completed for each exposure time. Adult WCRs were received from CROP CHARACTERISTICS (Farmington, Minn.).

dsRNA Feeding Before Mating:

Ten females were placed in one well with 11 pellets of treated artificial diet (2 μg dsRNA per pellet). Trays were transferred to a growth chamber with a temperature of 23±1° C., relative humidity >80%, and 16:8 L:D photoperiod. Females were transferred to trays containing fresh treated diet every other day for 10 days. On day 12 females were paired with 10 males and 22 plugs of untreated diet were provided. Males were removed after 4 days. Fresh untreated diet was provided every other day for 8 days. On day 22 females were transferred to egg cages containing autoclaved soil with 11 plugs of untreated artificial diet. Egg cages were placed back in the growth chamber and the diet was replaced on day 24. On day 26 females were removed from the soil cages and flash frozen for qPCR. Soil cages were transferred to a growth chamber with temperature 27±1° C., relative humidity >80% and 24 h dark. After 4 days the soil was washed using a #60 sieve to collect eggs from each cage. Eggs were treated with a solution of formaldehyde (500 μl formaldehyde in 5 ml of double distilled water) and methyl-(butycarbamoy)-2-benzimidazole carbamate (0.025 g in 50 ml of double distilled water) to prevent fungal contamination and placed in small petri dishes containing filter paper. Photographs were taken of each petri dish for egg counting using the cell counter function of Image J software (Schneider et al. (2012) Nat. Methods 9:671-5). Petri dishes with eggs were transferred to a small growth chamber with a temperature of 27±1° C., relative humidity >80%, and 24 h dark. Larval hatching was monitored daily for 15 days. Results of the percent total larvae that hatched are shown in FIG. 9B and the percent of total larvae that hatched is shown in FIG. 9A. Relative *brahma* expression of females was measured after receiving 6 times dsRNA and is shown in FIG. 10.

dsRNA Feeding Immediately after Mating:

Methods similar to those described above were used except that 10 males and 10 females were placed together in one well with 22 pellets of untreated artificial diet at the start of the study. Trays were transferred to growth chamber as described above. Fresh untreated diet was provided on day 3 and males were removed on day 5. Females were then transferred to treated artificial diet and maintained in the growth chamber. Fresh treated diet was provided every other day for 6 days. On day 12 females were transferred to egg cages containing autoclaved soil with 11 plugs of treated artificial diet. Egg cages were placed back in the growth chamber and fresh treated diet was provided on day 14. On day 16 all females were removed from the soil cages and flash frozen for qPCR. Soil cages and egg wash was conducted after 6 days as described above. Photographs were taken of each petri dish for egg counting. Larval hatching was monitored daily for 15 days. Results of eggs per female are shown in FIG. 9A and results of the percent total larvae that hatched are shown in FIG. 9B. Relative *brahma* expression of females was measured after receiving 6 times dsRNA and is shown in FIG. 10.

dsRNA Feeding Six Days after Mating:

Methods similar to those described above for dsRNA feeding immediately after mating except that insects received untreated artificial diet every other day until day 11 when females were transferred to treated diet. On day 12 females were transferred to egg cages containing autoclaved soil with 11 plugs of treated artificial diet. Egg cages were placed back in the growth chamber. Fresh treated diet was provided every other day from days 12-20. At day 22, all females were removed from the soil cages and flash frozen for qPCR. Soil cages and egg wash was conducted after 6 days as described above. Photographs were taken of each petri dish for egg counting. Larval hatching was monitored daily for 15 days. Larvae were counted and removed from the Petri dish each day. Results of eggs per female are shown in FIG. 9A and results of the percent total larvae that hatched are shown in FIG. 9B. Relative *brahma* expression was measured and is shown in FIG. 10.

Female mortality was recorded every other day for all treatments throughout the study.

Example 20: Duration of Exposure

Figure 11A:
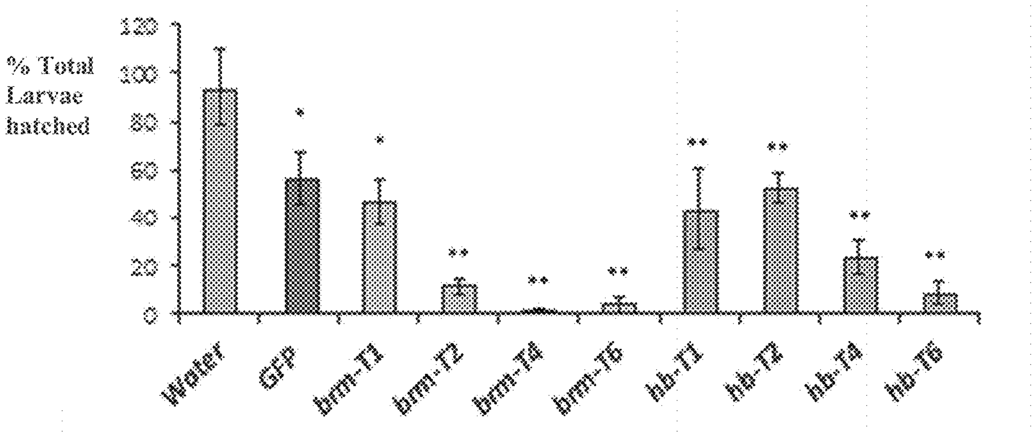
FIG. 11A illustrates a summary of data showing the effect of the duration of exposure to insects exposed to 2 μg of *brahma* or GFP dsRNA 1, 2, 4 or 6 times (brm-T1, -T2, -T4 or -T6).
Figure 11B:
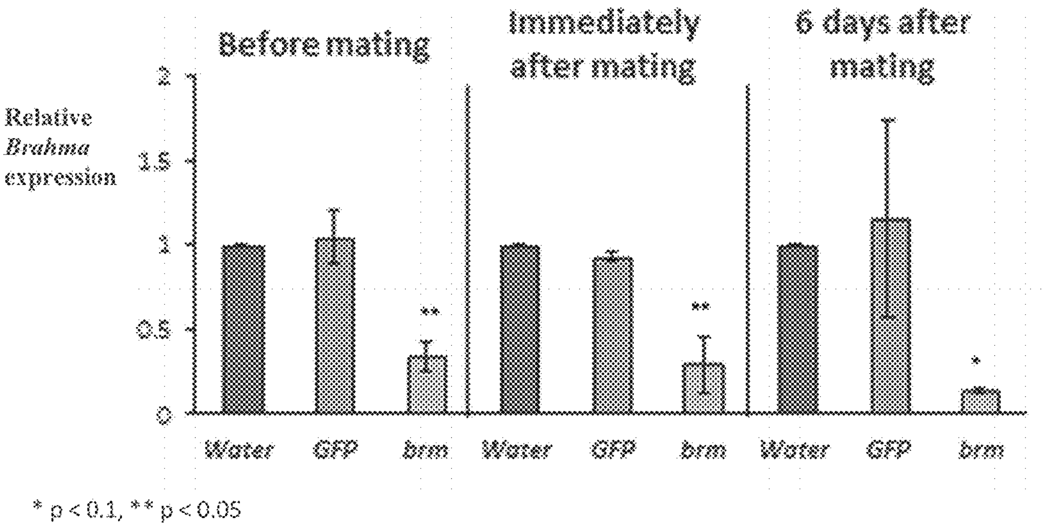
FIG. 11B illustrates the relative *brahma* expression measured on day 12 after the first exposure to 2 μg of *brahma* or GFP dsRNA. Comparisons performed with Dunnett's test, * indicates significance at p<0.1,  indicates significance at p<0.05, * indicates significance at p<0.001.

Virgin males and females were paired for a period of 4 days with untreated diet after which the mated females were exposed to 2 μg *brahma* dsRNA. To evaluate the effect of the duration of exposure insects were exposed to *brahma* or GFP dsRNA 1, 2, 4 or 6 times (shown as brm-T1, -T2, -T4 or -T6 in FIG. 11A and FIG. 11B). Four replications of 10 females and 10 males were completed per treatment. Adult males and females were received from CROP CHARACTERISTICS (Farmington, Minn.). Ten males and 10 females were placed together in one well with 20 pellets of untreated artificial diet. Trays were maintained in a growth chamber with a temperature of 23±1° C., relative humidity >80%, and 16:8 L:D photoperiod. New untreated artificial diet was provided on day 3. Males were removed on day 5 and females were transferred to a new tray containing 11 diet plugs per well with the respective treatment. On day 7, females were transferred to trays with new treated artificial diet and mortality was recorded. Females from 1 time (T1) of exposure treatment were transferred to untreated diet. On day 10 and 12 females were transferred to new trays with new treated artificial diet and mortality was recorded. Females from T1 and T2 were transferred to untreated diet. On day 14 females were transferred to egg cages containing autoclaved soil and new treated artificial diet was provided. Females from T1, T2 and T4 were provided untreated diet. On day 16, old diet was removed and new treated diet (11 plugs per cage) was added. Females from 1, 2 and 4 times of exposure were provided untreated diet. After 18 days all females were removed from the soil cages and flash frozen for qPCR. Soil cages were transferred to a growth chamber with a temperature of 27±1° C., relative humidity >80% and 24 h dark. Eggs were washed and photographs were taken of each petri dish as indicated for the timing of exposure. Hatched larvae were counted and removed from each Petri dish every day for 15 days. Results of the percent total larvae that hatched are shown in FIG. 11A. Relative *brahma* expression of females was measured and is shown in FIG. 11B.

Example 21: Ovarian Development

*D. v. virgifera* ovarian development was evaluated in females exposed to artificial diet treated with *brahma* dsRNA before mating and immediately after mating as described for the timing of exposure. Females were exposed to 2 μg *brahma* or GFP dsRNA, or water 6 times. Five females per treatment were collected one day after the last dsRNA exposure and stored in 70% ethanol for subsequent ovary dissections. Ovary dissections for all surviving females were performed under a stereomicroscope. Images were acquired with an Olympus SZX16 microscope, Olympus SDF PLAPO 2×PFC lens and the Olympus CellSens Dimensions software (Tokyo, Japan).

*D. v. virgifera* ovary dissections revealed no apparent differences in ovary development between females treated with water, GFP or *brahma* dsRNA; this was true for both unmated females as well as those dissected immediately after mating.

What may be claimed is:

1. An isolated nucleic acid molecule comprising a polynucleotide operably linked to a heterologous promoter, wherein the polynucleotide comprises SEQ ID NO:8, the complement of SEQ ID NO:8, SEQ ID NO:10, or the complement of SEQ ID NO:10.

2. The nucleic acid molecule of claim 1, wherein the polynucleotide is comprised in a vector.

3. A ribonucleic acid (RNA) molecule encoded by the nucleic acid molecule of claim 1.

4. The RNA molecule of claim 3, wherein the molecule is a double-stranded ribonucleic acid (dsRNA) molecule.

5. The dsRNA molecule of claim 4, wherein the dsRNA molecule is a hairpin RNA (hpRNA) molecule.

6. The RNA molecule of claim 3, wherein the molecule is a single-stranded RNA molecule.

7. The nucleic acid molecule of claim 1, wherein the heterologous promoter is functional in a plant cell.

8. A prokaryotic cell comprising the nucleic acid molecule of claim 1.

9. A eukaryotic cell comprising the nucleic acid molecule of claim 1.

10. A plant cell comprising the nucleic acid molecule of claim 7.

11. A transgenic plant comprising the nucleic acid molecule of claim 7.

12. A transgenic plant part comprising the nucleic acid molecule of claim 7.

13. A commodity product produced from the transgenic plant of claim 11, wherein the commodity product comprises a detectable amount of the polynucleotide.

14. The transgenic plant of claim 11, wherein a cell of the plant comprises a double-stranded ribonucleic acid (dsRNA) molecule encoded by the polynucleotide.

15. The cell of claim 10, wherein the cell is a *Zea mays* cell.

16. The transgenic plant of claim 11, wherein the plant is *Zea mays*.

17. The transgenic plant of claim 11, wherein the dsRNA molecule functions to inhibit a biological function within a *Diabrotica virgifera* pest when the *Diabrotica virgifera* pest ingests a part of the plant.

18. A method for controlling a *Diabrotica virgifera* pest population, the method comprising contacting a pest of the population with the dsRNA molecule of claim 4.

19. The method according to claim 18, wherein the dsRNA molecule is a hairpin RNA (hpRNA) molecule.

20. The method according to claim 18, wherein the dsRNA molecule is introduced into a male *Diabrotica virgifera* pest.

21. The method according to claim 18, wherein the dsRNA molecule is introduced into a female *Diabrotica virgifera* pest, the method further comprising releasing the female *Diabrotica virgifera* pest comprising the dsRNA molecule into the pest population, wherein mating between the female *Diabrotica virgifera* pest and male pests of the population produces fewer viable offspring than mating between other female pests and male pests of the population.

22. A method for controlling a *Diabrotica virgifera* pest population, the method comprising:

feeding the plant cell of claim 10 to a *Diabrotica virgifera* pest of the population, wherein the polynucleotide is expressed in the plant cell to produce a dsRNA molecule, functioning when ingested by the *Diabrotica virgifera* pest to inhibit a biological function of the *Diabrotica virgifera* pest or pest population.

23. A method of controlling *Diabrotica virgifera* pest infestation in a plant, the method comprising providing in the diet of a *Diabrotica virgifera* pest a double-stranded ribonucleic acid (dsRNA) molecule comprising as one strand a polyribonucleotide that is specifically hybridizable with SEQ ID NO:139, the complement of SEQ ID NO:139, SEQ ID NO: 140, or the complement of SEQ ID NO: 140.

24. The method according to claim 23, wherein the dsRNA molecule is a hairpin RNA (hpRNA) molecule, and the diet comprises a plant cell that expresses the hpRNA molecule.

25. A method for producing a transgenic corn plant, the method comprising:

introducing the nucleic acid molecule of claim 7 into a corn plant to produce a transgenic corn plant, wherein expression of the polynucleotide produces a dsRNA molecule that functions upon contact with a *Diabrotica virgifera* pest to inhibit a biological function within the pest when the pest ingests a portion of the corn plant.

26. The nucleic acid molecule of claim 1, further comprising a polynucleotide encoding a polypeptide from *Bacillus thuringiensis.*

27. The nucleic acid molecule of claim 26, wherein the polypeptide from *B. thuringiensis* is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

28. The plant cell of claim 10, wherein the cell comprises a polynucleotide encoding a polypeptide from *Bacillus thuringiensis.*

29. The plant cell of claim 28, wherein the polypeptide from *B. thuringiensis* is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, CytlA, and Cyt2C.

30. The transgenic plant of claim 11, wherein the plant comprises a polynucleotide encoding a polypeptide from *Bacillus thuringiensis.*

31. The transgenic plant of claim 30, wherein the polypeptide from *B. thuringiensis* is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

32. The method according to claim 23, wherein the method further comprises feeding the *Diabrotica virgifera* pest with an insecticidal polypeptide from *Bacillus thuringiensis.*

33. The method according to claim 32, wherein the insecticidal polypeptide from *B. thuringiensis* is selected from a group comprising Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C.

34. The transgenic plant part of claim 12, wherein the plant part is a seed.

35. The method according to claim 18, wherein contacting the *Diabrotica virgifera* pest with the dsRNA molecule comprises contacting the pest with a sprayable composition comprising the agent.

36. The method according to claim 18, wherein contacting the *Diabrotica virgifera* pest with the dsRNA molecule comprises feeding a plant cell comprising the dsRNA molecule to the pest.

37. The method according to claim 25, the method further comprising cultivating the corn plant.

38. The method according to claim 22, wherein feeding the plant cell to the *Diabrotica virgifera* of the population comprises providing a transgenic plant comprising the plant cell to the coleopteran pest population.

* * * * *